United States Patent [19]
Page et al.

[11] Patent Number: 6,020,476
[45] Date of Patent: Feb. 1, 2000

[54] DAZ: A GENE FAMILY ASSOCIATED WITH AZOOSPERMIA

[75] Inventors: David C. Page, Winchester; Renee Reijo, Allston; Richa Saxena, Cambridge; Trevor Hawkins, Somerville; Mary Pat Reeve, Arlington, all of Mass.

[73] Assignee: Whitehead Institute for Biomedical Research, Cambridge, Mass.

[21] Appl. No.: 08/742,185

[22] Filed: Oct. 30, 1996

Related U.S. Application Data

[63] Continuation-in-part of application No. 08/690,734, Jul. 31, 1996, Pat. No. 5,871,920, which is a continuation-in-part of application No. 08/310,429, Sep. 22, 1994, Pat. No. 5,695,935.

[51] Int. Cl.[7] .............................. C07H 21/04; C12Q 1/68
[52] U.S. Cl. ................... 536/23.5; 536/23.1; 536/24.31; 536/24.33; 435/6
[58] Field of Search ........................... 435/6, 91.2, 91.1; 536/23.1, 24.31, 24.33, 23.5

[56] References Cited

U.S. PATENT DOCUMENTS

| | | | |
|---|---|---|---|
| 5,695,935 | 12/1997 | Page et al. | 435/6 |
| 5,776,682 | 7/1998 | First et al. | 435/6 |
| 5,840,549 | 11/1998 | First et al. | 435/91.2 |
| 5,871,920 | 2/1999 | Page et al. | 435/6 |

OTHER PUBLICATIONS

Foote et al. Science 258: 60–66, 1992.
Lucotte et al. Nucleic Acids Research 13:8285, 1985.
Yen et al. Human Molecular Genetics 5: 2013–2017 (abstract provided), 1996.
Kun Ma et al., "A Y Chromosome Gene Family with RNA–Binding Protein Homology: Candidates for the Azoospermia Factor AZF Controlling Human Spermatogenesis", *Cell* 75:1287–1295 (1993).
Simon Foote et al., "The Human Y Chromosome: Overlapping DNA Clones Spanning the Euchromatic Region", *Science* 258:60–66 (1992).
Douglas Vollrath et al., "The Human Y Chromosome: A 43–Interval Map Based on Naturally Occurring Deletions", *Science* 258:52–59 (1992).
Renee Reijo et al., "Mouse Autosomal Homolog of DAZ, a Candidate Male Sterility Gene in Humans, Is Expressed in Male Germ Cells before and after Puberty", *Genomics* 35:346–352 (1996).
Howard J. Cooke et al., "A murine homologue of the human DAZ gene is autosomal and expressed only in male and femal gonads", *Hum. Molec. Genet.* 5(4):513–516 (1996).
Kim Yen Ngo et al., "A DNA Probe Detecting Multiple Haplotypes of the Human Y Chromosome", *Am. J. Hum. Genet.* 38:407–418 (1996).
G. Lucotte et al., "Y Chromosome DNA Polymorphisms in Two African Populations", *Am. J. Hum. Genet.* 45:16–20 (1989).
Renee Reijo et al., "Diverse spermatogenic defects in humans caused by Y chromosome deletions encompassing a novel RNA–binding protein gene", *Nature Genet.* 10:383–393 (1995).
P.H. Vogt et al., "Human Y chromosome azoospermia factors (AZF) mapped to different subregions in Yq11", *Hum. Mole. Genet* 5(7):933–943 (1996).
Colin Bishop et al., "Extensive Sequence Homologies Between Y and Other Human Chromosomes", *J. Mol. Biol.* 173:403–417 (1984).
Gérad Lucotte et al., "Nucleotide sequence of p49a, a genomic Y–specific probe with potential utilization in sex determination", *Molec. and Cell. Probes* 5:359–363 (1991).

*Primary Examiner*—Carla J. Myers
*Attorney, Agent, or Firm*—Hamilton, Brook, Smith & Reynolds, P.C.

[57] ABSTRACT

A small family of novel genes referred to as the DAZ gene family, present in interval 6D and/or 6E of the distal portion of the long arm of the human Y chromosome and on human chromosome 3. Alteration of a DAZ gene present in interval 6D and/or 6E of the distal portion of the long arm of the human Y chromosome is associated with reduced sperm count. Methods of diagnosis and treatment utilizing a DAZ gene, and antibodies that bind to the protein encoded by said genes.

12 Claims, 39 Drawing Sheets

```
3/1
TCA GCT GGG GTC TAC TCC GAG GGT TCG CCC GAC CTT GGT TTT CCT TAC ACC TTA GCC TTT
                                                          33/11                              63/21
GGC TCC TTG ACC ACT CGA GCC CCA CAG GTC

93/31
TTC CAG CGG ACT TCA CCA GCA GAC CCA GAA GTG GTG GGT GAA ACA CTG CCT CTG TTC CTC
                                                         123/41                              153/51
GAG CCT GTC GGG AGC TGC TGC CTG CCA

183/61
CCA CCA TGT CTG CTG CAA ATC CTG AGA CTC CAA ACT CAA CCA TCT CCA GAG AGG CCA GCA
                                        213/71                                    243/81
CCC AGT CTT CAT CAG CTG CAG CTA GCC AAG

273/91
GCT GGG TGT TAC CAG AAG GCA AAA TCG TGC CAA ACA CTG TTT TTT GTT GGT GGA ATT GAT
                          303/101                                   333/111
GAA ACT GAG ATT GGA AGC

363/121
TGC TTT GGT AGA TAC GGT TCA GTG AAA AGA AGT GAA GAT AAT CAC GAA TCG AAC TGG TGT
                                              393/131                                 423/141
TCC AAA GGC TAT GGA TTT GTT TCG TTT GTT

453/151
AAT GAC GTG GAT GTC CAG AAG ATT AGT AGG ATC ACA GAA TAC ATC TCC ATG GGT AAA AAG
                                  483/161                                     513/171
CTG AAG CTG GGC CCT GCA ATC AGG AAA CAA

543/181
AAG TTA TGT GCT CGT CAT GTG CAG CCA CGT CCT TTG GTA GTT AAT CCT CCT CCT CCA CCA
                              573/191                                603/201
CAG TTT CAG AAC GTC TGG CGG AAT CCA AAC

633/211
ACT GAA ACC TAC CTG CAG CCC CAA ATC ACG CCG AAT CCT GTA ACT CAG TAC GTT CAG TCT
                      663/221                              693/231
GCT GCA AAT CCT
```

FIG. 1

GAGTAATCAXATGCAXGTCATACTGAATTTGTACTGTATCACAGGTACTTCTTG

GAGAAGTGAAATGCTTGTGTTCAGACTATCAAAATTGTTAGCTTACAAATCAGG

TTTTAAAAACTTTTGGAAAGTCAGTATGTGCTTTTAAACACTTAAATGCAXGTC

TCAXTTTTTTTTTTTTTCCGXAGATATCTTAACATTCTTCAGTCTCGATTATGTG

TTACTTTAAACTATATATTAAACACAGACCCAGGTTCTAAATAAACATCTAATG

AAGAACAGCATCGTTAAGATAAAAACTAGAGAGTCTAATAATACAAGTTATAC

AGAAAGTTTCAGTGTGATTTCCAAATTCAGAATTTCAGTAATAGTGGAAAAACT

TTTAGCTTATATCACCCAGCACTCCCCATGAAACTAGATGCTGAGAGGCC

FIG. 2

| FIG. 3A | FIG. 3B |
|---|---|
| FIG. 3C | FIG. 3D |

| PATIENT NO. | Category |
|---|---|
| 2475 | Terminal Deletion |
| 1305 | Terminal Deletion |
| 1310 | Terminal Deletion |
| 1318 | Terminal Deletion |
| 2064 | Terminal Deletion |
| 746 | Terminal Deletion |
| 1788 | Terminal Deletion |
| 2240 | Terminal Deletion |
| 2168 | Terminal Deletion |
| 496 | Terminal Deletion |
| 2229 | Terminal Deletion |
| 1078 | Terminal Deletion |
| 1659 | Normal, Fertile |
| 2376 | Infertile |
| 2381 | Infertile |
| 2415 | Infertile |
| 2430 | Infertile |
| 2613 | Infertile |
| 2615 | Infertile |
| 2564 | Infertile |
| KLARD | Infertile |
| KUPAU | Infertile |
| MKB | Infertile |

FIG. 3C

AGTCGGCCTGCG

CTCC-TCAGCCTGGCGGTTCTACCTCCGAGGGTTCGCCCGCCCTTGGTTTTCCTTACACC

TTAGCCTTTGGCTCCTTTGACCACTCGAAGCCCCACAGCGTGTTCCAGCGGACTTCACCA

GCAGACCCAGAAGTGGTGGGTGAAACACTGCCTCTGTTCCTCCTTGAGCCTGTCGGGAGC

TGCTGCCTG----------------CCACCACCATGTCTGCTGCAAATCCTGAGACTCC

AAACTCAACCATCTCCAGAGAGGCCAGCACCCAGTCTTCATCAGCTGCAGCTAGCCAAGG

CTGGGTGTTACCAGAAGGCAAAATCGTGCCAAACACTGTTTTT--GTTGGTGGAATTGAT

GCTAGGATGGATGAAACTGAGATTGGAAGCTGCTTTGGTAGATACGGTTCAGTGAAA-GA

AGTGAAGATAATCACGAATCGAACTGGTGTGTCCAAAGGCTATGGATTTGTTTCGTTTGT

TAATGACGTGGATGTCCAGAA-GAT-AGTAGGA-TCACAGA-TACATTTCCAT-GGTAAA

FIG. 4 A

AGAGACTGATAAATTCCGTTGTTACTCAAGATGACTGCTTCAAGGGTAAAAGAGTGCATC

GCTTTAGAAGAAGTTTGGCAGTATTTAAATCTGTT-GGATCCTCTCAGCTATCTAGTTTC

ATGGGAAGTTGCTGGTTTTGAATATTAAGCTAAAAGTTTT-CCACTATTACAGAAATTCT

GAATTTTGGTAAATCACACTGAAACTTTCTGTATAACTTGTATTATTAGACTCTCTAGTT

TT-ATCTTAACACTGAAACTGTTCTTCATTAGATGTTTATTTAGAACCTGGTTCTGTGTT

TAATATATAGTTTAAAGTAACAAATAATCGAGACTGAAAGAATGTTAAGATTTATCTGCA

AGGATTTTTAAAAAATTGAAACTTGCATTTTAAAGTGTTTAAAAGCAAATTACTGACTTT

C-AAAAAGTTTTTAAAACCTGATTTGAAAGCTAACAATTTTGGATAGTCTGAACACAAG

CATTTCACTTCTCCAAGAAGTACCTGTGA-ACAGTACAATATTTCAGTATTGAGCTTTGC

ATTTATGATTTATC

FIG. 4 B

AAGCTGAAGCTGGGCCCTGCAATCAGGAAACAAAAGTTATGTGCTCGTCATGTGCAGCCA

CGTCCTTTGGTAGTTAATCCTCCTCCTCCACCACAGTTTCAGAACGTCTGGCGGAATCCA

AACACTGAAACCTACCTGCAGCCCCAAATCACGCCGAATCCTGTAACTCAGCACGTTCAG

GCTTATTCTGCTTATCCACATTCACCAGG-TCAGGTCATCACT-G-GATGTCAGTTGCTT

GTATATAATTATCAGGAA-TATCCTACTTATCCCGATTCACCATTTCAGGTCACCACTGG

ATATCAGTTGCCTGTATATAATTATC-AGCCATTTCCTGCTTA-TCCAAGTTCACCATTT

CAGGTCACTGCTGGATATCAGTTGCCTGTATATAATTATCAGGCATTTCCTGCTTATCCA

AGTTCACCATTTCAGGTCACCACTGGATATCAGTTGCCTGTATATAATTATCAGGCATTT

CCTGCTTATCCAAGTTCACCATTTCAGGTCACCACTGGATATCAGTTGCCTGTATATAAT

TATCAGGCATTTCCTGCTTATCCAAGTTCACCATTTCAGGTCACCACTGGATATCAGTTG

CCTGTATATAATTATCAGGCATTTCCTGCTTATCCAAATTCAGCAGTTCAGGTCACCACT

GGATATCAGTTCCATGTATACAATTACCAGATGCCACCGCAGTGCCCTGTTGGGGAGCAA

AGGAGAAATCTGTGGACCGAAGCATACAAATGGTGGTATCTTGTCTGTTTAATCCAGAGA

FIG. 4 C

```
   -120  ttgaccactcgaagcgcgcagcgggttccagcgacctcacagcagccgaccacagccctctgcctcctcagccttgtcaccgctcttgtggctctcctcagcctgacggtcgcgcttcctttctcttcatctttggctcct
      1  ATGTCTACTGCAAATCCTGAAACTCCAAACTCTCCAGAGAGCCAGCGCTCCATCTCCAGAGAGCCAGCCCAGAGGCCAAGGCTATATTTACCAGAAGGCAAATCATGCCAAAC
      1   M  S  T  A  N  P  E  T  P  N  S  T  I  S  R  E  A  S  T  Q  S  S  A  A  T  S  Q  G  Y  I  L  P  E  G  K  I  M  P  N 121  ACTGTTTTTGTTGGAGGAATTGATGTTAGGATGGATGAAACTGAGATTAGAAGCTTCTTTTGCTAGATATGGTTCAGTGAAAGAAGTCACTGATCGAACTGGTGTCCAAA
     41   T  V  F  V  G  G  I  D  V  R  M  D  E  T  E  I  R  S  F  F  A  R  Y  G  S  V  K  E  V  K  I  I  T  D  R  T  G  V  S  K 241  GGCTATGGATTTGTTTCATTTTTTAATGACGTGGATGTGCAGAAGATAAATTTCACAGATAAATTTCCATGGTAAAAAGCTGAAGCTGGGCCCTGCAATCAGAAAACAAAATTTATGT
     81   G  Y  G  F  V  S  F  F  N  D  V  D  V  Q  K  I  V  E  S  Q  I  N  F  H  G  K  K  L  K  L  G  P  A  I  R  K  Q  N  L  C 361  GCTTATCATGTGCAGCCACGTCCTCTTGTTTTTAATCATCCTCCCACAGTTTCAGAATGTCGACTAATCAAACACTGAAACTTATATGCAGCCCACCACGATGAATCCT
    121   A  Y  H  V  Q  P  R  P  L  V  F  N  H  P  P  P  Q  F  Q  N  V  W  T  N  P  N  T  E  T  Y  M  Q  P  T  T  M  N  P 481  ATAACTCAGTATGTTCAGGCATATCCTACTTACCCAAATTCACCAGGTGTTCAGGTCATCATCAGTGCCTGTATATAATTATCAGATCAGATTATATCAGATTATCAGATGCCACCACAGTGGCCTGTTGGGAGCAA
    161   I  T  Q  Y  V  Q  A  Y  P  T  Y  P  N  S  P  V  Q  V  I  T  G  Y  Q  L  P  V  Y  N  Y  Q  M  P  P  Q  W  P  V  G  E  Q 601  AGGAGCTATGTGTTACCTCCGGCTTATTCAGCTGTTAACTACCAGTGTAATGAAGTGATCAGGAGCTGAAGTTGTGCCAAATGAATGTTCAGTTCATGAAGCTCATGAAGCTCCACCCTCTGGA
    201   R  S  Y  V  V  P  P  A  Y  S  A  V  N  Y  H  C  N  E  V  D  P  G  A  E  V  V  P  N  E  C  S  V  H  E  A  T  P  P  S  G 721  AATGGCCCACAAAAGAAATCTGTGGACCGAAGCATACAAACGGTGGTATCTTGTCTGTTTAATCCAGAGAACAGACTGAGAAACTCTGTTGTTACTCAAGATGACTACTTCAAGATAAA
    241   N  G  P  Q  K  K  S  V  D  R  S  I  Q  T  V  V  S  C  L  F  N  P  E  N  R  L  R  N  S  V  V  T  Q  D  D  Y  F  K  D  K 841  AGAGTGCATCACTTTAGAAGAAGTCGGGCAATGCTTAAATCTGTTTGAtcctcctggcttatctagttacatggaagttgctggtttgaatattaagctaaaaggtttccactattat
    281   R  V  H  H  F  R  R  S  R  A  M  L  K  S  V  *   295

961  agaaattctgatttttggtaaatcacactcaaactttgtgtatagtgtattattagactctctagtttttattcttaaactgttcttcattagatgttcttcattagaactgttctgtgt
   1081  tgaaatatagttgaaagtaaaaaaaaataattgagactgaagaaaactaagattttatctgcaaggattttttaaaaattgcatttttaagtgtttaaaagcaaatactgattttcaaaaaa
   1201  tgtttttaaaaaactatttttgaaagttcagaaatttgttggctgaataacaaacattcacttctccaacaagtacctgaacagtacagtattgagcttttgcattatg
   1321  attctccagaaatttaccacacaagtcatttaaactgcattttaaactgaacttcaatatcagtgaactcaatatcagtttaaacccagcaaacagattca
   1441  aagcgaacagtcaatgtgggtcatatgtttattcaatatatttatcttttagctagaatacacacatatatatcctattgattatargtagtaattagataactaaatctgggc
   1561  ctaatttttaagagatccmagacaaactttactagtacataagcttctccatgaatcctcctcctttttggtaa   1644
```

FIG. 6

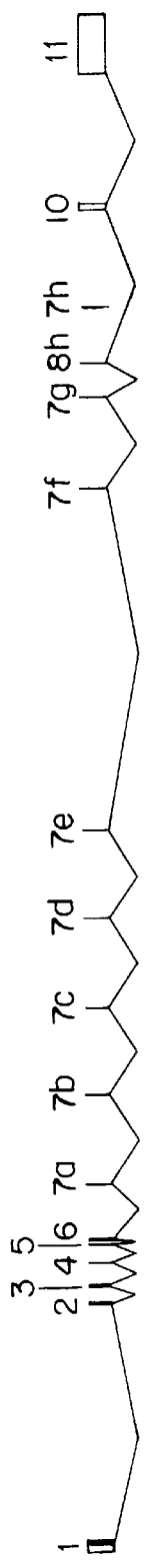
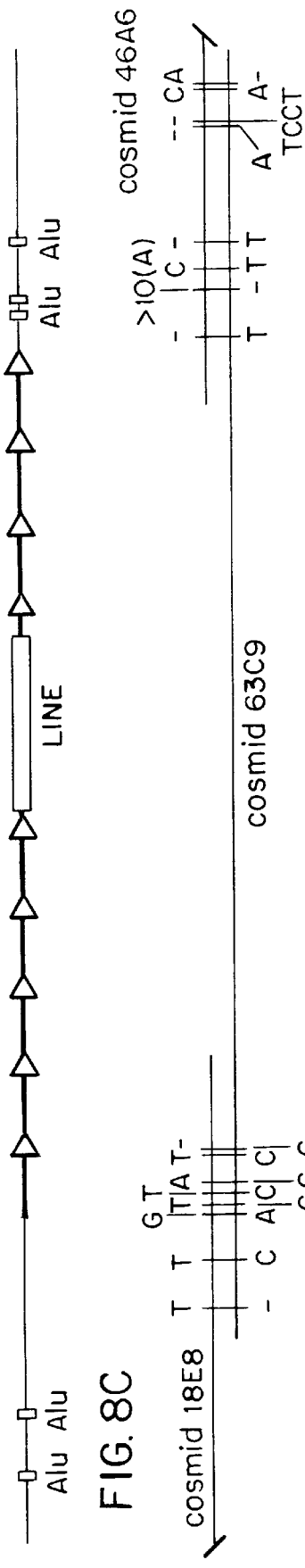
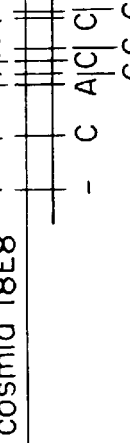
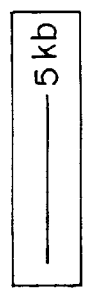
FIG. 8A
FIG. 8B
FIG. 8C
FIG. 8D
FIG. 8E

```
                       -217       Exon 1          3
       DAZH            tccgcctgcg........cgccatcATG
       DAZ             tcggcctgc.........caccaccATG gtgagttgaa 4         Exon 2        150
       DAZH            TCTACTGCAA........TGATGTTAGG
       DAZ  caaattacag TCTGCTGCAA........TGATGCTAGG gtattgtatt 151        Exon 3        242
       DAZH            ATGGATGAAA........TGTCCAAAGG
       DAZ  ttttccatag ATGGATGAAA........TGTCCAAAGG gtgagtaatt 243        Exon 4        294
       DAZH            CTATGGATTT........GATAGTAGAA
       DAZ  gcctttatag CTATGGATTT........GATAGTAGGA gtaagtaatc 295        Exon 5        358
       DAZH            TCACAGATAA........CAAAATTTAT
       DAZ  ctattttcag TCACAGATAC........CAAAAGTTAT gtgagtagga 359        Exon 6        498
       DAZH            GTGCTTATCA........GTATGTTCAG
       DAZ  ttttaaaaag GTGCTCGTCA........GCACGTTCAG gtaagaactg 499        Exon 7        570
       DAZH            GCATATCCTA........TAATTATCAG
         ┌ a ttatttcag GCTTACTCTG........TAATTATCAG gtaattgaag
         │ b ttatttcag GAATATCCTA........TAATTATCAG gtaatgtaag
         │ c ttctttcag GCATTTCCTG........CAATTATCAG gtaatgtaag
       DAZ│ d ttctttcag CCATTTCCTG........TAATTATCAG gtaatgtcag
         │ e ttctttcag GCATTTCCTG........CAATTATCAG gtaatgtaag
         │ f ttctttcag GCATTTCCTG........TAATTATCAG gtaatgtaag
         │ g ttctttcag GCATTTCCTG........CAATTATCAG gtaatgtaag
         └Ψh ttactttcag ACATATCCTA........CAATTACCAG gtaattgaag 571        Exon 8                       621
       DAZH            ATGCCACCAC........AGCAAAGGAG CTATGTTGTACCTCCG
         ┌ h tttttttaag ATGCCACCGC........AGCAAAGGAG gtaggttgtacctctggtgaa
         │Ψa ttaatttaag ATTCCACTGC........CGCAAAGGAG ttatgttgttcctccggtaaa
         │Ψb tttttttaag ATGCCACCAT........AGCAAAGGGA ttccgttcttgacgttaagtg
         │Ψc tttttttaag ATGCCACCAT........AGCAAAGGAT tatgttgtccttgacgttaag
       DAZ│Ψd atttttttaag ATTCCACCTT........AGCAAAGGGA ttatgttgtccttgacattaa
         │Ψe tttttttaaag ATGCCACCTT........AGCAAAGGGA ttatgttgtccttgacgttaa
         │Ψf ttttttcaag ATGCCACCAT........AGCAAAGGGA ttatgttttccttgatgttaa
         │Ψg tttttttaag ATGCCACCAT........AGCAAAGGGA ttatgttttccttgatgttaa
         └Ψi tttttttaag GTGCTACCGC........AGCAAAAGGG gttatggagtaaagtgaatta 622        Exon 9        735
       DAZH            GCTTATTCAG........CCCACAAAAG
       DAZΨ ttaaatatag GCTTATTCAG........CCCACAAAAG gcaaacatct 736        Exon 10       834
       DAZH            AAATCTGTGG........TTACATCAAG
       DAZ  tgtgtttcag AAATCTGTGG........TTACATCAAG gtatgaaagg 835        Exon 11
       DAZH            GATAAAAGAG........
       DAZ  tcttttccag GGTAAAAGAG........aataaa....
```

FIG. 9

Met Ser Ala Ala Asn Pro Glu Thr Pro Asn Ser Thr Ile Ser Arg Glu
Ala Ser Thr Gln Ser Ser Ser Ala Ala Ala Ser Gln Gly Trp Val Leu
Pro Glu Gly Lys Ile Val Pro Asn Thr Val Phe Val Gly Gly Ile Asp
Ala Arg Met Asp Glu Thr Glu Ile Gly Ser Cys Phe Gly Arg Tyr Gly
Ser Val Lys Glu Val Lys Ile Ile Thr Asn Arg Thr Gly Val Ser Lys
Gly Tyr Gly Phe Val Ser Phe Val Asn Asp Val Asp Val Gln Lys Ile
Val Gly Ser Gln Ile His Phe His Gly Lys Lys Leu Lys Leu Gly Pro
Ala Ile Arg Lys Gln Lys Leu Cys Ala Arg His Val Gln Pro Arg Pro
Leu Val Val Asn Pro Pro Pro Pro Gln Phe Gln Asn Val Trp Arg
Asn Pro Asn Thr Glu Thr Tyr Leu Gln Pro Gln Ile Thr Pro Asn Pro
Val Thr Gln His Val Gln Ala Tyr Ser Ala Tyr Pro His Ser Pro Gly
Gln Val Ile Thr Gly Cys Gln Leu Leu Val Tyr Asn Tyr Gln Glu Tyr
Pro Thr Tyr Pro Asp Ser Pro Phe Gln Val Thr Thr Gly Tyr Gln Leu
Pro Val Tyr Asn Tyr Gln Pro Phe Pro Ala Tyr Pro Ser Ser Pro Phe
Gln Val Thr Ala Gly Tyr Gln Leu Pro Val Tyr Asn Tyr Gln Ala Phe
Pro Ala Tyr Pro Ser Ser Pro Phe Gln Val Thr Thr Gly Tyr Gln Leu
Pro Val Tyr Asn Tyr Gln Ala Phe Pro Ala Tyr Pro Ser Ser Pro Phe
Gln Val Thr Thr Gly Tyr Gln Leu Pro Val Tyr Asn Tyr Gln Ala Phe
Pro Ala Tyr Pro Ser Ser Pro Phe Gln Val Thr Thr Gly Tyr Gln Leu
Pro Val Tyr Asn Tyr Gln Ala Phe Pro Ala Tyr Pro Asn Ser Ala Val
Gln Val Thr Thr Gly Tyr Gln Phe His Val Tyr Asn Tyr Gln Met Pro
Pro Gln Cys Pro Val Gly Glu Gln Arg Arg Asn Leu Trp Thr Glu Ala
Tyr Lys Trp Trp Tyr Leu Val Cys Leu Ile Gln Arg Arg Asp

FIG. 10

BASE COUNT
ORIGIN
```
   1 gatcctgatt actttgatat ttaaagtagg atttgacata ctctatcact tattggtgat
  61 aaataacgtc tgttttcttc ttagtccatt ttatttatgt gttagtttaa aagacatttt
 121 ctttgatgga aaataaagta acaaaatagt agtgaaatag ttcttcagtg tctctcattt
 181 attgacattt tctgtgtact tgaaatgtgt aggatatacc tcttcttctt ttttcttctc
 241 tgaacaatgg ctagagacaa agccctactt gtttctaaca tttacggtga gccattactg
 301 aatttgggtg tattcatgta tgctgcttcc tatatgtttt caaacaataa gtatttatcg
 361 aaacatataa gacatcgtac tgtccttctc cagttttgga ttgtacactg cccttagttt
 421 ttcgaaatga agtacagaaa aaaaacataa catctgtagg agaactacat attaccctgt
 481 aatattgtca aacacaaaac tatctggaag tatattgaca aagaaatagc aaatgtatta
 541 acttaactta cattgagatc tgtcttaatg gagccttacc agcagtgtaa gaaacaactt
 601 ctgggtgggc ataagtacac agtgtcagta aggtgaactt tgcctggtga aatagtcact
 661 actttgtcat ttgtgtgttc ccccgccccca cccaaggggg cttagcactt gacagagaat
 721 atttatttct tcctgaagtc attcattcat ttagaattct gcattgtttt atatagaaaa
 781 ttaataaata ttttaaagtt tttcattttt tttattttgg gaataatatt tttttctaat
 841 ttaaaaagat gttttaccat attcattctt tctgtaaact tactttcaga catatcctac
 901 ttatccaaat tcaccaggtc aggtcaccac tgggtgtcag ttgcctgtat gtaattatca
 961 ggtaattgaa gagggagtaa aatgatttgt tttcagatat tattgaagcc tttaacttgt
1021 ttatatgaat ttcccaaata gtgtgtcatt taaactagt gaaatgtacc taaaatttag
1081 gaaaacactt gcaatggtct agaatgaagc cctctgtatt atttagaagt aatgaattaa
1141 cattttgaca gggatatact tagcaataac ttttctgtaa aacagttttc tgagattcgt
1201 tgtccccttc tatatttcag cgtgtatttt ttcatctttt tcatcttttt atcatcccat
1261 tcttagagca cagaattcca attatatttt tattttaagc ttgctgcttc atgatagtag
1321 ttctctgggc ctcttttcat agatatgact acatctgtga cccataatca tatctatggt
1381 gataagtaat aaattgaaaa aactagtatc cttgagattt ccacaatgcc aactccagaa
1441 aattgggaaa atggcgaggt tttatgtata aagtaacaa gaacatcagg gattagaaac
1501 ataaagtact tctttttttt tttttactct gtttctttca ctttaataac aaatgagcca
1561 gcatgataag tgcttcaata ttgtgtatct catgagtttt tgaaaatgtg taggaatatt
1621 ttaatagttt tggtttcctt cttttattt ttttaaggtg ctaccgcagt ggcctgttgg
1681 ggagcaaaag gggttatgga gtaaagtgaa ttagtgaaac gtatacttcc tcatctttct
1741 tgactttttt ctatgccata tatgcctgta gatatttta aatggttctt tatattaatg
1801 ttttatgttt tgttacttta ttttaaccc aattataaac tcccatggga gcaacagtgc
1861 cttttgtct ctcacatttt tgtgtgctga aacagtggct ggtccacata atgataagtg
1921 ttcagttact tgttgataga ttatataatc caggaatggc ggtattaact ggctttagaa
1981 ttagcatgta tctgcctaga atatgcctct ggctttacta gccataaaac atttgttgag
2041 gagaaaccga aatgttttgc tattaattac tcttaaagag gaataggaat aaaacaagag
2101 tattacctct aatacaacag agctgctgtc ttacatcacg attggatatt tgaaggatat
2161 agtaagtgtt aaaattctca aacactcccc taactacatt tgtttcttag aatccttcta
2221 cctctgatta tgttgatacc tggaagacgt tttaaaacaa aaggctgcct taatgcattt
2281 caactttttcg tttaaaacaa ggtttctgaa gtaacacaat tgaatttcaa cacaacctac
2341 attgaaactt ttgataccag ctcacctttt tgaggaataa ataagtagct tttaaacgta
2401 tctgtattat ctgtttaatt acactttcat tattttaaat ataggcttat tcagctctta
2461 actgtcactg tagtgaagtt gatacaggag gtgatgttgt gctaaatgaa tgctcaattc
2521 atgaagctac cccacccctct ggaaatggcc cacaaaaggc aaacatctaa ttttgaattt
2581 ttttttacaat atatatttca tattttttc taatttgaat gacttttttt gagaagcaaa
2641 catttttgcc caaatttaaa aatgttagcc ataaatcatg gagcttaaat aatggactga
2701 tagtcagcag ttaatgtaaa ggttgttgaa atttcagata ccccaaattt tcagtatata
2761 cctaaagttt ctgattcagc aagtcctttc ctgtatttca gtttcactaa ttttaaaaag
2821 ccattcttta ataaatactg tattaatatg atttggcaga atgctatggg agggtttcct
2881 ctagaattct actcaaaaga agaattagta cgaattgtat gtccctttc ttttacaaca
2941 gttttgatct taagcagtga aaaataccat ttaaataagc attctctcca taacattata
3001 tgtggcagaa gtttccaaca gtggtgaagt cagtagtaat tattcaaaca ctgaaataga
3061 cagggttgtt tctttttttt atcattagtg caaatttctg taataacagt actgtcactc
3121 ctggcgtcac atatgttctg ttagataggt gggcgtgtgg aagtagttga tgtgctggta
3181 atatgtataa tacccaagaa gtcccattgc agtgtaaatt ccttgatttg atattggatt
3241 ttaaatgtg aataaatatg aaaacataac tcttacagta taattgtctg gttttgttct
3301 gagtatgttt tcttgaaaca ttggaattca cttagggatt taacaaattc agcttttaa
3361 accagtattc tatcgctaag gttctaaaat aattcttcga tttgtcagaa aacgtacata
3421 ctgaggatat gtggcaggaa ttatgaatca cattttatg aatttctttt ttttttgaga
3481 cagggtcttg cggtgtcgcc caggctggaa gtgcagtggt gtgatctcgg ctcactgcaa
```

FIG. 11 A

```
3541 cttctgtctc ctaggttcca gtaattctcc ctgcctcagc ctccccaata ggtggaatta
3601 caggcacccg tcacccagct aattttttgta ttttttagtg gagaaggggt ttcgccatgt
3661 tggccaggat agtcttgaac tcctgatatc aggtgatgcg tcctcctcgg cctcccaaag
3721 tgctgggatt agaggtgtga gccactgctc ccagcctctt ttagcattt tgcatttctt
3781 tggaaataaa ctgatatgtt cattaaacca tcaaaagaaa aaccaaaaca cacccttatt
3841 aagagtgagt gaaagaaaga gttgtcttta cattactgaa aacttctgtg tttcagaaat
3901 ctgtggaccg aagcatacaa atggtggtat cttgtctgtt taatccagag aagagactga
3961 taaattccgt tgttactcaa gatgactgct tcaaggtatg aaaggaatgg catgcataat
4021 taaaaagcac acttgttccc tctcaagtta gctgttttcc ttgtggcaca tgtattttgg
4081 gctttcttag aggaatttt tttcttttt ttttgttttg agacggagtc tcctctgtcg
4141 cccaggctgg agtgcagtga gtggcccat ctaggctcac tgcaagctcc acctcccagg
4201 tttacttaac gccattctcc tgcctcagcc ttccgagtag ctgggactac aggcgcccac
4261 caccacgccc agctaatttt ttgtattttt agtagagacg gggtttcacc gtgttagcca
4321 ggatggtctc gatctcctga cctcgtgatc cacctgcctc agcctcccaa agtgctggga
4381 ttacaggcat gagccaccgt gcccggccta gaacatttaa ttgaactgtt ggcatttgac
4441 tgtaacccag taaaccagtg tgggttttac ctggcagtat attttctgct gccgagcctt
4501 gatataatgt agtcaaattt agggaagaat cctgcagcag aaatttgtaa ttgaaagggt
4561 ttactagaga agagagttag ttgactacct tgaccaaata gtaaaataaa attttagata
4621 cagaaaggag atcttggctg ggtgcagagg ctcacgcctg taatcccaac actttggggg
4681 gctgaggtgg gtggattgct tgagctcagg agttcgaggc caccctgggt aacaaggcaa
4741 aacaccatct ctacaaaaaa atacaaaaat cagccagttg tgatggtaca tgcctgtagt
4801 gccaactact ccagaggagt ctgaggcagg aggatcgctt gagcctggga agttgaggct
4861 gcactgagcc atgattgtgc cgttgtagtc cagcctgggc aacagagtga gagaccttgt
4921 ctcaaaaaaa aaaaaaaaa aaaaaaaaa aaaaaaaaa gtagaactta atacatgcat
4981 attggactaa agaagaaa agaaatgatt tactcagatg atacacctga acagtgtgaa
5041 gggagaaaag gggtaaaatg aagcagtaaa aagttgagta gaaagagagg ttgattcaga
5101 gttggtgaag cggaagagaa tgtggctagt tgaattccag aaagatctga cttctgatcc
5161 cactttctat ccatgttgga tagataaatc ttttattaag gctctaattc ttacaagtct
5221 aaaatgagaa ggtacaggac taaaggtttc tgggtccctg tggttctaag tctataaata
5281 cgaaaaagaa ctaacttggt cagtccggtg ggagaaaaat attatggtta ataaagggaa
5341 ggtgttttt aaataacaat tttattaaaa taataccagt aatacaattt atgtatttaa
5401 aatgtgcact tcactgtttt ttcatatatt caaagttgtg caaccatgtc cacaatcaat
5461 tttagaatac ttaaatcacc tcaaaaatca ccccgtacc ttagcagtca cctgctattt
5521 tcctggaact tgtgtgtatc cctaggcaaa cactaattta cttttttcct ctaaggattt
5581 tcctgtcctg gagatttctt gtatatggaa tcatacataa tgatgtggca ttttgtgact
5641 ggatttttc actcagcata atgtttgtaa ggttcatcaa tattctagca cgtatcagaa
5701 cttaatcatt tctttttatt tgtagatatt accttattct gtttatgcat tcatctgtta
5761 aagacatttg gattatttcc acttttagc tgttataact aatgctgtga acattcatgt
5821 acaagttact gtggggacat acgtgcttac ctctcttgcg tatatacttg ggaatggaat
5881 tgctaagtca tatttaacct ttagtggaac tgccagattt gtcaaaactg ctacacact
5941 ttacattcaa aagaaaatgt ttaaccatca ctttgtgtct tacaacagaa ctagcttatt
6001 tttgtctgtg aatggatatg ggatgaagcc taagcctttt taaagggtta tattatgaat
6061 cttctgtata atgtagaaga gtagagccag atagcagaat taagttctta acatctttgc
6121 aacatggagt aaatatattt aaatttgaca tttgttctct tgttgcttcg ttctatatag
6181 atagtacaat ttagaaaaga aagaactgga attgtacatc agcttatctt gccgaaaatt
6241 ctgattacat tggtgtctac agtagtactt aagtgatttt caaagcagaa gatagttttt
6301 tgtgtttctt tctttctttc tttttttttt ttttgaggtg acctcatttg gtcatccagg
6361 ctggagtgca gtgtcgcaat cacagcttac tacaacctca aactcctgca ctcaagggat
6421 ccttctgcct cagcgtccca aataggacga cagacgtgca ccaccacact tagctagtta
6481 aaaagaaatt ttttttttt ttttttgagac agagtcccac tgtgtcaccc aggttggagt
6541 gcagtggtgc gatcttggct cactgcaagt tctgcctccc aggttcatgc cattctcctg
6601 cctcagcctc ccgagtggct gggactacag gtgcctgcca ccacgccag ctaatttttt
6661 gtgttttag tagagatggg gtttcatcgt gttagccagg atggtctcga tctcctgacc
6721 ttgtgatctg cccgcctcgg cctcccaaat tgctgggatt acaggtgtga gccaccgtgc
6781 ccagccaaaa gattttttt taagagagaa tcttactata ttgccctggc tcgtcttgaa
6841 ctcctgggct caagtgatcc tcctgcctca gcctcccaaa gtgctgggat tacaggcgta
6901 tgccaccatg tccagcccag aaaatatttt tttaaacttg agttctcacc tggtggtaga
6961 caaaagactc gctttgaaac ttccagagtt ttctgcttat tgggagagg aatcagaagt
7021 tggcatcctg cagttgtctg acatttagac ctattttaat tgactgcacg ttgttatatt
7081 gaattagaat gcctgagata ttttgaatg tatttacaat ttccatagcc gatttctctt
7141 cattgtctta gttatctagc cctttcacaa tcttgtttcc tacatgacct ctgaatatac
```

FIG. 11 B

```
7201 atgttggtga ccagttttct agattttaac ctaaattgat tatcactctt ttgacagatg
7261 aggtaacttc cagaagccac ttttatttat atgaaaatga aactgaagtc ttaaaaaaag
7321 ggcacagctt tgtagaaaag gaaatgttat tactcgttca ctcattccca ttcctccttg
7381 taagacctct cacttctctc tgccgtctg caggcaacat agagtgaaaa gaaagttttg
7441 catgtatttt aaagttttat cttcctttct aaagaatgat atgtcttcac aggttaatga
7501 tatgttcttc aaatgccaaa acttacatat tttaatctaa aaacacgaaa tttcagattg
7561 gagagcagtt cgcaagctgt agttggtatt aaatgcagtt caattagtga aaaaagtatt
7621 ctttacaatt acatttttcta ccagctgtct tgggacatt actgcaaaat tattaactaa
7681 gaagtacata aatgatact gagtttaagt cctttttattt ctcagtttac tggaatttgt
7741 tttatttaat tattgatttc ttttttttaac tgtttaataa aactagccat cttggtacat
7801 ttgttatccc agtgttcaaa tatgcttcct gaaaagaatc atcttttttt ctcattattt
7861 ataatgttta acccaaaac aaatggttta agttttgaca actttcagat ccatagtagt
7921 catcagaaat tttcagtaaa ataaaggac tatttctgtc ttttccaggg taaaagagtg
7981 catcgcttta aagaagttt ggcagtattt aaatctgttg gatcctctca gctatctagt
8041 ttcatgggaa gttgctggtt ttgaatatta agctaaaagt tttccactat tacagaaatt
8101 ctgaattttg gtaaatcaca ctgaaacttt ctgtataact tgtattatta gactctctag
8161 ttttatctta acactgaaac tgttcttcat tagatgttta tttagaacct ggttctgtgt
8221 ttaatatata gtttaaagta acaaataatc gagactgaaa gaatgttaag atttatctgc
8281 aaggattttt aaaaattga aacttgcatt ttaagtgttt aaaagcaaat actgacttc
8341 aaaaaagttt ttaaaacctg atttgaaagc taacaatttt gatagtctga acacaagcat
8401 ttcacttctc caagaagtac ctgtgaacag tacaatattt cagtattgag ctttgcattt
8461 atgatttatc tagaaattta cctcaaaagc agaattttta aaactgcatt tttaatcagt
8521 ggaactcaat gtatagttag ctttattgaa gtcttatcca aacccagtaa aacagattct
8581 aagcaaacag tccaatcagt gagtcataat gtttattcaa agtatttttat cttttatcta
8641 gaatccacat atgtatgtcc aattttgattg ggatagtagt taggataact aaaattctgg
8701 gcctaatttt ttaaagaatc aagacaaac taaactttac tgggtatata accttctcaa
8761 tgagttacca ttctttttta taaaaaaaat tgttccttga aatgctaaac ttaatggctg
8821 tatgtgaaat ttgcaaaata ctggtattaa agaacgctgc agcttttttta tgtcactcaa
8881 aggttaatcg gagtatctga aggaattgt ttttataaaa acattgaagt attagttact
8941 tgctataaat agatttttat ttttgttttt tagcctgtta tatttccttc tgtaaaataa
9001 aatatgtcca gaagaggcat gttgtttcta gattaggtag tgtcctcatt ttatattgtg
9061 accacacagc tagagcacca gagcccttt gctatactca cagtcttgtt ttcccagcct
9121 ctttactag tctttcagga ggtttgctct tagaactggt gatgtaaaga atggaagtag
9181 ctgtatgagc agttcaaagg ccaagccgtg aatggtagc aatgggatat aatacctttc
9241 taagggaaac atttgtatca gtatcatttg atctgccatg gacatgtgtt taaagtggct
9301 ttctggccct tctttcaatg gcttcttccc taaaacgtgg agactctaag ttaatgtcgt
9361 tactatgggc catattacta atgcccactg gggtctatga tttctcaaaa ttttcattcg
9421 gaatccgaag gatacagtct ttaaacttta gaattcccaa gaaggcttta ttacacctca
9481 gaaattgaaa gcaccatgac tttgtccatt aaaaaattat ccatagtttt tttagtgctt
9541 ttaacattcc gacatacatc attctgtgat taaatctcca gatttctgta aatgataacct
9601 acattctaaa gagttaattc taattattcc gatatgaccct taaggaaaag taaggaata
9661 aatttttgtc tttgttgaag tatttaatag agtaaggtaa agaagatatt aagtccctt
9721 caaaatggaa aattaattct aaactgagaa aaatgttcct actaccatt gctgatactg
9781 tctttgcata aatgaataaa aataaacttt ttttcttcaa atgtgttttt ggctttccga
9841 tgtaataatg taaaatggtg gggagttgcg tgggaactgt gtaacaaggt ttaaattcgt
9901 ataacaagct ttagattctt aaaatgcaga agtataaagt tcagtatact aatctgtctg
9961 agttagccca taaaagcaaa tgtaggtaca aagataagtt taagaggtgc atcaacagca
10021 gtgcagacta ggaatgctga tgaacacatc cgactctgct atctcacggc taaggtccct
10081 cacattttgg accctatgaa gcattttgtc tactgtacac tttgggccta gtctctagat
10141 catttatttc ggggtattgc agttgcctaa gggagcttaa ttttttttata ttgcaggtac
10201 ttcctgtgga taccataaaa aaaaaaatca gtaccgcttc ttctagcttt agtgttagta
10261 ctcagttcta taagctgagt ccagtggaga ggaaactcct cagacacgta tttcattagt
10321 tagtaagctt gctgattcat aaccagaaag ttgactccaa ggatacgcag gatagcaaac
10381 agtgctttct gcatcaccaa agattaaatt gtgatgttta gtgtccaata ataggcaaaa
10441 aattagtaat tcttttatgt gcctatgtgt atatatgtgt acatatgtgt ctatatatgc
10501 atatatttat ggttatgtac atactaacga ttatccagaa tatttggttc tagctgatca
10561 agctagtagg ttttcagtat tttcagaccc caaaactaga ctacatatgg tttaagatag
10621 ttgctttaca ccagcttgtt tctagtttcc tattaaatta ttaccacaaa aatctttgga
10681 attgaaaaat aacagttaag cactttttg taaaaagttc aagttatggt gaaatcaagc
10741 agctctaaaa aggttggtca cctccttaag tgtattctgc atgttggttt ttttcttttt
10801 ctaaaatcag attaccttta attcaaaata acttcagaat tggtagtacc tgtctggcaa
```

FIG. 11 C

```
10861 ggaagtcatt gactcttaaa aataaatact ccacagcatt tccctctcgt tataaagcac
10921 ctctagcccc ctcttcacta aattttcctt ggcttttttt taaaggtaaa ctgataaaaa
10981 tgggctgcca cattgcttaa tcgccttgcc tgctttcctt gctgtcagtt gagggtaatg
11041 aggagcagca acgataaggc agcgtgccac cttgctttca caaagatgcc aatagagaaa
11101 gtggggaaac ataagggaga aaaaagtagc agtattttac attgaccaag tcttgtgaat
11161 gggccagcta ttgagtatga tcatttggaa tccctagata aggattgctc ctgtacatat
11221 tttgataagt gtaatctatc ccttccaac atgtgtagta tgtctctgta tgtaactgat
11281 tgttgtgagc aattccttgc cactcaccaa agacagaact ttccatctgt agacagtaca
11341 ttttgtagta gaaaacaata gacataagaa gttcaaacta taaacatgtt tttgaatgct
11401 catgcaagat aatctgcata gcaaagaaat aatagacaat tcaacattgc atttagagtt
11461 aaaaacatct gtccagtatg gatgtagctg tgggccaatc ctaagtaaac gcaaaaaaaa
11521 aaaaaaaaaa aaaattgtct cttggtacag aagttgaaac taccactcta ccactgtaca
11581 attaaactct atggtcgctg tattttacgt ttttaactgg tctgaaacag ttctctagtt
11641 aagtctgtag ttcgttttcc caagacaagg ctttgtatct tacgtgcacc ttcattaatg
11701 ctgcatgcca ggaattccac atgaaacttc aagatgccgg ttcactaggt cttttccaca
11761 tgaaacttca agataccggt tcactaggtc tttaacaata gaacaaatac ttgcatgact
11821 gggatattca ggtcatgaac actccttata aatttgaagc aatagtaaca ttttaagcac
11881 tttggaaaat tggaggtttc ataccctca atcagatctt tttatagaat aacaaaaata
11941 cactaaggtt ctaatcacat ctattgtctt tgcccaaaat aacatggata gagacacact
12001 ccattctggc tcaatcttag atgaaactcc agaagaaagg cagttgataa tgatacagcc
12061 aggccagctg tttaagtgga cgtgtcccct ctgcccttgt acatttgttt aaaaattttg
12121 ataggactct tcccgcctcc ttcacaccct ccataaatct gactagggcc ataagaatgg
12181 agagaggtaa tttaaaaggc agaggacatt tttctccttg tttttaccta tgctgatccc
12241 ctacctggtg ttggagcagc ttcactgtga gtaaaatctg aacagtgttt aagcagtaaa
12301 cccactatat tgaggaaagc gtgacctgca cttttttttt tttttttttt cctgaacatg
12361 acttggttgt tgctcatcat tttggttggt gatgggtctt tgacaaaccg atatgctcac
12421 catccaaagt tgtgtccatg tttagatcag cgcagtattc gatagggcac gtttcctcaa
12481 gataccaatt ttacagggaa gtcaaagagc atcagagcta tcataagggg tgttttcag
12541 aagccaaatc ctgggcccca ttctcagatg ctcttattct aatgctctgg atgggcccag
12601 taatctgcat ttttaacatg tgccccaggt gattctgacc actgtaacat actttgagaa
12661 atatggcctc agttggggag ctctcattag atcatctcaa gctaccctg gatttaggat
12721 agaaacagcc ctgtcaggtc aactatgact ttcataaagg attccgttgg cttaattcac
12781 cgaattcatc tttccctgcc aagcccgtgc ctgggaatgc agctgtcca caggcaagag
12841 tgactcatga atgggctgaa atagattgaa tagaaagttt gaaaccaag acttgtggcc
12901 agaaatcagt gacaggaggg agtgactaca gaggcaaagc tggattccaa ggccaagagc
12961 aggcaagcca agggtgaggg actaggctcg agtgggaaag ggcagagtgg atatcctggg
13021 gacagagaca ctgtgtttgc ctcctggagt gaagaactat gcctttgact cacttgacac
13081 actttacaaa tagtattacc catggttttt agaaaagtat ggcctgtcat tgctcctttt
13141 cctgctgtgg aattaactaa tacctcttaa caccttaag caagaatgat aataacagat
13201 caatatcaaa aaaatatgtt gagatcaagt tccagagaca gccttaggca tttgatatcc
13261 atattctttt tgtatatgtc tgtgttttaa aatttcacat ttagttcact caaaagtata
13321 aaaatatttta tttaaagaat aataaatacc caagttggct tgagaaatag aacatttcat
13381 taattaaaaa atatgccctc cctgatcaca ccctcttcct ccccaagaag aagaaaccac
13441 ctaaattgaa ttttggttta atcatctgct gaataaaatg tttcttttca caatattttg
13501 aactttaaga gaacatatac tgaaactatt tttttttttt tttttttggc acattgttag
13561 actcatccgt gttgactggg agattctatt tatttttcact gcttttttagt tgtatcagtt
13621 gaatatttta cggtttgtta ttccccttgc tgggggacaa ttgactttta tttttttgttt
13681 taaaatttta aatgtaaatt gtgttgattc gttgattgct gttacaaact atgctcctac
13741 gaacattgtt aaatgcctct gatcacttag gtactagaat gtcataaaaa agagtgaact
13801 ttaaatccca gccccaaata cttcctgagt aagcttggac gagcttctca ctgagtcttg
13861 gtttcctcct ctgtaaaaca acaatactag tatctacttt atagtgttac tatgagatta
13921 tttggggcaa cacatcaatg tggttagctt cccatccaca gatctaccca cctgcatccc
13981 actcaaaccc acctaagttt tctgcagcct ttacatttca gtaactagaa cttcccacgt
14041 ggtctgtgta tagagcagcc atggtttggt gaatgactgt gtcctgaaat gtagtctttt
14101 gcgtatcttc tttggtagta ggaaacagct cattatgcta ggctcttcag gatattttct
14161 agaatagttc ccttttttct gagagggcct tgaatgagta gaacactaac aaatgagtga
14221 aataatggta cataggccag cattccctaa gcacaatttc tgttttcct tcatgaaatg
14281 ctggaggtgg caggcaggat tcatatccc attcttctca tcacatgcat actccctgaa
14341 atttgtatag gattttaggg ttttcagagc tacttcgtat atatgatttc gtttggtctt
14401 cgtcaactcc tttgaagtgc tagacatgtc taggttttag gtgtgatttt cttaaattta
14461 cacaccctgg gattcagata aataagaaac tgagacttga catctgggcc attgcttttt
```

FIG. 11 D

```
14521 atactatctc atagatagca gactctccaa atcaaaatac agaaatattt ttactaatac
14581 ataataatta tacacattta tgggatatct gtgacaattt catgcttcca tgcaatgtgt
14641 ggtgatcaaa acagggtaac tgggatatcc atcacctcaa acatttatca tttctttgtg
14701 tggggagcat tttctaccta tttggaacta cacaataaat tattgttaac tatagtcacc
14761 ctcctgtgct gtcaaacact agaacttatt ccttctaact gtattttgt atccagtaaa
14821 caacctccct taattcccgt cccccaacc caacactcac tctctatagc ctctgttaac
14881 tactgttcta cactttacct ccatgagatc aattattttg gctcccacat atgagtgaga
14941 ataaagacat ttgtctttct gtgcctggtt tatttcactt aaaataatgt ccttggttcc
15001 atccgtgttg ctgcaaatga ccggacctca tccttttaa cggctcaata gtactccatt
15061 gtgtagatgt accacatttt ctttatgcat tcatctgttg acggatactt aggctggttc
15121 caaatcttgg atattgtgaa cagtactgca ataaacgtga gagtgcagag atctcttcaa
15181 catgccatgc tgttttgtt actcctacag ttttgcagta cattttgaaa ttcgctagcg
15241 tgatgccttc agctttattc ttttgactca gtattgcttt cgctacttgg agtcttttgt
15301 ggttccatag aattttatga ttttttttc taatttctat gaagaagtat ttggcatttt
15361 cacggggatt gcatgaaatc tgtagatcac ttttggcaga attggttatt ttaacaatat
15421 taattcttcc aacctgtgaa catggggttg gggtgtcttt ctactttttt gtgtaatctt
15481 taatttattt tgtaagtttt ttaatagttt tccttgtaga ggttttatc tcattggtta
15541 aatttattcc tagatacttt attttatttt ttatacctat tataaacggg attgctttct
15601 tgattatttt ttcctgctgg ctgcttgttg gtacacagaa agtctagtgg tttttgtata
15661 ttaattttgt gtactgcaaa tttactgaat tcacttatca cttctgaaag tttttttggt
15721 ggagttttaa gggttttgtg tctgcaaaca aatttactga attcatttat gactactgaa
15781 agttttttgg tggagtttta aaggttttat atctgcaaac agggacaatt tgacttcttc
15841 ctttccaatc tggatgctct ttttttttccc ttgcctaatt gctgtggcta gaacttctgg
15901 tactatgctg aataaaagtt gtgaagtgga tattttttgtc tcttccgtat gttagaggaa
15961 atcctttgaa ttttttccctg ttcagtatga tgttggttgt gggtttatta tatatggcct
16021 ttattgtgtt cagatatatt ccttttacgt ctgacttgtg gagagttttt atcatgaagc
16081 cctgttgaat tttatcaaat gtttttttctg catctattga gatgatcaca tggttttttgt
16141 tcttcactct gtcaatgcga tgtatcatat ttaagttggt ttgcatatgt ggaaacatcc
16201 tgtcattttg ttaattattt tctggttggt ttgtataacc tttgttgatt tctttcttat
16261 tgtttatcat tgcagtttag tattttcctg tagtgataaa gtttgattgt ttttcctttc
16321 tcccttgtat atctgctcta ctgggatgaa tcccttgcat ccctgggata aatcccactt
16381 ggtcatgggg aatgatcttt ttaatgtgct gttggtttca gtttcttagt atttggttga
16441 ggttttttgc gtttctgtta atcagagata ctggtctata gttttctttt tttgttgtgt
16501 ccttgtctgg atttggtatc agagtaatgc tgacctcaaa taatgaactt tgaagaattc
16561 tcttcaactt tctggaaggg tttgagaaga attgctatta tttatttaaa tttgtggtgt
16621 aattcagcat tgaagccctc agttcctcag ttatttgatg ggaggctgtt tattacagat
16681 tcaatcttct tactcataat tggtctgttc aggttttcta tttctttttt tttttttttt
16741 tttttttttt ttttttgag agggagtctc tctctgtcac ccaggctgga gtgcagtggt
16801 gcaatctcgg ctcactgcaa actcctcctt ccgggttcat gccagtctcc tgcctcagac
16861 tcctgagtag ctgggactac gggcacctgt catgatgccc agctaacttt tttgtatttt
16921 tagtagagat ggggtttcac cgtgttagcc aggatggtct ccatctcctg acctcattat
16981 ccgcccgcct ctgcctctca aagtgctggg attacagctg tgagccaccg tgcccggccc
17041 gtgttttcta tttcttactg gttcaatctt ggtaggtttt atgtgtccag gaatttgtct
17101 atttctttct gctaggttct ctgattttt ggtgtatagt tgttcagaat agtctgtaat
17161 gatcctttat atttctctgg tagtctccta tttcatttct gattttattt atttgagtct
17221 tttctctttt tattcttggt ttgtgtagct aaccgtttgc aaatttgtt tacctttttca
17281 caaaaccaac tttttctttt gttgatcttc tgtattttta tagtccccat tttatttctg
17341 ctctgatctt cattatgttt ttcttctact aattttggtc atggtttgct cttactttc
17401 tagttccttg atatgcatcg ttaggttttt aattttattt ccacttttcg gatacaggta
17461 tttattgctg taagttttcc tcttaaaatg gctttgttgt atcgcatagg ttttcaaatg
17521 ttgctgtttt catttgtttc cagaaatttt taaattatcg ttttaatttt ttcatttgac
17581 ttctcattca ggagcatgtt gtttaatttc catgtatttg tgtaatttca aaagttactc
17641 ttgttatcga tttctagttt tattccattg tgattaagag aagatactta ccatgatttc
17701 agttcattta aatttgttga aacttaattg tgtggatgaa catgtggtct gtccccaaga
17761 acagtccatg tgcagaattt actgatgaaa agcatgtgta ttctgcagct attggatgaa
17821 atgttctaga aatgtctgtt aggtctgtct ggtctcagat tcatttcctg ttaaatgttt
17881 ctttgttggt ttctgtatat atatatatat atatatatgt atatatatag atatctgtct
17941 aatgcagaga gtgagtgttg gaagtcccca actattacta tattgaagtc tatctcaccc
18001 tttagattta ataatatttg gtttttatat atctgggtgc tctgatgttg ggtgaatata
18061 tattcacaat tgttatatcc tctggctcaa ttggacccct tatcattaca taatgacctt
18121 tttggtctct tttacagtt tttgacttga agtctgtttc atttgatatg tatagctact
```

FIG. 11 E

```
18181 ctaattcact tttggttttg gttcacatgg aatatctttt tctgttcctt cactttcagt
18241 ctatgtaatc acacaagtgt ctttacaggt gaagtcagtt acttgtaggc agcatccagt
18301 tgggtaattt ttttttttt tttcaatcca ttctgctagc ctaagtcttt tatgtgagga
18361 atttaatctg tttacattca aggtattact gataggtgag gacttactcc tgtcattttg
18421 ttaattattt tcttgttgtt ttgtatatcc tttgttcatt tatttctgcc ttattgttta
18481 tcgttgcagt ttggtcattt ctatagtgat acgatttgat tattattcct tttgttgtat
18541 atctgctcta ccagtgatct ttatacttgt atatgtctct gtaatagtga tcatcatctt
18601 tttacttcca gatgtaggac ttccttaacc atttcttgta aggccagtct agcactgatg
18661 gactccctca gttttttgctt gctttaggca gactttattt ctccctcatt tatgaaggat
18721 tgctttgctg ggaatagcat tcttgactga actttctttt tttttttttt tttttttag
18781 cacgttgaat tatatcatct catttctcc tggcctgtaa gacttctgca gagaaatcca
18841 ctactagtct aatggagatg cccttatatg tgacttgatg cttttctctt gcttttgtag
18901 agaaagactt tcacgtgcat ctgagtttta gtgtgccagt tgagaagggt gcagtgactc
18961 tttttcaaga tagttgaagt ggtatggcct cattcagctt ctttggctgc attcaatatc
19021 agcagtagct gtgagtacct cagttgccta ggccatacaa gtttgtggta gtgatgatgg
19081 cataagttgt taataacctc catatcaaag gctttggggg ttttcttcat tctcattttc
19141 cacacactgg ggagatttag acaagagtat cctttctgga ttcaggtctg acatggccta
19201 taagtagcta tagcagtgct gggttccagg tttaggtgct ccaaatggct atggtgctag
19261 ggtcctaggc tcaaggtttc atgaactatg tgtggcactt gggtcttggg gtgcctgttt
19321 attctctgtg gtgaggttga atgcaggttg cccaaagagc caggatctgt gactctgagg
19381 tacccctag cagcttggtt acagggattt gggttgtagc tgtgattcta tccctagtgg
19441 ccagggagca gcactggacc aactctggag aagaagggt gctctggatg tttgggccta
19501 gggagcaggg tagtgctgca attcaggaac ccaagccaat aggtatcagt ggcaatgtgg
19561 gtcccattgt agtagtagta gtggtagtag tagtagtagt agtagtagta gtagtagttg
19621 tagctgtagt agtagtagta gttgttgtag ttgttgtagt tgtagtagta atagttgttg
19681 tagtggcagt agtagtgact ctagaccttg tgatggtgga gtcagcagta ttccagattc
19741 tgtgaggcca ggtgtagcag tagcaagtac cctgaatagt ggagcacagc tgtcctttgg
19801 gccctgttag gcaggaaaca gcactgtgat gatttttactt tccagggaga ggggtgtctc
19861 agcagctccc gctcttggtg gctagtccag ctctccaggg aattaggata ctagagttgt
19921 ttggcctgta gggcagactg tctcagttca gccacggttt tgcctctctg tgatgcaagg
19981 tactacagca gtttagctca gcttggccag ggcactgatt ccccaggtgg cccagagacc
20041 attttctggg atacagggca ctgctaaaac ttaggcacag ggaggcatga ctgctcaaag
20101 tgactaaggt attgttttct tggaggcagg gtactgtttc agatctggcc tgaggagtta
20161 ggggaagagt aggtggatca gctccacctc cacttggccc caggagaagt gtgtaagaga
20221 tgcttatagc tcaccttggg gatgttcagt cactaggctg ggggtgtttt ggtggcagtt
20281 tagcctcagg gatgaagggg acctgtgcct acttgaaccc tgagcacgac acactccagc
20341 cgtaggtcta gctgcaagat ggtatagcac agtagacatg tgggccacag aggagaacat
20401 agtgttagct acttctctga agggagcaca gctttgtgaa ctctagacag ctccttcagg
20461 tgggcttagg tagtgcctgt gaggaccgta gggcacctct gccatggtga ggtctgtgga
20521 tgtccaaggt gttgatcggg gttgctggtg ttctcttgct tacctcctca ctgtatgaag
20581 aagttcctct ttgttcctag cttatctcaa tttgggatg gagtggtgaa ggcctggcat
20641 ttccttccat tctctttgtg gctgttctgt ttctgtgctc atcagggttc ctgctattcc
20701 tctgagtttc tctggaactc tccttcagtt actctcatta aaacgtagtg ttttttttagt
20761 ctttctggca tctgtgatgg agacaagctc taggggcttc tagtcagcct tgctcttaat
20821 taatccaaga gacagaaata tttttgactg ggctttatga aagctataac taggactata
20881 atgcgaaatg gacaacttaa aattggaggg agaaaaaaat tcagttagaa taggttgagc
20941 taaaatttac catgtgtcag caggctctgt acaaaattgc attaagtaac tcccctcatt
21001 taatccttac aacaccctag tgaagttata tattgttctt attttttata tatgggaaca
21061 caaatactta cactataaaa tatcttacct aatgtcacag agctagttag ctacagagtc
21121 aggggtctga ctgcagagcc ccccagttta ccaccctaaa ttcctctgtc acttaaactt
21181 caatcccatc tcactccatg ccctttcttt agaaggcagt ggtttacaca aacagatct
21241 gatttgttta aatatggag aatcttttaa aaaaataatt tgttgaggtg aaattaaaat
21301 aatgaaatta accattttaa agtagcacta agtagattca taatgtctta caaacagcac
21361 ctctatctta gttctaaaat gttttcatca tgccgaagta aaaatacctt taagccgttt
21421 tcccccatcc ctctgcaact gcaatcgctg gaaaccacct aggtgcactc ttacctttc
21481 tggatatttc gtataaattg aatcatgcag tatgtgatgt tttatctgct ttcacttagc
21541 atgttttctt cacttagcat acattgcagc aggtatccaa tacttcattc cttttcatgg
21601 ttgaataata ttccgttccg tgaatatacc acattatgtt tatccattcc ccctgctgga
21661 cttttgggct gtttctacct tttgattatt gtaaatagtg ctgctatgaa catgtgtgca
21721 catgtactta tttatgagtc cctattttct tcttttttaa tactttttatt ttaggtttgg
21781 gggtacatgt gaaggcgtgt tacacagata aactcatgtc atgggagtgt tgttgtaca
```

FIG. 11 F

```
21841 gattatttca tcacccagga attaaaccca gtacccaaca gttaccttt  ctgctcctct
21901 ctctcctccc accctcctgc ctgaagtgcg cctcagtgcc tgttgtttcc ttctttgtat
21961 tcacaagttc tcatcattta gctcccactt ataagtgaga acatgcagta tttggttttc
22021 tgttcctgca ctagttgct  gaggataatg gcctccagct ccatccactt cctgcaaaag
22081 acatgatctt gttctttctg tatggctacg tagtatttga tagtgtatac gtaccacatt
22141 tgctttatcc aatttgtcat tgatgggcat ttaggttgat tccttgtttt tgctattgtg
22201 aatagtgctg caatgaacat ttgtgtgcat ttgtctttaa ggcagaatga tttatattcc
22261 tctgggtata ttcccagtaa ttggattgtt gggtcgaatg gcagttctgc ttttagctgt
22321 ttgagggatt gccgtaccgc ttttcataag ggttgaatga atttacactc caccaatggt
22381 gtataagggt tccctttct  ctgcaacctc actagcatct gttattttt  gttgagttcc
22441 gatttttaat tctctggggt gtatacacag caatgaactt aagggtcgta tggtaattgt
22501 gtgtttaatc atttgagaga ttgccaaact gttttccaca gcagctgaac catattacgt
22561 tataaccagc aatgtacaag ttctgatttc tcaccagcac ttgttaattt tccatttaaa
22621 aaaagtatag ctatcctaga ggctgtgaag tgatacttta ttgtggcctt tatttgcatt
22681 tccctactga ctaatggtat tgaacatttg taaaacatgt ttgtttgcca tttgtatata
22741 ttctttatag aaatatctat tcagtccttt gctccttttt aaattggatt gttaggtttt
22801 ttgtagttga gttgttaaaa gttgtttata tgtatgttct caatactaga tctttattaa
22861 aatatgattc acaattattt tcacccattt tgtaggctgg attttttactt tcttggtaat
22921 gtccttcctt tgatgcataa aattttaaaa ttttgacaaa ataatttta  tctattttg
22981 tttttcatgc ttttggtgtc atatgtaata atctattgct gaatccactt tgaagaagat
23041 ttacacctgt gtttcttcg  aaggggtaca gttttagctt ttatatttag gttattgatt
23101 catcttgagt taacatttta tatagtatga agtagggtct cgactttctt cttttgcatt
23161 tggatattca gttgtcccag catcattaaa gacaattctt tcccccactg aaaggtcttg
23221 gtaccttttt gtttgttgaa tagtgattga aatcacttta gcttaatcca aacaatcagt
23281 gagacaagga agtgctggga ctctgcccca tgttttcttg atatgtctgt catccatgca
23341 ggttcttctc aaggttcaaa gaagaaccca agttcttctt tgaacccaag gttcaaagcc
23401 ccatcccaag tgtcctcctc tccactggct gcttctccta ttagtaacag actctaaagt
23461 tgaggaagtc accagattct tctccctagt ccagacccac aagatggttc cttgttgtta
23521 gcaaggatac caactggatg ccatgggtct cattcaggcc cattcacagc cttgttggtt
23581 tcactatttt ttccttcctc cttttaattt taacaggttc attgcaatat aattactgta
23641 cataaactgc acatattaaa attgtacacc ttgctgagtt tgacatatg  tatacaactg
23701 tgaaaccatc acaacagtga agataagaaa cattcccatc atctcattgt aattcattcc
23761 ccaacccacc ctcaactaat aatctgtttt ctgtcactat gaattacttc aagctttcta
23821 gaagtttata taaatggaat catacagtat atacccttta gtctgtgaat tctctcattt
23881 ctcataatga tttttagatt cgtctgtgtt gttgcatgta tcaatagttt cttccttttt
23941 attgctgagt agtatttcat aataaagatt ttacacaatt tgtgtatccg ttcttatact
24001 gatggtcatt tgggctattt cacgtttggg gctattgcaa acaaaggtgc tactaacatt
24061 agtgtgtaag tctttgtgta gatgtatgct tttatttctt ttgggcaaag acccaggaat
24121 tgaacagcaa ggtcctatgt taggtgcatt ttaagttttt aaagaaattt ccacgcattt
24181 tctggaaaca cacaagaata aattaacata ttcttatctc ttgtcatctt tgtgctacta
24241 taatatttgg aggttctttt aaaaataaat gtgtacatct ttgtctccta tgcctttgat
24301 tgcctggagc agatttgttt gttcttttt  gcaccttcaa ttcctaagac agtcctttgc
24361 ataaaaggat ggttaatcag ctttggatga acgaatgtca gataatggct tatctgaacc
24421 aaaatgaatg agagggcaaa attggagagg atgagaggag tagaataggt aaataaataa
24481 aataacactg tctttaaaa  ttatgcacat aattcatgat ggaaaaagat ccaaaaataa
24541 agagtagctt aaagaagaaa ataaaaatca tccatgatcc ttcatagtca ctctttaaaa
24601 aattattttg ttgtttatt  ttctccccaa tattctctta aagttaaggc cactagttct
24661 caactcttcc tacacatcag actactcagg aagctctttt aaataggtcc aatgtctgga
24721 ttccattaga gattctaatt ttaattggtc tgaggtggag tctgggtgtc aatagttttt
24781 ttttttttaa tcaatctttc aaaggtagtg atttacatac aacaaatgc  atttattta
24841 agtgtacagt tcaatgagtt ttgacaagta tgtatcctcc ctataaacac tgctctaatc
24901 aagtatacaa tatttccatc atcttcaaat accccacatt tcatcccagg caacccctga
24961 tctggcttgt tactatagat taatggtgat tattcaagaa tttcatataa acagaaccta
25021 acagtctggc ttctttcact cagcatgttt atcagagtca tcatattgtt acatatatcc
25081 atagtttatt cttttcact  actgattagt atttcattgt atggaggtac cacattttgt
25141 ttatccattc acctcttgat ggacatctgg gctgtttgca cgtattgact gttaggaata
25201 gagcttctat gtgcgttctt ataagtcttt gtgtggagat atgttttcat ttctcttggg
25261 taaatgtgta ggagtagaat tgctgggtct tatggtaagt gtctgtttaa ctttataaga
25321 aatttacaaa tcattttct  ttttttcttt ttttccaag  acagaatctt gttctgcctc
25381 ccagacttga gtgcaatggc gcgatctcga ctcactgcaa cctcggcctc ccaggttcaa
25441 gcaattctcc tgcctcagtc ttctgaatag ctgggattac aggcacgtgc caccatgccc
```

FIG. 11 G

```
25501 gggtaatttt tgtgttttta gtagaggcgt tgttttcacc atgttggcca ggctggtctc
25561 caactcctaa cctcgtgatc taccctcctc ggcctaccaa agtgctggga ttacagccat
25621 gagccactgt gcctaacctc caaaccattt ttcaaagtag ttgtactatt tcacacatcc
25681 accagtgatg tgtgagtgtt cagttgtcct acatttttgc cacaccacca atattgtcag
25741 tatcttaaat ttaaaccatt ataggggtca ttagcagttt ctaaaagctc ccctagaaat
25801 gtgtacttct ctgtatataa tacatagtaa aaagtgaaga aaaataact ctcgaaatga
25861 ttgtaatgtg cagtcaatat tgagaaccac tgagaaccac tgagcaagac tagaccgaca
25921 agtcccaagt atttaaataa tgacatattt tcatttgtgc gttattttt tcttacccat
25981 tcatttattc aaaaataact atactagctc tatactaagt gttggcaaca tagagatcta
26041 caacaatatt tttctgccct caagaagctg acaaatttct tttttctctt aagaaaacaa
26101 aatttcacct gtgtgaccac agtcatttca gacaatttag tttttaattg gtctttctca
26161 gtattgtgca gcccaggcct tgagtcgatc ttgatgaggg ggaaaaagta acgggatcat
26221 tcatggtatt tgagatgttg ctttcttgat tttactcttt tccttccctg cttcctgtct
26281 cccgtatttg ctttcataca taattcagct ttgggaacag tgtctttaaa tgaagtcacc
26341 acatgagcca taacaatata aataaaacaa aaatactttg cctctggaat tggcactttg
26401 gtgactgcac tccatagagg ctatggctga tttctaattt ttgtatttta ttttctcct
26461 ttgtttcttt gatataggaa atcttcagta aaaagcatat tctaataaaa ataagactaa
26521 ctagtgtaac attataaaat cctctccaga agcctattaa ataagtatag tagatgggta
26581 aaaaataata tggcccataa accctacaaa actcacaagt aaaattatgt aatcaaattg
26641 taaaatattc tcttatttgc tattaaatgt acactataaa aaagactttg aaattgtaca
26701 ataatgttta cctccttgga attgttagaa ataagtacat aatacttaat ttctgtgcag
26761 aattttttta atattctaag aattgttaag gtcagtgtga gaagtgttaa cattggctgc
26821 cacttgctta caaaagaggt tctacataca gcaactgata ggagattcca ttttccttt
26881 tactggggct ttagtgattt cagagactcc aacattcttg tgaaaaattg actatagaag
26941 tccaataatg agtagaaagt tatttgtcta gctgtcggtt taaagaaatt tcatccccaa
27001 cataggtggc tttccatcaa gaaaatattt tccagcacaa tctcaagcca atttaatccc
27061 ttgattgtat tctgtaccat gcagcaaagc cagtttccat gtttgctgtg tttaatttta
27121 tttcactgaa ctttcttttc actgcaattc tttccttatt ttcattgttt ttacacaaat
27181 tagattcatt gatcagtttt tttgtatcac attaattttt ccttatttag tttcaaccac
27241 tgcaattttt gcttttgttt tccaaatcca aatctctctg acatcaaatt ttgcaagtct
27301 aaatgtaaag aaaatgtctt ttgcagcaac ttgggtgtaa ctgaggcca ttattccaaa
27361 tgaagtaact taagaatgga gatgcagaaa ccatgtgttc tcagttataa gtgagagcta
27421 agctataagg acacaaagac attcagagtt atacaatgga catcagagaa tcaaaagggg
27481 gagaaggtgg gtgaggcatg agggctaaaa gctgcatatt gggtacgata tacactactc
27541 aggtgatggg tgcactaaaa tttcagactt caccactata caattcatcc atgtaacaaa
27601 aaaccacgtg caccctaaa gctatcgaaa taaaaaataa aaacaaaaac aaaaaataaa
27661 atttgaatgc atttatcaa aaggatgcga gccttctttc cattttaac caatagcatt
27721 gttgccatgt gtggtatcat ctgttgtcag ttttattta tgctgattat ttctaccagc
27781 cgtaacaatt gggaaatagg caaaagttg gttgtattta ttcctagat aatcaataac
27841 aaacttcaga gcaatctaat gagacagagt tataggtgca cagaagaaga agaaaagcta
27901 cagtgtgtg gagcatggat ggctaaactc ctggttaact cgatggggtc aaaaggacaa
27961 atgtggggca gagttcagat cttttgacag ggtcaacgga tctggcatca gtccctggct
28021 gctctcttct aagtttcag tcgtgctctt ctccattcct caccagaccc ctggcctctt
28081 tggagctgcc tggacaggag ctctcctggc ctctggcaaa ctcctggctg ggttgcggat
28141 ggaaattcct ggtacccta gttgagttca tacaagctga acgttttcaa aaggaactaa
28201 tttacttga gccaactaaa caaaactgaa atacacacag aaaatacaaa agcacagaaa
28261 tagatgaggg ttccatgcca tgggcatttt aatcatgtgt atcaagaacc tttatagagt
28321 tcatgtctgg cccagccaat ccacttctag gaagttatct caaggtgatg tactggatat
28381 gagttgaaag atgtgtatac gacgtattta tcaacaaaaa ttggaacaag gtaaatatgt
28441 tctgatagag gaataattca aatagagtat tttcatacca tttaatactc agctacgaag
28501 cagggctggt aaacttttct ggaaaagaat agatagtaag tattgtagat ttgtgggcca
28561 tatggtgtct gtcagaaata atcgattctg ctattgtagc acagcaatgg gcatagatag
28621 tacataaagg aatcagcaca ttcatgttcc aataaaactt tgttaattta ccaaaaaaaa
28681 aaaaaacaca aacccaggt ggaattggct tatgagcctt aatttgcaga ccctggttt
28741 acagagatga tatggatttg tatttactga caaagagagc tgattataat atactattgg
28801 gcaaaaacaa agcagatac tagtatagca tttatggtat gatgtcactt atgcaaaatg
28861 aagattgata tatatata tatatata tatatata tatatatc agtagagaag
28921 tgtctagaag gatgttcagc aaatactaac gaagatatta tcactaggtt gaagaatttg
28981 agatgatttt tttcctttat ttgttttcac attttttcat tactagaaaa aatatttta
29041 tttaataatt catactcttt gacagagtac ttccacggtt gttgttgggg ttgccgcaca
29101 gctgtgaagc ctgtgcagtt gcacacttcc aggagatgcc atcacatgga ctacaatgtg
```

FIG. 11 H

```
29161 aaggattccc ccagagttgt gtggcgaggc agtcttccca cctcccattc tctgttcagc
29221 tctgtccaat taattcagca agcatttgtt tgtcatctac tacactagac attgttctag
29281 acagaaatat cgggaaacaa agcatacaaa aatgtttgcc cttgtagtgc tttatgttct
29341 agtgaaggag aaagatgata aggagaataa agagtgacac atatgcaagc ttcctggagg
29401 tcaagtagcc cagttttttgg cagagggaat agccagtggg aagaaggcag gcagggcaaa
29461 tatttacaac cctcgtttta cagaagagaa cattggaact tagggaggtt taagggatgg
29521 ctgagggtca gaacgtggtc agcaccagaa gcaaggcctt tcaattgcaa ggtcagggtt
29581 ccttccacac tgggacaaga ggcagcacct gcaagataag gtagaggtga atgaacctag
29641 gtggctttag ttagattctg cagacttta tgacaggcca atgcatataa atgataatag
29701 ctgacatcac attaagaaaa agatgcagca tctcatgaga tctactacat gctcctgatt
29761 aggaaaagga atgttgaaaa atagcactga gtttataaaa atagcgttta gggtgtaatt
29821 ctcatttttt tagtacatga atgcttaaga aagatgttca tcaaatgtta gcaatgctta
29881 ttacttgatg gtaggatttc aaagagtttt aaattttctt ctttattctt ttctgaattg
29941 tttgagtttt ttgcaatgga agtgtgaaaa cagaagaaat aaaaaagttt gatgttagaa
30001 agataccatt aagctaacat ttacacactc tgtgctgttc cacagcacct gtagtaccac
30061 tatttctttg taaattcttc cagggcagag actgtgtttt attcattctt ctttgcccag
30121 catgtggaac ctcctacaaa acaagcattc aacagggttt gtggaacaaa tgcaaagtgc
30181 atttgcgaac tgcagcttat ataatctaca acagacacct agggggctc aggaatgaca
30241 cgaacagttt ccagccgaag ggaatttcat tttctttct agttggagtt tccatggcac
30301 ccagaagacc agggatcctg gtaagaaagt tttaaaacgc tgaagtggta agtttgtaaa
30361 tttgtgatac ctggtgtcaa gtcctacttc aggaatctac aaaaattggg ccttttgaat
30421 agaagtgttt tagtgaataa tgagtgatgt ggcaacttat tctgataata tttcaatcta
30481 gcttttgct tttaatggta gttgccattt ctattgggct gcatcattcc caggaaagcc
30541 ttcttttaaa atcagtacag gatgtgtgca tcctaataca aaaatcccaa atccagaaat
30601 gcccctgaat ctgaaagttt tcagtgcta atatgagata gtgaaacctt gctttcaga
30661 tggttcagtg tacaaaaaca ttgtttcata gacaaaatta tttaaggtgt tgtataaaat
30721 tactttcaga ctatgtgcct aaggtatata tgaaacataa atgaattcca tgtttagatt
30781 tgggtctcac tcccagatat ctcattatat atatgcaaat attccaaaat caaaatcaaa
30841 aacaaacaaa caaaaaaacc gccaaatccg aaacacttct ggtttcaagc attttggaga
30901 agggattttc agcctctccc tagagattaa tttgtttgat gtggtcaatt gcctgattat
30961 tcaaactcct caaaaagtgc aggtctttcc tccataccac ctgtttaggt tttgaatagt
31021 ttagaaaaaa aaataagtga ctgtctttaa gtcattgatt aaaagttaat agccttaaaa
31081 tgtttccatt cctatttat tacaaagtat tgctcgaaac aagttttaat agtgagaagg
31141 aaagttgtca cccataggtt taggcacaat ttttcagtct cctttactca cttagcatta
31201 gactagaaac actttcccaa tgatttttg aatacttgtg tagcatttga acttgtagat
31261 gaccacactg tacaaaacca ttgcagaatt agcatacatt catattagtg ttagtttttt
31321 agtgattttt aattgaacag ggaaatttta catatttggc tctattctgt aactacaagc
31381 aaaattctaa ctgacttttc cctctttcag attcttaatt attaaactca tctgaccatt
31441 tttattttta tttatttaat tgacaaagag cgtatatact caaggtgtac aatgcaatta
31501 tttgatatgc ctaaattagg ttggtgcaat tagtttgcac caacctaata cattgtataa
31561 ttactacaat caaattaatt aatacataca ttatcaccca tgctatacat tagattctca
31621 gaaattgctc atcttataac tgaaagtttg tccccttttgg tcaaaatcta cccatttccc
31681 ccaccgccat tccctggcaa ctgccatggt actctatgtt ttgatgagtt caactctctt
31741 atattctgca tataatacac tgttgaccct gaacagcgt ggagtttgag cactgacccc
31801 tgcatagtcg caaatcagca tataactttt tcttaaggca tggggtctca ctatgtttcc
31861 cagactgggc cttgaattac cttggcctta aacttgatt ctccaaaagc ttaactacta
31921 atagcctact attgaccaat agccttacca ataacgtaaa cacttgatta acatgtattt
31981 tgtatatgta ttatatactg tatttgtacg ctaaagtaaa ctatagaaaa gatggtgtta
32041 ttaagaaaat cataaggaaa agaaaatata tttactattc cttaagtcaa agcggagagg
32101 tcttcatact ccttgtgttc ctattgggta gactgaggaa gagaaggaag aggaggattg
32161 gtcttgctgt ctcagatgtg acagaaacag aagaaaattc acatataagt ggacctgtac
32221 cattcaaact catgatgttc tattagtcta tgtgtttgtt tttatgccag taccatactc
32281 tttagattaa catagctttg taacatagtt tgaaatcagg aaatgtgatg cctccagctt
32341 cgctcttctt tctcaagatt gctttggtca ggttttttg tggttccata tgaatcttag
32401 aattatttt tctctatctg tgaagaatgc tgccattgga attttgatag agtttgcaat
32461 gaacctatag atcaccttgg gtagtatgga tattttaata atattaattc tgatacatga
32521 acatgtgatg tctttctttt tatttgtgtc atcttcaatt tattttctca gtgttttata
32581 tgctgatatt taaacttctt ggttaaatgt attcctaagt aattttattg tgcttgttgc
32641 tattgtaagt aggattgttt tctttctttc ttttttcagat aatttgttgg tgctgtatag
32701 aagtgcaatt cattgttcaa ttcccaccag tgattgagaa cgtgcggtgt tggttttttt
32761 gtccttgcga tagtttgctg agaatgatgg tttccagctt catccatgtc tctacaaagg
```

```
32821 acatgaactc atcatttttt atggcagcat agtattccat ggtgtatatg tgccacattt
32881 tcttaatcca gtctatcatt gttggagtta atgggtgcag cacaccaaca tggcacatgt
32941 atacatatgt aacaaacctg cacgttgtgc acatgtaccc taaaacttaa agtataataa
33001 taataataat aataataata ataatgaaag aattgcaatt caattttaat gttgattttg
33061 gtattctgga actttactga attctctttt taggtctaac agttttttgg tggagtttct
33121 gtatacaagg tcatgtcatc tacggagaca attttgcttc ttcctttctg atttggatat
33181 ttttatttc tttttcttgc ctaactgctc taggtagcac ttgtggtact atgcacaata
33241 gaagtggtga gtgtgggcac ccttgttcct gatcatagaa gaaagcttt ctgcttttta
33301 ccattgggta tgatgttggc tgtgggcttg tccaatatgg catttattct gttgaggaac
33361 attccttgca tacctaattt ggtgagagtt ttaacagcat tttgaagtat aagtgacata
33421 aaataaacag catatgtatc tagtgtacaa tttgataagt tttgacatac gtatataccc
33481 atgaagccga tcaatatagt gaacataaac atcatcccaa aaggtatcct tgtgctcctt
33541 tgtaatctct ccttcctgtc tctctccatg taccctcttc tcaggcaacc actgatctcc
33601 tttctgtcat acagattggt tttaattgtc tagaggcata taccaatgta ataatacaat
33661 aagtagttta ttttggtgtg gcttctttta ttcagcataa ttactttaac attcattcat
33721 attgttgtat gtatccatag accttttttt ttttttttt tttttttttg ctgaatagta
33781 tttcattgta tgaatacacc aacatttctt tatctagtta cctgttatgg acatttgggt
33841 tgttttcagt gtgagacttt tacaaataaa gctgctataa acatttatat atgagtcact
33901 ttatgatacg cttttagttc tcttggatat acaagtgctg gatcacatag caggaatacg
33961 tctgactttt taagaaactg caggttttcc attttcgtt tccaacagta tatcagttct
34021 aattcctcca cctccttgac aacatttggt attgtcaatc tttttaaatt tagctattgt
34081 ggtaggcata taatgctttt aacttgtatt ttcctaacta ctaatgattt tgaacatctt
34141 ttcatatgct tatttcccat ccctgtatct tctttgtgga agtatctgtt caagtattt
34201 gcccattgtt ttattgtttt tctaactcga ttttgagagt acttataca ttctggatga
34261 aggttgttat cagacatatt ctgtgcaaat attttctccc agtctggctt gttttctcat
34321 tctcttagta gcatcatctg aagaacagaa gttttgaatt tgatgaaat ccagtttatc
34381 agtttgttct tttatggatc atgcttttgg tgttacagct aagaaatctt tgcccagtgc
34441 aaagtcacaa agatttttctt ttagaaatgt tatcgttttt ggttctaac ttaggcctgt
34501 gacccatttt tcagttcatt tctaggtata gtgtgaagta tggattttgc atatggtaac
34561 caattattct agcaccattt gttgaaaaga ctgtcctttc tccacttaat tacatttgca
34621 catttgtaaa cacaaacaca cagacagaca gacagacaca cacacacaca cacacacaca
34681 cacacacaca cacacacccc atatatattt aggtctcttt ctgggctctc tatatttttt
34741 aatgatatcc cttgtctatt gtgatgtcaa tacccactat tttggttact gtagcttagt
34801 aataagtcta gacgtgagac agtgttaatc cgcctagttc ttcttttccc aaattgtttt
34861 gtctagtatg gttccttttc atttccacat taatcttaga gtcagcttgt caatttctat
34921 aaaatgtctg ctagggtttt gattgtgatt ccattgaatc cataatttgg agataattgg
34981 catattaata ataatgagtc ttttaatcca taaacatggt ctatctctcc atttatatag
35041 gtccttaatt tcttttggca atgtattata gtttatagtg tacacatctt tcacatttta
35101 tgtcagattt atccctatgt atttcatatt tttatgttat tcaaagtatt tttaaaattt
35161 caacttgtga ttgttctttg ctagtctgta gaaatacagt tgatttttta ttgatatttt
35221 atcctaaaac cttagctaaa atcaattatt acttctaact ttttgtgtt tctattagat
35281 tttctagata gatagtcatg ttggctatat ataaagacag ttttatttct tccattctgg
35341 atgcatttt ttcatgtctg attatatgtt ccagtatctc cagcacaagg ttgaatacaa
35401 gtggtgagag cagacatcct tgtcttagtc ctgatcacag aggaaatgca ttcagtcttt
35461 tatcatgaag taagttttta gctatagatt tttcatagat gctgtattat tcaggagtct
35521 ccagaggaac agaactaata ggagagatgt gtatatgaaa gggaattat taaggagtat
35581 tgactcacat gatcacaagg tgaaatccca tgataggccg tctacaagct gacgagcaag
35641 aaagcccagt ccaagcccca aaacctcaaa aataggaag ccaacagtgc cgccttcagt
35701 ctgtggccga aggcctgaga gcccttagca aaccactggc atcaagcctg agactccaaa
35761 agctgaaaaa catgcactcc gatgttgag ggcaggaagc atccagcaca ggagaaagat
35821 gaaagccgga aggctcagca agtctagttc ttccatgttc ttctgcctgc tttattctag
35881 ctgtgctggc agctgattag attgtggcca cccagaatga gggtgggtct gcctctccca
35941 gtctactgac tcaaatgtta atctcctttg gcaacaccct cacagacaca cccaggaaca
36001 ctacttcgca tccttcaagc tagtcaagtt aatactcagt attaaccatc acagatgccc
36061 tttatcagtt tgaggaaatg cttttctatg cttagtttgc tgaaagtttt tatttaataa
36121 tacatgttag attttttgtta cctgcttttt ctgtgtcttt tgagatgatc atgtgattta
36181 tctctttgct aacatggaga attgtactga tttattttca gtgtaaaatc atcctgaatt
36241 cctaggaagt aaaatcccaa tttatcatga tattgtattc ttttataga ttttgaattc
36301 agcttgctaa aatttttatt tttttcttct atattcatga agaatcttgg cctatagttt
36361 gcttttttgt taacatctta gtaaggtttt tgtgccatgg taattctggt ctcttacaaa
36421 tattccctgc ctcataagtt ctctgggata gtttgtatag aattggtatt atttcttcat
```

FIG. 11 J

```
36481 taaatgtttg gcagaattca ctggcaaagc tatctgggtc tcaaatctcc tttgtgggaa
36541 gatttctaac tacaaattga aaattttttac atttatttt atttgtacat ttatttattt
36601 tctgagatgg agtgtctctc tgtcacctag gctggagccc agtggtgcga tctcagctca
36661 ctgcaacctc tgtctcctgg gttcaagcaa ttcttctgcc ccagtctccc ttgcagctgg
36721 gattacaggt gtgtgccacc atgcccagct aatttgtttg aattttaat agagacaggg
36781 ttttgccatg ttagtcaggc tggtcttgaa cttctgactt cagatgatcc acctgtctca
36841 gcctcccagt gtgttgggat tacaggcgtg agccaccgtg cacacctat attgattttt
36901 tttttaaat ataaggctat tatctgtttc tttgtgactg agctttgata ttttatatgt
36961 tttaggacat ttgttaattt catttccatt gtaaaattta tgggcataaa attttacaag
37021 tgatattccc tttttatact ttttaatatc ttagaaacca ctgatacca ttctctcatt
37081 cctaatgtga aaaattttga tctctccttt ttcctaatca atctatcttg agatttatcc
37141 attttctttt gctttgtttt tttttttttt ttcctctctg agatggagat tcagtcttgt
37201 tgcccaggct gcagtgcaat gggttgatct cggctcaatg gggcaacctc cgcctcctgg
37261 gttcaggcaa ttctcctgcg tcaacatcct gagtagttgg gattacaggt gtgcaccacc
37321 aagcccagct aattttgca tttttcagta gagatggtgt ctcaccatat tggtcaggct
37381 catttagaac tcctgacctc aggtgatcca cctgcctgg ccttccaaag tgttgggatt
37441 tcaggcatga gccagtgtgc ccaactccat tttattttc ttgtcaagaa accaactttg
37501 tttttgttga ttttctctat ttttgtcttc tattttattg atttctcttt tgatctttat
37561 tatttcctac tgtctgcttc ctttgagttt aatgtgcact cttgttttta ttatttattt
37621 cttgtgatgg atcctgaggt cattgccttg aatcatttt ttttttttt gtaaaatagg
37681 tatttggtgt tatacagttc cattagtatt agtattagat gccaaacatt agtggcatcc
37741 tacaaattct tatatactgt attttcattt tcactcacct cagaatattt tgtaatttcc
37801 cttttgattt cttcttgaa ctgtgagtta tttagaagca tgttatttag tttctagata
37861 tttgggtatt tttcagttat ccctcttcta ttgatttcta atttaatttc actgtggtca
37921 aagaacatat ttgtatgact tgaatctttt tacgtatatt gagaatggtt ttatggctca
37981 gaatgtagtt ggtctttgta aatgcccat gtgtacttga aaataatata tattctgctg
38041 ccattggatg gagtgttgta aaaatgtcaa ttaggagttg tttgatagta ttgttcaaat
38101 ctgttatatc cttgctgatt ttctgtccac ttgttctatt aattatcgag aaaggattat
38161 tgaaattccc agctacaatt atggatgtgt ttatttctcc ttacaatcta ttagttttg
38221 cctcatgtat ttgaagcact gttatgaagt acctaaaccc ttaggattgt cacattttca
38281 ttaactgacc aatttgtcat gctgaaatga ctctctgcct acggtaacat ttttcactct
38341 aagatttact tctttagta tattaatata gcctctgtcg agggctcagc tggagagaga
38401 gctgagctgc caggttttaa cgtggtcagt taagaaaacg gccaaactta aaaagaaaaa
38461 aaaaaagaa accatcaaga ctttattcac ttatgcaaca gtataagcaa gaagcaaaaa
38521 aggaagaagt gccagctccc agaatgttcc atgttttccc ccatggagca gctcagagga
38581 ggggagtttg gggtatgggg atgatcatct ccctgcttag cgagacggac tgccgaacat
38641 gagcctcctg ctatttcgct gttgctggga atttatggac cctgtggtga agggtgggag
38701 tttggggaag gctaggagtg aagatactt aatactgagg accgcggagg cggaggttgt
38761 tgcagtgagc cgagatcgcg ccactgcact ccatcctaag cgacagcatg agactcagtc
38821 tcaaaaaaaa aaaaaaaaaa aaaaaagag gaagaagagg aggaggagga gggaggggga
38881 ggaggaggag gaggagaatg agaagaaaag aaaaagaag aagaagaaga ggaagaaggg
38941 gaagaagaag agaaggaagc ggaagaggaa gaagaagaag gagaagagga agaagaagaa
39001 gaagcagaag aagaagaaga ggaggaagaa gaagaagaag agagaaaagc atgttttttca
39061 ggttactctc aagaagttgg tgtctagtag aggcagccaa gaaagacctc tgccaggacc
39121 ctcctgatcc ggggacctct gcatggacgt atctgggctg ggaatgcagg tatgtgtaag
39181 aacataagtg cgggggacg tgagtctttg atacaactcc cctaggggac tgtgtgctct
39241 ggttctggtt gtgcaccgag gccggtgggg aggacccatg aacaaactt gtggtaaggc
39301 ctttgtagtg gctgaaaact cacacacaga gttgggtttt ggctctcaga aaactgctca
39361 gccactccag cttcctcttg gccagtgtca gcaatggcat acccttgtca aaacttagac
39421 tatttggcca ggccccgtgg ctcatgcctg taatgccggt actttgggag gctggggcag
39481 gtggatcctg agcgcaggag tttgagaaca gcctggcctc aagaaaaaaa aatttttttt
39541 cacttttaac ccatttgtgt ctttatattt taaagtgcat ctcttgcagg cagcacaaag
39601 ttgtcttgca ttttatcca atctgacagt ctgcctttta atgggctaa ttggactatt
39661 tttatttaaa cttttttatct gtaatggcta acttcactc tatcacattg gcatttgttt
39721 cttatttgtt ccacctgttc tttgttcctt ttttcctccc tctctgtctt attttagatt
39781 aattggatta atttagatta actggattga tttgaattag ttgagtattt ttatgatcta
39841 tttttatctc ctttatagac ttattagctt taactctttg ttttattatt ttagtggtag
39901 catacatctt ttcttatcac gatatatttt gagggatact atacctcttc atatgtggta
39961 tgatatcctc aaatgggtat acttctattt ctccccccac cagcctttat gttattgttt
40021 ttgtcttcca atttatataa gtcataaccc ctataataca tggttattat ttatgtttaa
40081 atagccaatt atctcttatt tggtaatttt tattgtgata aaatatacat aacataaaat
```

FIG. 11 K

```
40141 ttaccatttt aactgttatc agtggtgaat ccacacaaga ctgcagcaac ctcaattctt
40201 acctccttca gaagaaagaa ttcaaccaaa gggaataagg cagagggaga aactgaggca
40261 agcttaaggg aaggagtgaa agtttattaa gaagttttag agcaagaatg aaaggaagtg
40321 aagtacgctt ggaagagggg caagcgggtg acttgagaga tcaagtgcaa ggtttgaccg
40381 ttgacttggg ttttatgct tctggggtga ttgtgccctt ctcccctgat ccttcccttg
40441 gggtggcctg ccagcactta ggaggggcca cgtgtgcagt gtgtttacta aagttgtatt
40501 caggccgcct tgaaacattt ttcccttacc ggttgagtat tccctaagga aggtgaggta
40561 ccagttaatt ccaccatttt gcctcttagt gtgcatgctt gagttcactc acccaactcc
40621 tgccatctaa tcaggaagct gctgatcatc agtttcaggt gttttctatc tattgggaga
40681 ctgcgtttcc ctggcgctgg ctgcaaccaa ttattatttt agagacagtt taacaaccac
40741 ctcactatca ccttatggtc gcctgacatt cctggtgaag agggccctct ccttccctgc
40801 tcatgtctgc ctaactacct atggtaacaa aagcttttt ttttttttt tttttgaggc
40861 aaggtcttgc tctgtcaccc caggtgtcgt gcagtgggc aatcatggtt cactgcaacc
40921 tcaacctcca gggctcaatt gatcctccca ccttagcctc ctgagtagcc aggactacgg
40981 gtgtgtgcca ccacacctgg ctaatttctg tatttttgt agagacagga tttgccttgt
41041 tgcttaggct ggtcttgaat tcctggggtc aagctatctg ttggtctctg cctcccaaag
41101 tgtgggatt taggtgtga accactgtgc ctagaccccc aaattatctt tttttcagag
41161 acagtgtgat agttctcaaa ctatcaccta acattcctgg taggagagga aagatctctc
41221 tcttgcccca gtcatgcctg tctaactacg tgtaactagt tagctcagct tactgttata
41281 attttctca ctgatagaat tttgcaaag cactttcaa tactaccaaa ataaatagta
41341 atcaaccact tggaaagcat ttagaagtaa ctgaagtccc tacttacacc aaatgaggaa
41401 aagccaaact acactgtggg acacactgta agtccctgca tcagtcagct gttgctgtgc
41461 aaacacctcc tcaagactcg gcaggataaa gcaatgacca tttataattg ctcacatgtc
41521 tgcaggtcag ctgcttttg gctgaccgag gcagggctta gctaggctgg ctctgcagcg
41581 tgtgtctctc attctcctcc tgtggcaaac aatggcagat gacaatggca aatgtggaaa
41641 gcctttaaag aagaaatctc ataaggagtt ccctgtcact cccattcatc tcagtctttc
41701 agccaaagca agtgatatgg ccaaacccca tatcaagggg tggggaaata taatttgctt
41761 atttattagg agcaaagtca catggtggtc attgcagaat gggttgaatg acataaccta
41821 tcatcagccc tgaagaaact catcattcat ttccttcctc aagactcccc tcatccgggc
41881 atctccagat cttactcttt cccacactct gtatcaaaca gtccactcac actagctacc
41941 ctgcttcctt tggcaccctc tttccactag ataacctgtt cactcagcat ttctattttc
42001 atttgcatct ccacccttgt cccattaccc cagcagctca cagaggaccc tgacagaata
42061 ggcaaaaccc agaagttggg tgggtagata atgtgtgaaa gctcacacgg ttctgacgcc
42121 tccttgacgc agcacattac tagcgaatga catgtatagg gcctggggtg tttgcagaac
42181 caaatcaggt gtggaggaaa ttatatgtaa ataccctccat gggtgtgtga ttgtatcata
42241 cctcaccata acaaagctca aatgacattt catttccaaa tgtggctagg tttccctgtg
42301 ttatatgtcg ttgaaagcca gtataaataa atatctgtga aagtcctagc tgactgcctg
42361 ctttgtttct gccactaaac tgtaagctcc tcatgaacag agtgtttctg tacaattcac
42421 tagctgtctc tatctttacc tcacagccaa tccacaaatg aacgctgtca gccttgcccc
42481 ccatcatatc ccaaccatcc atgtctggct actccattgc tagtccaacc gaagcccctt
42541 gcatctcatg cctgggttat ttcacagcct tctaggctgg taactcccgc tgctactgtg
42601 cctggctcca gtctattctg tacatggtga agaggatcct ttgaaaaatg gataaaatga
42661 gtagcaaatt gtgtttctcc tgcactcaga atcctcctct ggctcctcac tgtaacctct
42721 ggcttcagta gttacggcaa atatttaaaa gtcagcctgc aggaagaacc ctgatttact
42781 gagttttcca atgttagtag tataaatact catcatggcc aattttaagc tggcttcttt
42841 ccttcactcc gtccctccct cctcccttc tcccctcctt ctcttctccc ctctttcctt
42901 catttcctcc ctccctccct catttcttct gtccttctct ccttcccttc ctttccttct
42961 cacgtccttc tttccttctt tccctcctcc cgtcctttct tccctattct ctgcctccta
43021 ctctagaatt gacatttcat gacaggcaat ccatgtctgt cttagttatt gcttagaagt
43081 acctggcaca taatggaagg ctcagtacat atttcttgaa caaatagttg actaattgaa
43141 tagatgatcc tttcttaatt ctgtaccagg atttaagaat tattcaaaga agatgtcatt
43201 gttttaaaat gaccaagtac tgctcagcac tttcaagttc acaaagcatg cctcatgcat
43261 catctctatg atctgtaccc gggtgccatc ctgagaagct gggaaaggct tttctcttcc
43321 tcctcacttt acaaatgagg aaacaaagac tcagagggat ggaggttccc gctcaaggcc
43381 aaacagtaag tatgtatcca caagtctgac tctcagtctg gcagtcttct cagtggtctc
43441 caggaactgt ttagctcttg ggggatctc ataagggaag cctggaggct tcagggagag
43501 ctgtcccaag gaagaggaga gaaacacatg gtggcgagga aggaggattg acgaccaggg
43561 aaggccttac gtaggcctct accaggctga gcctctggtg tcaggccagt aacatagtaa
43621 ttcaggtccc caatcctgat tctgtctcta gattcccact aacctcccca cagacatgga
43681 gcattgagcc ccccttcccc acttatagag taccccagat agcataggct ccacacctag
43741 cacccacctt cttgcaagtc tatagcaatg agcagcagag cgccagctga gatcc
```

FIG. 11 L

BASE COUNT
ORIGIN
```
   1 gatctctagt aaagctgtgt agaatcagta acttctaggc tctaattaac aaagcaggaa
  61 ccctcctttc ttattaactt ctataacatt actgtgttca aaaagataac gcagtttctt
 121 ttgtcttttg ttttctttca gacaggtata tgtgtaatag ctttctcttt tgcagcattt
 181 tgtactgaca tttgtgaagt caacagcact tcaccaatga ttttttaaatt aatgatgtgt
 241 catagtttcc tgatgtgtca attagttctt aattaaaatt ttttcaaaat aagtcagcta
 301 aatagtgaag ccaaaaaaga aacttgaaaa caaatcggct gaaaataaat tcaaataaca
 361 ggacactaac ttacattggc acaccacttg taccacttta tacgtacaaa atgaattcac
 421 agatgtgatc tcatgtcatt ctcaaagcac tttgcccaca gatacatagc tggcaagtag
 481 gtggcttata accacttacc tgtaagggac ataaacctag atctcctgac tgaattattt
 541 gtttcactat gctatattgt ttctccaacg tatatattac ttatgaatac tacttcagaa
 601 aattttacat taaccttaga gtctgctgtg aaagaataa agacagttct gatcagaatc
 661 tagaaaatta gtgagttata tgtatgtgtt tttttatctg aaaataaaga tggtatcatt
 721 tatatctatc agcccactgt gaaaatcaga attatcagtc agactgattc cgtgttactc
 781 aggaagaaaa atgttatttc aaaagatgct ttgaacaccc tagcgttagg gaagaggatt
 841 gtaacaaatt ggtttaaaac gttgaggctt atttttcttt tggtgggct tttttttttt
 901 ttttttttt taagatttat ctttagtcta ctcagtaaag tgaaaagttg tttatgaata
 961 tagaacagga tgattttaat aactttaatt tttacaaatc taaactctct agttttgggt
1021 gtctttttta actacttcac gtagtacttt cacaaatact aaatgggtat tcttccacag
1081 cattatacaa gactcggtga tgagcggcac taggtttaag aaagtactgt atccttcggt
1141 taaaattcca tgctgatgta ctctgataag tttaaatcct gagcctgaac tgagctgcac
1201 tggtgactga attacaatga aagtaattta tataaaaatat acttaaaata caaaaatggt
1261 atttcacatt atgtatgggt tttgcctgca tacgtaatta tgatgtctac tttccaaatt
1321 acagtctgct gcaaatcctg agactccaaa ctcaaccatc tccagagagg ccagcaccca
1381 gtcttcatca gctgcagcta gccaaggctg ggtgttacca gaaggcaaaa tcgtgccaaa
1441 cactgttttt gttggtggaa ttgatgctag ggtattgtat tcgtacctca tttttacctt
1501 aacatacatc atgaacaatg ggatgtgggc cctgttacaa acttaaattt ttttttgtac
1561 ttcctggagg tttagaattg cttttaggtt tgacccatag gtactaaaaa tatctttgac
1621 aaagggctgc tggtcattcg gggataaatg ggggagaaat ttccacctca tggtagtaaa
1681 attgtagtaa agttgaaatt tttgaatgct gaattttac tctgacgttc agttcttttc
1741 catagatgga tgaaactgag attggaagct gctttggtag atacggttca gtgaagaag
1801 tgaagataat cacgaatcga actggtgtgt ccaaggggtg agtaatttta tcaaaaatat
1861 gtgaactcca gtcacctatt ctataagtat cagacaagac ttcaaaactg atattctgac
1921 ccttgtataa atgcaatatt ctgcagtgtt aatttctttc acgtagggga taaaaggcta
1981 ttaccagttc ttctatttga ccatttttct aatgtttgta tttaaatgtc tccagtttct
2041 atttcataca gatgagttaa tcagttttct caaataattg ttttcttcat acactgcaga
2101 gcatcttaaa ttttaaccac cttgtcttag acagtaagtt aaactcaggt tcacagatat
2161 gaattctttg ctaatcaata aagttgtcac actgccctaa tcctagcaca ttttgacata
2221 gttctgctta agaaaagtg gtatttgtag aggatctgtc atgtacatct agcaaatac
2281 ttatcatggt atattattcg tcttttgtca tgaccacttc tgtatataga atagtagacc
2341 ttctgaacca cgtactgtat gatggtgatt ttatgcttca tttgtctgcc tttatagcta
2401 tggatttgtt tcgtttgtta atgacgtgga tgtccagaag atagtaggag taagtaatct
2461 aatagaaaaa tctcttattt atcttattgc tacaacgttt agtgtcagtg atacactcgg
2521 acttgtgtaa aatttgggga aagacacact tcctgttcaa aatccaaact cagagtaacc
2581 tcacgtagct tgtttgatcc tgtttatttt tgactggaca cctagtttca tgaactacag
2641 acaggaaggg ttggagacag ggtgatggaa agttttgat caactttcac ttgatgcctc
2701 ttgacactga ttagagtagt aagggtaagt aaggtagctt cgtgatgaca aattttaatt
2761 tggtgcgtag ttgtccccga tcttctatga tgataggtac tttagaagac ttcaggtgtt
2821 tacccaagtc ttggaagcta acacttgaaa attgattcta gttttgttaa cggttctatt
2881 ttcagtcaca gatacatttc catggtaaaa agctgaagct gggccctgca atcaggaaac
2941 aaaagttatg tgagtaggaa aagaaatggt tcttttctga cccgtgtagc ttttcaaata
3001 actaaaaata ggcttttttc ttcttgcttt ttaaaaaggt gctcgtcatg tgcagccacg
3061 tcctttggta gttaatcctc ctcctccacc acagtttcag aacgtctggc ggaatccaaa
3121 cactgaaacc tacctgcagc cccaaatcac gccgaatcct gtaactcagc acgttcaggt
3181 aagaactgct tatgttcctg ttctcttgtt tattctagtc atccttccct ctgtggaatt
3241 gtatctacac tttccatagt aagtggcaat agaatccctg tttgaacagt gtgagtaacg
3301 ggaaatctgt tacttttgtt agaaatttct tattcttcgt gttcgtcatt tgagctaaga
3361 atcttctgta tacttggcga agctttctct tagaaatgac ctctgtagac acatgaacaa
3421 atctcttcct atctctgcct ctttcacctc atataactag tcctaaagta tttggaagca
3481 gccctcctta tgtgtctgcc tagtttattg ttctctaagg ttagcagtta acctagctat
3541 tctttacttg cagtgatttc cagatgcctc ctcatataaa ttgcttgact tctgggtata
```

FIG. 12 A

```
3601 ttctggttct gggatgggta gatttctgat ctcttttgct ctatctagaa atcccgtgag
3661 tttctggcac gtaatttctc tgatgctggt tgctttgata tttaaagtag gatttgacat
3721 actcttgtca cttactggtg ataaataacg tttagtttgt tcttcgttca ttttatttat
3781 gtgttagttt ttaaaaagag gttttcttcg atggaaaata aagtaaccaa atagtagtga
3841 attagttctt caatgtctct catttgttga cattttccat gtacttgaaa cgtgtggggt
3901 acacctcttc ttcttttttcc ttctctgagc aatggctaga agaaaagccc tacttgtttg
3961 tagcatttac tgtgagccat tactgaatgt gggtgtattg atgaatgatg ctacctgtat
4021 gttttttaatc agtaagtatt tattgaaaag tagaagacat tatactgtct ctttttccagc
4081 tgtggcttac ttactgccct taatttgtgg aaaagaagta cagagaaagc cgtaacatct
4141 gccgaagaac tacagtatta ccctataata tcatcagata gcaaacagtc tagaagtatt
4201 ttgccaaaga aagagcaaat gtattatttt aacttacgtt gaaatctatc ttaatagagc
4261 cttatcagca gcgtaagaaa taacttctgg gtgggcataa gtacacagta taaatatggt
4321 agactttggc cggtgcaaca gtcacttgtt ttgtcatttg tctcttcccc ctccccgccc
4381 aaagggtagc acttgacaga gaatatttgt ttcttcatgt cagtcattca tttagaaatc
4441 tgtatttctg tatgtagaaa ataattacc atttcaaggt ttttcgtatt tttgttattt
4501 tgggaatgat atttctttct agttaaagaa aatgttttac cgtattaatc cattctttct
4561 gtaaacttta ttttcaggct tactctgctt atccacattc accaggtcag gtcatcactg
4621 gatgtcagtt gcttgtatat aattatcagg taattgaaga gggagtaaga tgatttactt
4681 tcagctacta ttgaggcctc aacttgctta tacaaattgc ttgataggt tgtccttta
4741 aactagtgaa ctgtacctaa aatttaagaa atcacttaga attagtgtaa tgaggacctc
4801 tgttttgttt agaagtgatg aaataagatt ttgacaggag ggtacttagc aataactttt
4861 ccgtagaaca atttctgaga tttggtgttc ccttctttgt ttcagcatgt attttgttat
4921 ctttgctgtc aaagagctga acatccaga ctgactttcc tgaatcttgt agagatacag
4981 agtgaaataa aagctttacc gaattcttag agcacagaat ttcagttgta tttttatttt
5041 agcttgctgc ttcatgatag cagttctctg gtctctttt caatggtaca actattatct
5101 gtgacccata attgtatctg tggtaacaaa ttcaaagaat taatatcttt gagggttcca
5161 caattctgtt tccataaaat tgggaaaaag gtgaggtttt ctgtgtagaa gtaacaacaa
5221 gaacttggg gattagaaac ctaaagtact tcttttttct attctgtttc ttttattata
5281 acaaaggagc catcatgata aatactccaa tattatgtaa ctcatgtgtt tttgaaaacg
5341 tgtaggagta tttaaataat tgtggttact tttttttttt tttttttttt tttttaattt
5401 aagattccac tgcactggcc tgttggggcg caaaggagtt atgttgttcc tccggtaaag
5461 cgaatgagtg aaacatatac ctgctcttct ttcttgattt tttgtgtggc acatatgcct
5521 ataaatattt ttaatgattc tttatattga tgtgttaacg ttttgttact ttcttttttaa
5581 cccaattata atctcccatg ggagaaacag tgcctttttc tctctcaggt ttttgtatgc
5641 ttaagcaatg gcttctccaa attatgacaa gtgttcagtt acttgtcgat agattattta
5701 atctaagaaa ggtagtccta atgtggcttt atctaagaaa ggtagtatta atttggcttt
5761 agaatagcat gtatctgatg agaatctgca tctggatgta ccaaccataa aaaatttcat
5821 aaagagaaac agaaatgttt tgctgttaat tactcttaaa taagaatagg attaaaaaga
5881 gtattacctc tataacacct gagctgcttt cccccatata actaaaatat ttaaaagcag
5941 ttctcctcat gtgtctgcct gctttattct tctctaagtt tagcagttaa tccaggtatt
6001 ctttatttga aatgatttcc agatgcctct gcatattaaa ttgctgactt ccagatatat
6061 tctggttctg gaatgggtag atttctgata tgttttaggt atctgtaaat cccgcaagtt
6121 tctggcatgt agtgtctctg atccttgtta gtttgctatt taaagtagat ttgacatatt
6181 ctgtcactta ctggtggtaa ataacgttta ttttcttctt agttcatttt atttatatct
6241 tagtttaaaa gacatttct ttgatggaaa ataaagtaac agaatagtag tgaagtagtt
6301 atattcagtg tttctcattt gttgacattt tccctgtact tgaaacatgt acggtatacc
6361 tcatcttctt tttccttctg tgaacaatgg ctggaataaa agccctactt ctatcattta
6421 ctgtgagcca ttactgaatc tgggtgtatt gatgcatgct gcttacctat atgtgttgaa
6481 acaataagta tttattgaaa catatgagac attatactgt ctctttttcca gtattggatt
6541 ctatactgca cttagttttt caacatgaag tacagaaaac gccgtaaatt ctgcagaact
6601 acgtattacc ttataatatt gtcaaataca catcagtctg gaagcatttt tacagggaaa
6661 tagcaaatgt attaatttaa cttacattga actctgtctt aatgcagcct tatcaccagt
6721 gcaagaaata acttctgggt gggcataagt acacaataa agtaaggtta actttgcctg
6781 gtgtcatagc cagttctttt gacatttgtc tgttccccct ccacgcccaa ccatagcact
6841 tgaccgagaa taatacgttc ttcataaatc agtcagtcac ttacaattct acattgttgc
6901 agatagaaaa ataattagta tttcgaaatt tttcatagtt ttgttatatt gggactaatt
6961 cttcctaatt aaaaataatg ttttaacgta ttaattcatt ctttctgtat aatttatttt
7021 caggaatatc ctacttatcc cgattcagca tttcaggtca ccactggata tcagttgcct
7081 gtatataatt atcaggtaat gtaagaggga gtaaatgat ttgctttcag gtattattgg
7141 ggcctttaac tttttttagac aaatttcctg aacagttggt cattttaaac tagtgaagtg
7201 tacctaaaat ttaaggaaac acttagaatt agtgtagaat gaagacatct gtcttatta
7261 gaagtaatga agtagtattt tgagaggaat atacctggca ataacatttc tgtagaagag
```

FIG. 12 B

```
 7321 atttctgaga tgtggtgttc tctcctttac ttctggatgt agttttcatc tttactgtga
 7381 aatagctgaa tgaaacatcc aaactgactt tcatgaattt tcttagggag atagagtgaa
 7441 ataaatttct gctgcacttt tcagagcaca gaatcccaat tacattttca ttttagctgg
 7501 ctgtttgaag atagtaattc tctggatctc ttttcataga tacaagtata tctatgaccc
 7561 ataattatat ctatggtaat aaactgaaag aggtagtatc ttggaggttt ccacattgcc
 7621 aactcctgaa atttggaga aagatgaagt ttcaaatata aaagtaagaa gaatgtcatg
 7681 gactagaaac atgatgtact taagttttcc tttctgttac ttttattata ataaaaaagg
 7741 agacagcagg ataaggactt caatattgtg tttctcatga gttttgaaa atgtgtagga
 7801 atactttaat agttttggtg tccttttttt tttttttttt tttttttta agatgccacc
 7861 ataggggcct gttggggagc aaagggattc cgttcttgac gttaagtgaa ttagccaaac
 7921 atagacttcc tgttcattct tgattttttt ccatgtcata tatgcctata aatatttta
 7981 agtgattctt tatattaatt ttttgtcgt tgttactttc ttgttaaccc gattatgaac
 8041 tcccatggga gcaagagtgc cttttttgcc ctcaggtttt tatgtgccta agcaatggca
 8101 ggtccacata atgatagact atataatcac agaaaagtag tattcacttg actttagaat
 8161 tatcacgtat ctgccaataa tctgcctctg gctttaccag caatagaaaa tttatagaag
 8221 agaaacagaa ttgctttgct gttaatgacg cttaaataag aacaggagtg aacgagagta
 8281 ttacctccaa atcaccggag ctgctttccc ccttataagc agttcctaaa gtgaatgaaa
 8341 gcagctctcc ttatgtgtct gcctacttta ttcttcggta agtttagcag ttcatctagc
 8401 tatcctttat ttgaaatgat ttccagatgc ctcctcatat aaattgctga cttctggata
 8461 tttcctggtt ctggaatggg tagatttctg atgtggttta gtatatatat gtaaaccccg
 8521 tgagcttctg gcatctaatt tctctgatcc tggttacatt gatatttaaa gtagggtttg
 8581 acatactctg tcacctactg ttgataaata acgtttatat tcttcttagt tcatttatt
 8641 gacgtgttag ctttaaagac attttctttg acggaaaatg aagtaacaaa ataatagtga
 8701 aatagttatg cagtgtctct aatttgttga tattttccat gtacttgaaa cttgtatggt
 8761 atacctcttc ttttttccttc tctgaacaat ggctagaaaa aaagtcctac tttttctgt
 8821 catttactgt gaggcatcac tgattctggg tgtattcatg tatgctgcta cctgtatgtt
 8881 ttcaaacaat aagaatttat tgaaacatgt aagacattat actttctctt ctccagtatt
 8941 ggatcataga ctgcacttag ttttttcgtaa tgaagtacag acaaagccat aacatctgtc
 9001 gaactacata ttaccctata atattgtctg atacaaaaca gtctagaaat attcttacag
 9061 agaaattgca aatgtattaa tttaacttac cttgcaatct ctcttaatgg agccttacca
 9121 ccagtgtaag aaataacgtc tgggtgtgaa taagtacaca gtataaggta aactttggtg
 9181 aagtagtcaa ttcttttgtc atttgttccc ccttcacacc catagtgtag cacttgacct
 9241 agaatctttc tttcttcata aagtcagtca ttcatttgga attctgcatt gttgtacgta
 9301 gaaaaaggat attttacctt ttgtaatatt tttgttatat tgggaattat atttctttgt
 9361 aattttaaaa agtggtttac catattcatt ttttttctgca acctttcttt tcagccattt
 9421 cctgcttatc caagttcacc atttcaggtc actgctggat atcagttgcc tgtatataat
 9481 tatcaggtaa tgtaagaagg agtaaaatga tttactttca ggtattattg aggcattcaa
 9541 cttgtttata caaatttcct gaatagctgg tcatttaaa ttagtgaagt gtacctaaaa
 9601 tttaaggaaa cacgtagaag tagtgtagaa tgaagacctc tgtcttattt agaagtaatg
 9661 aagtagtatt ttgagaggaa tatacttggc aataacttt ctgtagaaga gatttctgag
 9721 atgtggtgtt ctcttcttta tttctggatg cagttttcat ctttactgtg aaatagctga
 9781 atgaaacatc caaactgact ttcatgaatt ttcttaggga gatagagtga ataaatttta
 9841 tgctgcactt tcagagcac agaatcccaa ttacattttc atttagctgg ctgtttgaa
 9901 gatagtaatg ctctggatct cttttcatag atacaagtat atctatgacc cataattaca
 9961 tctatggtaa gaaactgaaa gaggtagtat ctttgaggtt ccaccttgc caactcccga
10021 aatttggag aaaggtgaag tttccaatat aaaagtaaca agaatgtcat ggactagaaa
10081 cataaagtac ttaagtttc cttctgtta cttttattat aatgaaaaag gagacagctg
10141 gataagtact tcaatgttgt atttctcatg tgttttgaa aatgtgtagg aatacatata
10201 atactttcgg tgtccttttt ttttctttct ttttctttct tttttttttt taagatgcca
10261 ccataaggtc ctgttgggga gcaaaggatt atgttgtcct tgacgttaag tgaattagcc
10321 aaacatagat ttcctgttca ttcttgattt ttttccatgt catatatgcc tataaatatt
10381 tttaagtgat tcttatat aattttttg ttgttgttac tttcttgtta acccgattat
10441 aaactcccat gggagcaaga gtgccttttt agccctccagg ttttatgtg gttaagcaat
10501 ggcaggtcca tataatgaca gactatataa tcaaagaaag gtagtgttca tgtgacttta
10561 caattagcat gtatctgcat agaatctgcc tctggcttta ccagcaatag aatatttata
10621 gaagagaaac agaaatgctt tgctgttaat gacgcttaaa tgaataggg agtaaacgag
10681 agtattaccg ccaaatcacc ggagctgctt tccccttat aaccagttcc taaagtgaat
10741 gaaagcagct cccccttatgt gtctgcctac tttattcttt ggtaagtta gcagttcatc
10801 tagctattct ttatttgaaa tgatttccgg atgcctcctc atataaattg ctgacttctg
10861 gaaatattct tcttctggaa tgggtagatt tctgatgtgg tttagtatat atataaaccc
10921 cgtgagcttc tggcgtctaa tttctctgat tctggttaca ctgatattta agtagggtt
10981 tgacatactc catcacttaa tgttgataac taacctttat attcttctta gttcgtttta
```

FIG. 12 C

```
11041 tttatgtgtt agcttaaaag acattttctt tgatggaaaa tgaagtaaca aaataatagt
11101 gaaatagttc tgcggttgtc tctaatttcg tgatattttc catgtacttg aaacatgtat
11161 ggtatacctc ttcttttcc ttctctgaac aatggctaga aaaaagcct tacttgtttc
11221 tgtcatttac tgtgagcgat tactgaatct gggtgtattc atgtatgctg ctacctgtat
11281 gttttcagat aataaaatt ttttgaaaca tataagacat tatactttct cttgtccagt
11341 attggattat agactgcact tagttttcg taatgaagta cagacaaagc cataacatct
11401 gtcaaactat atattgtcct ataatattgt ctgatacaaa acagtctaga aatattctga
11461 cagggaaata gcaaatgtat taatttaact taccttgcaa tctctcttaa tggagcctta
11521 ccaccagtgt aagaaataac ttctgggtgt gaataagtac acagtataag gtaaactttg
11581 gtgaaatagt caattctttt gtcattagtt cccccttcac tcccaaagtg tagcacttgt
11641 catagaatct ttctttcttc ataaagtcag tcattcattt agaattctgc attattgtat
11701 gtagaaaaac aatattttac ctattttgt tatattcaga attatatttc tttctaattt
11761 taaaaaaatg gtttaccgta ttcatttttt tctggaacct ttcttttcag gcatttcctg
11821 cttatccaaa ttcaccattt caagtcgcca ctggatatca gttccctgta tacaattatc
11881 aggtaatgtc agagggagta aaatgatttg cttttaggta ttattgaggc ctttaacttg
11941 ttcatacaaa tttcctgaat agttgctcat tttaaactag tgaattgtac ctaaaattta
12001 aggaaacact tagtgtagaa tgaagacctc tgtgttattt agaataatga ggtagtattt
12061 tgacaggaat atacttggca ataacttttc tgtagaacag atttctgaga tttggtgttc
12121 tcttcttcat ttctggatgt agttttcatc tttactgtca aatagctaaa tgaaacgtcc
12181 aaagtgtctt tcatgaattt tcttagggag atagactgaa ataaaattat gctgcacttt
12241 tcagagcaca gaatcccaat tacattttca ttttagctgg ctgtttgaag atagtaatgc
12301 tctggatctc ttttcataga tacaagtgta tctgtgaccc ataattatat ctatggtaat
12361 aaactgaaag agctagtatc tttgaggttt ccacattgcg aaatcccgaa aatgtggaga
12421 gagctgaagt ttccaatgta aaagtaacaa gaatgtcatg gactagaaac ataaagtatt
12481 tgagttttcc tttctgttac ttttattaca ataaaaaagg agacagcagg ataagtactt
12541 taatattgtg tttctcatgt gttttgaaa atgtgtagta atacttcaat agttttggtt
12601 tccttttatt tattaattga ttttttaaga ttccaccttta ggggcctgtt gggtagcaaa
12661 gggattatgt tgtccttgac attaagggaa ttagccaaac atagacttcc tgttcattct
12721 tgattttttt ccatgtcata tatgcctaca aatatttta agtgacttt tatgttaatg
12781 ttttttttgt tgttgtttcc ttcttgttaa cccgattata aactcccatg gcagcaacag
12841 tgccttttt gtcctcaggt ttttatgtgc ttaagcaatg gcaggtctac ataatgatag
12901 actatataat caaagaaagg gagtattcac gtgactttag aattgcatg tgtctgcaca
12961 gaatatgcct ctggctttac cagcagtaga aaatttatag aagagaaaca gaaatgcttt
13021 gctgttaatg acgcctaaat aagaagagga gtaaaggaga gtattacctc caactcaccg
13081 gagctgcttt ccccttata agcagttcct aaagtgaatg aaagcagctc tccttatgtg
13141 tctgcctact ttattcttcg gtaagtttag cagtttatct agctatcctt tatttgaaat
13201 gattgccaca tgcctcctca tataaatggc tgacttctgg atatattctg gttctggaat
13261 gggcagattt ctgacgtggt ttagtatata tatataaacc cggtgagttt ctggcatgta
13321 atttctctga tcgtggttac attgatattt aaagtagggt ttgacatagt gtgtcactta
13381 ctgttgataa atatcgttta ttttcttctt agttcatttc attgatgtgt tagcttaaaa
13441 gacattttct ttgacagaaa atgaagtaat gaaataatag tgaaatcgtt ctgctgtgtc
13501 tctaatttgt tgatattttc catgtacttg aaacatgtat ggtatacctc ttcttttcc
13561 ttctctgaac catggctaga aaaaagccc tacttgtttc tctcgtttac tgtgagcat
13621 tagtgattct gggtgtattc atgtatgctg ctacctgtat gttttcaaac aataagaatt
13681 tgttgaaaca tgtcagacat tatactttt attctccagt attggaatat agactgcaat
13741 tagtttttg gaatgaaata cagacaaagc cataacatct atagaactac atattaccct
13801 acaatattgt ctgatacaaa acagtctgga aatattctta cagcgaaatt gcaaatgtat
13861 tgatttacct tacattgcaa tctgtcttag tggaaccta tcaccagtgt aagacataat
13921 ttctgggtgt gaataagtac acagtataag gtaaattttg gtgaagtagt cagttctttg
13981 tcatttgttc cccttcaca cccaaagtgt agcacttgac atagaatctt tctttcctca
14041 taaagtcatt catttggaat tctgcattgt tgtatgtaga aaaggatat tttccgtttt
14101 gtaatatttt tcttatattg ggaattatat ttctttctaa tttaaaatg tggtttacca
14161 tattcatttt ttctgcaacc ttttcaggca tttcctgctt atccaaattc accagttcag
14221 gtcaccactg gatatcagtt gcctgtatac aattatcagg taatgtaaga ggtagtaaaa
14281 tggtttgctt tcaggtatta ttgaggcctt taacttgtt atagaaattt cctgaatagt
14341 tggtcatttt taactagtga agtgtcccta aaattaagg aaagacttag tgtagaatga
14401 agacctctgt cttatttaga agtaatgaag taatatttt acaggaatat ccttggcaat
14461 aacatttgtg tagaagagat ttctgagatt tggtgtcccc ttcttcatt gtggatatag
14521 ttttcatctt tgctgtcaaa tagctgaatg aaacatccaa actgactttc atgaatttt
14581 ttagggagat agagtgaaat aaaattatga tccacttttc agagcacaga attccaatta
14641 tattttcatt ttagctggct gtttgacggt agtcattctc aggatctctt ctcatagata
14701 caagtatatc tatgacccat aactatatct atggtaataa actgaaagag ctagtatttt
```

FIG. 12 D

```
14761 tgaggtttcc acattgccaa ctcccaaaaa tttggagaaa ggtgaagatt caaatttaaa
14821 gtaacaagaa tgtcatggac aagaaacata aagtacttaa gttttccttt ctgttacttt
14881 tattataata aaaaaggaga cagcggaata agtacttcaa tactgtgttt ctcatgtgtg
14941 tttgaaaata tgtaggaata gtttaatagt tttggtttcc tttttttttt ttttttttaa
15001 agatgccacc ttaggggcct gttggggagc aaagggatta tgttgtcctt gacgttaagg
15061 gaattagcca acatagact tcctgttcat tcttgatttt ttttccatgt catatatgcc
15121 tataaatatt tttaagtgac tctctatatt aatgtttgtt gttgttgttg ttactttctt
15181 gttaacccga gtataaactc ccatggcagc aacagtgcct tttttgccct cagggtttta
15241 tgtgcttaag caatggcagc tccacataat gatagactat ataatcaaag aaaggtaata
15301 ttcacgtgac tttagaatta gcatgtagct gcatagaatc tgcctctgc tttaccagca
15361 gtagtaaatt tatagaagag aaacagaaat gctttgctgt taattatgct taaataagaa
15421 tagaagtaaa ggagagtatt acctgacaat caccagagca gctttccccc gtataagcag
15481 ttcctaaagt gaatgaaagc agctctcctt atgtgtctgc ctactttatt cttccgtaag
15541 tttagcaatt catctagcta tcctttattt gaaatgattt ccagatgcct cctcatataa
15601 attgctgact tctggatata ttctggttct ggaatgggta gatttctgat gtgatttagt
15661 atatatatat aaaccgcttg agtttctggc atctaatttc tctgatcctg gtgacattga
15721 tatttaaagt aggggtttgac atactctatc acttactgtt gataaataac gtttatattc
15781 ttcttagttc atttcattga tgtgttagct taaaagacat tttctttgat ggaaaatgta
15841 gtaacaaaat aatagtgaaa tagttctgca gtgtttctaa tttgttgata ttttccatgt
15901 acttgaaaca tgtatggtat acctcttatt tttccttctc tgaacaatgg gtagaagaaa
15961 agctctactt gttactgtca tttactgtga gccattactg aatctgggtg tattcatgta
16021 tgctactgcc tgtatgtttt caaacaataa gcatttattg aaacatataa gacattatac
16081 ttcctcttct ccagtattgg attatagact gcacttagtt ttttggaatg aagtacagac
16141 aaagccataa catctataga actacatatt accctataat attgtctgat acaaaacagt
16201 ctagaaatat tcttacagca aattgcaaat gtattaattt aacttacatt gcaatctgtc
16261 ttaatggagc cttatcacca gtgtaagaaa taacttctgg gtgtgaataa gtacacagta
16321 taaggtaaac tttggtgaag tagtcaattc ttttttttt taaattatg ctttaagttt
16381 tagggtccat gtgcacattg tgcaggttag ttccatatgt atacatgtgc catgctggtg
16441 ctctgcaccc tctaactcct catctagcat taggtatatc tcccagtgct atccctcccc
16501 cctccccca ccccacaaca gtccccagag tgtgatatat cccttcctgt gtccatgtga
16561 tctcattgtt caattcccac ctatgagtga gaatatgcgg tgtttggttt tttgttcttg
16621 cgatagttta ctgagaatga tgatttccaa tttcatccat gtccctacaa aggacatgaa
16681 gtcatcattt tttatggcgg catagtattc catggtgtat atgtgccaca ttttcttaat
16741 ccagtctatc attgttggac atttgggttg gttccaagtc tttgctattg tgaataatgc
16801 cgcaataaac atacgtgtgc atgtgtcttt atagcagcat gatttatagt cctttgtgta
16861 tacccccagt aatgggatgg ctgggtcaaa tgctatttcc agttctagat ccctgaggaa
16921 tcgccacact gacttccaca atggttgaac tagtttacag tcccgccaac agtgtaaaag
16981 tgttcctgtt tctccacatc ttctccagca cctgttgtct cctgactttt aaatgattgc
17041 cattctaact ggtgtgagat ggtatctcac tgtggttttg atttgcattt ctctgatggc
17101 cagtgatgat gagcattttt tcatgtgttt tttggctgca taaatgtctt cttttgagaa
17161 gtgtctgttc atgtccttca cccactttt gatgaggttg tttgttttt cttgtaaatt
17221 tgttttagct cattgtagat tctggatatt agccctttgt cagatgagta ggttgtgaaa
17281 attttctccc attttgtagg ttgcctgttc actctgatgg tagtttcttt ttctgtgcag
17341 aagctcttta gtttaattag atcccatttg tcaattttgt cttttattgc cattgctttt
17401 ggtgttttag acgtgaagtc ctcgcctatg cctatgtcct gaatggtaat gcctaggttt
17461 tcttctaggg tttttatggt tttacgtcta acgtttaagt ctttaatcca tcttgaattg
17521 attttttgtat aaggtgtaag gaagggatcc agtttcagct ttctacatat ggctagccag
17581 ttttcccagc accatttatt aaatagggaa tccttccccc attgcttgtt tttctcaggt
17641 ttgtcaaaga tcagatagtt gtagatatgc ggcgttattt ctgagggctc tgttctgttc
17701 cattgatcta tatctctgtt ttggtaccag taccatgctg ttttggttac tgtagccttg
17761 tagtatagtt tgaagtcagg tagtgtgatg cctccagctt tgttcttttg cttaggatt
17821 gacttggcaa tgcgggctct tttttggttc catgtgaact ttaaagtagt tttttccaat
17881 tctgtgaaga aaggcattgg tagcttgatg gggatggcat tgaatctgta aattaccttg
17941 ggcagtatgg ccattttcac gatattgatt cttcctactc atgagcatgg aatgttcttc
18001 catttgtttg tatcctcttt tatttccttg agcagtggtt tgtagttctc cttgaagagg
18061 tccttcacat cccttgtaag ttgatttcct aggcatttta ttccctttga agcaattgtg
18121 aatgggagtt cactcatgat tgggctctct gtttgtctgt tgttggtgta taagaaagct
18181 tgtgattttt gtacattgat tttgtatcct gagactttgc tgaagttgct tatcagctta
18241 aggagatttt gggctgagac aatgggggttt ctagatata taatcatgtt gtctgcaaac
18301 agggacaatt tgacttcctc cttttcctaat tgaataccct ttatttcctt ctcctgccta
18361 attgccctgg ccagaacttc caacactatg ttgaatagga gtggtgagag agggcatccc
18421 tctcttgtgc cagttttcaa agggaatgct tccagttttt gcccattcag tatgatattg
```

FIG. 12 E

```
18481 gctgtgggtt tgtcatagat agctcttact attttgaaat acgtcccatc aatacctaat
18541 ttattgagag tttttagcat gaagggttgt tgaattttgt caagggcttt ttctgcatct
18601 attgagataa tcatgtgttt tttgtctttg gttctgttta tatgctggat tacatttatt
18661 gatttgcgta tattgaacca gccttgcatc ccagcgatga agcccacttg atcatggtgg
18721 ataagctttt tgatgtgccg ctggattcgt tttgccagta ttttattgag gattttttgca
18781 tcaatgttca tcaaggatat tggtctaaaa ttctcttttt tggttgtgtc tctgcctggc
18841 tttggtatca gaatgatgct ggcctcataa aatgagttag ggaggattct gtcttttttct
18901 gttgattgga atagtttcag aaggaatggt accagttcct ccttgtacct ctggtagaat
18961 tcggctgtga atccatctgg tcctggactg tttttggttg gtgagctatt gattattgcc
19021 acaatttcag ctcctgttat tggtctattc agagattcaa cttcttcctg gtttagtctt
19081 gggagagtgt atgtgtcgag gagtttatcc atttcttcta gattttctag tttatttgcg
19141 tagaggtgtt tgtagtattc tctgatggta gtttgtattt ctgtgtgatc agtggcgata
19201 tccccttttat catttttttat tgcgtctatt ggattcttct ctcttttttt ctttattagt
19261 cttgctagcg gtctgtcact tttgttgatc ctttcaaaaa accagctcct ggattcatta
19321 attttttgaa gggttttttg tgtctctatt tccttcagtt ctgctctgat cttagttatt
19381 tcttgccttc tgctagcttt tgactgtgtt tgctcttgct tttctagttc ttttaattgt
19441 gatgttacgg tgtcaatttt ggatctttcc tgctttctct tgtgggcatt tagtgctata
19501 aatttccctc tacacactgc tttgaatgca tcccagagat tccggtatgt tgtgtctttg
19561 ttctcgttgg tttcaaagaa catctttatt tctgccttca ttttgttatg tacccagtag
19621 tcattcagga gcaggttgtt cagtttccat gtagttgagt ggttttgagt gagattctta
19681 atcctgagtt ctagtttgat tgcactgtgg tctgagagat agtttgttat aatttctgtt
19741 cttttacatc cgctgaggag agctttactt cccagtatgt ggtcagtttt ggaataggtg
19801 tggtgtggtg ctgaaaaaaa atgtatattc tgttgatttg gggtggagag ttctgtagat
19861 gtctattagg tccacttggt gcagagctga gttcaattcc tgggtatcct tgttgacttt
19921 ctgtctcgtt gatctgtcta atgttgacag tggggtgtta aagtctccca ttattaatgt
19981 gtgggagtct aagtctcttt gtaggtcact caggacttgc tttatgaatc ttggtgctcc
20041 tgtattgggt gcatatatat ttaggatagt tagctcttct tgttgaattg atccctttac
20101 cattatgtaa tggccttctt tgtctctttc gatctttgtt ggtttaaagt ctgttttatc
20161 agagactagg attgcaaccc ctgcctttt tgtttttcca tttgcttggt agatcttcct
20221 gcatcctttt attttgagcc tatgtgtgtc tctgcacgtg agatgggttt cctgaataca
20281 gcacactgat gggcttgac tcttatcca gttgccagt ctgtgctttt taattggagc
20341 atttagtcca ttgacattta aagttaatat tgtttatgtat gaatttgatc ctgtcattat
20401 gatgttagct ggttatttg cttgttagtt gatgcagttt cttcctagtc tcgatggtct
20461 ttacattttg gcatgatttt gcagcggctg gtaccggttg ttcctttcca tgtttagtgc
20521 ttccttcagg agctcttata aggcaggctt ggtggtgaca aaatctctca gcatttgctt
20581 gtctgtaaag tatttttttt ctccttcgct tatgaagctt agtttggctg gatatgaaat
20641 tctgggttga aaattatttt cttaagaat gttgaatatt ggcccccact ctcttctggc
20701 ttgtagggtt tctgccgaga gatccactgt tagtctgatg ggcttccctt tgagggtaac
20761 ccgaccttc tctctggctg cccttaacat ttttccttc atttcaactt tggtgaatct
20821 gacaattatg tgtcttggag ttgctcttct cgaggagtat ctttgtggtg ttctctgtat
20881 ttcctgaatc tgaacgttgg cctgccttgc tagattgggg aagttctcct ggataaatatc
20941 ctgcagagtg ttttccagct tggttccatt ctcccgatca ctttcaggta caccaagcag
21001 acgtagattt ggtcttttca catagtccca tatttcttgg aggctttgct catttcgttt
21061 tattcttttt tctccaaact tccttctca cttcatttca ttcatttcat cttccattgc
21121 tgatacccttt tcttccagtt gatcgcatca gctcctgagg cttctgcatt cttcacgtag
21181 ttcttgagcc ttggttttca gctccatcag ctcctttaag cacttctctg tattggttat
21241 tctagttata cattcttcta cattttttt ttccaaagtt ttcaacttct ttgcctttgg
21301 tttgaatgtc ctcccgtagc tcagagtaat tgatcgtct gaagccttct tctctcagct
21361 cgtcaaagtc attctccatc cagctttgtt ccgttgctgg tgaggaactg cgttcctttg
21421 gaggaggaga ggtgctctgc ttttagagt tccagtttt tctgttctgt ttttccccc
21481 tctttgtggt tttatctact tttggtcttt gatgatggtg atgtacagat gggttttgg
21541 tgtggatgtc ctttctgttt gttagttttc cttctaactg agaggaccct cagctgcagg
21601 tctgttggaa tacccctgccg tgtgaggtgt cagtgtgccc ctgctggggg gtgcctccca
21661 gttaggctgc tcggggggtc aggggtcagg gacccacttg aggaggcagt ctgcccgttc
21721 tcagatctcc agctgcgtgc tgggagaacc actgctctct tcaaagctgt cagacagggt
21781 catttaagtc tgcagaggtt actgctgtct ttttgtttgt ctgtgccctg ccctagagg
21841 tggagcctac agaggcaggc aggcctcctt gagctgtggt gggctccacc cagttggagc
21901 ttccctgcgg cttgtttac ctaatcaagc ctgggcaatg gcgggcgccc ctccccagc
21961 ctcgttgccg ccttgcagtt tgatctcaga ctgctgtgct agcaatcagt gagactgcgt
22021 gggcgtagga ccctccgagc caggtgcggg ataatctca gtggtgtgcc gttttttaag
22081 cccgtcggaa aagcgcagta tcgggtggg agtgacccga ttctccaggt ggcatccgtc
22141 acccctttct ttgactcaga agggaactcc ctgaccgctt gcgcgtccca agtgaggcaa
```

FIG. 12 F

```
22201 tgcctcgccc tgcttccgct cgcacgcggt gagcccaccc actgacctgc gcccactgtc
22261 tggcactccc tagtgagatg aacccggtac ctcagatgga aatgcagaaa tcacccgtct
22321 tcggcgtcgc tcacgctggg agctgtagac tggagctgtt cctattcggc catcttggct
22381 cctcccccac ccccctttt tttcaagat gccaccatag gggcctgttg gggagcaaag
22441 ggattatgtt ttccttgatg ttaagtgaat tagccaaaca tagacttcct gttcattctt
22501 ggttttttc cacgtcgtat atgcctatta ctattttaa gtgatttta tatcaatgtt
22561 ttagtttatt tttactttt cttgttaacc cgattataaa ctcccatggg agcaacagtg
22621 cctttttgc cctgaggttt tatttgctt aagcaatggc aggtccactt aatgatagac
22681 catatcatca aagaaggta gtattcatgt ggcttttgaa ttagcatgca tctgcgtaga
22741 ttctgcctct ggctttacca gcaacagaaa atttgtagaa cagagacaga aatgctttgc
22801 tgttaattgc gcttaaataa gaataggagt aaacgagagt attacctcca aagcaccaga
22861 gctgcttcc tcctctaaa cagttcctaa agtgaatgaa agcagctctc cttatgtgtc
22921 tgcctacttc attcttcggt aagtttaaca gttcatctag ctacccttta tttgaaatga
22981 tttccagatg cctcctcata taaattgctg acttctggat atattctggt tcgggaatgg
23041 gtagatttct gatgtggttt agtaggtata taaatcccgt gagcttcttg catctaattt
23101 ctctgatcct gcttacactg atatttaaag taggttttga catactccat cacttaatgt
23161 tgataaagga cgtttatatt cttcttagtt cgttttattt atgtgttagc tttaaagaca
23221 ttttctttga cggaaagtga agtaacaaaa taatagtcga atagttctgc cgtgtctcta
23281 atttgttgat attttccatg tacttgaaac atgtatggta cacctcttct ttttccttct
23341 ctgaacaatg gctagaaaaa aaaccctact tctttctgtc atttactgtg aggcattact
23401 gaatctgggt gtattcatgt atgctgctac ctgtatgttt tcaaacaata agaattcatt
23461 gaaacatata agacattata ctttctcttc tccagtattg gattatagac tgcacttagt
23521 tttccggaat gaagtacaga caaagccata acgcgtgtac aactacacat tgtcctataa
23581 tattgtctga taaaaaacag tgtagaaata ttctgacagg gaaatagcaa atgtattaat
23641 ttaacttacc ttgcaatctc tcttaatgga gccttatcac cagtgtaaga aataacgtct
23701 gggtgtgaat acgtacacag tataaggtaa actttggtga agtcgtcaat tcttttgtca
23761 tttcttcccc cttcacagcc aaagtgtagc acttgacatg gaatctttct ttcttcataa
23821 atcagtcatt catttggaat tctgcattgt tgtatgtaga aaacgatat tttcccttct
23881 gtaatattgt tgttatattg ggaattatat ttctttgtaa ttttaaaaag tggtttacca
23941 tattcatttt tttctgccaa ccttctttt caggcatttc ctgcttatcc aagttcacca
24001 tttcaggtca ccactgatca tcagttgcct gtatataatt atcaggtaat gtaagaagga
24061 gtaaaattat ttgctttcag gtattattga ggccttaac ttgtttatac aaatttccgg
24121 aatagttggt cattttaaac tagtgaagtg tacctaaaat ttaaggaaac acttagaatt
24181 agtgtagaat gaagacctct gtcttattga gaagtaatga agtcgaattt tgacaggaat
24241 atacttggga ataactttcc tgtagaacag atttctgaga tttggtgtcc cattcttcat
24301 ttctggatgt agttttcatc tttactgtca aataactgaa tgaaacatcc aaactgactt
24361 tcatgaattt tcttagggag atagagtgaa ataaaattat gacccacttt gcagagcaca
24421 gaattccaac tatatttca ttttagctgg ctgtttcacg atagcaattc tctgggtctc
24481 ttttcacaga tacaagtaca tctatgccca ataattatat ctatggtaat aaactgaaag
24541 agctagtatc tttgaggttt ccacattgcc aactcccgaa aatgtggaga agggtgaagt
24601 ttctaatata aaagtaacaa gaatgtcatg gactagaaac ataaagtact caagttttcc
24661 tttctgttac ttgtattata ataaaaagg agacagcagg ataagtgctt caatattgtg
24721 tttctcatgt gttttttgaaa atgtgtagga atattttaat agttttggtt tccttttttt
24781 ttttttttt aagatgccac catagggggcc tgttggggag caaagggatt atgttttcct
24841 tgatgttaag tgaattagcc aaacatagac ttcctgttca ttcttggttt ttttccacgt
24901 cgtatatgcc tattactatt tttaagtgat ttttatatca atgtttagt ttatttttt
24961 actttcttgt taacccgatt ataaactccc atgggagcaa cagtgccttt tttgccctga
25021 ggttttatt tgcttaagca atggcaggtc cacttaatga tagaccatat catcaaagaa
25081 aggtagtatt catgtggctt ttgaattagc atgcatctgc gtagattctg cctctggctt
25141 taccagcaac agaaatttg tagaacagag acagaaatgc tttgctgtta attgcgccta
25201 aataagaata ggagtaaacg agagtattac ctccaaagca ccagagctgc tttcctcctt
25261 ataaccagtt cctaaagtga atgaaagcag ctctccttat gtgtctgcct acttcattct
25321 tcggtaagtt taacagttca tctagctacc ctttatttga atgatttcc agatgcctcc
25381 tcatataaat tgctgacttc tggatatatt ctggttcggg aatgggtaga tttctgatgt
25441 ggtttagtag gtatataaat cccgtgagct tcttgcatct aatttctctg atcctgctta
25501 cactgatatt taaagtaggt tttgacatac tccatcactt aatgttgata aaggacgttt
25561 atattcttct tagttcgttt tatttatgtg ttagctttaa agacattttc tttgacggaa
25621 aatgaagtaa caaaataata gtccaatagt tctgcagtgt ctcaattttg ttgatattt
25681 ccatgtactt gaaacatgta tggtacacct cttctttttc cttctctgaa caatggctgg
25741 aaaaaagcc tacttgttt ctgtcattta ctgtgcggca ttactgaatc agggcatatt
25801 catgtgtgct gctacctgta tgttttcaaa caataagaat tcattgaaac atataagaca
25861 ttatactttc tcttctccag tattggatta tagactgcac ttagtttttt ggaatgaagt
```

FIG. 12 G

```
25921 acaaacatag cactaatatc tatagaacta catattaccc tttaatattg tctgatacaa
25981 aacagtctag aaatattctg acattgaaat agcaaatgta taaatttaac ttacattgca
26041 atctgtctta atggagcctt atcaccggtg taagaaagaa tttctgggtg tgaataagta
26101 cacagtataa ggtaaacttt ggtgaaatag tcaattcttt tgtcatttgt tcccccttca
26161 cacccaaagt gtggcacatg acatagacta tttcttcttt cataaagtca gtcattcatt
26221 tagaattctg cattgttgta tgtagaaaaa tgatatttta acgtttttaa tatttttgtt
26281 acattgggaa tgatatttct ttctaatttt aaaaaatggt ttaccatatt ctttttttc
26341 tgccaccttt cttttcaggc atttcctgct tatccaaatt cagcagttca ggtcaccact
26401 ggatatcagt tccatgtata caattaccag gtaatgtaag aaggaatgaa atgatttgct
26461 ttcaggtatt attgaggcct ttaacttgtt tatacaaatt tcctgaatag ttggtcattt
26521 taaactagtg aagtgtacct aatatttaag gaaacactta gaattagtgt agaatgaaga
26581 cctctgtctg atttagaagt aatgaggtaa tattttgaca ggaatgtact tggcaataac
26641 ttttctgtag aacagttttc tgagatttga cccttctata tttcaggata tagttttcat
26701 ctttgctgtc aaatagctga atgaaacctc caggatgact ttcatgaatt ttttagggat
26761 atagagtaaa taaaattatt acccaattct tagagcacat aattcaaatt atagtttcat
26821 ttagtaggct gtttcccgac aattgttgtc tggttctctt tcatagtag agaggactct
26881 atctatgacc aataatcata tgtagcataa taagttcaaa gtagtaacat ctttgagatt
26941 tccacaatgc caaatccaaa aattggggaa aaggtgtggt tcgtatttg tatgtggaag
27001 taacaacaag aatgtcagga attagaacca taaagtactt ctttttttcca ttgtctttct
27061 tttattataa taacaaagga gccagcatag gtacttcaat attttatata tcatttgttt
27121 ttgaaaatgt ttatgaatat ttgaataatt ttgttttcct atttttttt taagatgcca
27181 ccgcagtgcc ctgttgggga gcaaaggagg taggttgtac ctctggtaaa gtgaattagc
27241 ctaccatgta cttctgttct ttctggatta ttttccatat catttatgcc ttataaatat
27301 tttaaatgat tcttttatatt aatgtgttac attttgttac tttcttttta acccagttac
27361 aatctcccat gggtgcaaca gtgccttttt ctctctcagg ttttttgtgtg cttaaggagt
27421 ggctggtcca cataataagt gttcagttac ttgttgatag actgtgtaat ctaagaaaga
27481 tagtattaat gtcactttag aattagcatg tatctgcgta gggtctgcct ctggttttac
27541 cagccacaaa aaatttgttg aagagaaaca gaaatgtttt gctgttaatt actcttaaat
27601 aagaatagga ataaaaaaag agtattaccct ctaaaatacc tgaacttctt tcccccatta
27661 tacctagttc tgaaaacatt tgaaagcagc tgttctaatg tttctgccta gtttattctt
27721 taaggatagc gattaatcta gctcttcttt acttgcaatg atttccagtt gactcctcat
27781 ataaactgct gacttcggga tatattctcg gtctggaatg tatagatttc tgacctattt
27841 tactgtacct ataaatcctg tgaatttctg gcatgtaatt tctctgatcc tgattacttt
27901 gatatttaaa gtaggatttg acatactcta tcacttattg gtgataaata acgtctgttt
27961 tcttcttagt ccatttttatt tatgtgttag tttaaaagac attttctttg atggaaaata
28021 aagtaacaaa atagtagtga aatagttctt cagtgtctct cattttattga cattttctgt
28081 gtacttgaaa tgtgtaggat atacctcttc ttcttttttc ttctctgaac aatggctaga
28141 gacaaagccc tacttgtttc taacatttac ggtgagccat tactgaattt gggtgtattc
28201 atgtatgctg cttcctatat gttttcaaac aataagtatt tatcgaaaca tataagacat
28261 cgtactgtcc ttctccagtt ttggattgta cactgccctt agttttcga aatgaagtac
28321 agaaaaaaaa cataacatct gtaggagaac tacatattac cctgtaatat tgtcaaacac
28381 aaaactatct ggaagtatat tgacaaagaa atagcaaatg tattaactta acttacattg
28441 agatctgtct taatggagcc ttaccagcag tgtaagaaac aacttctggg tgggcataag
28501 tacacagtgt cagtaaggta aactttgcct ggtgaaatag tcactacttt gtcatttgtg
28561 tgttcccccg ccccacccaa aggggcttag cacttgacag agaatattta ttcttcctg
28621 aagtcattca ttcatttaga attctgcatt gttttatata gaaaattaat aaatatttta
28681 aagttttca tttttttttat tttgggaata atatttttt ctaatttaaa aagatgtttt
28741 accatattca ttctttctgt aaacttactt tcagacatat cctactatc caaattcacc
28801 aggtcaggtc accactgggt gtcagttgcc tgtatgtaat tatcaggtaa ttgaagaggg
28861 agtaaaatga tttgttttca gatattattg aagcctttaa cttgtttata tgaatttccc
28921 aaatagtgtg tcattttaaa ctagtgaaat gtacctaaaa tttaggaaaa cacttgcaat
28981 ggtctagaat gaagccctct gtattattta gaagtaatga attaacattt tgacagggat
29041 atacttagca ataacttttc tgtaaaacag ttttctgaga ttcgttgtcc ccttctatat
29101 ttcagcgtgt attttttcat cttttttcatc ttttttatcat cccattctta gagcacagaa
29161 ttccaattat atttttattt taagcttgct gcttcatgat agtagttctc tgggcctctt
29221 ttcatagata tgactacatc tgtgacccat aatcatatct atggtagtaa gtaataaatt
29281 gaaaaaacta gtatccttga gatttccaca atgccaactc cagaaaattg ggaaaatggc
29341 gaggttttat gtataaaagt aacaagaaca tcagggatta gaaacataaa gtacttcttt
29401 ttttttttt actctgtttc tttcacttta ataacaaatg agccagcatg ataagtgctt
29461 caatattgtg tatctcatga gtttttgaaa atgtgtagga atattttaat agttttggtt
29521 tccttctttt tatttttta aggtgctacc gcagtggcct gttggggagc aaagggggtt
29581 atggagtaaa gtgaattagt gaaacgtata cttcctcatc tttcttgact tttttctatg
```

FIG. 12 H

```
29641 ccatatatgc ctgtagatat ttttaaatgg ttctttatat taatgttttta tgttttgtta
29701 ctttattttt aacccaatta taaactccca tgggagcaac agtgccttttt tgtctctcac
29761 attttttgtgt gctgaaacag tggctggtcc acataatgat aagtgttcag ttacttgttg
29821 atagattata taatccagga atggcggtat taactggctt tagaattagc atgtatctgc
29881 ctagaaatatg cctctggctt tactagccat aaaacatttg ttgaggagaa accgaaatgt
29941 tttgctatta attactctta aagaggaata ggaataaaac aagagtatta cctctaatac
30001 aacagagctg ctgtcttaca tcacgattgg atatttgaag gatatagtaa gtgttaaaat
30061 tctcaaacac tcccttaact acatttgttt cttagaatcc ttctacctct gattatgttg
30121 atacctggaa gacgttttaa aacaaaggc tgccttaatg catttcaact tttcgtttaa
30181 aacaaggttt ctgaagtaac acaattgaat ttcaacacaa cctacattga aactttgat
30241 accagctcac cttttttgagg aataaataag tagcttttaa acgtatctgt attatctgtt
30301 taattacact ttcattattt taaatatagg cttattcagc tcttaactgt cactgtagtg
30361 aagttgatac aggaggtgat gttgtgctaa atgaatgctc aattcatgaa gctaccccac
30421 cctctggaaa tggcccacaa aaggcaaaca tctaattttg aatttttttt acaatatata
30481 tttcatattt ttttctaatt tgaatgactt tttttgagaa gcaaacattt ttgcccaaat
30541 ttaaaaatgt tagccataaa tcatggagct taaataatgg actgatagtc agcagttaat
30601 gtaaaggttg ttgaaatttc agatacccca aattttcagt atatacctaa agtttctgat
30661 tcagcaagtc cttcctgta tttcagtttc actaattta aaaagccatt ctttaataaa
30721 tactgtatta atatgatttg gcagaatgct atgggagggt ttcctctaga attctactca
30781 aaagaagaat tagtacgaat tgtatgtccc ttttctttta caacagtttt gatcttaagc
30841 agtgaaaaat accatttaaa taagcattct ctccataaca ttatatgtgg cagaagtttc
30901 caacagtggt gaagtcagta gtaattattc aaacactgaa atagacaggg ttgtttcttt
30961 tttttatcat tagtgcaaat ttctgtaata acagtactgt cactcctggc gtcacatatg
31021 ttctgttaga taggtgggcg tgtggaagta gttgatgtgc tggtaatatg tataatacc
31081 aagaagtccc attgcagtgt aaattccttg atttgatatt ggattttaaa atgtgaataa
31141 atatgaaaac ataactctta cagtataatt gtctggtttt gttctgagta tgttttcttg
31201 aaacattgga attcacttag ggatttaaca aattcagctt tttaaaccag tattctatcg
31261 ctaaggttct aaaataattc ttcgatttgt cagaaaacgt acatactgag gatatgtggc
31321 aggaattatg aatcacattt ttatgaattt cttttttttt ttgagacagg gtcttgcggt
31381 gtcgcccagg ctgaagtgc agtggtgtga tctcggctca ctgcaacttc tgtctcctag
31441 gttccagtaa ttctccctgc ctcagcctcc caataggtg gaattacagg cacccgtcac
31501 ccagctaatt tttgtatttt ttagtggaga aggggtttcg ccatgttggc caggatagtc
31561 ttgaactcct gatatcaggt gatgcgtcct cctcggcctc ccaaagtgct gggattagag
31621 gtgtgagcca ctgctcccag cctcttttag catttttgca tttctttgga aataaactga
31681 tatgttcatt aaaccatcaa aagaaaaacc aaaacacacc ttattaaga gtgagtgaaa
31741 gaaagagttg tctttacatt actgaaaact tctgtgtttc agaaatctgt ggaccgaagc
31801 atacaaatgg tggtatcttg tctgttaat ccagagaaga gactgataaa ttccgttgtt
31861 actcaagatg actgcttcaa ggtatgaaag gaatggcatg cataattaaa aagcacactt
31921 gttccctctc aagttagctg ttttccttgt ggcacatgta ttttgggctt tcttagagga
31981 atttttttc tttttttttt gttttgagac ggagtctcct ctgtgcgccc aggctggagt
32041 gcagtgagtg gccccatcta ggctcactgc aagctccacc tcccaggttt acttaacgcc
32101 attctcctgc ctcagccttc cgagtagctg ggactacagg cgcccaccac cacgcccagc
32161 taattttttg tatttttagt agagacgggg tttcaccgtg ttagccagga tggtctcgat
32221 ctcctgacct cgtgatccac ctgcctcagc ctcccaaagt gctgggatta caggcatgag
32281 ccaccgtgcc cggcctagaa catttaattg aactgttggc atttgactgt aacccagtaa
32341 accagtgtgg gttttacctg gcagtatatt ttctgctgcc gagccttgat ataatgtagt
32401 caaatttagg gaagaatcct gcagcagaaa tttgtaattg aaagggttta ctagagaaga
32461 gagttagttg actaccttga ccaaatagta aaataaaatt ttagatacag aaaggagatc
32521 ttggctgggt gcagaggctc acgcctgtaa tcccaacact tgggggggct gaggtgggtg
32581 gattgcttga gctcaggagt tcgaggccac cctgggtaac aaggcaaaac accatctcta
32641 caaaaaaata caaaaatcag ccagttgtga tggtacatgc ctgtagtgcc aactactcca
32701 gaggagtctg aggcaggagg atcgcttgag cctgggaagt tgaggctgca ctgagccatg
32761 attgtgccgt tgtagtccag cctgggcaac agagtgagag accttgtctc aaaaaaaaaa
32821 aaaaaaaaaa aaaagtaga acttaataca tgcatattgg actaaagaga agaaagaaa
32881 tgatttactc agatgataca cctgaacagt gtgaagggag aaaggggta aaatgaagca
32941 gtaaaaagtt gagtagaaag agaggttgat tcagagttgg tgaagcggaa gagaatgtgg
33001 ctagttgaat tccagaaaga tctgacttct gatcccactt tctatccatg ttggatagat
33061 aaatctttta ttaaggctct aattcttaca agtctaaaat gagaaggtac aggactaaag
33121 gtttctgggt ccctgtggtt ctaagtctat aaatacgaaa aagaactaac ttggtcagtc
33181 cggtgggaga aaaatattat ggttaataaa gggaaggtgt tttttaaata acaattttat
33241 taaaataata ccagtaatac aatttatgta tttaaaatgt gcacttcact gttttttcat
33301 atattcaaag ttgtgcaacc atgtccacaa tcaattttag aatatttaaa tcacctcaaa
```

FIG. 12 I

```
33361 aatcaccccc gtaccttagc agtcacctgc tattttcctg gaacttgtgt gtatccctag
33421 gcaaacacta atttactttt ttcctctaag gattttcctg tcctggagat ttcttgtata
33481 tggaatcata cataatgatg tggcattttg tgactggatt ttttcactca gcataatgtt
33541 tgtaaggttc atcaatattc tagcacgtat cagaacttaa tcatttcttt ttatttgtag
33601 atattacctt attctgttta tgcattcatc tgttaaagac atttggatta tttccacttt
33661 ttagctgtta taactaatgc tgtgaacatt catgtacaag ttactgtggg gacatacgtg
33721 cttacctctc ttgcgtatat acttgggaat ggaattgcta agtcatattt aacctttagt
33781 ggaactgcca gatttgtcaa aactggctac acactttaca ttcaaaagaa aatgtttaac
33841 catcactttg tgtcttacaa cagaactagc ttattttgt ctgtgaatgg atatgggatg
33901 aagcctaagc cttttttaaag ggttatatta tgaatcttct gtataatgta gaagagtaga
33961 gccagatagc agaattaagt tcttaacatc tttgcaacat ggagtaaata tatttaaatt
34021 tgacatttgt tctcttgttg cttcgttcta tatagatagt acaatttaga aaagaaagaa
34081 ctggaattgt acatcagctt atcttgccga aaattctgat tacattggtg tctacagtag
34141 tacttaagtg attttcaaag cagaagatag tttttttgtgt ttctttcttt ctttcttttt
34201 ttttttttttg aggtgacctc atttggtcat ccaggctgga gtgcagtgtc gcaatcacag
34261 cttactacaa cctcaaactc ctgcactcaa gggatccttc tgcctcagcg tcccaaatag
34321 gacgacagac gtgcaccacc acacttagct agttaaaaag aaatttttttt ttttttttttt
34381 tgagacagag tcccactgtg tcacccaggt tggagtgcag tggtgcgatc ttggctcact
34441 gcaagttctg cctcccaggt tcatgccatt ctcctgcctc agcctcccga gtggctggga
34501 ctacaggtgc ctgccaccac gcccagctaa ttttttgtgt tttagtaga gatgggggttt
34561 catcgtgtta gccaggatgg tctcgatctc ctgaccttgt gatctgcccg cctcggcctc
34621 ccaaattgct gggattacag gtgtgagcca ccgtgcccag ccaaaagatt ttttttaag
34681 agagaatctt actatattgc cctggctcgt cttgaactcc tgggctcaag tgatcctcct
34741 gcctcagcct cccaaagtgc tgggattaca ggcgtatgcc accatgtcca gcccagaaaa
34801 tattttttta aacttgagtt ctcacctggt ggtagacaaa agactcgctt tgaaacttcc
34861 agagtttttct gcttatttgg gagaggaatc agaagttggc atcctgcagt tgtctgacat
34921 ttagacctat tttaattgac tgcacgttgt tatattgaat tagaatgcct gagatatttt
34981 tgaatgtatt tacaatttcc atagccgatt tctcttcatt gtcttagtta tctagcccctt
35041 tcacaatctt gtttcctaca tgacctctga atatacatgt tggtgaccag ttttctagat
35101 tttaacctaa attgattatc actcttttga cagatgaggt aacttccaga agccactttt
35161 atttatatga aaatgaaact gaagtcttaa aaaaagggca cagcttttgta gaaaaggaaa
35221 tgttattact cgttcactca ttcccattcc tccttgtaag acctctcact tctctctgca
35281 cgtctgcagg caacatagag tgaaaagaaa gttttgcatg tatttttaaag ttttatcttc
35341 ctttctaaag aatgatatgt cttcacaggt taatgatatg ttcttcaaat gccaaaactt
35401 acatatttta atctaaaaac acgaaatttc agattggaga gcagttcgca agctgtagtt
35461 ggtattaaat gcagttcaat tagtgaaaaa agtattcttt acaattacat tttctaccag
35521 ctgtctttgg gacattactg caaaattatt aactaagaag tacataaaat gatactgagt
35581 ttaagtcctt ttatttctca gtttactgga atttgtttta tttaattatt gatttcttttt
35641 tttaactgtt taataaaact agccatcttg gtacatttgt tatcccagtg ttcaaatatg
35701 cttcctgaaa agaatcatct tttttttctca ttatttataa tgtttaaacc caaaacaaat
35761 ggtttaagtt ttgacaactt tcagatccat agtagtcatc agaaattttc agtaaaataa
35821 aaggactatt tctgtctttt ccagggtaaa agagtgcatc gctttagaag aagtttggca
35881 gtatttaaat ctgttggatc ctctcagcta tctagtttca tgggaagttg ctggttttga
35941 atattaagct aaaagtttc cactattaca gaaattctga attttggtaa atcacactga
36001 aactttctgt ataacttgta ttattagact ctctagtttt atcttaacac tgaaactgtt
36061 cttcattaga tgtttattta gaacctggtt ctgtgtttaa tatatagttt aaagtaacaa
36121 ataatcgaga ctgaaagaat gttaagattt atctgcaagg attttttaaaa aattgaaact
36181 tgcattttaa gtgtttaaaa gcaaatactg actttcaaaa aagttttttaa aacctgattt
36241 gaaagctaac aattttgata gtctgaacac aagcatttca cttctccaag aagtacctgt
36301 gaacagtaca atatttcagt attgagcttt gcatttatga tttatctaga aatttacctc
36361 aaaagcagaa ttttttaaaac tgcattttta atcagtggaa ctcaatgtat agttagcttt
36421 attgaagtct tatccaaacc cagtaaaaca gattctaagc aaacagtcca atcagtgagt
36481 cataatgttt attcaaagta ttttatcttt tatctagaat ccacatatgt atgtccaatt
36541 tgattgggat agtagttagg ataactaaaa ttctgggcct aattttttaa agaatccaag
36601 acaaactaaa ctttactggg tatataacct tctccaatgag ttaccattct ttttttataaa
36661 aaaaaattgtt ccttgaaatg ctaaacttaa tggctgtatg tgaaatttgc aaaatactgg
36721 tattaaagaa cgctgcagct ttttttatgtc actcaaaggt taatcggagt atctgaaagg
36781 aattgttttt ataaaaacat tgaagtatta gttacttgct ataaatagat ttttattttt
36841 gttttttagc ctgttatatt tccttctgta aaataaaata tgtccagaag aggcatgttg
36901 tttctagatt aggtagtgtc ctcattttat attgtgacca cacagctaga gcaccagagc
36961 ccttttgcta tactcacagt cttgttttcc cagcctcttt tactagtctt tcaggaggtt
37021 tgctcttaga actggtgatg taaagaatgg aagtagctgt atgagcagtt caaaggccaa
```

FIG. 12 J

```
37081 gccgtggaat ggtagcaatg ggatataata cctttctaag ggaaacattt gtatcagtat
37141 catttgatct gccatggaca tgtgtttaaa gtggctttct ggcccttctt tcaatggctt
37201 cttccctaaa acgtggagac tctaagttaa tgtcgttact atgggccata ttactaatgc
37261 ccactggggt ctatgatttc tcaaaatttt cattcggaat ccgaaggata cagtctttaa
37321 actttagaat tcccaagaag gctttattac acctcagaaa ttgaaagcac catgactttg
37381 tccattaaaa aattatccat agttttttta gtgcttttaa cattccgaca tacatcattc
37441 tgtgattaaa tctccagatt tctgtaaatg atacctacta tctaaagagt taattctaat
37501 tattccgata tgaccttaag gaaaagtaaa ggaataaatt tttgtctttg ttgaagtatt
37561 taatagagta aggtaaagaa gatattaagt ccctttcaaa atggaaaatt aattctaaac
37621 tgagaaaaat gttcctacta cctattgctg atactgtctt tgcataaatg aataaaaata
37681 aactttttttt cttcaaatgt gttttttggct ttccgatgta ataatgtaaa atggtgggga
37741 gttgcgtggg aactgtgtaa caaggtttaa attcgtataa caagctttag attcttaaaa
37801 tgcagaagta taaagttcag tatactaatc tgtctgagtt agcccataaa agcaaatgta
37861 ggtacaaaga taagtttaag aggtgcatca acagcagtgc agactaggaa tgctgatgaa
37921 cacatccgac tctgctatct cacggctaag gtccctcaca ttttggaccc tatgaagcat
37981 tttgtctact gtacactttg ggcctagtct ctagatcatt tatttcgggg tattgcagtt
38041 gcctaaggga gcttaatttt tttatattgc aggtacttcc tgtggatacc ataaaaaaaa
38101 aaaatcagta ccgcttcttc tagctttagt gttagtactc agttctataa gctgagtcca
38161 gtggagagga aactcctcag acactcctgt atttcattag ttagtaagct tgctgattca
38221 taaccagaaa gttgactcca aggatacgca ggatagcaaa cagtgctttc tgcatcacca
38281 aagattaaat tgtgatgttt agtgtccaat aataggcaaa aaattagtaa ttcttttatg
38341 tgcctatgtg tatatatgtg tacatatgtg tctatatatg catatattta tggttatgta
38401 catactaacg attatccaga atatttggtt ctagctgatc aagctagtag gttttcagta
38461 ttttcagacc ccaaaactag actacatatg gtttaagata gttgctttac accagcttgt
38521 ttctagtttc ctattaaatt attaccacaa aaatctttgg aattgaaaaa taacagttaa
38581 gcactttttt gtaaaaagtt caagttatgg tgaaatcaag cagctctaaa aaggttggtc
38641 acctccttaa gtgtattctg catgttggtt ttttttcttt tctaaaatca gattacctt
38701 aattcaaaat aacttcagaa ttggtagtac ctgtctggca aggaagtcat tgactcttaa
38761 aaataaatac tccacagcat ttccctctcg ttataaagca cctctagccc cctcttcact
38821 aaatttttct tggctttttt ttaaaggtaa actgataaaa atgggctgcc acattgctta
38881 atcgccttgc ctgctttcct tgctgtcagt tgagggtaat gaggagcagc aacgataagg
38941 cagcgtgcca ccttgctttc acaaagatgc caatagagaa agtggggaaa cataagggag
39001 aaaaaagtag cagtatttta cattgaccaa gtcttgtgaa tgggccagct attgagtatg
39061 atcatttgga atccctagat aaggattgct cctgtacata ttttgataag tgtaatctat
39121 cccttcccaa catgtgtagt atgtctctgt atgtaactga ttgttgtgag caattccttg
39181 ccactcacca aagacagaac tttccatctg tagacagtac attttgtagt agaaaacaat
39241 agacataaga agttcaaact ataaacatgt ttttgaatgc tcatgaaaga taatctgcat
39301 agcaaagaaa taatagacaa ttcaacattg catttagagt taaaaacatc tgtccagtat
39361 ggatgtagct gtgggccaat cctaagtaaa cgcaaaaaaa aaaaaaaaaa aaaattgtct
39421 cttggtacag aagttgaaac taccactcta ccactgtaca attaaactct atggtcgctg
39481 tattttacgt ttttaactgg tctgaaacag ttctctagtt aagtctgtag ttcgttttcc
39541 caagacaagg cttttgtatct tacgtgcacc ttcattaatg ctgcatgcca ggaattccac
39601 atgaaacttc aagatgccgg ttcactaggt cttttccaca tgaaacttca agataccggt
39661 tcactaggtc tttaacaata gaacaaatac ttgcatgact gggatattca ggtcatgaac
39721 actccttata aatttgaagc aatagtaaca ttttaagcac tttggaaaat tggaggtttc
39781 ataaccctca atcagatctt tttatagaat aacaaaaata cactaaggtt ctaatcacat
39841 ctattgtctt tgcccaaaat aacatggata gagacacact ccattctggc tcaatcttag
39901 atgaaactcc agaagaaagg cagttgataa tgatacagcc aggccagctg tttaagtgga
39961 cgtgtcccct ctgcccttgt acatttgttt aaaaatttttg ataggactct tcccgcctcc
40021 ttcacaccct ccataaatct gactaggccc ataagaatgg agagaggtaa tttaaaaggc
40081 agaggacatt tttctccttg tttttaccta tgctgatccc ctacctggtg ttggagcagc
40141 ttcactgtga gtaaaatctg aacagtgttt aagcagtaaa cccactatat tgaggaaagc
40201 gtgacctgca cttttttttt ttttttttc ctgaacaaga cttggttgtt gctcatcatt
40261 ttggttggtg atgggtcttt gacaaaccga tatgctcacc atccaaagtt gtgtccatgt
40321 ttagatcc
```

FIG. 12 K

DAZ: A GENE FAMILY ASSOCIATED WITH AZOOSPERMIA

RELATED APPLICATIONS

This application is a Continuation-in-Part application of U.S. application Ser. No. 08/690,734, filed Jul. 31, 1996, now U.S. Pat. No. 5,871,920 which is a Continuation-in-Part application of U.S. application Ser. No. 08/310,429, filed Sep. 22, 1994 U.S. Pat. No. 5,695,935. The teachings of these prior applications are incorporated herein in their entirety.

FUNDING

Work described herein was supported by grant RO1-HGOO257 from the National Institute of Health, National Center for Human Genome Research, funding from the Howard Hughes Foundation, funding from March of Dimes Birth Defects Foundation and funding from the Damon Runyon-Walter Winchell Foundation Cancer Research Fund. The United States Government has certain rights in the invention.

BACKGROUND OF THE INVENTION

Male infertility is a concern for many couples. Worldwide studies have shown that 2%–7% of all couples have experienced difficulty in achieving conception or are unable to bear children, especially as they near the end of their reproductive life. (Sara A., *Advances in Fertility and Sterility, Proc. Twelfth World Congress Fer. Steril.* 4:91–92 (1987)). Furthermore, among men who seek help or advice at fertility clinics, slightly more than 10% are diagnosed as having oligospermia or azoospermia of unknown origin. (Hargreave, T. B., *The Management of Male Infertility*, T. B. Hargreave and T. E. Soon, eds. (Singapore: PG Publishing, pp. 2–21, 1990)). At this time, little is known about the causes of reduced spermatogenesis and, although various treatments are available, improved methods are still needed.

XY sex chromosomes are found in a multitude of species throughout the animal kingdom. It is thought that XY chromosomes arose independently in many evolutionary lineages, in each case deriving from an ordinary autosomal pair. According to prevailing theories, once recombination between nascent X and Y chromosomes becomes restricted, the gene content of the Y chromosome declines steadily and inexorably. Degeneration of the Y chromosome is well documented in Drosophila (Rice, *Science* 263:230–232 (1994); Steinemann & Steinemann, *Proc Natl. Acad. Sci. USA* 89:7591–7595 (1992)), and has been shown to be an ongoing process even among mammals, which are generally considered to exhibit extreme differentiation of the X and Y chromosomes. The few genes that persist on highly differentiated Y chromosomes are thought to be relics of this common ancestry with the X chromosome. According to this view, Y-chromosomal genes were once, or still are, shared with the X chromosome (Rice, *BioScience* 46:331–343 (1996)).

SUMMARY OF THE INVENTION

This invention pertains to a family of genes referred to herein as the DAZ gene family. As described herein, multiple copies of the DAZ gene, more than 99% identical in DNA sequence and having many degenerate exons, are tightly clustered in the same region of the Y chromosome. Furthermore, the invention relates to a functional DAZ homolog, DAZH, located on human chromosome 3. The entire gene family, comprising the DAZ genes located on the Y chromosome and on chromosome 3, appears to be expressed exclusively in germ cells. DNA sequence analysis has revealed that the Y-chromosomal DAZ gene cluster arose during primate evolution by transposition of the autosomal gene to the Y chromosome, exon amplification and pruning within the transposed gene, and amplification of the modified gene.

This invention also pertains to an isolated DAZ gene present in interval 6D and/or 6E of the distal portion of the long arm of the human Y chromosome, whose alteration is associated with reduced sperm count. The invention particularly pertains to a DAZ gene having the DNA sequence of SEQ ID NO: 15. This DAZ gene, which appears to be testis-specific, is approximately 3.1 kb in size, and encodes a protein homologous in certain domains to several RNA binding proteins. This gene (having a CDNA sequence of SEQ ID NO: 15) is referred to herein as the DAZ gene.

The present invention also relates to methods of diagnosing reduced sperm count associated with alteration of a DAZ gene present in interval 6D and/or 6E of the distal portion of the long arm of the Y chromosome, and particularly to a method of diagnosing reduced sperm count associated with alteration of the DAZ gene comprising the nucleotide sequence of SEQ ID NO: 15. In one embodiment of the present method, deletion of the gene is assessed, such as by a hybridization method in which a nucleotide sequence (nucleic acid sequence) which hybridizes to a DAZ gene described herein (or portion of that gene) is used to assess Y chromosomal DNA for the presence or absence of the gene. For example, lack of hybridization of the nucleotide sequence used to assess a DNA sample obtained from a male who has a reduced sperm count indicates that the gene is deleted and that the reduced sperm count is associated with the deletion. The present invention also relates to nucleotide sequences for use as probes or primers for methods of diagnosing reduced sperm count associated with alteration of a DAZ gene described herein.

The present invention further relates to the protein encoded by genes which are members of the DAZ gene family, which includes the amino acid sequence of the RNA binding domains conserved among members of the family of RNA binding proteins. This invention also relates to a method of treating reduced sperm count, such as by a gene therapy method in which a DAZ gene described herein, or a gene portion which encodes a functional protein, is introduced into a man whose sperm count is reduced and in whom the gene is expressed and the encoded protein replaces the protein normally produced or enhances the quantity produced.

Novel genes described herein which are members of the DAZ gene family, have been designated the DAZ and DAZH genes. DAZ has been shown to be altered in men whose sperm count is reduced. The complete DAZ cDNA sequence (SEQ ID NO: 15) is shown in FIG. 4, and the predicted amino acid sequence (SEQ ID NO: 98) of the DAZ gene is shown in FIG. 10. The DAZ gene is located within the 6D and/or 6E deletion interval, appears to encode a testis-specific transcript, is present in a single copy on the Y chromosome of higher primates, and probably has a homologue in lower mammals. The DAZH cDNA sequence (SEQ ID NO: 96) and predicted amino acid sequence (SEQ ID NO: 97) are shown in FIG. 6. The DAZH gene appears to be expressed exclusively in germ cells.

Thus, this invention has application to several areas. It may be used diagnostically to identify males with reduced sperm count in whom a DAZ gene has been altered. It may also be used therapeutically in gene therapy treatments to remedy fertility disorders associated with alteration of a DAZ gene. The present invention may also be useful in designing or identifying agents which function as a male contraceptive by inducing reduced sperm count. This invention also has application as a research tool, as the nucleotide sequences described herein have been localized to interval 6D and/or 6E of the distal portion of the long arm of the human Y chromosome and can therefore serve as markers for these intervals.

BRIEF DESCRIPTION OF THE DRAWINGS

FIG. 1 is a partial nucleotide sequence (SEQ ID NO: 1) of a gene which is a member of the DAZ gene family.

FIG. 2 is a partial nucleotide sequence (SEQ ID NO: 2) of a gene which is a member of the DAZ gene family; the partial sequence represented by SEQ ID NO: 2 is 5' of the partial sequence represented by SEQ ID NO: 1.

FIGS. 3A, 3B, 3C and 3D show a map of patient deletions and YAC clones spanning the entire interval. The numbers proceeded by "yS" along the top margin are sequence-tagged sites (STS). The letters "na" indicate that the site was not analyzed.

FIGS. 4A, 4B and 4C indicate the DAZ cDNA sequence (SEQ ID NO: 15).

FIG. 6 shows the DAZH cDNA sequence (GenBank accession number U65918; SEQ ID NO: 96) and predicted amino acid sequence (SEQ ID NO: 97). The single 24-amino acid "DAZ repeat" is underlined. Arrowheads above the nucleotide sequence depict probable locations of ten introns. Numbering of nucleotides and amino acids begins with the first in-frame AUG codon.

FIGS. 8A, 8B, 8C, 8D and 8E show a schematic representation of genomic DNA sequence from the DAZ gene cluster on the human Y chromosome. FIG. 8A shows the DAZ transcription unit. Exons are numbered according to the scheme outlined in FIG. 9. Coding regions are in black, while UTRs are in white. Region 7h is potentially an exon, but it has not been identified in sequenced clones. FIG. 8B depicts pseudoexons within the DAZ transcription unit. FIG. 8C shows the sequence backbone having nine tandem repeats of a 2.4-kb unit, interrupted at one point by a 6.1-kb LINE element. Alu repeats are also indicated. FIG. 8D shows three cosmids from which the sequence was derived. Nucleotide differences between 18E8 and overlapping portion of 63C9 or between 63C9 and overlapping portion of 46A6 are listed. Deletions are indicated with a dash. Sequencing of the 5' portion of cosmid 18E8 is in progress; all of cosmid 46A6 (43,795 nucleotides) was sequenced, but only 12 kb is represented. FIG. 8E shows the locations of the DYS1 plasmids p49f and p49a (Bishop et al., *J. Mol. Biol.* 173:403–417 (1984); Lucotte and Mariotti, *Molec. and Cell Probes* 5:359–363 (1991)).

FIG. 9 depicts the exons and pseudoexons of the human DAZ and DAZH genes. The figure is arranged in 11 tiers corresponding to the 11 exons of DAZH. In each tier the DAZH exon is shown in the top line, and below are shown all homologous regions, both exons and pseudoexons, in DAZ cosmids 18E8 (exon 1 through pseudoexon 8b) and 63C9 (exon 2 through exon 11). DAZH translated sequences (and homologous portions of DAZ) are capitalized. DAZ exon 8h is 16 nucleotides shorter at its 3' end than DAZH exon 8, apparently because a single nucleotide substitution created a new splice donor site in DAZ.

FIG. 10 depicts the amino acid sequence (SEQ ID NO: 98) of the DAZ gene predicted from the DNA sequence of SEQ ID NO: 15.

FIGS. 11A–L depict the genomic DNA sequence of the DAZ gene (SEQ ID NO: 101; GeneBank Accession No. AC000022) present in cosmid 46A6.

FIGS. 12A–K depict the genomic DNA sequence of the DAZ gene (SEQ ID NO: 102; GeneBank Accession No. AC000021) present in cosmid 63C9.

DETAILED DESCRIPTION OF THE INVENTIon

The present invention pertains to a small family of novel genes referred to as the DAZ gene family, present in interval 6D and/or 6E of the distal portion of the long arm of the human Y chromosome and on human chromosome 3. Alteration of a DAZ gene present in interval 6D and/or 6E of the distal portion of the long arm of the human Y chromosome is associated with reduced sperm count.

As described herein, the Y chromosomes of infertile males, their fathers and normal males have been studied. Among 71 infertile males, 8 males have been identified who have de novo overlapping interstitial deletions on the distal long arm of the Y-chromosome; no such deletions were detected in normal males. The size of the deletion interval which contains this gene, approximately 3.1 kb in size, is approximately 500 kb. The DAZ gene appears to be part of a small gene family (herein termed the DAZ gene family) whose members are located in the same region of the Y chromosome; there also appears to be a related gene on chromosome 3 (DAZH). The gene family members located on the Y chromosome are more than 90 percent identical at the DNA level to the DAZ gene. The DAZH gene is 87–94 percent identical at the DNA level to the DAZ gene; the most highly conserved regions exhibit about 94 percent identity. Partial nucleotide sequences of a gene which is a member of the DAZ gene family are shown in FIGS. 1 and 2 (SEQ ID NOS: 1 and 2). Accordingly, the present invention pertains to genes, particularly human genes, which are at least 87 percent, and more preferably at least 94 percent, identical at the DNA level to the DAZ gene having a nucleotide sequence of SEQ ID NO: 15.

Figures 3, 3A:
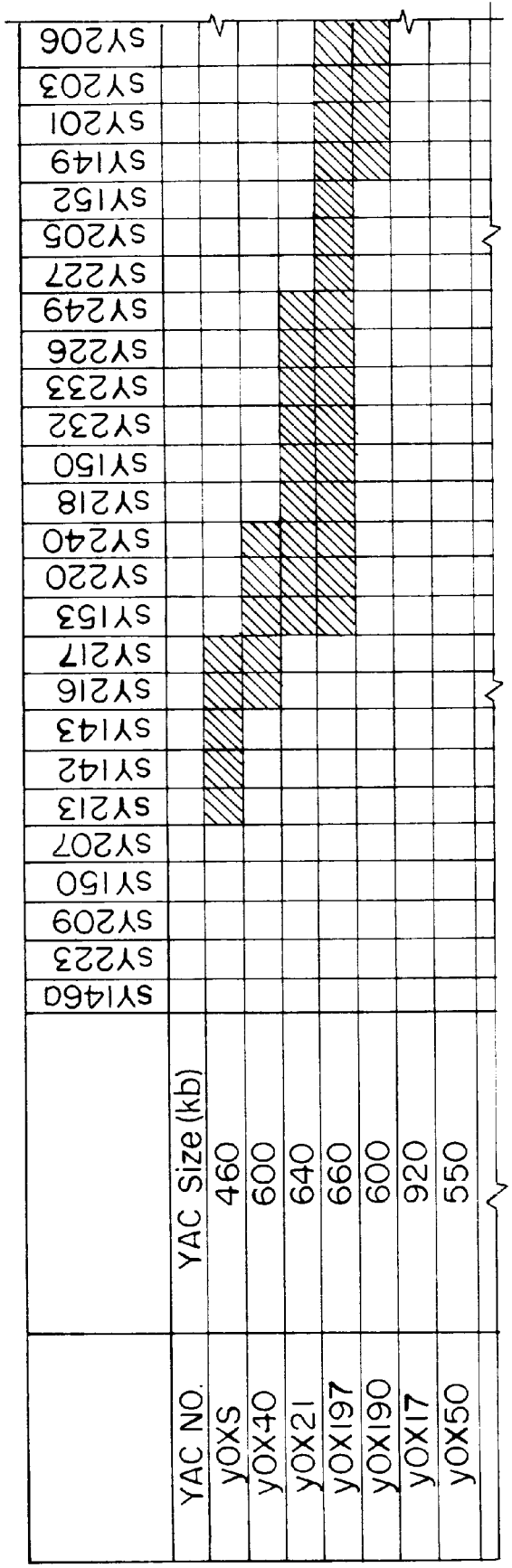
Figure 3B:
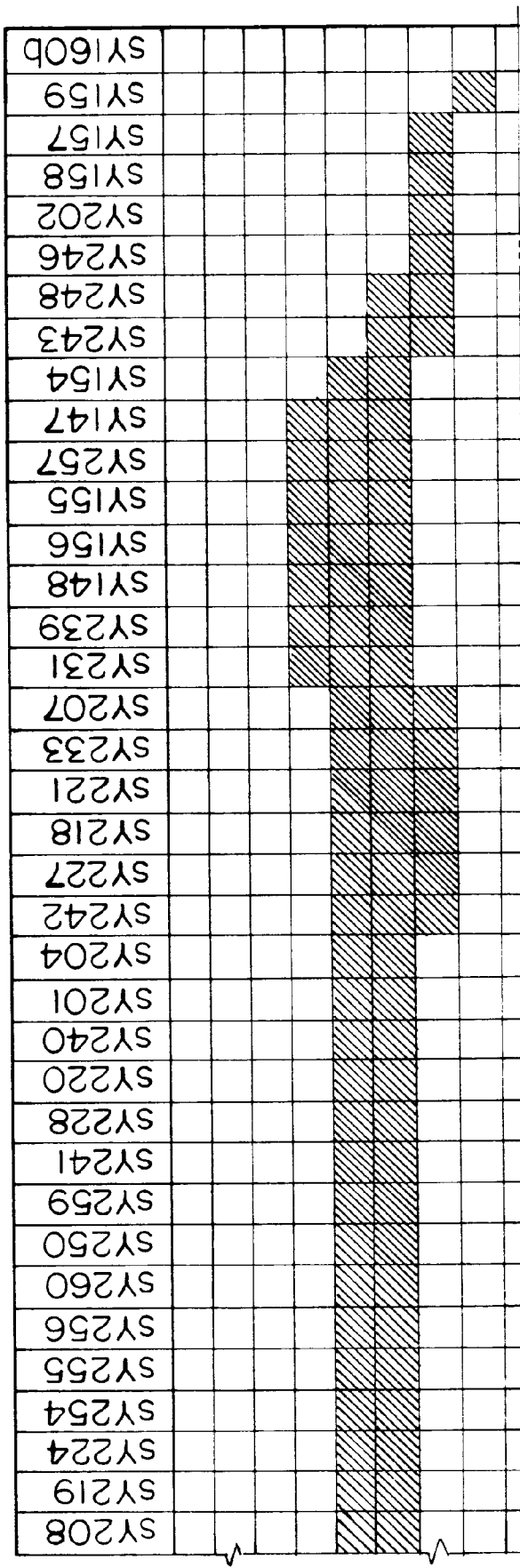
Figure 3D:
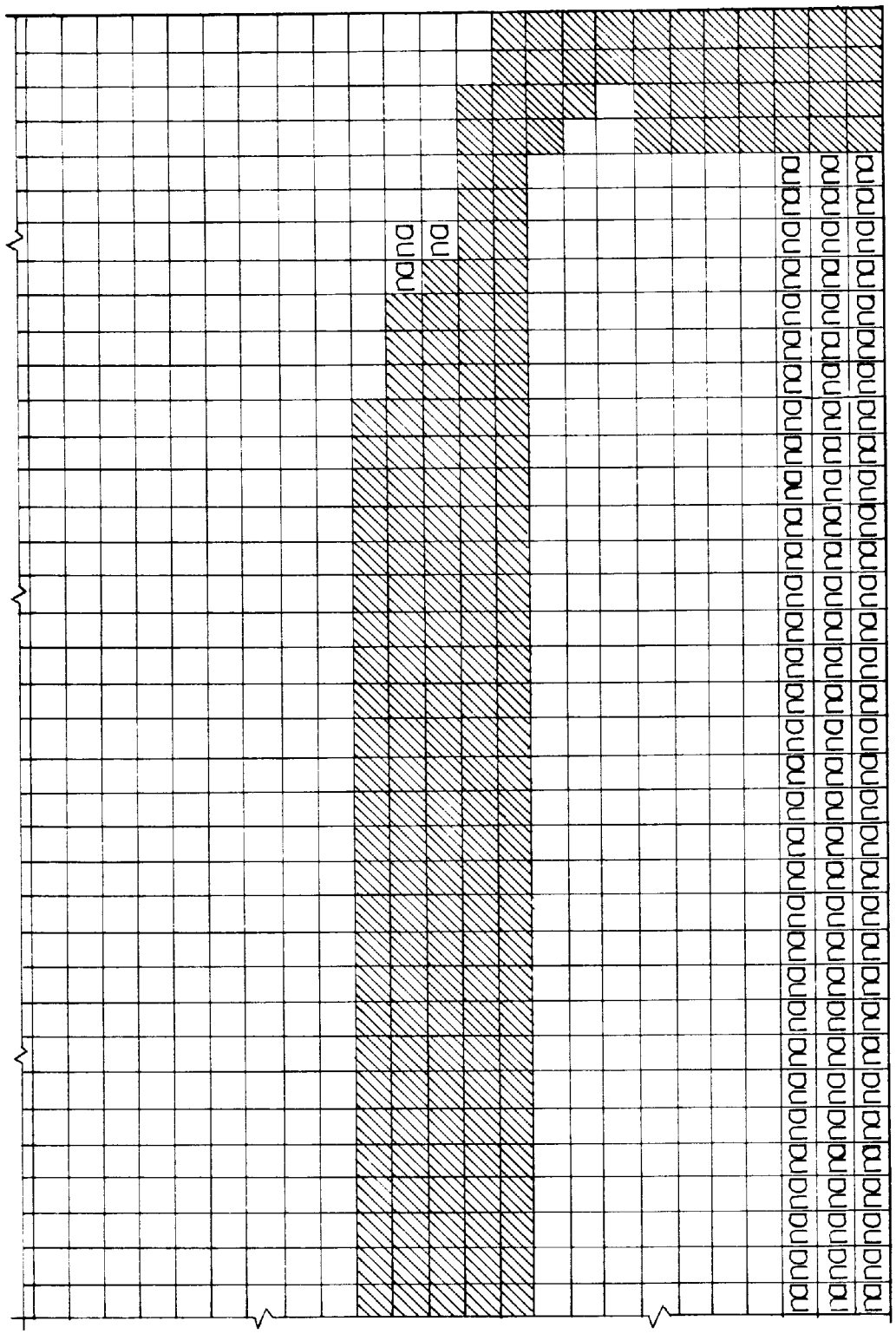

In order to identify the DAZ gene, whose alteration is associated with reduced sperm count, the relevant deletion interval was analyzed for transcription units by using markers in the deletion interval, identifying yeast artificial chromosomes (YACs) that span the region (see FIG. 3), obtaining 5-fold cosmid coverage of the interval, and using exon-trapping of cosmids to identify sequences with coding potential.

The present invention also pertains to novel methods for diagnosing and treating reduced sperm count associated with an alteration of a member of the DAZ gene family. The present invention also has utility as a research tool, since the gene described herein, or a portion thereof, serves as a marker for the 6D deletion interval of the long arm of the Y chromosome to which it is localized. The cDNA sequence (SEQ ID NO: 15) of the DAZ gene is shown in FIG. 4.

Terms used throughout the Specification are understood to have their art-recognized meaning unless otherwise defined. As used herein, the term "alteration of the gene" includes disruption of the gene (deletion of one or more nucleotides, addition of one or more nucleotides, or change in one or more nucleotides) and loss of the gene. Azoospermia is defined as a condition wherein the concentration of sperm in a semen sample is 0 to occasional sperm per ml, and oligospermia is defined as a condition wherein the concentration of sperm in a semen sample ranges from occasional to less than 20 million per ml. Reduced sperm count is understood to encompass both oligospermia and azoospermia, i.e., a sperm count of less than 20 million per ml, including total absence of sperm. As used herein, an "isolated" gene or nucleotide sequence is intended to mean a gene or nucleotide sequence which is not flanked by DNA sequences which normally (in nature) flank the gene or nucleotide sequence. Thus, an isolated gene or nucleotide sequence can include a gene or nucleotide sequence which is biologically isolated or synthesized chemically or by recombinant means.

Furthermore, as defined herein, "the DAZ gene" is intended to mean a gene comprising the nucleotide sequence of SEQ ID NO: 15. "A DAZ gene" is intended to mean one of the multiple copies of the DAZ gene, more than 99% identical in DNA sequence and littered with degenerate exons, which are tightly clustered in the same region of the Y chromosome. A gene which is a member of the DAZ gene family includes the DAZ gene (comprising SEQ ID NO: 15), any one of the multiple copies of the DAZ gene which are tightly clustered in the same region of the Y chromosome ("a DAZ gene"), and the DAZ homolog located on human chromosome 3 (DAZH).

The DAZ gene of the present invention was identified by searching the relevant deletion interval for transcription units by combining additional new markers with known markers over the deletion interval, identifying yeast artificial chromosomes which span the region, obtaining five-fold cosmid coverage of the interval and using exon-trapping of cosmids to identify sequences with coding potential. Once this candidate gene was identified, it was characterized to determine if it fit the profile of a gene whose alteration is associated with reduced sperm count. As described further below, the DAZ gene is located exclusively within the deletion interval, has a testis-specific transcript and is present in a single copy on the Y chromosome.

Partial sequence analysis of other cDNA clones from the same human adult testis library, identified by hybridization with DAZ probes, suggested that they were derived from a single transcription unit that was homologous but not identical to DAZ; this homologous gene is referred to herein as DAZH (DAZ homolog). Complete sequence analysis of two DAZH cDNA clones revealed that they were collinear and shared a single long open reading frame (FIG. 6). This transcript appears to encode a protein of 295 amino acids, with a molecular weight of 33,170. As discussed herein below, the predicted DAZ and DAZH proteins are similar but nonidentical.

It was then determined whether DAZH, like DAZ, mapped to the human Y chromosome. Using PCR assays specific to DAZH, products of identical size were obtained using human male or female genomic DNAs as templates, suggesting that the gene is autosomal or X-chromosomal. DAZH was mapped using two methods. By in situ hybridization of genomic BAC clones to human metaphase spreads, DAZH was localized to the distal short arm of chromosome 3. This localization was independently confirmed and refined by PCR analysis of whole-genome radiation hybrid panels.

Human DAZH appears to be expressed in adult testis, as indicated by recovery of clones from a cDNA library prepared from this tissue. To confirm this result and to determine whether DAZH is transcribed elsewhere, a DAZH-specific probe was hybridized to Northern Blots of RNAs from 16 different human tissues. RT-PCR analysis was also carried out on five different human tissues using DAZH-specific primers. These studies revealed that DAZH is abundantly expressed in the adult testis, where a 3.5-kb transcript is readily detected by Northern blotting, and is expressed at a lower level in the adult ovary, where a DAZH-specific RT-PCR product is observed. No evidence of transcription was observed in the other tissues examined.

Figure 7:
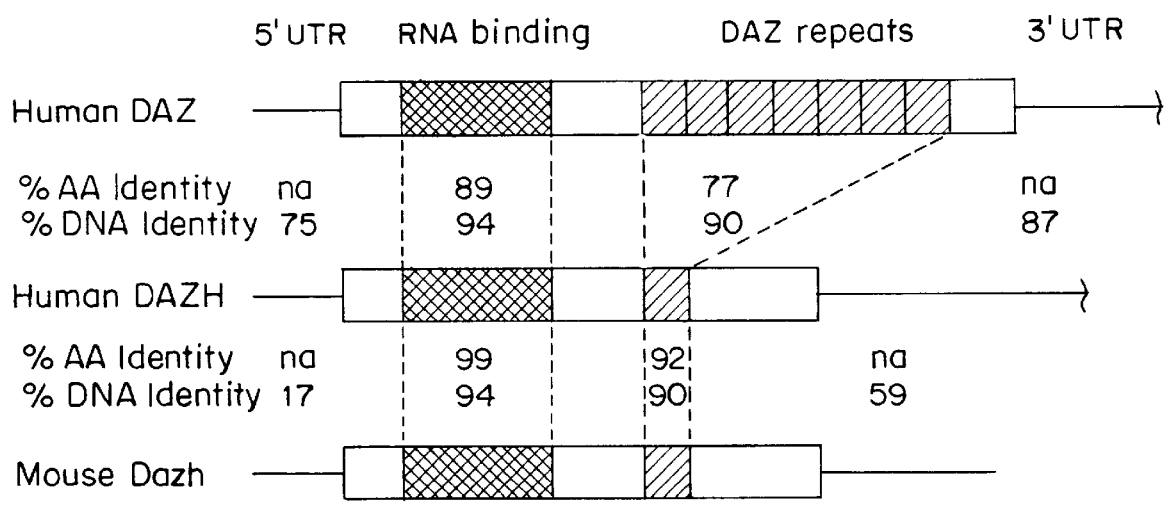
FIG. 7 shows a comparison of human DAZ, human DAZH and mouse Dazh transcripts and encoded proteins. Percentage nucleotide and amino acid identities are shown for the following regions: 5' untranslated region (UTR), RNA binding domain, DAZ repeats, and 3' UTR ("na" indicates not applicable).

Comparative analyses of predicted protein and underlying cDNA sequences for human DAZH, human DAZ and mouse Dazh provide unexpected insights into the evolution of this gene family. The three proteins have quite similar structures, with overall sequence similarity being greatest between the products of the human DAZH and mouse Dazh genes (FIG. 7). Indeed, within the 82-residue RNA-binding domain, the products of human DAZH and mouse Dazh, both autosomal, differ by only one amino acid substitution, while both differ from human Y-encoded DAZ at nine residues. While the human Y-encoded protein includes seven tandemly arrayed "DAZ repeats", each 24 amino acids in length, the mouse and human DAZH proteins contain only one such unit (FIG. 7).

At first glance, these protein comparisons seem to suggest that, during evolution, the ancestors of DAZ and DAZH diverged from a single common protein before the separation of the murine and human lineages; in this case, the DAZ gene must have been lost or diverged beyond the point of cross-hybridization during murine evolution. However, an examination of the cDNA sequences themselves clearly indicated a very different evolutionary course. Especially revealing were analyses of the genes' untranslated regions (UTRs), which are presumably subject to less intense selective pressures than are coding sequences and should evolve more rapidly. In their UTRs, the human DAZH and human DAZ transcripts exhibit a remarkably high degree of nucleotide sequence identity (75% and 87%, respectively, in 5' and 3' UTRs). A far lower degree of UTR sequence identity is observed between human DAZH and mouse Dazh (17% and 59%, respectively, for 5' and 3' UTRs). These UTR comparisons strongly suggested that the human DAZ and DAZH genes evolved from a single gene after, not before, the separation of the murine and human lineages. Thus, the DAZ gene must have encoded a protein much like human or mouse DAZH, given that the mouse (and fly) proteins show greater similarity to human DAZH than to human DAZ. Homology between human chromosome 3, where human DAZH maps, and mouse chromosome 17, where mouse Dazh maps, has not been reported previously. On the basis of this analysis, it was tentatively concluded that an ancestral, autosomal DAZH gene, still extant in humans, mice and flies, gave rise to Y-chromosomal DAZ during human evolution, after the separation of the human and murine lineages. The Y-encoded DAZ protein must have evolved relatively rapidly as compared with its highly conserved, autosomally-encoded ancestor, DAZH.

The DAZ Gene Cluster on the Y Chromosome

To better understand the structure and evolution of the human DAZ gene family the nucleotide sequence of about 100 kb of the AZF region of the human Y chromosome was determined (FIG. 8). The particular cosmids sequenced were chosen, based on restriction fingerprinting and hybridization with DAZ oligonucleotides, to overlap modestly and to collectively span an entire DAZ transcription unit. The cosmids derived from flow-sorted Y chromosomes originating from a single normal male. As described herein, this sequence analysis confirmed the above-outlined model of an autosomal-to-Y transposition, revealed that the DAZ transcription unit had been shaped by an unprecedented process of exon amplification and pruning, and demonstrated that the AZF region contains multiple copies of DAZ. No genes other than DAZ were detected in the sequenced region. Vogt and Colleagues have suggested that a second gene or gene family, designated SPGY, is found in the vicinity of DAZ in this AZF region. No sequence analysis of SPGY has been reported. However, Vogt and Colleagues have reported two SPGY oligonucleotide sequences that yield a human genomic PCR product of 460 bp (Vogt et al., *Hum. Mole. Genet.* 5:933–9439 (1996)). Perfect matches to both oligonucleotides are found with DAZ exon 11 (nucleotides 8373–8398 and 8804–8829 in cosmid 46A6; see FIGS. 11A–L, SEQ ID NO: 101), where they span a region of 457 base pairs.

Among the most evident features of the sequenced region is an array of nine tandem repeats of a 2.4 kb unit, comprising half of cosmid 63C9 (FIG. 8D, center). These tandem repeats are interrupted at one point by a 6 kb LINE element, but they otherwise exhibit 77 to 96% sequence identity. As judged by numerous PCR assays on genomic DNAs from normal and AZF-deleted human males, these repeats appear to be specific to the AZF region of the Y chromosome.

The DAZ transcription unit appears to contain at least 16 exons and to span about 42 kb, including all nine tandem repeats. Located upstream of the 2.4 kb repeats are exon 1, which ends immediately 3' of the initiator codon, exons 2 through 5, which encode the RNA-binding domain, and exon 6. Each of the next seven exons (denoted 7a through 7 g) is 72 bp in length, encodes a single "DAZ repeat" of 24 amino acids, and falls within a 2.4 kb genomic repeat. Thus, seven of the first eight 2.4 kb tandem repeats appear to correspond, one to one, to the seven tandem "DAZ repeats" previously noted in the encoded protein (Reijo et al., *Nature Genet.* 10:383–393 (1995)). The sixth tandem repeat is interrupted by the LINE element and lack a 72-bp exon, apparently deleted at the site of the LINE's insertion. Curiously, the subsequent exon (exon 8) falls within the eight of the none 2.4-kb tandem repeats, but its nucleotide and encoded amino acid sequences are unrelated to those of exons 7a through 7g. The last two exons of DAZ are located 3' of the tandem repeat array. A 3' poly(A) tail has yet to be identified in any DAZ cDNA clone. However, in the genomic DNA, a putative polyadenylation signal (AATAAA) is found 1.85 kb 3' of the 5'boundary of exon 11, and RT-PCR studies confirm that mature DAZ transcripts end shortly 3' of this polyadenlyation signal.

Finally, the three sequenced cosmids, all derived from a single individual's Y chromosome, were compared in detail. Slight sequence differences were detected among the three cosmids in regions of overlap, strongly suggesting that the cosmids represent distinct, though highly similar, copies of DAZ. Cosmids 18E8 and 63C9 appear to overlap by 8 kb, including exons 2 through 7b, but actually differ at eight nucleotides in this region (FIG. 8D). Similarly, cosmids 63C9 and 46A6 appear to overlap by 12 kb, including exons 10 and 11, but actually differ at eight sites (FIG. 8D). None of the nucleotide substitutions predicts an amino acid substitution or alters a splice site. Since the three cosmids derive from a single individual, and thus a single Y chromosome, these sequence differences cannot be attributed to allelic variation but must instead lead to a conclusion that they represent distinct copies of DAZ with approximately 99.9% sequence identity.

The 72-bp repeat unit (the DAZ repeat) in the DAZ cDNA shows a remarkable sequence similarity to human DYS1, an extraordinarily polymorphic family of Yq-specific sequences first described in 1984 and widely exploited since that time in population genetic studies (Bishop et al., *J. Mol. Biol.* 173:403–417 (1984); Ngo et al., *Am. J. Hum. Genet.* 38:407–418 (1986); Lucotte et al., *Am. J. Hum. Genet.* 45:16–20 (1989)). A database search for DNA sequences related to the DAZ genomic locus revealed more extensive similarity to DYS1; there is near identity between the entirety of a sequenced segment (750 bp; plasmid p49a; Lucotte and Mariotti, *Molec. and Cell. Probes* 5:359–363 (1991)) of human DYS1 and the fourth of the nine 2.4 kb repeats in DAZ.

These findings prompted an examination of the relationship of DYS1 to DAZ and eventually led to an equation of the two. First, an EcoRI restriction map of a DYS1 cosmid is strikingly similar to that of DAZ cosmid 63C9. PCR assays flanking DAZ exons 4, 5, 6 and 7a yielded products of the expected size when amplified from a DYS1 clone. As a final test of the equation, Southern blots of TaqI-digested genomic DNAs from three AZF-deleted men and their relatives were probed with plasmid 49f, the DYS1 probe most widely used in population genetic studies. In normal male relatives, the expected array of Y-specific TaqI fragments, both polymorphic and monomorphic, were observed. However, in the three AZF-deleted men, all Y-specific bands were absent, demonstrating that all DYS1 sequences are, like the DAZ gene cluster, located in the AZF region. The only DYS1-homologous fragments remaining in the AZF-deleted men are two autosomal fragments that correspond to DAZH as confirmed by TaqI digestion of DAZH BAC clones. Thus, it was concluded that the DAZ gene cluster and the highly polymorphic DYS1 sequences are one and the same.

A Transcription Unit With Many Vestigial Exons

The DAZH coding region (FIG. 6) exhibits about 90% nucleotide sequence identity to the sequenced portion of the AZF region (FIG. 8), allowing a prediction of the likely locations of all DAZH introns (FIGS. 6 and 9) and a further exploration of the evolutionary relationship of the Y-chromosomal DAZ and the autosomal DAZH transcription units. This analysis substantiated that while the DAZH gene appears to have a conventional structure, the DAZ transcription unit is a contorted derivative littered with degenerate exons. Indeed, scattered among the exons of a single DAZ transcription unit (e.g., that largely encompassed by cosmid 63C9) are nine sequence segments that bear unmistakable similarity to DAZH exons yet consist of nothing more than vestigial remains of those exons. These degenerate, vestigial exons are referred to herein as "pseudoexons", by analogy to "pseudogenes". Eight of the nine pseudoexons are relics of DAZH exon 8 and are found in the 2.4 kb tandem repeats that comprise the central half of the DAZ transcription unit. The remaining pseudoexon (a descendant of DAZH exon 9) is found between the last of the 2.4 kb repeats and exon 10. All nine DAZ pseudoexons share two properties that distinguish them from true DAZ exons. First, their 5' or 3' splice sites have degenerated (FIG. 9). Second, these pseudoexons have not been found in any of the DAZ cDNA clones sequenced as described herein, suggesting that they are excised (as components of introns)

during processing of DAZ transcripts. The exon 7 derivative within the last of the 2.4 kb repeats may represent a tenth pseudoexon, as it has not been detected in any of the DAZ cDNA clones sequenced as described herein, though its splice sites appear to be intact.

Transposition, Amplification and Pruning

An examination of all available sequence information for the human Y-chromosomal DAZ and autosomal DAZH genes, cDNAs and encoded proteins suggests the following sequence of evolutionary events:

Transposition

A complete copy of the DAZH transcription unit was transposed from an autosome (now human chromosome 3) to the Y chromosome during primate evolution. This transposition occurred sometime prior to the splitting of the orangutan and human lineages, as indicated by the presence of male-specific, DAZ-homologous sequences in both species.

Expansion and Pruning of Transcription Unit

Within the newly transposed gene, a 2.4 kb genomic segment encompassing exons 7 and 8 was tandemly amplified, eventuating in a long array such as that observed in cosmid 63C9. In most of the amplified units, however, one or both of the exons degenerated or was deleted. For example, early in the course of the amplification process, a repeat unit arose in which exon 8 had been incapacitated by splice site mutations or other degenerative changes, and subsequent amplification of this unit gave rise to the present string of 2.4 kb repeats harboring a functional derivative of DAZH exon 7 and a vestige of DAZH exon 8. Only in the penultimate repeat were both exons 7 and 8 preserved. The transposed descendant of DAZH exon 9 degenerated without amplification. With this one exception, the pruned DAZ transcription unit retained one or more functional descendants of each DAZH exon.

Gene Amplification

The emerging DAZ transcription unit, having undergone internal duplications and substantial pruning, was amplified so that small numbers of transcription units exist in close proximity in the AZF region of the human Y chromosome. The present data provides direct evidence for the existence of at least two or three copies of DAZ exhibiting 99.9% sequence identity (two if nonoverlapping cosmids 18E8 and 46A6 derive from the same copy of DAZ). This is a minimum estimate of gene copy number; the true number of DAZ copies may be greater. Indeed, when either DAZ or DAZH probes are hybridized to human genomic Southern blots, the resulting male-specific DAZ bands are far more intense than the male-female-common DAZH bands, even though the DAZH gene is present in two copies per cell, unlike the Y chromosomal gene.

Given the well-documented polymorphism of the synonymous DYS1 sequence family, it is anticipated that the sequence of some DAZ gene copies may be more diverged, at least in some individuals. In fact, 11 nucleotide differences were observed between DAZ cDNA (GenBank Accession No. U21663) and genomic sequences, eight of these differences being in exons 7d and 7e. These differences could reflect sequence divergence among DAZ gene copies on a single Y chromosome, or they could reflect true polymorphisms that distinguish the individuals from whom cDNA and genomic libraries were prepared.

Preservation of Function

The DAZ gene cluster on the human Y chromosome arose from an autosomal ancestor, DAZH, via a series of structural transformations whose complexity could not have been anticipated. Nonetheless, it appears that the newly emergent Y gene cluster retained key functional characteristics of its autosomal ancestor. First, the sequence of the encoded protein was largely preserved. The products of DAZ and DAZH appear to be RNA-binding proteins whose sequences are, apart from the 24-residue tandem repeats in DAZ, quite similar throughout much of their lengths. Such preservation of the bulk of the mature transcript's reading frame is a remarkable outcome given that the DAZ transcription unit encompasses 26 exons and pseudoexons, as compared with 11 exons in DAZH.

Second, it appears that both the ancestral and the more recently derived members of the DAZ gene family are expressed exclusively in germ cells. Like its mouse homolog (*Dazh/Dazla*; Reijo et al., *Genomics* 35:346–352 (1996); Cooke et al., *Hum. Molec. Genet.* 5:513–516 (1996)), human DAZH is abundantly transcribed in adult testes and at a lower level in adult ovaries, while human DAZ, absent in females, is transcribed exclusively in testes. As demonstrated by the absence of transcripts in germ-cell deficient mice (white-spotted and Steel mutants), Dazh expression in testes is restricted to germ cells, and these mutant studies have recently been extended to ovaries, with identical results (J. Seligman, R. R., D. C. P., unpublished results). Thus, in both humans and mice, germ cells appear to be the only site of expression of the DAZ gene family.

It seems likely that the products of the ancestral gene, autosomal DAZH, and its derivative, Y-chromosomal DAZ, interact with similar or identical RNA targets in the same cell types. The similar azoospermic phenotypes associated with human DAZ deletions and with loss-of-function mutations in the Drosophila homolog suggest that the germ cell functions of the DAZ protein family may have been conserved throughout much of metazoan evolution. In humans, partial redundancy of Y-chromosomal DAZ and autosomal DAZH function could contribute to the variable nature of the spermatogenic defects caused by AZF deletion.

Conversely, mutations in DAZH could be responsible for spermatogenic defects in some men with intact Y chromosomes.

Evolution of the Y Chromosome

The case of human DAZ contradicts the prevailing view that most, if not all, Y-chromosomal genes were once shared with the X chromosome. The results presented herein strongly affirm that much of the gene content of the Y chromosome reflects the Y's common ancestry and ongoing meiotic and functional relationship with the X. A substantial fraction of human Y chromosomal genes and DNA sequences have X homolog (Vollrath et al., *Science* 258:52–59 (1992); Foote et al., *Science* 258:60–66 (1992); Affara et al., *Cytogenet. Cell Genet.* 73:33–76 (1996)). However, these results suggest that the Y chromosome's evolution and gene content may also be influenced by a process that is independent of the X chromosome. It is possible that the direct acquisition of autosomal genes that enhance male fertility is an important component of Y chromosome evolution. Selective pressures would favor this process, particularly if the genes transposed to the Y were of little or no benefit to females, and most especially if they diminished female fitness.

DAZ represents the first unambiguous example of autosome-to-Y transposition of a germ-cell factor, but diverse observations suggest that there may be other cases. Several other genes or gene families on the human, mouse or Drosophila Y chromosomes are expressed specifically in testes, where they likely function in spermatogenesis, and exhibit no evidence or Y homology. The human Y-chromosomal gene GBY, postulated to function in germ cell development in normal males but to cause germ cell tumors in sex-reversed XY females (Page, *Development* 101 *Suppl:*151–155 (1987)), may represent a "sexually antagonistic" locus that enhances male fitness but diminishes female fitness. Though not definitive, these observations suggest the possibility of autosome-to-Y transposition of male fertility factors may be a recurrent theme in Y chromosome evolution.

Regardless of chromosomal origin, genes transposed to the nonrecombining portion of the Y chromosome would inevitably face and likely succumb to powerful degenerative forces during subsequent evolution. Perhaps the rate of acquisition of male fertility factors approximates the rate of subsequent degeneration, resulting in an evolutionary steady state. In contrast to the extreme evolutionary stability of the X chromosome, at least in mammals, individual male fertility factors would not be long-lived, in an evolutionary sense, on the Y chromosome.

The present invention also includes the nucleotide sequences described herein, and their complements, which are useful as hybridization probes or primers for an amplification method, such as polymerase chain reaction (PCR), to show the presence, absence or disruption of the gene of the present invention. Probes and primers can have all or a portion of the nucleotide sequence (nucleic acid sequence) of the gene described herein or all or a portion of its complement. For example, sequences shown in Tables 1, 3 and 4 (SEQ ID NOS: 3–8 and 19–90) can be used, as well as the nucleotide sequence of SEQ ID NO: 15 or its complement. The probes and primers can be any length, provided that they are of sufficient length and appropriate composition (i.e., appropriate nucleotide sequence) to hybridize to all or an identifying or characteristic portion of the gene described or to a disrupted form of the gene, and remain hybridized under the conditions used. Useful probes include, but are not limited to, nucleotide sequences which distinguish between the DAZ gene and an altered form of the DAZ gene shown, as described herein, to be associated with reduced sperm count (azoospermia, oligospermia). Generally, the probe will be at least 7 nucleotides, while the upper limit is the length of the gene itself, e.g., up to about 40,000 nucleotides in length. Probes can be, for example, 10 to 14 nucleotides or longer; the length of a specific probe will be determined by the assay in which it is used.

In one embodiment, the present invention is a method of diagnosing reduced sperm count associated with an alteration in the gene referred to herein as the DAZ gene. Any man may be assessed with this method of diagnosis. In general, the man will have been at least preliminarily assessed, by another method, as having a reduced sperm count. By combining nucleic acid probes derived either from the isolated native sequence or cDNA sequence of the gene, or from the primers disclosed in Table 2, with the DNA from a sample to be assessed, under conditions suitable for hybridization of the probes with unaltered complementary nucleotide sequences in the sample but not with altered complementary nucleotide sequences, it can be determined whether the patient possesses the intact gene. If the gene is unaltered, it may be concluded that the alteration of the gene is not responsible for the reduced sperm count. This invention may also be used in a similar method wherein the hybridization conditions are such that the probes will hybridize only with altered DNA and not with unaltered sequences. The hybridized DNA can also be isolated and sequenced to determine the precise nature of the alteration associated with the reduced sperm count. DNA assessed by the present method can be obtained from a variety of tissues and body fluids, such as blood or semen. In one embodiment, the above methods are carried out on DNA obtained from a blood sample.

The invention also provides expression vectors containing a nucleotide (nucleic acid) sequence present in interval 6D of the distal portion of the long arm of the human Y chromosome, whose alteration is associated with reduced sperm count, and encoding a protein or peptide, which is operably linked to at least one regulatory sequence. "Operably linked" is intended to mean that the nucleotide sequence is linked to a regulatory sequence in a manner which allows expression of the nucleotide sequence. The term "regulatory sequence" includes promoters, enhancers, and other expression control elements (see, e.g., Goeddel, *Gene Expression Technology: Methods in Enzymology* 185, Academic Press, San Diego, Calif. (1990)). It should be understood that the design of the expression vector may depend on such factors as the choice of the host cell to be transformed and/or the protein or peptide desired to be expressed. For instance, the peptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17).

Prokaryotic and eukaryotic host cells transfected by the described vectors are also provided by this invention. For instance, cells which can be transfected with the vectors of the present invention include, but are not limited to , bacterial cells such as E. col, insect cells (baculovirus), yeast and mammalian cells, such as Chinese hamster ovary cells (CHO).

Thus, a nucleotide sequence described herein can be used to produce a recombinant form of the protein via microbial or eukaryotic cellular processes. Production of a recombinant form of the protein can be carried out using known techniques, such as by ligating the oligonucleotide sequence into a DNA or RNA construct, such as an expression vector, and transforming or transfecting the construct into host cells, either eukaryotic (yeast, avian, insect or mammalian) or prokaryotic (bacterial cells). Similar procedures, or modifications thereof, can be employed to prepare recombinant proteins according to the present invention by microbial means or tissue-culture technology.

The present invention also pertains to pharmaceutical compositions comprising the proteins and peptides described herein. For instance, the peptides or proteins of the present invention can be formulated with a physiologically acceptable medium to prepare a pharmaceutical composition. The particular physiological medium may include, but is not limited to, water, buffered saline, polyols (e.g.; glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous polypeptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents.

This invention also has utility in methods of treating disorders of reduced sperm count associated with alteration of the DAZ gene or a member of the DAZ gene family. These genes may be used in a method of gene therapy, whereby the gene or a gene portion encoding a functional protein is inserted into cells in which the functional protein is expressed and from which it is generally secreted to remedy the deficiency caused by the defect in the native gene.

The invention described herein also has application to the area of male contraceptives, since alteration of the DAZ gene produces the functional effects which are desirable in a male contraceptive, e.g., failure to produce sperm without other apparent physiological consequences. Thus, the present invention also relates to agents or drugs, such as, but not limited to, peptides or small organic molecules which mimic the activity of the altered DAZ gene product. Alternatively, the agent or drug is one which blocks or inhibits the activity or function of the unaltered DAZ gene (e.g., an oligonucleotide or a peptide). The ideal agent must enter the cell, in which it will block or inhibit the function of the DAZ gene, directly or indirectly.

The present invention is also related to antibodies which bind a protein or peptide encoded by all or a portion of the intact genes of the present invention, as well as antibodies which bind the protein or peptide encoded by all or a portion of a disrupted form of the gene. For instance, polyclonal and monoclonal antibodies which bind to the described polypeptide or protein are within the scope of the invention. A mammal, such as a mouse, hamster or rabbit, can be immunized with an immunogenic form of the protein or peptide (an antigenic fragment of the protein or peptide which is capable of eliciting an antibody response). Techniques for conferring immunogenicity on a protein or peptide include conjugation to carriers or other techniques well known in the art. The protein or peptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)). Such antibodies are useful as diagnostics for the intact or disrupted gene, and also as research tools for identifying either the intact or disrupted gene.

The invention will be further illustrated by the following non-limiting exemplifications:

EXAMPLES

Azoospermic Males

Figures 5A, 5B, 5C:
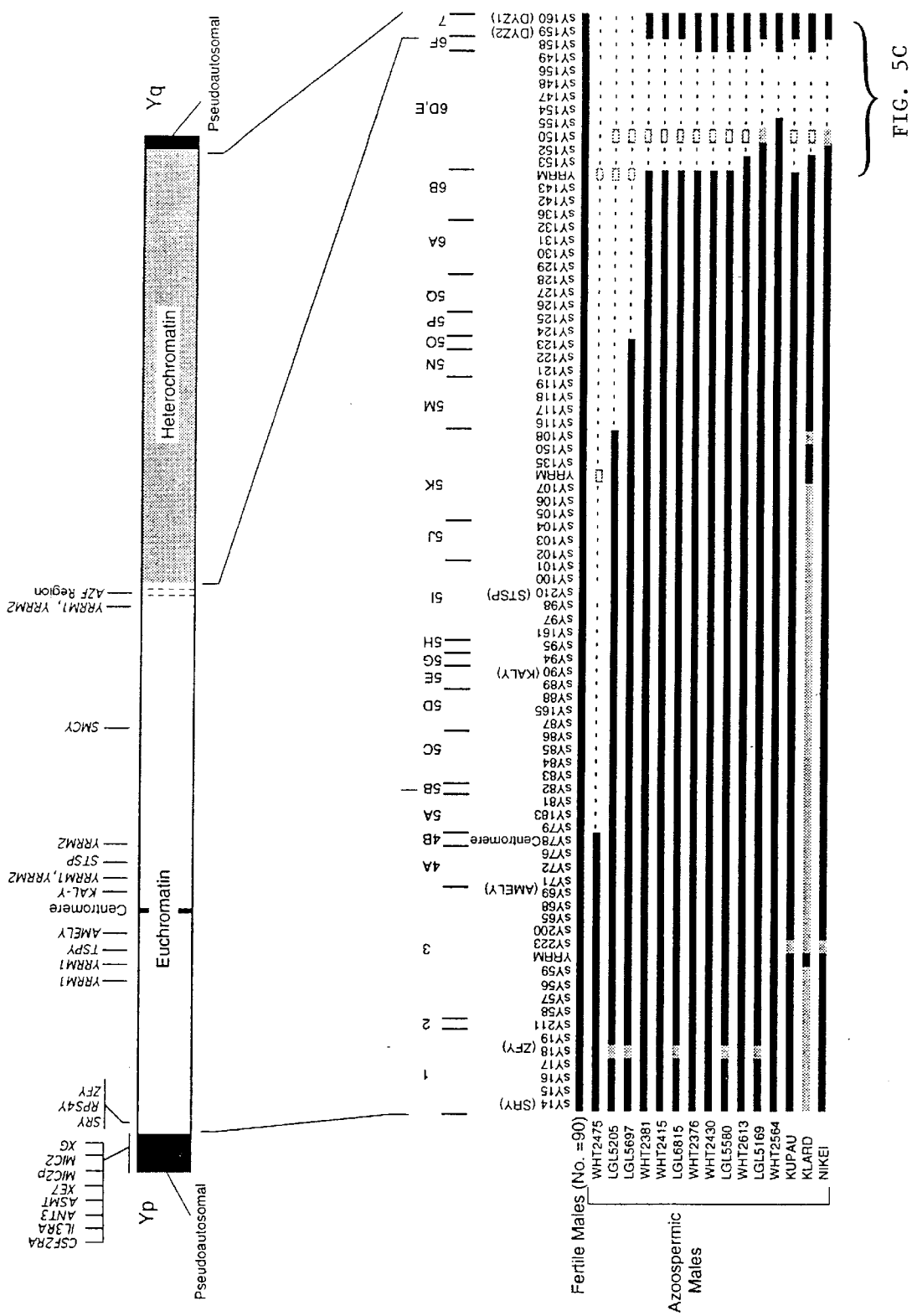
FIGS. 5A, 5B and 5C show the chromosomal STSs, both new and previously published, which were tested for in DNA samples from men with reduced sperm count.
Figure 5C:
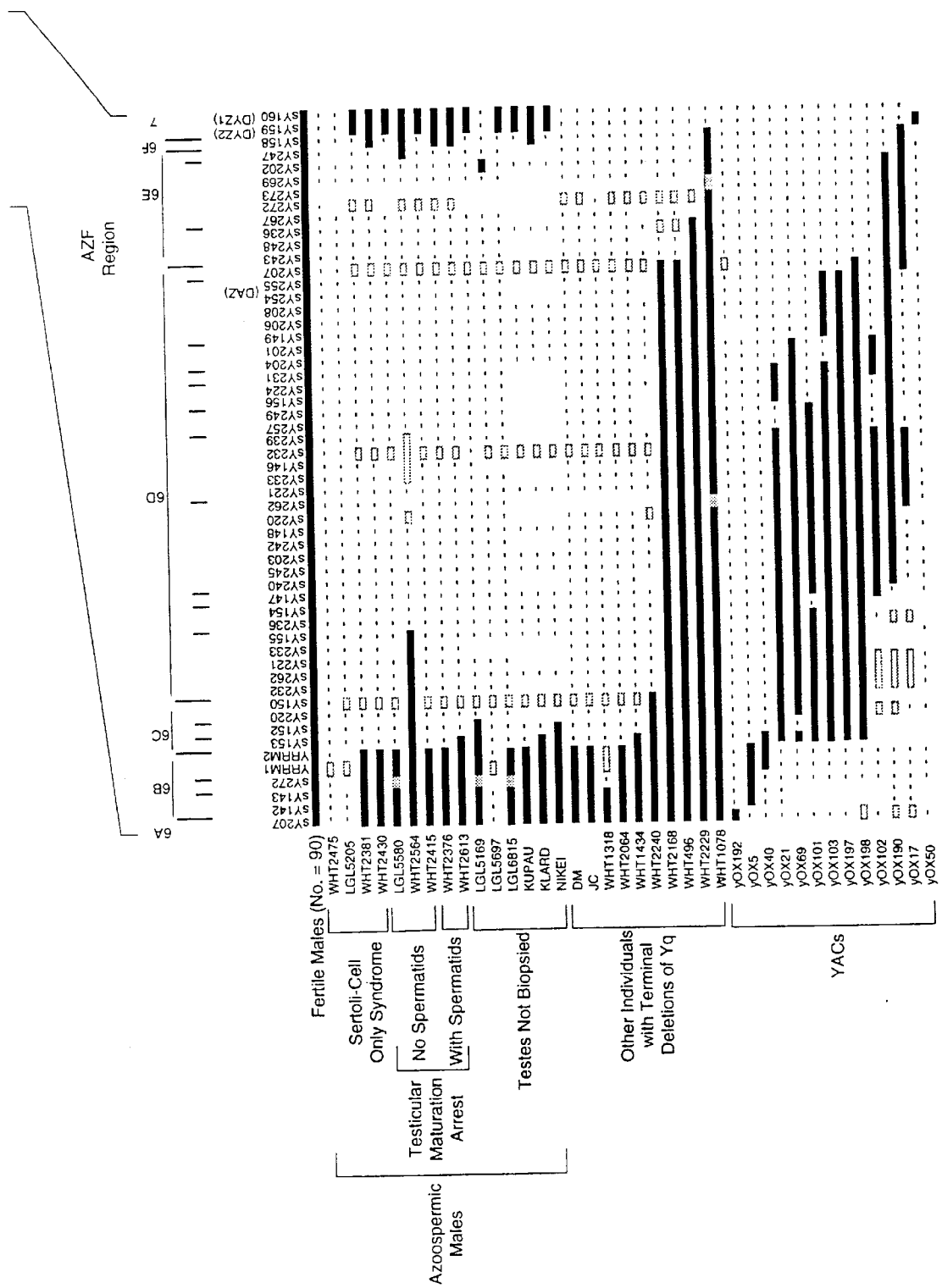

Blood samples were obtained from 71 infertile human males who had testes biopsies. These biopsies showed 32 patients with Sertoli-cell only syndrome, 30 patients with Testicular Maturation Arrest, and 3 patients with both Sertoli-cell only and Testicular Maturation Arrest. Six additional undiagnosed azoospermic males were examined as well. Sequence-tagged sites (STS) from existing Y chromosome maps (Foote, et al., *Science*, 258:60–66, (1992)), were incorporated with new STSs to serve as markers to assay (FIGS. 5A, 5B and 5C). The Y chromosomes of the 71 patients were studied for abnormalities, especially deletions. The presence of each marker was determined by polymerase chain reaction (PCR) amplification and scoring the presence of the product after agarose gel electrophoresis. The PCR conditions consisted of a 5 minute cycle at 94° C., 35 cycles consisting of 1 minute at 94° C., 1.5 minutes at 58° C. and 1 minute at 72° C, and a final 5 minutes at 72° C. Absence of a marker indicated deletion of the region of the chromosome corresponding to that STS. Nine patients were found to have deletions in the Y chromosome. Six of the fathers of these 9 males were screened and no deletions were found, indicating a de novo mutation. The deletions in 8 of the 9 patients were found to be overlapping and within the 6D deletion interval of the Y chromosome (D. Vollrath et al., *Science* 258:52–59 (1992)). The one non-overlapping deletion was more proximal on the chromosome, possibly indicative of another gene or region for future study.

Yeast artificial chromosomes (YACs) that spanned the 6D interval were identified. The ends of these YACs were sequenced by ABI automated sequencing to isolate new markers to refine the Y chromosome maps. Additional markers were constructed using subtraction techniques (Rosenberg et al. (1994)). Pooled markers were then used as probes to obtain 5-fold cosmid coverage from the Lawrence Livermore Chromosome Y Cosmid Library LLOYCN03"M". This produced 124 cosmids, 76% of which contain STSs that fall in the 6D deletion interval. Sixty cosmids were subcloned from yOX17, a 920-kb YAC spanning most of the deletion region. Three P1 clones containing marker sy202 were obtained from Genome Systems to provide fuller coverage of the distal region.

Cosmid #316 (Lawrence Livermore address: Plate 35, row G, column 3), cosmid #325 (Lawrence Livermore address: Plate 48, row D, column 5) and cosmid #330 (Lawrence Livermore address: Plate 59, row H, column 4) were obtained by hybridization. These cosmids were subcloned into exon-trapping vector pSPL3, a vector containing splice donor and acceptor sites. This vector was then transfected into mammalian COS-7 cells according to the exon-trapping system of GibcoBRL/Life Technologies, Cat. No. 18449-017. The exon-trapped exons were then amplified and sequenced using polymerase chain reactions (PCR) and automated sequencing.

The results of the exon-trapping and sequencing indicated that there was one clear cut transcription unit in the interval of interest. The blood DNA of the 8 patients was then probed with a pair of primers from within the gene to confirm that this sequence was indeed missing in males with reduced sperm count. Table 1 list primers used to confirm that this gene is missing in infertile men with reduced sperm counts. Study of tissue from the spleen, thymus, prostate, ovary, small intestine, colon, leukocytes and testis indicate that the DAZ transcript is primarily expressed in the testis.

TABLE 1

| OLIGO NO. | SEQUENCE | EXON CLONE# | PAIR WITH | PRODUCT SIZE | Yspec. larger | sY No. |
|---|---|---|---|---|---|---|
| 3115 | GGGTGTTACCAGAAGGCAAA (SEQ ID NO: 3) | ET316-13;-10 | 3116 | 400 | yes | 254 |
| 3116 | GAACCGTATCTACCAAAGCAGC (SEQ ID NO: 4) | ET316-13;10 | 3115 | 400 | | |
| 3123 | GTTACAGGATTCGGCGTGAT (SEQ ID NO: 5) | ET325-17 | 3124 | 125 | yes | 258 |

TABLE 1-continued

| OLIGO NO. | SEQUENCE | EXON CLONE# | PAIR WITH | PRODUCT SIZE | Yspec. larger | sY No. |
|---|---|---|---|---|---|---|
| 3124 | CTCGTCATGTGCAGCCAC (SEQ ID NO: 6) | ET325-17 | 3123 | 125 | | |
| 3125 | GCTGCAAATCCTGAGACTCC (SEQ ID NO: 7) | 330-13/23 | 3126 | 102 | yes | 255 |
| 3126 | TTTGCCTTCTGGTAACACCC (SEQ ID NO: 8) | 330-13/23 | 3125 | 102 | | |

The sequenced exons produced by the exon-trapping. system were then used in a hybridization screen against a Clonetech genomic adult human cDNA XDR2 testes library. One hundred cDNAs were obtained, and two, which contained the same primer bands (#3115-16 and #3125-26) as seen in the original blood sample, were sequenced. The nucleotide sequences of these cDNAs (#66B and 98B) are shown in FIG. 1 (SEQ ID NO: 1) and FIG. 2 (SEQ ID NO: 2).

The sequenced exons were also analyzed by GRAIL, FASTN and BLAST to identify potential coding regions and/or homology with known sequences. From this resulting data, it was determined that the DAZ gene is a member of the gene family encoding RNA binding proteins such as poly-A binding protein, hnRNPa1, sex lethal, and a previously identified Y-chromosome gene, YRRM. The nucleotide sequence bears little resemblance to any of these family members, but the RNA binding domains are conserved at the protein level. The closest relative appears to be poly-A binding protein (see Table 2).

TABLE 2

| | RNA Binding Domain | |
|---|---|---|
| | RNP2 | RNP1 |
| RNA BINDING CONSENSUS SEQUENCE: | LFVGNL (SEQ ID NO:9) or IYIKGM (SEQ ID NO:10) | KGYGFVXF (SEQ ID NO:12) |
| POLY-A BINDING PROTEIN: | LFVGNL | KGYGFVNF (SEQ ID NO:13) |
| DAZ: | LFVGGI (SEQ ID NO:11) | KGYGFVSF (SEQ ID NO:14) |

The results of a Northern Blot performed on the exons obtained from exon-trapping showed that the total gene is approximately 3.1 kb. The three cDNAs currently sequenced, #66B, 93B and 98B (pDP #1575, #1576 and #1577), contain a total of 2.5 kb of the sequence. The rest of the sequence was obtained by probing a Clonetech genomic adult human cDNA XDR2 testes library with the ends of the known sequences and using PCR to amplify and sequence the sequence obtained thereby. A RACE protocol (5'-Amplifinder; Clontech) was used to capture the 5' portion of the DAZ transcript. Human adult testis RNA was employed as the starting template and the following two DAZ oligonucleotides were used as gene-specific primers: AAC-GAAACAAATCCATAGCCTTTG (SEQ ID NO: 16) for cDNA synthesis and CTCGCTCGCCCAGAACCGTATC-TACCAAAGCA (SEQ ID NO: 17) for secondary amplification. The resulting PCR product (approximately 500 bp) were cloned (TA cloning system; Invitrogen) and sequenced.

Testing for Y-specific STSs

Many Y chromosomal STSs which were tested for (FIGS. 5A–C) were described previously (Vollrath et al., Science 258:52–59 (1992)). The remaining STSs are listed in Table 3 and were generated by nucleotide sequencing of 1) ends of YAC inserts, 2) YAC subtraction products,or 3) exon trapping products. YAC-insert ends were captured by inverse PCR (Haldi et al., Genomics 24:478–484 (1995)) following digestion with HaeIII, AluI and TaqI. Oligonucleotide primers were selected so that nearly all PCR assays could be carried out under identical conditions (Vollrath et al., Science 258:52–59 (1992)). YRRM primers were as described in Ma et al. (Cell 75:1287–1295 (1993) and corrected in Kobayashi et al. (Hum. Mol. Genet. 3:1965–1967 (1994)).

Human genomic DNAs were prepared from blood or lymphoblastoid cell lines. PCR was performed in v-bottom, 96-well plates (MJ Research) in 20 μl volumes in 1.5 mM MgCl$_2$, 5 mM NH$_4$Cl, 10 mM tris (pH 8.2), 50 mM KCl, 100 μM dNTP's, with 1 unit of Taq DNA polymerase, 100 to 200 ng of human genomic DNA per reaction, and each primer at 1 μM. Thermocycling usually consisted of an initial denaturation of 5 minutes at 94° C.; 35 cycles of 1 minute at 94° C., 1.5 minutes at 58° C., 1 minute at 72° C.; and, finally, 5 minutes at 72° C. As indicated in Table 3, certain primer pairs were annealed at 62° C (indicated with an asterisk). Reactions were stored at 4° C. until they were loaded onto 2 to 4% agarose gels for analysis.

TABLE 3

| STS | Left Primer | Right Primer | Product Size (bp) |
|---|---|---|---|
| sY201* | TGTTGTACGTAGAAAAAGGATATTTTACC (SEQ ID NO: 30) | ATATGGTAAACCACTTTTTAAAATTGCCA (SEQ ID NO: 31) | 99 |
| sY02 | ACAGTTTGAAATGAAATTTTAAATGTGTT (SEQ ID NO: 32) | TGACAAAGTGAGACCCTACTACTA (SEQ ID NO: 33) | 121 |
| sY03 | AAGGATATTTTACCTTTGGTAAT (SEQ ID NO: 34) | GTGGAGCAGTGACCTGAAAT (SEQ ID NO: 35) | 157 |
| sY204 | CCTTTGGTAATATTTTGGTTATAT (SEQ ID NO: 36) | ACTTGGATAA GCAGGAAATG GCTG (SEQ ID NO: 37) | 119 |
| sY206 | ACAGAATTTCAGTTGTATTTTTATTT | ACCCTCCAAGATATTAATTCTTTG | 143 |

TABLE 3-continued

| STS | Left Primer | Right Primer | Product Size (bp) |
|---|---|---|---|
| | (SEQ ID NO: 38) | (SEQ ID NO: 39) | |
| sY207 | AATTAAAGGACCCTTAAATTCATT (SEQ ID NO: 40) | CCTCTGAAAGATTAATATATGGTTCT (SEQ ID NO: 41) | 153 |
| sY208 | GGACATAGTCCTGCTTAAGAAAAGTGG (SEQ ID NO: 42) | ACGTGGTTCAGGAGGTCTACTATTCTA (SEQ ID NO: 43) | 140 |
| sY220 | ATGGGTGAGAAGCCTGATTGT (SEQ ID NO: 44) | TGGGAAAGCCTGAACTGCC (SEQ ID NO: 45) | 109 |
| sY221 | GTAAGCCCCAGATACCCTCC (SEQ ID NO: 46) | AAATTGTTTGGAAAAGGACACC (SEQ ID NO: 47) | 113 |
| sY224 | ATAGTTAGTTTTGTGGTAACAT (SEQ ID NO: 48) | CATAGCCTCTATGCAGATGGG (SEQ ID NO: 49) | 158 |
| sY231 | ATTGATGTGTTGCCCCAAT (SEQ ID NO: 50) | AGAGTGAACTTTAAATCCCAGCC (SEQ ID NO: 51) | 149 |
| sY232 | GACTCTACCACTTGGGCTCAATTT (SEQ ID NO: 52) | AGATGTACCCAAGGCCACTG (SEQ ID NO: 53) | 91 |
| sY233 | AGTTAGTAAGCCCCAGTTATCCTCC (SEQ ID NO: 54) | TTTGGAAAAGGACACCTTATTAGCCA (SEQ ID NO: 55) | 115 |
| sY236 | CCCCATCGGTAAACCAAATCA (SEQ ID NO: 56) | CCCATTGAAGTTTCAAGGTGTCA (SEQ ID NO: 57) | 94 |
| sY239 | CATTCATCTTCCCTTTTGAAGG (SEQ ID NO: 58) | ATGCAAGTCGCAGGAAATCT (SEQ ID NO: 59) | 200 |
| sY240 | TCAAATAGCAGCAATTTAATAT (SEQ ID NO: 60) | GCACCTGAAGAGCTGCTTG (SEQ ID NO: 61) | 247 |
| sY242 | ACACAGTAGCAGCGGGAGTT (SEQ ID NO: 62) | TCTGCCACTAAACTGTAAGCTCC (SEQ ID NO: 63) | 233 |
| sY243 | GTTTCTTCATAAGCAACCAAATTG (SEQ ID NO: 64) | CAGATTATGCCACTGCCCTT (SEQ ID NO: 65) | 118 |
| sY245 | TTACTTCCTTAAGTCAAAGCGG (SEQ ID NO: 66) | CTGAGACAGCAAGACCAATCC (SEQ ID NO: 67) | 101 |
| sY247 | CTGGACAAAGCCTTGGAAAA (SEQ ID NO: 68) | CTGCATGTCAATTGTGGGAC (SEQ ID NO: 69) | 114 |
| sY248 | CATTGGCATGAATGTGTATTC (SEQ ID NO: 70) | CTCTGGGACAAGTGTTCCTT (SEQ ID NO: 71) | 94 |
| sY249 | GACAAAGGGCTGATGATTTA (SEQ ID NO: 72) | CATCACCTTTACTTTTTAAATGG (SEQ ID NO: 73) | 114 |
| sY254* | GGGTGTTACCAGAAGGCAAA (SEQ ID NO: 74) | GAACCGTATCTACCAAAGCAGC (SEQ ID NO: 75) | 107 |
| sY255* | GTTACAGGATTCGGCGTGAT (SEQ ID NO: 76) | CTCGTCATGTGCAGCCAC (SEQ ID NO: 77) | 126 |
| sY257 | AGGTTGTTTGGCCTTGAGC (SEQ ID NO: 78) | TCTATGATCTGTACCCGGTGC (SEQ ID NO: 79) | 123 |
| sY262 | AGCTCACTGCAAGCAACAGA (SEQ ID NO: 80) | CCACCATCCCCCTTCTTC (SEQ ID NO: 81) | 100 |
| sY267 | GAATGTGTATTCAAGGACTTCTCG (SEQ ID NO: 82) | TACTTCCTTCGGGGCCTCT (SEQ ID NO: 83) | 102 |
| sY269 | CTCTGGGACAAGTGTTCCTTG (SEQ ID NO: 84) | CATTGGCATGAATGTGTATTCA (SEQ ID NO: 85) | 94 |
| sY272 | GGTGAGTCAAATTAGTCAATGTCC (SEQ ID NO: 86) | CCTTACCACAGGACAGAGGG (SEQ ID NO: 87) | 93 |
| sY273 | GGTCTTTAAAAGGTGAGTCAAATT (SEQ ID NO: 88) | AGACAGAGGGAACTTCAAGACC (SEQ ID NO: 89) | 95 |

Individual Y-derived YACs (Foote et al., *Science* 258:60–66 (1992)) were also tested for STSS, in which case 5 to 10 ng of total yeast genomic DNA were employed as template and an annealing temperature of 62° C. was used.

YAC subtraction

The subtraction protocol of Rosenberg et al. (*Proc. Natl. Acad. Sci. USA* 91:6113–6117 (1994)) was modified for use with YAC DNAs. DNAs from 66 overlapping YACs spanning most of the Y chromosome's euchromatic region (Foote et al., *Science* 258:60–66 (1992)) were separated from yeast chromosomes by pulsed-field electrophoreses on 1.2% low-melt agarose gels, excised and purified using Geneclean (Bio 101). "Tracer" was prepared using DNA pooled from eight overlapping YACs (yOX69, yOX101, yOX102, yOX103, yOX104, yOX190, yOX192, yOX198) blanketing the AZF region. 100 ng of this DNA was digested with SAu3A and ligated to Sau3A-compatible PCT adapter (an equimolar mixture of GACACTCTCGAGACATCAC-CGTCC (SEQ ID NO: 90 and phosphorylated GATCG-GACGGTGATGTCTCGAGAGTG (SEQ ID NO: 91). "Drivers" were prepared from total yeast genomic DNA (strain AB1380) and from DNA pooled from 58 YACs spanning the remainder of the euchromatic portion of the Y chromosome. Yeast genomic DNA (1 µg) or pooled YAC DNA (100 ng) was sonicated to an average length of 1 kb, treated with Klenow fragment of DNA polymerase to produce blunt ends, and ligated to blunt-end PCR adapter (an equimolar mixtures of AATTCTTGCGCCTTAAACCAAC (SEQ ID NO: 94 and phosphorylated GTTGGTTTAAG-GCGCAAG (SEQ ID NO: 95). Tracer and driver DNAs were then amplified separately using oligonucleotides Ol25 and OL31DB, respectively, as PCR primers (*Proc. Natl. Acad. Sci. USA* 91:6113–6117 (1994)). Subtractive hybridizations were carried out as previously described after combining the following in a total volume of 4 µl: 4 ng of amplified tracer DNA; 7 µg of amplified, biotinylated YAC driver DNA; 3 µg of amplified, biotinylated yeast genomic driver DNA; 20 µg of yeast tRNA; 5 µg of oligonucleotide OL30; and 2 μg of oligonucleotide OL25. Individual products of subtraction were sequenced after digesting bulk product with Sau3A and cloning into the BamHI site of plasmid pBluescript KS(+)(Stratagene). To increase the sequence complexity of the subtraction product, an additional round of subtractive hybridization was performed using, as a third driver, 2 μg of DNA from 130 subtraction clones that had been pooled, amplified, and biotinylated as described above. The resulting subtraction product, in bulk, was radiolabeled and hybridized to high-density arrays of an 11,700-clone, Y-enriched cosmid library (LL0YNC03; Human Genome Center, Lawrence Livermore National Laboratory, Livermore, Calif.) according to the procedure of Holland et al. (*Genomics* 15:297–304 (1993)), resulting in identification of 120 cosmid clones.

Exon trapping

Substrates for exon trapping (Duyk et al., *Proc. Natl. Acad. Sci. USA* 87:8995–8999 (1990)) included 120 cosmids identified by hybridization to YAC subtraction product, 60 cosmids constructed by subcloning YAC yOX17 in Super-Cos1 (Stratagene), and three P1 clones identified by commercial screening (Genome Systems). These genomic clones were digested with BamHI and BglII, individually subcloned into pSPL3 (Gibco-BRL) and transfected into COS7 cells. After 48 hours growth, RNA was harvested using Trizol (Gibco-BRL). cDNA was synthesized, and clones that contained potential intron-exon boundaries were identified by PCR using primers flanking the cloning sites. These exon trapping products were sequenced, and from these sequences STSs wee developed.

Characterization of potential exons Exon trapping products whose corresponding STSs were male-specific and mapped to the AZF region were further characterized, including exon 325.7 (subcloned as plasmid pDP1593), which proved to derive from the DAZ gene. To confirm male specificity and to look for evidence of transcription, potential exons were labeled with $^{32}$P-dCTP by random priming and hybridized to Southern and Northern blots as previously described (Fisher et al., *Cell* 62:1205–1218 (1990)). Putative exons were then used as hybridization probes in screening a cDNA library (HL1161X, Clontech) constructed by oligo (dT) priming of mRNA from the testes of four human adults; hybridization (at 47° C.) and washing conditions were as published (Fisher et al., *Cell* 62:1205–1218 (1990)). Nucleotide sequencing of DAZ cDNA clones was performed as previously described (Fisher et al., *Cell* 62:1205–1218 (1990)). Since the composite length of DAZ cDNA clones was considerably shorter than the 3.5-kb transcript observed on Northern blots, a RACE protocol (5'-Amplifinder; Clontech) was used to capture the 5' portion of the DAZ transcript. Human adult testis RNA was employed as a starting template and the following two DAZ oligonucleotides as gene-specific primers: AACGAAACAAATCCAT-AGCCTTTG (for cDNA synthesis; SEQ ID NO: 92) and CTCGCTCGCCCAGAACCGTATCTACCAAAGCA (for secondary amplification; SEQ ID NO: 93). The resulting PCR-products (approximately 500 bp) were cloned (TA cloning system; Invitrogen) and sequenced.

Oligospermic Males

Idiopathic oligospermia, defined as the presence of less than 20 million sperm per ml of semen, is the most common cause of male infertility. About three to four percent of men have severe defects in sperm production resulting in oligospermia, a principal or contributing factor in perhaps one fifth of infertile couples. Progress toward medical therapies to correct oligospermia has been slow, at least in part, because the etiology of the disorder is not understood. In particular, little is known about the possible contributions of genetic factors.

The wide range of testicular histologies observed in azoospermic men with AZF deletions allowed for the possibility that less severe spermatogenic defects could also be caused by AZF's absence. What if the Azoospermia Factor is not absolutely required for completion of spermatogenesis? Though the AZF gene or gene family was originally defined and more recently mapped in the context of azoospermia, it was questioned whether the gene's absence might sometimes result in oligospermia. Indeed, in a few cases, Y chromosomal variants have been reported in oligospermic men (Kobayashi et al., *Hum. Mol. Genet.* 3:1965–1967 (1994)), but in no case prior to the current study was the variant shown to be a de novo mutation, and thus no causal link could be established. In searching for such definitive evidence of causality, these studies were further focused on men with severe oligospermia.

Screening for Y Chromosomal Deletions

Severely oligospermic men were screened for Y chromosome deletions using DNA probes. Cytologically, the Y chromosome consists of a euchromatic region and a heterochromatic region. As the heterochromatin appears to be dispensable with regard to fertility (Andersson et al., *Hum. Genet.* 79:2–7 (1988); Borgaonkar and Hollander, *Nature* 230:52 (1971)), the concentration was on the euchromatin, for which a comprehensive map of ordered DNA landmarks and overlapping recombinant DNA clones has been assembled (Vollrath et al., *Science* 258:52–59 (1992); Foote et al., *Science* 258:60–66 (1992)). Genomic DNAs were prepared from peripheral blood samples (Page et al., *Cell* 51:1091–1104 (1987)) from 35 men with total motile sperm counts (per ejaculate) of 40,000 to 1 million. Using the polymerase chain reaction (PCR), each oligospermic man was tested for the presence of 118 Y-DNA landmarks (more precisely, STSs, or sequence-tagged sites) previously shown to blanket the euchromatic region of the Y chromosome. Two precautions were taken to minimize false negative results. First, only PCR assays that reliably gave positive results when tested on 90 fertile men were used. Second, an STS was not recorded as absent from a patient unless at least three successive attempts at PCR amplification yielded negative results.

Sperm DNA

In the case of patient WHT2712, spermatozoa were purified from ejaculate by centrifugation on a MiniPercoll gradient (Ord et al., *Hum. Reprod.* 5:987–989 (1990)). To prepare DNA, 50,000 sperm were incubated for 1 hour at 37° C. in 20 μl of a solution containing 0.05 mg/ml proteinase K, 50 mM KCl, 10 mM Tris pH 8.3, 1.5 mM MgCl$_2$, 20 mM dithiothreitol, and 1.7 μM sodium dodecyl sulfate. Proteinase K was then inactivated by heating the samples to 85° C. for 5 minutes, and 100 μl of PCR mix (containing 1.5 mM MgCl$_2$, 5 mM NH$_4$Cl, 10 mM Tris (pH 8.2), 50 mM KCl, and 100 μM dNTP's) was added to each sample (Gyllensten et al., *PCR Protocols* 1:300–306 (1990), Innis et al., eds.). This sperm DNA was tested for a subset of the Y-chromosomal landmarks by PCR.

Y-chromosomal STSs

Most of the Y-chromosome STSs which were tested for (FIGS. 5A–5C), as well as the PCR and electrophoresis conditions employed, were described previously (Vollrath et al., *Science* 258:52–59 (1992); Reijo et al., *Nature Genet.* 10:383–393 (1995)). Six new STSs were developed for this study, and their designations and oligonucleotide primer sequences are shown in Table 4.

TABLE 4

| STS | Gene | Left Primer | Right Primer | Product Size (bp) |
|---|---|---|---|---|
| sY277 | DAZ | GGGTTTTGCCTGCATACGTAATTA (SEQ ID NO: 18) | CCTAAAAGCAATTCTAAACCTCCAG (SEQ ID NO: 19) | 275 |
| SsY279 | DAZ | CCACCTCATGGTAGTAAAATTGTA (SEQ ID NO: 20) | CTCTTATTTATCTTATTGCTACAACG (SEQ ID NO: 21) | 150 |
| sY283 | DAZ | CAGTGATACACTCGGACTTGTGTA (SEQ ID NO: 22) | GTTATTTGAAAAGCTACACGGG (SEQ ID NO: 23) | 375 |
| sY274 | RPS4Y | TTAAGGGGACAGTATTTCAACTTC (SEQ ID NO: 24) | CCACATTTAAACTGAGTACAGTCC (SEQ ID NO: 25) | 350 |
| sY238 | ZFY | AACAAGTGAGTTCCACAGGG (SEQ ID NO: 26) | GCAAAGCAGCATTCAAAACA (SEQ ID NO: 27) | 350 |
| sY276 | AMELY | CCTACCGCATCGTGAATTTC (SEQ ID NO: 28) | TCTGTATGTGGAGTACACATGG (SEQ ID NO: 29) | 200 |

Identification and Characterization of DAZH

DAZH-Specific PCR Assay

A single pair of primers, one located in DAZH exon 8 (GGAGCTATGTTGTACCTCC; SEQ ID NO: 99) and the other in DAZH exon 9 (GTGGGCCATTTCCAGAGGG; SEQ ID NO: 100), was used in PCR screening of a BAC library, in typing of radiation hybrids and in RT-PCR assays. These primers yield a 128-bp product from DAZH cDNA clones and a 0.8-kb product from human genomic DNA. This assay does not co-amplify DAZ genomic or cDNA sequences; in DAZ, the homolog of DAZH exon 9 is a pseudoexon (FIG. 9). PCR was performed in 20 μl volumes of 1.5 mM MgCl$_2$, 5 mM NH$_4$Cl, 10 mM Tris (pH 8.3), 50 mM KCl, 100 μM dNTPs, with 1 U Taq DNA polymerase and 1 μM of each primer. Thermocycling conditions were an initial denaturation of 3 minutes at 94° C.; 35 cycles of 1 minute at 94° C., 1.5 minutes are 56° C., 1 minute at 72° C.; and, finally, 5 minutes at 72° C. RT-PCR (cDNA cycle kit, Invitrogen, San Diego, California) was performed on 100 ng of total RNA from each of five human tissues (Clontech, Palo Alto, Calif.).

Chromosomal Fluorescence In Situ Hybridization

DAZH clone 30K13 was isolated from the human genomic BAC library of Shizuya et al. (*Proc. Natl. Acad. Sci. USA* 89:8794–8797 (1992)) (Research Genetics, Huntsville, Alabama) by PCR screening. Thus BAC was labeled with biotin-11 dATP by nick translation (Gibco BRL, Gaithersburg, Maryland). Metaphase chromosomes were prepared from human male lymphocytes using 75 mM KCl as hypotonic buffer and methanol/acetic acid (3:1 v/v) as fixative. Hybridization was carried out as previously described (Chance et al., *Cell* 72:143–151 (1993)) and signals were detected using a commercial system (Vector, Burlingame, Calif.). The slides were blocked with goat serum, incubated with fluorescein avidin DCS, and rinsed in 4x SSC, 0.03% Triton. Slides were then incubated with biotinylated anti-avidin D and rinsed again. A second incubation with fluorescein avidin DCS was followed by a final rinse. Chromosomes were banded using Hoechst 33258-actinomycin staining and propidium iodide counterstaining. Chromosomes and hybridization signals were visualized by fluorescence microscopy using a dual band pass filter (Omega, Brattleboro, Vt.).

Radiation Hybrid Mapping

DNAs from the 93 hybrid cell lines of the GeneBridge 4 panel (Gyapay et al., *Hum. Molec. Genet.* 5:339–346 (1996))(Research Genetics) were tested for DAZH by PCR. Analysis of the results unambiguously positioned DAZH with respect to the radiation hybrid framework map constructed at the Whitehead/MIT Center for Genome Research (Hudson et al., *Science* 270:1945–1954 (1995)).

Northern and Southern Blotting

A DAZH-specific hybridization probe was derived from DAZH cDNA clone pDP1648 by PCR using the primers described above. This probe, labeled by incorporation of $^{32}$P-dCTP during PCR, was hybridized overnight to Northern blots of human tissue RNAs (Clontech, Palo Alto, Calif.) at 65° C. in 1 M sodium phosphate (pH 7.5), 7% SDS. Blots were washed three times for 20 minutes each at 57° C. in 0.1x SSC, 0.1% SDS.

For Southern blotting the purified insert of DYS1 plasmid p49f (Bishop et al., *J. Mol. Biol.* 173:403–417 (1984)) was $^{32}$P-labeled by random-primed synthesis and hybridized overnight using the conditions just described, except that blots were washed at 42° C. in 2x SSC, 0.1% SDS.

Genomic DNA Sequencing

AZF-region cosmids were selected from a Y-enriched library (LL0YNC03) constructed at the Human Genome Center, Lawrence Livermore National Laboratory, Livermore, California. A complete description of the methodology employed in sequencing cosmids 63C9, 46A6 and 18E8 is in preparation (T. L. H. et al., in preparation); the nucleotide sequence of cosmid 46A6 is shown in FIGS. 11A–L (SEQ ID NO: 101), and the nucleotide sequence of cosmid 63C9 is shown in FIGS. 12A–K (SEQ ID NO: 102). Briefly, M13 and pUC libraries were prepared from each cosmid, and standard dye-primer based shotgun sequencing methods were used to obtain six-fold coverage, on average, of the cosmid insert. The sequence was completed using primer-directed chemistries and directed reverse reads. Further information on the sequencing project can be found at http://www.genome.wi.mit.edu.

De Novo AZF Deletions in Two Oligospermic Men

Y chromosome deletions were detected in two men, both of whom were severely oligospermic and had poor sperm motility and morphology. In the first patient, WHT2615, repeated semen analyses yielded sperm counts of 50,000 to 100,000 per ml, with 20 to 30% of sperm motile and 10% of sperm with normal morphology. In the second patient, WHT2712, repeated semen analyses yielded sperm counts of 40,000 to 90,000 per ml, with 30 to 40% of sperm motile and 10 to 25% of sperm with normal morphology. Apart from infertility, these two unrelated individuals were in good health.

In both WHT2615 and WHT2712, deletions of small, interstitial portions of Yq, the long arm of the Y chromosome, were discovered. In both men the presence of the bulk of the Y chromosome was detected, including the sex-determining gene SRY as well as RPS4Y, ZFY, YRRM, TSPY, AMELY, the centromere, and the heterochromatic region. However, in WHT2615 and WHT2712, the absence of 43 and 44, respectively, of the 118 Y-chromosomal STSs (sequence-tagged sites) tested were detected. The absent STSs are all clustered in the AZF region, the portion of Yq commonly deleted in azoospermic men, and they include the DAZ gene. The Yq deletions observed in the two oligospermic men overlap substantially, not only with each other but also with the deletions previously observed in azoospermic men.

If the Yq deletions actually caused the severe oligospermia in WHT2615 and WHT2712, then one would expect the deletions to represent new mutations not present in their fathers. Both fathers were found to carry intact Y chromosomes, leading to the conclusion that the deletions of the AZF region are the cause of oligospermia in these two cases.

AZF-Deleted. Y-Bearing Sperm

The Y-DNA tests described in the previous section were all performed on blood, a conventional and readily accessible source of DNA for genetic testing. However, the finding of AZF-region deletions in leukocytes from oligospermic men raised important questions about the DNA in their sperm. If AZF if absolutely required for completion of spermatogenesis, then one might suppose that the sperm produced by the two oligospermic men under study could carry either an X or an intact Y chromosome, but never an AZF-deleted Y chromosome. This would be possible if the two oligospermic men under study are testicular mosaics for a cell line with an intact Y chromosome, in which case the de novo AZF deletions reported would have arisen as somatic mutations, after fertilization, rather than in the fathers' germlines. On the other hand, if these oligospermic men produce some sperm carrying AZF deleted Y chromosomes, issues of genetic counseling would arise, since efforts to father children via intracytoplasmic sperm injection or other in vitro fertilization techniques might propagate the Y-chromosomal defect and the infertility for which it is responsible.

To test these possibilities, DNA studies were carried out on the rare sperm produced by one of the two AZF-deleted oligospermic men, WHT2712. Sperm DNA prepared from an unrelated, fertile control man and from WHT2712 were tested for a subset of Y-chromosomal STS located within and just outside the region deleted in WHT2712's leukocytes. As expected, the fertile man's sperm carried an intact Y chromosome. oligospermic male WHT2712 was also found to produce Y-bearing sperm, but these carry a deletion of the AZF region—the same deletion that was found in his blood.

Thus, it was found that severe oligospermia is caused, in some cases, by newly arising deletions on the Y chromosome. These deletions are of interstitial, submicroscopic portions of the Y chromosome's long arm (Yq); they encompass the entirety of the previously defined Azoospermia Factor (AZF) region and include the DAZ gene; and they are not present in the fathers of the oligospermic men. This last observation is crucial in that it establishes that these deletions were not inconsequential polymorphisms (Nakahori et al., *Hum. Molec. Genet.* 3:1709 (1994)) but were in fact the cause of oligospermia. The Yq deletions we observed in two oligospermic men are remarkably similar in location and extent to those we had reported in azoospermic men with Sertoli-cell-only syndrome or complete testicular maturation arrest, indicating that these disorders are not etiologically distinct (when associated with Yq deletions) but represent clinically diverse manifestations of the same underlying genetic cause.

Equivalents

Those skilled in the art will recognize or be able to ascertain, using no more than routine experimentation, many equivalents to the specific embodiments of the invention described specifically herein. Such equivalents are intended to be encompassed in the scope of the following claims.

The invention claimed is:

1. An isolated nucleotide sequence which specifically hybridizes to a DNA sequence selected from the group consising of:
   a) SEQ ID NOS: 96, 99, 100, 101 and 102; and
   b) the complement of SEQ ID NOS: 96, 99, 100, 101 and 102.

2. An isolated nucleotide sequence which encodes a protein comprising the amino acid sequence of SEQ ID NO: 98.

3. An isolated nucleotide sequence comprising a nucleotide sequence selected from the group consisting of:
   a) SEQ ID NOS: 96, 99, 100, 101 and 102; and
   b) the complement of SEQ ID NOS: 96, 99, 100, 101 and 102.

4. An isolated nucleotide sequence comprising the nucleotide sequence of SEQ ID NO: 96.

5. An isolated nucleotide sequence which encodes a protein comprising the amino acid sequence of SEQ ID NO: 97.

6. An isolated nucleotide sequence comprising the nucleotide sequence of SEQ ID NO: 101.

7. An isolated nucleotide sequence comprising a nucleotide sequence comprising at least one DAZ repeat.

8. An isolated nucleotide sequence comprising the nucleotide sequence of SEQ ID NO: 102.

9. An isolated nucleotide sequence which specifically hybridizes to a DNA sequence selected from the group consising of:
   a) SEQ ID NO: 3; and
   b) the complement of SEQ ID NO: 3.

10. An isolated nucleotide sequence which specifically hybridizes to a DNA sequence selected from the group consising of:

a) SEQ ID NOS: 16–31 and 34–95; and b) the complement of SEQ ID NOS: 16–31 and 34–95.

11. An isolated nucleotide sequence comprising a nucleotide sequence selected from the group consisting of:

a) SEQ ID NO: 3; and b) the complement of SEQ ID NO: 3.

12. An isolated nucleotide sequence comprising a nucleotide sequence selected from the group consisting of:

a) SEQ ID NOS: 16–31, 34–95; and b) the complement of SEQ ID NOS: 16–31 and 34–95.

* * * * *

UNITED STATES PATENT AND TRADEMARK OFFICE
CERTIFICATE OF CORRECTION

PATENT NO.   : 6,020,476                              Page 1 of 1
DATED        : February 1, 2000
INVENTOR(S)  : David C. Page, Renee Reijo, Richa Saxena, Trevor Hawkins, and Mary Pat Reeve It is certified that error appears in the above-identified patent and that said Letters Patent is hereby corrected as shown below:

Column 137,
Line 64, delete "the complement of SEQ ID NOS:96,99,100,101 and 102" and insert -- a nucleotide sequence fully complementary to one of SEQ ID NOS: 96,99,100,101, and 102 --.

Column 138,
Line 67, delete "consising" and insert -- consisting --.

Signed and Sealed this

Fourteenth Day of August, 2001

Attest:

NICHOLAS P. GODICI
Attesting Officer
Acting Director of the United States Patent and Trademark Office

SEQUENCE LISTING (1) GENERAL INFORMATION:

(iii) NUMBER OF SEQUENCES: 102

(2) INFORMATION FOR SEQ ID NO:1:

(i) SEQUENCE CHARACTERISTICS:
      (A) LENGTH: 975 base pairs
      (B) TYPE: nucleic acid
      (C) STRANDEDNESS: double
      (D) TOPOLOGY: linear (xi) SEQUENCE DESCRIPTION: SEQ ID NO:1:

```
TCAGCTGGGG TCTACTCCGA GGGTTCGCCC GACCTTGGTT TTCCTTACAC CTTAGCCTTT      60

GGCTCCTTGA CCACTCGAGC CCCACAGGTG TTCCAGCGGA CTTCACCAGC AGACCCAGAA     120

GTGGTGGGTG AAACACTGCC TCTGTTCCTC CTTGAGCCTG TCGGGAGCTG CTGCCTGCCA     180

CCACCATGTC TGCTGCAAAT CCTGAGACTC CAAACTCAAC CATCTCCAGA GAGGCCAGCA     240

CCCAGTCTTC ATCAGCTGCA GCTAGCCAAG GCTGGGTGTT ACCAGAAGGC AAAATCGTGC     300

CAAACACTGT TTTTTGTTGG TGGAATTGAT GCTAGGATGG ATGAAACTGA GATTGGAAGC     360
```

```
TGCTTTGGTA GATACGGTTC AGTGAAAAGA AGTGAAGATA ATCACGAATC GAACTGGTGT       420

TCCAAAGGCT ATGGATTTGT TTCGTTTGTT AATGACGTGG ATGTCCAGAA GATTAGTAGG       480

ATCACAGAAT ACATCTCCAT GGGTAAAAAG CTGAAGCTGG GCCCTGCAAT CAGGAAACAA       540

AAGTTATGTG CTCGTCATGT GCAGCCACGT CCTTTGGTAG TTAATCCTCC TCCTCCACCA       600

CAGTTTCAGA ACGTCTGGCG GAATCCAAAC ACTGAAACCT ACCTGCAGCC CCAAATCACG       660

CCGAATCCTG TAACTCAGTA CGTTCAGTCT GCTGCAAATC CTGAGACTCC AAACTCAACC       720

ATCTCCAGAG AGGCCAGCAC CCAGTCTTCA TCAGCTGCAG CTAGCCAAGG CTGGGTGTTA       780

CCAGAAGGCA AAATCGGCCA AACACTGTTT GGTGGTGGAA TCGATGCTAG GATGGATGAA       840

ACTGAGATTG GAAGCTGCTT TGGTAGATAC GGCTCAGAGA AAGAAGTGAA GATATCACGA       900

TTCGAACTGG TGTGTCCAAG CTATGGATT CGGCTCGTTG TTAATGACGT CGTGTTCAGA        960

AAGATAGTAG GAGTA                                                       975

(2) INFORMATION FOR SEQ ID NO:2:

(i) SEQUENCE CHARACTERISTICS:
        (A) LENGTH: 428 base pairs
        (B) TYPE: nucleic acid
        (C) STRANDEDNESS: double
        (D) TOPOLOGY: linear (xi) SEQUENCE DESCRIPTION: SEQ ID NO:2:

GAGTAATCAN ATGCANGTCA TACTGAATTT GTACTGTATC ACAGGTACTT CTTGGAGAAG        60

TGAAATGCTT GTGTTCAGAC TATCAAAATT GTTAGCTTAC AAATCAGGTT TTAAAAACTT       120

TTGGAAAGTC AGTATGTGCT TTTAAACACT TAAATGCANG TCTCANTTTT TTTTTTTTTC       180

CGNAGATATC TTAACATTCT TCAGTCTCGA TTATGTGTTA CTTTAAACTA TATATTAAAC       240

ACAGACCCAG GTTCTAAATA AACATCTAAT GAAGAACAGC ATCGTTAAGA TAAAAACTAG       300

AGAGTCTAAT AATACAAGTT ATACAGAAAG TTTCAGTGTG ATTTCCAAAT TCAGAATTTC       360

AGTAATAGTG GAAAACTTT TAGCTTATAT CACCCAGCAC TCCCCATGAA ACTAGATGCT       420

GAGAGGCC                                                               428

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:3:

GGGTGTTACC AGAAGGCAAA                                                   20

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:4:

GAACCGTATC TACCAAAGCA GC                                                22

(2) INFORMATION FOR SEQ ID NO:5:

(i) SEQUENCE CHARACTERISTICS:
```

(A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:5:

GTTACAGGAT TCGGCGTGAT                                                  20

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (xi) SEQUENCE DESCRIPTION: SEQ ID NO:6:

CTCGTCATGT GCAGCCAC                                                    18

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:7:

GCTGCAAATC CTGAGACTCC                                                  20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:8:

TTTGCCTTCT GGTAACACCC                                                  20

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Leu Phe Val Gly Asn Leu
1               5

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Ile Tyr Ile Lys Gly Met
1               5

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Leu Phe Val Gly Gly Ile
1               5
```

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Lys Gly Tyr Gly Phe Val Xaa Phe
1               5
```

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Lys Gly Tyr Gly Phe Val Asn Phe
1               5
```

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Lys Gly Tyr Gly Phe Val Ser Phe
1               5
```

(2) INFORMATION FOR SEQ ID NO:15:

(i) SEQUENCE CHARACTERISTICS:
        (A) LENGTH: 1848 base pairs
        (B) TYPE: nucleic acid
        (C) STRANDEDNESS: single
        (D) TOPOLOGY: linear (xi) SEQUENCE DESCRIPTION: SEQ ID NO:15:

```
AGTCGGCCTG CGCTCCTCAG CCTGGCGGTT CTACCTCCGA GGGTTCGCCC GCCCTTGGTT      60
TTCCTTACAC CTTAGCCTTT GGCTCCTTTG ACCACTCGAA GCCCCACAGC GTGTTCCAGC     120
```

```
GGACTTCACC AGCAGACCCA GAAGTGGTGG GTGAAACACT GCCTCTGTTC CTCCTTGAGC      180

CTGTCGGGAG CTGCTGCCTG CCACCACCAT GTCTGCTGCA AATCCTGAGA CTCCAAACTC      240

AACCATCTCC AGAGAGGCCA GCACCCAGTC TTCATCAGCT GCAGCTAGCC AAGGCTGGGT      300

GTTACCAGAA GGCAAAATCG TGCCAAACAC TGTTTTTGTT GGTGGAATTG ATGCTAGGAT      360

GGATGAAACT GAGATTGGAA GCTGCTTTGG TAGATACGGT TCAGTGAAAG AAGTGAAGAT      420

AATCACGAAT CGAACTGGTG TGTCCAAAGG CTATGGATTT GTTTCGTTTG TTAATGACGT      480

GGATGTCCAG AAGATAGTAG GATCACAGAT ACATTTCCAT GGTAAAAGAG ACTGATAAAT      540

TCCGTTGTTA CTCAAGATGA CTGCTTCAAG GGTAAAAGAG TGCATCGCTT TAGAAGAAGT      600

TTGGCAGTAT TTAAATCTGT TGGATCCTCT CAGCTATCTA GTTTCATGGG AAGTTGCTGG      660

TTTTGAATAT TAAGCTAAAA GTTTTCCACT ATTACAGAAA TTCTGAATTT TGGTAAATCA      720

CACTGAAACT TTCTGTATAA CTTGTATTAT TAGACTCTCT AGTTTTATCT TAACACTGAA      780

ACTGTTCTTC ATTAGATGTT TATTTAGAAC CTGGTTCTGT GTTTAATATA TAGTTTAAAG      840

TAACAAATAA TCGAGACTGA AAGAATGTTA AGATTTATCT GCAAGGATTT TTAAAAAATT      900

GAAACTTGCA TTTTAAAGTG TTAAAAGCAA ATTACTGACT TTCAAAAAAG TTTTTAAAAC      960

CTGATTTGAA AGCTAACAAT TTTGGATAGT CTGAACACAA GCATTTCACT TCTCCAAGAA     1020

GTACCTGTGA ACAGTACAAT ATTTCAGTAT TGAGCTTTGC ATTTATGATT TATCAAGCTG     1080

AAGCTGGGCC CTGCAATCAG GAAACAAAAG TTATGTGCTC GTCATGTGCA GCACGTCCT      1140

TTGGTAGTTA ATCCTCCTCC TCCACCACAG TTTCAGAACG TCTGGCGGAA TCCAAACACT     1200

GAAACCTACC TGCAGCCCCA AATCACGCCG AATCCTGTAA CTCAGCACGT TCAGGCTTAT     1260

TCTGCTTATC CACATTCACC AGGTCAGGTC ATCACTGGAT GTCAGTTGCT TGTATATAAT     1320

TATCAGGAAT ATCCTACTTA TCCCGATTCA CCATTTCAGG TCACCACTGG ATATCAGTTG     1380

CCTGTATATA ATTATCAGCC ATTTCCTGCT TATCCAAGTT CACCATTTCA GGTCACTGCT     1440

GGATATCAGT TGCCTGTATA TAATTATCAG GCATTTCCTG CTTATCCAAG TTCACCATTT     1500

CAGGTCACCA CTGGATATCA GTTGCCTGTA TATAATTATC AGGCATTTCC TGCTTATCCA     1560

AGTTCACCAT TTCAGGTCAC CACTGGATAT CAGTTGCCTG TATATAATTA TCAGGCATTT     1620

CCTGCTTATC CAAGTTCACC ATTTCAGGTC ACCACTGGAT ATCAGTTGCC TGTATATAAT     1680

TATCAGGCAT TTCCTGCTTA TCCAAATTCA GCAGTTCAGG TCACCACTGG ATATCAGTTC     1740

CATGTATACA ATTACCAGAT GCCACCGCAG TGCCCTGTTG GGGAGCAAAG GAGAAATCTG     1800

TGGACCGAAG CATACAAATG GTGGTATCTT GTCTGTTTAA TCCAGAGA                 1848

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

AACGAAACAA ATCCATAGCC TTTG                                             24

(2) INFORMATION FOR SEQ ID NO:17:

(i) SEQUENCE CHARACTERISTICS:
        (A) LENGTH: 32 base pairs
```

(B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:17:

CTCGCTCGCC CAGAACCGTA TCTACCAAAG CA                              32

(2) INFORMATION FOR SEQ ID NO:18:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:18:

GGGTTTTGCC TGCATACGTA ATTA                                      24

(2) INFORMATION FOR SEQ ID NO:19:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:19:

CCTAAAAGCA ATTCTAAACC TCCAG                                     25

(2) INFORMATION FOR SEQ ID NO:20:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:20:

CCACCTCATG GTAGTAAAAT TGTA                                      24

(2) INFORMATION FOR SEQ ID NO:21:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:21:

CTCTTATTTA TCTTATTGCT ACAACG                                    26

(2) INFORMATION FOR SEQ ID NO:22:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:22:

CAGTGATACA CTCGGACTTG TGTA                                      24

(2) INFORMATION FOR SEQ ID NO:23:

(i) SEQUENCE CHARACTERISTICS:

(A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:23:

GTTATTTGAA AAGCTACACG GG                                               22

(2) INFORMATION FOR SEQ ID NO:24:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:24:

TTAAGGGGAC AGTATTTCAA CTTC                                             24

(2) INFORMATION FOR SEQ ID NO:25:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:25:

CCACATTTAA ACTGAGTACA GTCC                                             24

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:26:

AACAAGTGAG TTCCACAGGG                                                  20

(2) INFORMATION FOR SEQ ID NO:27:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:27:

GCAAAGCAGC ATTCAAAACA                                                  20

(2) INFORMATION FOR SEQ ID NO:28:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:28:

CCTACCGCAT CGTGAATTTC                                                  20

(2) INFORMATION FOR SEQ ID NO:29:

(i) SEQUENCE CHARACTERISTICS:
            (A) LENGTH: 22 base pairs (B) TYPE: nucleic acid
         (C) STRANDEDNESS: single
         (D) TOPOLOGY: linear (xi) SEQUENCE DESCRIPTION: SEQ ID NO:29:

TCTGTATGTG GAGTACACAT GG                                            22

(2) INFORMATION FOR SEQ ID NO:30:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:30:

TGTTGTACGT AGAAAAAGGA TATTTTACC                                     29

(2) INFORMATION FOR SEQ ID NO:31:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:31:

ATATGGTAAA CCACTTTTTA AAATTGCCA                                     29

(2) INFORMATION FOR SEQ ID NO:32:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:32:

ACAGTTTGAA ATGAAATTTT AAATGTGTT                                     29

(2) INFORMATION FOR SEQ ID NO:33:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO:33:

TGACAAAGTG AGACCCTACT ACTA                                          24

(2) INFORMATION FOR SEQ ID NO:34:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO:34:

AAGGATATTT TACCTTTGGT AAT                                           23

(2) INFORMATION FOR SEQ ID NO:35:

(i) SEQUENCE CHARACTERISTICS:
         (A) LENGTH: 20 base pairs
         (B) TYPE: nucleic acid (C) STRANDEDNESS: single
          (D) TOPOLOGY: linear (xi) SEQUENCE DESCRIPTION: SEQ ID NO:35:

GTGGAGCAGT GACCTGAAAT                                             20

(2) INFORMATION FOR SEQ ID NO:36:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:36:

CCTTTGGTAA TATTTTGGTT ATAT                                        24

(2) INFORMATION FOR SEQ ID NO:37:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:37:

ACTTGGATAA GCAGGAAATG GCTG                                        24

(2) INFORMATION FOR SEQ ID NO:38:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (xi) SEQUENCE DESCRIPTION: SEQ ID NO:38:

ACAGAATTTC AGTTGTATTT TTATTT                                      26

(2) INFORMATION FOR SEQ ID NO:39:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:39:

ACCCTCCAAG ATATTAATTC TTTG                                        24

(2) INFORMATION FOR SEQ ID NO:40:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:40:

AATTAAAGGA CCCTTAAATT CATT                                        24

(2) INFORMATION FOR SEQ ID NO:41:

(i) SEQUENCE CHARACTERISTICS:
          (A) LENGTH: 26 base pairs
          (B) TYPE: nucleic acid
          (C) STRANDEDNESS: single (D) TOPOLOGY: linear (xi) SEQUENCE DESCRIPTION: SEQ ID NO:41:

CCTCTGAAAG ATTAATATAT GGTTCT                                              26

(2) INFORMATION FOR SEQ ID NO:42:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:42:

GGACATAGTC CTGCTTAAGA AAAGTGG                                             27

(2) INFORMATION FOR SEQ ID NO:43:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:43:

ACGTGGTTCA GGAGGTCTAC TATTCTA                                             27

(2) INFORMATION FOR SEQ ID NO:44:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:44:

ATGGGTGAGA AGCCTGATTG T                                                   21

(2) INFORMATION FOR SEQ ID NO:45:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:45:

TGGGAAAGCC TGAACTGCC                                                      19

(2) INFORMATION FOR SEQ ID NO:46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:46:

GTAAGCCCCA GATACCCTCC                                                     20

(2) INFORMATION FOR SEQ ID NO:47:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:47:

AAATTGTTTG GAAAAGGACA CC                                                    22

(2) INFORMATION FOR SEQ ID NO:48:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:48:

ATAGTTAGTT TTGTGGTAAC AT                                                    22

(2) INFORMATION FOR SEQ ID NO:49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:49:

CATAGCCTCT ATGCAGATGG G                                                     21

(2) INFORMATION FOR SEQ ID NO:50:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:50:

ATTGATGTGT TGCCCCAAT                                                        19

(2) INFORMATION FOR SEQ ID NO:51:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:51:

AGAGTGAACT TTAAATCCCA GCC                                                   23

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:52:

GACTCTACCA CTTGGGCTCA ATTT                                                  24

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:53:

AGATGTACCC AAGGCCACTG                                             20

(2) INFORMATION FOR SEQ ID NO:54:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:54:

AGTTAGTAAG CCCCAGTTAT CCTCC                                       25

(2) INFORMATION FOR SEQ ID NO:55:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:55:

TTTGGAAAAG GACACCTTAT TAGCCA                                      26

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:56:

CCCCATCGGT AAACCAAATC A                                           21

(2) INFORMATION FOR SEQ ID NO:57:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:57:

CCCATTGAAG TTTCAAGGTG TCA                                         23

(2) INFORMATION FOR SEQ ID NO:58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:58:

CATTCATCTT CCCTTTTGAA GG                                          22

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:59:

ATGCAAGTCG CAGGAAATCT                                              20

(2) INFORMATION FOR SEQ ID NO:60:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:60:

TCAAATAGCA GCAATTTAAT AT                                           22

(2) INFORMATION FOR SEQ ID NO:61:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:61:

GCACCTGAAG AGCTGCTTG                                               19

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:62:

ACACAGTAGC AGCGGGAGTT                                              20

(2) INFORMATION FOR SEQ ID NO:63:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:63:

TCTGCCACTA AACTGTAAGC TCC                                          23

(2) INFORMATION FOR SEQ ID NO:64:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:64:

GTTTCTTCAT AAGCAACCAA ATTG                                         24

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:65:

CAGATTATGC CACTGCCCTT                                               20

(2) INFORMATION FOR SEQ ID NO:66:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:66:

TTACTTCCTT AAGTCAAAGC GG                                            22

(2) INFORMATION FOR SEQ ID NO:67:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:67:

CTGAGACAGC AAGACCAATC C                                             21

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:68:

CTGGACAAAG CCTTGGAAAA                                               20

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:69:

CTGCATGTCA ATTGTGGGAC                                               20

(2) INFORMATION FOR SEQ ID NO:70:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:70:

CATTGGCATG AATGTGTATT C                                             21

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:71:

CTCTGGGACA AGTGTTCCTT                                               20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:72:

GACAAAGGGC TGATGATTTA                                                20

(2) INFORMATION FOR SEQ ID NO:73:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:73:

CATCACCTTT ACTTTTTAAA TGG                                            23

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:74:

GGGTGTTACC AGAAGGCAAA                                                20

(2) INFORMATION FOR SEQ ID NO:75:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:75:

GAACCGTATC TACCAAAGCA GC                                             22

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:76:

GTTACAGGAT TCGGCGTGAT                                                20

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:77:

CTCGTCATGT GCAGCCAC                                                    18

(2) INFORMATION FOR SEQ ID NO:78:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:78:

AGGTTGTTTG GCCTTGAGC                                                  19

(2) INFORMATION FOR SEQ ID NO:79:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:79:

TCTATGATCT GTACCCGGTG C                                               21

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:80:

AGCTCACTGC AAGCAACAGA                                                 20

(2) INFORMATION FOR SEQ ID NO:81:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:81:

CCACCATCCC CCTTCTTC                                                   18

(2) INFORMATION FOR SEQ ID NO:82:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:82:

GAATGTGTAT TCAAGGACTT CTCG                                            24

(2) INFORMATION FOR SEQ ID NO:83:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:83:

TACTTCCTTC GGGGCCTCT                                                  19

(2) INFORMATION FOR SEQ ID NO:84:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:84:

CTCTGGGACA AGTGTTCCTT G                                                  21

(2) INFORMATION FOR SEQ ID NO:85:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:85:

CATTGGCATG AATGTGTATT CA                                              22

(2) INFORMATION FOR SEQ ID NO:86:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:86:

GGTGAGTCAA ATTAGTCAAT GTCC                                        24

(2) INFORMATION FOR SEQ ID NO:87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:87:

CCTTACCACA GGACAGAGGG                                                  20

(2) INFORMATION FOR SEQ ID NO:88:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:88:

GGTCTTTAAA AGGTGAGTCA AATT                                        24

(2) INFORMATION FOR SEQ ID NO:89:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:89:

AGACAGAGGG AACTTCAAGA CC                                              22

(2) INFORMATION FOR SEQ ID NO:90:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:90:

GACACTCTCG AGACATCACC GTCC                                              24

(2) INFORMATION FOR SEQ ID NO:91:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:91:

GATCGGACGG TGATGTCTCG AGAGTG                                            26

(2) INFORMATION FOR SEQ ID NO:92:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:92:

AACGAAACAA ATCCATAGCC TTTG                                              24

(2) INFORMATION FOR SEQ ID NO:93:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:93:

CTCGCTCGCC CAGAACCGTA TCTACCAAAG CA                                     32

(2) INFORMATION FOR SEQ ID NO:94:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:94:

AATTCTTGCG CCTTAAACCA AC                                                22

(2) INFORMATION FOR SEQ ID NO:95:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:95:

GTTGGTTTAA GGCGCAAG                                                     18

(2) INFORMATION FOR SEQ ID NO:96:

```
    (i) SEQUENCE CHARACTERISTICS:
        (A) LENGTH: 1858 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 217..1100

(xi) SEQUENCE DESCRIPTION: SEQ ID NO:96:

TCCGCCTGCG CTCCTCAGCC TGACGGTCCG CCTTTCGGGG CTCCTCAGCC TTGTCACCCG      60

CTCTTGGTTT TCCTTTTCTC TTCATCTTTG GCTCCTTTGA CCACTCGAAG CCGCGCAGCG     120

GGTTCCAGCG GACCTCACAG CAGCCCCAGA AGTGGTGCGC CAAGCACAGC CTCTGCTCCT     180

CCTCGAGCCG GTCGGGAACT GCTGCCTGCC GCCATC ATG TCT ACT GCA AAT CCT       234
                                       Met Ser Thr Ala Asn Pro
                                         1               5

GAA ACT CCA AAC TCA ACC ATC TCC AGA GAG GCC AGC ACC CAG TCC TCA       282
Glu Thr Pro Asn Ser Thr Ile Ser Arg Glu Ala Ser Thr Gln Ser Ser
             10                  15                  20

TCA GCT GCA ACC AGC CAA GGC TAT ATT TTA CCA GAA GGC AAA ATC ATG       330
Ser Ala Ala Thr Ser Gln Gly Tyr Ile Leu Pro Glu Gly Lys Ile Met
         25                  30                  35

CCA AAC ACT GTT TTT GTT GGA GGA ATT GAT GTT AGG ATG GAT GAA ACT       378
Pro Asn Thr Val Phe Val Gly Gly Ile Asp Val Arg Met Asp Glu Thr
     40                  45                  50

GAG ATT AGA AGC TTC TTT GCT AGA TAT GGT TCA GTG AAA GAA GTG AAG       426
Glu Ile Arg Ser Phe Phe Ala Arg Tyr Gly Ser Val Lys Glu Val Lys
 55                  60                  65                  70

ATA ATC ACT GAT CGA ACT GGT GTG TCC AAA GGC TAT GGA TTT GTT TCA       474
Ile Ile Thr Asp Arg Thr Gly Val Ser Lys Gly Tyr Gly Phe Val Ser
                 75                  80                  85

TTT TTT AAT GAC GTG GAT GTG CAG AAG ATA GTA GAA TCA CAG ATA AAT       522
Phe Phe Asn Asp Val Asp Val Gln Lys Ile Val Glu Ser Gln Ile Asn
             90                  95                 100

TTC CAT GGT AAA AAG CTG AAG CTG GGC CCT GCA ATC AGG AAA CAA AAT       570
Phe His Gly Lys Lys Leu Lys Leu Gly Pro Ala Ile Arg Lys Gln Asn
         105                 110                 115

TTA TGT GCT TAT CAT GTG CAG CCA CGT CCT TTG GTT TTT AAT CAT CCT       618
Leu Cys Ala Tyr His Val Gln Pro Arg Pro Leu Val Phe Asn His Pro
     120                 125                 130

CCT CCA CCA CAG TTT CAG AAT GTC TGG ACT AAT CCA AAC ACT GAA ACT       666
Pro Pro Pro Gln Phe Gln Asn Val Trp Thr Asn Pro Asn Thr Glu Thr
135                 140                 145                 150

TAT ATG CAG CCC ACA ACC ACG ATG AAT CCT ATA ACT CAG TAT GTT CAG       714
Tyr Met Gln Pro Thr Thr Thr Met Asn Pro Ile Thr Gln Tyr Val Gln
                 155                 160                 165

GCA TAT CCT ACT TAC CCA AAT TCA CCA GTT CAG GTC ATC ACT GGA TAT       762
Ala Tyr Pro Thr Tyr Pro Asn Ser Pro Val Gln Val Ile Thr Gly Tyr
             170                 175                 180

CAG TTG CCT GTA TAT AAT TAT CAG ATG CCA CCA CAG TGG CCT GTT GGG       810
Gln Leu Pro Val Tyr Asn Tyr Gln Met Pro Pro Gln Trp Pro Val Gly
         185                 190                 195

GAG CAA AGG AGC TAT GTT GTA CCT CCG GCT TAT TCA GCT GTT AAC TAC       858
Glu Gln Arg Ser Tyr Val Val Pro Pro Ala Tyr Ser Ala Val Asn Tyr
     200                 205                 210

CAC TGT AAT GAA GTT GAT CCA GGA GCT GAA GTT GTG CCA AAT GAA TGT       906
His Cys Asn Glu Val Asp Pro Gly Ala Glu Val Val Pro Asn Glu Cys
215                 220                 225                 230
```

-continued

```
TCA GTT CAT GAA GCT ACT CCA CCC TCT GGA AAT GGC CCA CAA AAG AAA       954
Ser Val His Glu Ala Thr Pro Pro Ser Gly Asn Gly Pro Gln Lys Lys
                235                 240                 245

TCT GTG GAC CGA AGC ATA CAA ACG GTG GTA TCT TGT CTG TTT AAT CCA      1002
Ser Val Asp Arg Ser Ile Gln Thr Val Val Ser Cys Leu Phe Asn Pro
            250                 255                 260

GAG AAC AGA CTG AGA AAC TCT GTT GTT ACT CAA GAT GAC TAC TTC AAG      1050
Glu Asn Arg Leu Arg Asn Ser Val Val Thr Gln Asp Asp Tyr Phe Lys
                265                 270                 275

GAT AAA AGA GTG CAT CAC TTT AGA AGA AGT CGG GCA ATG CTT AAA TCT GT   1100
Asp Lys Arg Val His His Phe Arg Arg Ser Arg Ala Met Leu Lys Ser
    280                 285                 290

TTGATCCTCC TGGCTTATCT AGTTACATGG GAAGTTGCTG GTTTTGAATA TTAAGCTAAA    1160

AGGTTTCCAC TATTATAGAA ATTCTGAATT TTGGTAAATC ACACTCAAAC TTTGTGTATA    1220

AGTTGTATTA TTAGACTCTC TAGTTTTATC TTAAACTGTT CTTCATTAGA TGTTTATTTA    1280

GAAACTGGTT CTGTGTTGAA ATATAGTTGA AAGTAAAAAA ATAATTGAGA CTGAAAGAAA    1340

CTAAGATTTA TCTGCAAGGA TTTTTTAAAA ATTGGCATTT TAAGTGTTTA AAAGCAAATA    1400

CTGATTTTCA AAAAAATGTT TTTAAAAACC TATTTTGAAA GGTCAGAATT TTGTTGGTCT    1460

GAATACAAAC ATTTCACTTC TCCAACAAGT ACCTGTGAAC AGTACAGTAT TTACAGTATT    1520

GAGCTTTGCA TTTATGATTT CTCCAGAAAT TTACCACAAA AGCAAAATTT TTAAAACTGC    1580

ATTTTTAATC AGTGGAACTC AATATATAGT TAGCTTTATT GAAGTCTTCT TATCTAAACC    1640

CAGCAAAACA GATTCAAAGC GAACAGTCCA ATCAGTGGGT CATATGTTTA TTCAAAATAT    1700

TTTATCTTTT AGCTAGAATC CACACATATA TATCCTATTT GATTAGGTAG TAATTAGATA    1760

ACTAAAATTC TGGGCCTAAT TTTTTAAAGA ATCCAGACAA ACTAAACTTT ACTAGGTACA    1820

TAAGCTTCTC CATGAATCAC CATCCTCCTT TTTGGTAA                            1858
```

(2) INFORMATION FOR SEQ ID NO:97:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO:97:

```
Met Ser Thr Ala Asn Pro Glu Thr Pro Asn Ser Thr Ile Ser Arg Glu
 1               5                  10                  15

Ala Ser Thr Gln Ser Ser Ala Ala Thr Ser Gln Gly Tyr Ile Leu
            20                  25                  30

Pro Glu Gly Lys Ile Met Pro Asn Thr Val Phe Val Gly Gly Ile Asp
        35                  40                  45

Val Arg Met Asp Glu Thr Glu Ile Arg Ser Phe Phe Ala Arg Tyr Gly
    50                  55                  60

Ser Val Lys Glu Val Lys Ile Ile Thr Asp Arg Thr Gly Val Ser Lys
65                  70                  75                  80

Gly Tyr Gly Phe Val Ser Phe Phe Asn Asp Val Asp Val Gln Lys Ile
                85                  90                  95

Val Glu Ser Gln Ile Asn Phe His Gly Lys Lys Leu Lys Leu Gly Pro
            100                 105                 110

Ala Ile Arg Lys Gln Asn Leu Cys Ala Tyr His Val Gln Pro Arg Pro
        115                 120                 125
```

```
Leu Val Phe Asn His Pro Pro Pro Gln Phe Gln Asn Val Trp Thr
130                 135                 140

Asn Pro Asn Thr Glu Thr Tyr Met Gln Pro Thr Thr Met Asn Pro
145                 150                 155                 160

Ile Thr Gln Tyr Val Gln Ala Tyr Pro Thr Tyr Pro Asn Ser Pro Val
                165                 170                 175

Gln Val Ile Thr Gly Tyr Gln Leu Pro Val Tyr Asn Tyr Gln Met Pro
            180                 185                 190

Pro Gln Trp Pro Val Gly Glu Gln Arg Ser Tyr Val Val Pro Pro Ala
        195                 200                 205

Tyr Ser Ala Val Asn Tyr His Cys Asn Glu Val Asp Pro Gly Ala Glu
    210                 215                 220

Val Val Pro Asn Glu Cys Ser Val His Glu Ala Thr Pro Pro Ser Gly
225                 230                 235                 240

Asn Gly Pro Gln Lys Lys Ser Val Asp Arg Ser Ile Gln Thr Val Val
                245                 250                 255

Ser Cys Leu Phe Asn Pro Glu Asn Arg Leu Arg Asn Ser Val Val Thr
            260                 265                 270

Gln Asp Asp Tyr Phe Lys Asp Lys Arg Val His His Phe Arg Arg Ser
        275                 280                 285

Arg Ala Met Leu Lys Ser
    290
```

(2) INFORMATION FOR SEQ ID NO:98:

(i) SEQUENCE CHARACTERISTICS:
        (A) LENGTH: 366 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

```
Met Ser Ala Ala Asn Pro Glu Thr Pro Asn Ser Thr Ile Ser Arg Glu
1               5                   10                  15

Ala Ser Thr Gln Ser Ser Ser Ala Ala Ala Ser Gln Gly Trp Val Leu
            20                  25                  30

Pro Glu Gly Lys Ile Val Pro Asn Thr Val Phe Val Gly Gly Ile Asp
        35                  40                  45

Ala Arg Met Asp Glu Thr Glu Ile Gly Ser Cys Phe Gly Arg Tyr Gly
    50                  55                  60

Ser Val Lys Glu Val Lys Ile Ile Thr Asn Arg Thr Gly Val Ser Lys
65                  70                  75                  80

Gly Tyr Gly Phe Val Ser Phe Val Asn Asp Val Asp Val Gln Lys Ile
                85                  90                  95

Val Gly Ser Gln Ile His Phe His Gly Lys Lys Leu Lys Leu Gly Pro
            100                 105                 110

Ala Ile Arg Lys Gln Lys Leu Cys Ala Arg His Val Gln Pro Arg Pro
        115                 120                 125

Leu Val Val Asn Pro Pro Pro Pro Gln Phe Gln Asn Val Trp Arg
    130                 135                 140

Asn Pro Asn Thr Glu Thr Tyr Leu Gln Pro Gln Ile Thr Pro Asn Pro
145                 150                 155                 160

Val Thr Gln His Val Gln Ala Tyr Ser Ala Tyr Pro His Ser Pro Gly
                165                 170                 175
```

```
Gln Val Ile Thr Gly Cys Gln Leu Leu Val Tyr Asn Tyr Gln Glu Tyr
            180                 185                 190
Pro Thr Tyr Pro Asp Ser Pro Phe Gln Val Thr Thr Gly Tyr Gln Leu
            195                 200                 205
Pro Val Tyr Asn Tyr Gln Pro Phe Pro Ala Tyr Pro Ser Ser Pro Phe
210                 215                 220
Gln Val Thr Ala Gly Tyr Gln Leu Pro Val Tyr Asn Tyr Gln Ala Phe
225                 230                 235                 240
Pro Ala Tyr Pro Ser Ser Pro Phe Gln Val Thr Thr Gly Tyr Gln Leu
            245                 250                 255
Pro Val Tyr Asn Tyr Gln Ala Phe Pro Ala Tyr Pro Ser Ser Pro Phe
            260                 265                 270
Gln Val Thr Gly Tyr Gln Leu Pro Val Tyr Asn Tyr Gln Ala Phe
            275                 280                 285
Pro Ala Tyr Pro Ser Ser Pro Phe Gln Val Thr Thr Gly Tyr Gln Leu
            290                 295                 300
Pro Val Tyr Asn Tyr Gln Ala Phe Pro Ala Tyr Pro Asn Ser Ala Val
305                 310                 315                 320
Gln Val Thr Thr Gly Tyr Gln Phe His Val Tyr Asn Tyr Gln Met Pro
            325                 330                 335
Pro Gln Cys Pro Val Gly Glu Gln Arg Arg Asn Leu Trp Thr Glu Ala
            340                 345                 350
Tyr Lys Trp Trp Tyr Leu Val Cys Leu Ile Gln Arg Arg Asp
            355                 360                 365

(2) INFORMATION FOR SEQ ID NO:99:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:99:

GGAGCTATGT TGTACCTCC                                              19

(2) INFORMATION FOR SEQ ID NO:100:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:100:

GTGGGCCATT TCCAGAGGG                                              19

(2) INFORMATION FOR SEQ ID NO:101:

(i) SEQUENCE CHARACTERISTICS:
         (A) LENGTH: 43795 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:101:
```

-continued

```
GATCCTGATT ACTTTGATAT TTAAAGTAGG ATTTGACATA CTCTATCACT TATTGGTGAT      60

AAATAACGTC TGTTTTCTTC TTAGTCCATT TTATTTATGT GTTAGTTTAA AAGACATTTT     120

CTTTGATGGA AAATAAAGTA ACAAAATAGT AGTGAAATAG TTCTTCAGTG TCTCTCATTT     180

ATTGACATTT TCTGTGTACT TGAAATGTGT AGGATATACC TCTTCTTCTT TTTTCTTCTC     240

TGAACAATGG CTAGAGACAA AGCCCTACTT GTTTCTAACA TTTACGGTGA GCCATTACTG     300

AATTTGGGTG TATTCATGTA TGCTGCTTCC TATATGTTTT CAAACAATAA GTATTTATCG     360

AAACATATAA GACATCGTAC TGTCCTTCTC CAGTTTTGGA TTGTACACTG CCCTTAGTTT     420

TTCGAAATGA AGTACAGAAA AAAAACATAA CATCTGTAGG AGAACTACAT ATTACCCTGT     480

AATATTGTCA ACACAAAAC TATCTGGAAG TATATTGACA AAGAAATAGC AAATGTATTA      540

ACTTAACTTA CATTGAGATC TGTCTTAATG GAGCCTTACC AGCAGTGTAA GAAACAACTT     600

CTGGGTGGGC ATAAGTACAC AGTGTCAGTA AGGTGAACTT TGCCTGGTGA AATAGTCACT     660

ACTTTGTCAT TTGTGTGTTC CCCCGCCCCA CCCAAAGGGG CTTAGCACTT GACAGAGAAT     720

ATTTATTTCT TCCTGAAGTC ATTCATTCAT TTAGAATTCT GCATTGTTTT ATATAGAAAA     780

TTAATAAATA TTTTAAAGTT TTTCATTTTT TTTATTTTGG GAATAATATT TTTTTCTAAT     840

TTAAAAAGAT GTTTTACCAT ATTCATTCTT TCTGTAAACT TACTTTCAGA CATATCCTAC     900

TTATCCAAAT TCACCAGGTC AGGTCACCAC TGGGTGTCAG TTGCCTGTAT GTAATTATCA     960

GGTAATTGAA GAGGGAGTAA AATGATTTGT TTTCAGATAT TATTGAAGCC TTTAACTTGT    1020

TTATATGAAT TTCCCAAATA GTGTGTCATT TTAAACTAGT GAAATGTACC TAAAATTTAG    1080

GAAAACACTT GCAATGGTCT AGAATGAAGC CCTCTGTATT ATTTAGAAGT AATGAATTAA    1140

CATTTTGACA GGGATATACT TAGCAATAAC TTTTCTGTAA AACAGTTTTC TGAGATTCGT    1200

TGTCCCCTTC TATATTTCAG CGTGTATTTT TTCATCTTTT TCATCTTTTT ATCATCCCAT    1260

TCTTAGAGCA CAGAATTCCA ATTATATTTT TATTTTAAGC TTGCTGCTTC ATGATAGTAG    1320

TTCTCTGGGC CTCTTTTCAT AGATATGACT ACATCTGTGA CCCATAATCA TATCTATGGT    1380

GATAAGTAAT AAATTGAAAA AACTAGTATC CTTGAGATTT CCACAATGCC AACTCCAGAA    1440

AATTGGGAAA ATGGCGAGGT TTTATGTATA AAAGTAACAA GAACATCAGG GATTAGAAAC    1500

ATAAAGTACT TCTTTTTTTT TTTTTACTCT GTTTCTTTCA CTTTAATAAC AAATGAGCCA    1560

GCATGATAAG TGCTTCAATA TTGTGTATCT CATGAGTTTT TGAAAATGTG TAGGAATATT    1620

TTAATAGTTT TGGTTTCCTT CTTTTTATTT TTTTAAGGTG CTACCGCAGT GGCCTGTTGG    1680

GGAGCAAAAG GGGTTATGGA GTAAAGTGAA TTAGTGAAAC GTATACTTCC TCATCTTTCT    1740

TGACTTTTTT CTATGCCATA TATGCCTGTA GATATTTTA AATGGTTCTT TATATTAATG     1800

TTTTATGTTT TGTTACTTTA TTTTTAACCC AATTATAAAC TCCCATGGGA GCAACAGTGC    1860

CTTTTTGTCT CTCACATTTT TGTGTGCTGA ACAGTGGCT GGTCCACATA ATGATAAGTG     1920

TTCAGTTACT TGTTGATAGA TTATATAATC CAGGAATGGC GGTATTAACT GGCTTTAGAA    1980

TTAGCATGTA TCTGCCTAGA ATATGCCTCT GGCTTTACTA GCCATAAAAC ATTTGTTGAG    2040

GAGAAACCGA AATGTTTTGC TATTAATTAC TCTTAAAGAG GAATAGGAAT AAAACAAGAG    2100

TATTACCTCT AATACAACAG AGCTGCTGTC TTACATCACG ATTGGATATT TGAAGGATAT    2160

AGTAAGTGTT AAAATTCTCA AACACTCCCT TAACTACATT TGTTTCTTAG AATCCTTCTA    2220

CCTCTGATTA TGTTGATACC TGGAAGACGT TTTAAAACAA AAGGCTGCCT TAATGCATTT    2280

CAACTTTTCG TTTAAAACAA GGTTTCTGAA GTAACACAAT TGAATTTCAA CACAACCTAC    2340

ATTGAAACTT TTGATACCAG CTCACCTTTT TGAGGAATAA ATAAGTAGCT TTTAAACGTA    2400
```

-continued

```
TCTGTATTAT CTGTTTAATT ACACTTTCAT TATTTTAAAT ATAGGCTTAT TCAGCTCTTA    2460

ACTGTCACTG TAGTGAAGTT GATACAGGAG GTGATGTTGT GCTAAATGAA TGCTCAATTC    2520

ATGAAGCTAC CCCACCCTCT GGAAATGGCC CACAAAAGGC AAACATCTAA TTTTGAATTT    2580

TTTTTACAAT ATATATTTCA TATTTTTTTC TAATTTGAAT GACTTTTTTT GAGAAGCAAA    2640

CATTTTTGCC CAAATTTAAA AATGTTAGCC ATAAATCATG GAGCTTAAAT AATGGACTGA    2700

TAGTCAGCAG TTAATGTAAA GGTTGTTGAA ATTTCAGATA CCCCAAATTT TCAGTATATA    2760

CCTAAAGTTT CTGATTCAGC AAGTCCTTTC CTGTATTTCA GTTTCACTAA TTTTAAAAAG    2820

CCATTCTTTA ATAAATACTG TATTAATATG ATTTGGCAGA ATGCTATGGG AGGGTTTCCT    2880

CTAGAATTCT ACTCAAAAGA AGAATTAGTA CGAATTGTAT GTCCCTTTTC TTTTACAACA    2940

GTTTTGATCT TAAGCAGTGA AAAATACCAT TTAAATAAGC ATTCTCTCCA TAACATTATA    3000

TGTGGCAGAA GTTTCCAACA GTGGTGAAGT CAGTAGTAAT TATTCAAACA CTGAAATAGA    3060

CAGGGTTGTT TCTTTTTTTT ATCATTAGTG CAAATTTCTG TAATAACAGT ACTGTCACTC    3120

CTGGCGTCAC ATATGTTCTG TTAGATAGGT GGGCGTGTGG AAGTAGTTGA TGTGCTGGTA    3180

ATATGTATAA TACCCAAGAA GTCCCATTGC AGTGTAAATT CCTTGATTTG ATATTGGATT    3240

TTAAAATGTG AATAAATATG AAAACATAAC TCTTACAGTA TAATTGTCTG GTTTTGTTCT    3300

GAGTATGTTT TCTTGAAACA TTGGAATTCA CTTAGGGATT TAACAAATTC AGCTTTTTAA    3360

ACCAGTATTC TATCGCTAAG GTTCTAAAAT AATTCTTCGA TTTGTCAGAA AACGTACATA    3420

CTGAGGATAT GTGGCAGGAA TTATGAATCA CATTTTTATG AATTTCTTTT TTTTTTGAGA    3480

CAGGGTCTTG CGGTGTCGCC CAGGCTGGAA GTGCAGTGGT GTGATCTCGG CTCACTGCAA    3540

CTTCTGTCTC CTAGGTTCCA GTAATTCTCC CTGCCTCAGC CTCCCCAATA GGTGGAATTA    3600

CAGGCACCCG TCACCCAGCT AATTTTTGTA TTTTTTAGTG GAGAAGGGGT TTCGCCATGT    3660

TGGCCAGGAT AGTCTTGAAC TCCTGATATC AGGTGATGCG TCCTCCTCGG CCTCCCAAAG    3720

TGCTGGGATT AGAGGTGTGA GCCACTGCTC CCAGCCTCTT TTAGCATTTT TGCATTTCTT    3780

TGGAAATAAA CTGATATGTT CATTAAACCA TCAAAAGAAA AACCAAAACA CACCCTTATT    3840

AAGAGTGAGT GAAAGAAAGA GTTGTCTTTA CATTACTGAA AACTTCTGTG TTTCAGAAAT    3900

CTGTGGACCG AAGCATACAA ATGGTGGTAT CTTGTCTGTT TAATCCAGAG AAGAGACTGA    3960

TAAATTCCGT TGTTACTCAA GATGACTGCT TCAAGGTATG AAAGGAATGG CATGCATAAT    4020

TAAAAAGCAC ACTTGTTCCC TCTCAAGTTA GCTGTTTTCC TTGTGGCACA TGTATTTTGG    4080

GCTTTCTTAG AGGAATTTTT TTTCTTTTTT TTTTGTTTTG AGACGGAGTC TCCTCTGTCG    4140

CCCAGGCTGG AGTGCAGTGA GTGGCCCCAT CTAGGCTCAC TGCAAGCTCC ACCTCCCAGG    4200

TTTACTTAAC GCCATTCTCC TGCCTCAGCC TTCCGAGTAG CTGGGACTAC AGGCGCCCAC    4260

CACCACGCCC AGCTAATTTT TTGTATTTTT AGTAGAGACG GGGTTTCACC GTGTTAGCCA    4320

GGATGGTCTC GATCTCCTGA CCTCGTGATC CACCTGCCTC AGCCTCCCAA AGTGCTGGGA    4380

TTACAGGCAT GAGCCACCGT GCCCGGCCTA GAACATTTAA TTGAACTGTT GGCATTTGAC    4440

TGTAACCCAG TAAACCAGTG TGGGTTTTAC CTGGCAGTAT ATTTTCTGCT GCCGAGCCTT    4500

GATATAATGT AGTCAAATTT AGGGAAGAAT CCTGCAGCAG AAATTTGTAA TTGAAAGGGT    4560

TTACTAGAGA AGAGAGTTAG TTGACTACCT TGACCAAATA GTAAAATAAA ATTTTAGATA    4620

CAGAAAGGAG ATCTTGGCTG GGTGCAGAGG CTCACGCCTG TAATCCCAAC ACTTTGGGGG    4680

GCTGAGGTGG GTGGATTGCT TGAGCTCAGG AGTTCGAGGC CACCCTGGGT AACAAGGCAA    4740
```

-continued

```
AACACCATCT CTACAAAAAA ATACAAAAAT CAGCCAGTTG TGATGGTACA TGCCTGTAGT    4800

GCCAACTACT CCAGAGGAGT CTGAGGCAGG AGGATCGCTT GAGCCTGGGA AGTTGAGGCT    4860

GCACTGAGCC ATGATTGTGC CGTTGTAGTC CAGCCTGGGC AACAGAGTGA GAGACCTTGT    4920

CTCAAAAAAA AAAAAAAAA AAAAAAAAA AAAAAAAAA GTAGAACTTA ATACATGCAT       4980

ATTGGACTAA AGAAGAAA AGAAATGATT TACTCAGATG ATACACCTGA ACAGTGTGAA      5040

GGGAGAAAAG GGGTAAAATG AAGCAGTAAA AAGTTGAGTA GAAAGAGAGG TTGATTCAGA    5100

GTTGGTGAAG CGGAAGAGAA TGTGGCTAGT TGAATTCCAG AAAGATCTGA CTTCTGATCC    5160

CACTTTCTAT CCATGTTGGA TAGATAAATC TTTTATTAAG GCTCTAATTC TTACAAGTCT    5220

AAAATGAGAA GGTACAGGAC TAAAGGTTTC TGGGTCCCTG TGGTTCTAAG TCTATAAATA    5280

CGAAAAAGAA CTAACTTGGT CAGTCCGGTG GGAGAAAAAT ATTATGGTTA ATAAAGGGAA    5340

GGTGTTTTTT AAATAACAAT TTTATTAAAA TAATACCAGT AATACAATTT ATGTATTTAA    5400

AATGTGCACT TCACTGTTTT TTCATATATT CAAAGTTGTG CAACCATGTC CACAATCAAT    5460

TTTAGAATAC TTAAATCACC TCAAAAATCA CCCCCGTACC TTAGCAGTCA CCTGCTATTT    5520

TCCTGGAACT TGTGTGTATC CCTAGGCAAA CACTAATTTA CTTTTTTCCT CTAAGGATTT    5580

TCCTGTCCTG GAGATTTCTT GTATATGAAA TCATACATAA TGATGTGGCA TTTTGTGACT    5640

GGATTTTTTC ACTCAGCATA ATGTTTGTAA GGTTCATCAA TATTCTAGCA CGTATCAGAA    5700

CTTAATCATT TCTTTTTATT TGTAGATATT ACCTTATTCT GTTTATGCAT TCATCTGTTA    5760

AAGACATTTG GATTATTTCC ACTTTTTAGC TGTTATAACT AATGCTGTGA ACATTCATGT    5820

ACAAGTTACT GTGGGACAT ACGTGCTTAC CTCTCTTGCG TATATACTTG GGAATGGAAT     5880

TGCTAAGTCA TATTTAACCT TTAGTGGAAC TGCCAGATTT GTCAAAACTG GCTACACACT    5940

TTACATTCAA AAGAAAATGT TTAACCATCA CTTTGTGTCT TACAACAGAA CTAGCTTATT    6000

TTTGTCTGTG AATGGATATG GGATGAAGCC TAAGCCTTTT TAAAGGGTTA TATTATGAAT    6060

CTTCTGTATA ATGTAGAAGA GTAGAGCCAG ATAGCAGAAT TAAGTTCTTA ACATCTTTGC    6120

AACATGGAGT AAATATATTT AAATTTGACA TTTGTTCTCT TGTTGCTTCG TTCTATATAG    6180

ATAGTACAAT TTAGAAAAGA AAGAACTGGA ATTGTACATC AGCTTATCTT GCCGAAAATT    6240

CTGATTACAT TGGTGTCTAC AGTAGTACTT AAGTGATTTT CAAAGCAGAA GATAGTTTTT    6300

TGTGTTTCTT TCTTTCTTTC TTTTTTTTTT TTTTGAGGTG ACCTCATTTG GTCATCCAGG    6360

CTGGAGTGCA GTGTCGCAAT CACAGCTTAC TACAACCTCA AACTCCTGCA CTCAAGGGAT    6420

CCTTCTGCCT CAGCGTCCCA AATAGGACGA CAGACGTGCA CCACCACACT TAGCTAGTTA    6480

AAAAGAAATT TTTTTTTTTT TTTTTGAGAC AGAGTCCCAC TGTGTCACCC AGGTTGGAGT    6540

GCAGTGGTGC GATCTTGGCT CACTGCAAGT TCTGCCTCCC AGGTTCATGC CATTCTCCTG    6600

CCTCAGCCTC CCGAGTGGCT GGGACTACAG GTGCCTGCCA CCACGCCCAG CTAATTTTTT    6660

GTGTTTTTAG TAGAGATGGG GTTTCATCGT GTTAGCCAGG ATGGTCTCGA TCTCCTGACC    6720

TTGTGATCTG CCCGCCTCGG CCTCCCAAAT TGCTGGGATT ACAGGTGTGA GCCACCGTGC    6780

CCAGCCAAAA GATTTTTTTT TAAGAGAGAA TCTTACTATA TTGCCCTGGC TCGTCTTGAA    6840

CTCCTGGGCT CAAGTGATCC TCCTGCCTCA GCCTCCCAAA GTGCTGGGAT TACAGGCGTA    6900

TGCCACCATG TCCAGCCCAG AAAATATTTT TTTAAACTTG AGTTCTCACC TGGTGGTAGA    6960

CAAAAGACTC GCTTTGAAAC TTCCAGAGTT TTCTGCTTAT TTGGGAGAGG AATCAGAAGT    7020

TGGCATCCTG CAGTTGTCTG ACATTTAGAC CTATTTTAAT TGACTGCACG TTGTTATATT    7080

GAATTAGAAT GCCTGAGATA TTTTTGAATG TATTTACAAT TTCCATAGCC GATTTCTCTT    7140
```

```
CATTGTCTTA GTTATCTAGC CCTTTCACAA TCTTGTTTCC TACATGACCT CTGAATATAC    7200

ATGTTGGTGA CCAGTTTTCT AGATTTTAAC CTAAATTGAT TATCACTCTT TTGACAGATG    7260

AGGTAACTTC CAGAAGCCAC TTTTATTTAT ATGAAAATGA AACTGAAGTC TTAAAAAAAG    7320

GGCACAGCTT TGTAGAAAAG GAAATGTTAT TACTCGTTCA CTCATTCCCA TTCCTCCTTG    7380

TAAGACCTCT CACTTCTCTC TGCACGTCTG CAGGCAACAT AGAGTGAAAA GAAAGTTTTG    7440

CATGTATTTT AAAGTTTTAT CTTCCTTTCT AAAGAATGAT ATGTCTTCAC AGGTTAATGA    7500

TATGTTCTTC AAATGCCAAA ACTTACATAT TTTAATCTAA AAACACGAAA TTTCAGATTG    7560

GAGAGCAGTT CGCAAGCTGT AGTTGGTATT AAATGCAGTT CAATTAGTGA AAAAAGTATT    7620

CTTTACAATT ACATTTTCTA CCAGCTGTCT TTGGGACATT ACTGCAAAAT TATTAACTAA    7680

GAAGTACATA AAATGATACT GAGTTTAAGT CCTTTTATTT CTCAGTTTAC TGGAATTTGT    7740

TTTATTTAAT TATTGATTTC TTTTTTTAAC TGTTTAATAA AACTAGCCAT CTTGGTACAT    7800

TTGTTATCCC AGTGTTCAAA TATGCTTCCT GAAAAGAATC ATCTTTTTTT CTCATTATTT    7860

ATAATGTTTA AACCCAAAAC AAATGGTTTA AGTTTTGACA ACTTTCAGAT CCATAGTAGT    7920

CATCAGAAAT TTTCAGTAAA ATAAAAGGAC TATTTCTGTC TTTTCCAGGG TAAAAGAGTG    7980

CATCGCTTTA GAAGAAGTTT GGCAGTATTT AAATCTGTTG GATCCTCTCA GCTATCTAGT    8040

TTCATGGGAA GTTGCTGGTT TGAATATTA AGCTAAAAGT TTTCCACTAT TACAGAAATT    8100

CTGAATTTTG GTAAATCACA CTGAAACTTT CTGTATAACT TGTATTATTA GACTCTCTAG    8160

TTTTATCTTA ACACTGAAAC TGTTCTTCAT TAGATGTTTA TTTAGAACCT GGTTCTGTGT    8220

TTAATATATA GTTTAAAGTA ACAAATAATC GAGACTGAAA GAATGTTAAG ATTTATCTGC    8280

AAGGATTTTT AAAAAATTGA AACTTGCATT TTAAGTGTTT AAAAGCAAAT ACTGACTTTC    8340

AAAAAAGTTT TTAAAACCTG ATTTGAAAGC TAACAATTTT GATAGTCTGA ACACAAGCAT    8400

TTCACTTCTC CAAGAAGTAC CTGTGAACAG TACAATATTT CAGTATTGAG CTTTGCATTT    8460

ATGATTTATC TAGAAATTTA CCTCAAAAGC AGAATTTTTA AAACTGCATT TTTAATCAGT    8520

GGAACTCAAT GTATAGTTAG CTTTATTGAA GTCTTATCCA AACCCAGTAA AACAGATTCT    8580

AAGCAAACAG TCCAATCAGT GAGTCATAAT GTTTATTCAA AGTATTTTAT CTTTTATCTA    8640

GAATCCACAT ATGTATGTCC AATTTGATTG GGATAGTAGT TAGGATAACT AAAATTCTGG    8700

GCCTAATTTT TTAAAGAATC CAAGACAAAC TAAACTTTAC TGGGTATATA ACCTTCTCAA    8760

TGAGTTACCA TTCTTTTTTA TAAAAAAAAT TGTTCCTTGA AATGCTAAAC TTAATGGCTG    8820

TATGTGAAAT TTGCAAAATA CTGGTATTAA AGAACGCTGC AGCTTTTTTA TGTCACTCAA    8880

AGGTTAATCG GAGTATCTGA AAGGAATTGT TTTTATAAAA ACATTGAAGT ATTAGTTACT    8940

TGCTATAAAT AGATTTTTAT TTTTGTTTTT TAGCCTGTTA TATTTCCTTC TGTAAAATAA    9000

AATATGTCCA GAAGAGGCAT GTTGTTTCTA GATTAGGTAG TGTCCTCATT TTATATTGTG    9060

ACCACACAGC TAGAGCACCA GAGCCCTTTT GCTATACTCA CAGTCTTGTT TTCCCAGCCT    9120

CTTTTACTAG TCTTTCAGGA GGTTTGCTCT TAGAACTGGT GATGTAAAGA ATGGAAGTAG    9180

CTGTATGAGC AGTTCAAAGG CCAAGCCGTG AATGGTAGC AATGGGATAT AATACCTTTC    9240

TAAGGGAAAC ATTTGTATCA GTATCATTTG ATCTGCCATG GACATGTGTT TAAAGTGGCT    9300

TTCTGGCCCT TCTTTCAATG GCTTCTTCCC TAAAACGTGG AGACTCTAAG TTAATGTCGT    9360

TACTATGGGC CATATTACTA ATGCCCACTG GGGTCTATGA TTTCTCAAAA TTTTCATTCG    9420

GAATCCGAAG GATACAGTCT TTAAACTTTA GAATTCCCAA GAAGGCTTTA TTACACCTCA    9480
```

```
GAAATTGAAA GCACCATGAC TTTGTCCATT AAAAAATTAT CCATAGTTTT TTTAGTGCTT      9540

TTAACATTCC GACATACATC ATTCTGTGAT TAAATCTCCA GATTTCTGTA AATGATACCT      9600

ACATTCTAAA GAGTTAATTC TAATTATTCC GATATGACCT TAAGGAAAAG TAAAGGAATA      9660

AATTTTTGTC TTTGTTGAAG TATTTAATAG AGTAAGGTAA AGAAGATATT AAGTCCCTTT      9720

CAAAATGGAA AATTAATTCT AAACTGAGAA AAATGTTCCT ACTACCTATT GCTGATACTG      9780

TCTTTGCATA AATGAATAAA AATAAACTTT TTTTCTTCAA ATGTGTTTTT GGCTTTCCGA      9840

TGTAATAATG TAAAATGGTG GGGAGTTGCG TGGGAACTGT GTAACAAGGT TTAAATTCGT      9900

ATAACAAGCT TTAGATTCTT AAAATGCAGA AGTATAAAGT TCAGTATACT AATCTGTCTG      9960

AGTTAGCCCA TAAAAGCAAA TGTAGGTACA AGATAAGTT TAAGAGGTGC ATCAACAGCA      10020

GTGCAGACTA GGAATGCTGA TGAACACATC CGACTCTGCT ATCTCACGGC TAAGGTCCCT      10080

CACATTTTGG ACCCTATGAA GCATTTTGTC TACTGTACAC TTTGGGCCTA GTCTCTAGAT      10140

CATTTATTTC GGGGTATTGC AGTTGCCTAA GGGAGCTTAA TTTTTTTATA TTGCAGGTAC      10200

TTCCTGTGGA TACCATAAAA AAAAAAATCA GTACCGCTTC TTCTAGCTTT AGTGTTAGTA      10260

CTCAGTTCTA TAAGCTGAGT CCAGTGGAGA GGAAACTCCT CAGACACGTA TTTCATTAGT      10320

TAGTAAGCTT GCTGATTCAT AACCAGAAAG TTGACTCCAA GGATACGCAG GATAGCAAAC      10380

AGTGCTTTCT GCATCACCAA AGATTAAATT GTGATGTTTA GTGTCCAATA ATAGGCAAAA      10440

AATTAGTAAT TCTTTTATGT GCCTATGTGT ATATATGTGT ACATATGTGT CTATATATGC      10500

ATATATTTAT GGTTATGTAC ATACTAACGA TTATCCAGAA TATTTGGTTC TAGCTGATCA      10560

AGCTAGTAGG TTTTCAGTAT TTTCAGACCC CAAAACTAGA CTACATATGG TTAAGATAG      10620

TTGCTTTACA CCAGCTTGTT TCTAGTTTCC TATTAAATTA TTACCACAAA AATCTTTGGA      10680

ATTGAAAAAT AACAGTTAAG CACTTTTTTG TAAAAAGTTC AAGTTATGGT GAAATCAAGC      10740

AGCTCTAAAA AGGTTGGTCA CCTCCTTAAG TGTATTCTGC ATGTTGGTTT TTTTCTTTTT      10800

CTAAAATCAG ATTACCTTTA ATTCAAAATA ACTTCAGAAT TGGTAGTACC TGTCTGGCAA      10860

GGAAGTCATT GACTCTTAAA AATAAATACT CCACAGCATT TCCCTCTCGT TATAAAGCAC      10920

CTCTAGCCCC CTCTTCACTA AATTTTTCTT GGCTTTTTTT TAAAGGTAAA CTGATAAAAA      10980

TGGGCTGCCA CATTGCTTAA TCGCCTTGCC TGCTTTCCTT GCTGTCAGTT GAGGGTAATG      11040

AGGAGCAGCA ACGATAAGGC AGCGTGCCAC CTTGCTTTCA CAAAGATGCC AATAGAGAAA      11100

GTGGGAAAC ATAAGGGAGA AAAAAGTAGC AGTATTTTAC ATTGACCAAG TCTTGTGAAT      11160

GGGCCAGCTA TTGAGTATGA TCATTTGGAA TCCCTAGATA AGGATTGCTC CTGTACATAT      11220

TTTGATAAGT GTAATCTATC CCTTCCCAAC ATGTGTAGTA TGTCTCTGTA TGTAACTGAT      11280

TGTTGTGAGC AATTCCTTGC CACTCACCAA AGACAGAACT TTCCATCTGT AGACAGTACA      11340

TTTTGTAGTA GAAAACAATA GACATAAGAA GTTCAAACTA TAAACATGTT TTTGAATGCT      11400

CATGCAAGAT AATCTGCATA GCAAAGAAAT AATAGACAAT TCAACATTGC ATTTAGAGTT      11460

AAAAACATCT GTCCAGTATG GATGTAGCTG TGGGCCAATC CTAAGTAAAC GCAAAAAAAA      11520

AAAAAAAAAA AAAATTGTCT CTTGGTACAG AAGTTGAAAC TACCACTCTA CCACTGTACA      11580

ATTAAACTCT ATGGTCGCTG TATTTTACGT TTTTAACTGG TCTGAAACAG TTCTCTAGTT      11640

AAGTCTGTAG TTCGTTTTCC CAAGACAAGG CTTTGTATCT TACGTGCACC TTCATTAATG      11700

CTGCATGCCA GGAATTCCAC ATGAAACTTC AAGATGCCGG TTCACTAGGT CTTTTCCACA      11760

TGAAACTTCA AGATACCGGT TCACTAGGTC TTTAACAATA GAACAAATAC TTGCATGACT      11820

GGGATATTCA GGTCATGAAC ACTCCTTATA AATTTGAAGC AATAGTAACA TTTTAAGCAC      11880
```

```
TTTGGAAAAT TGGAGGTTTC ATAACCCTCA ATCAGATCTT TTTATAGAAT AACAAAAATA   11940

CACTAAGGTT CTAATCACAT CTATTGTCTT TGCCCAAAAT AACATGGATA GAGACACACT   12000

CCATTCTGGC TCAATCTTAG ATGAAACTCC AGAAGAAAGG CAGTTGATAA TGATACAGCC   12060

AGGCCAGCTG TTTAAGTGGA CGTGTCCCCT CTGCCCTTGT ACATTTGTTT AAAAATTTTG   12120

ATAGGACTCT TCCCGCCTCC TTCACACCCT CCATAAATCT GACTAGGCCC ATAAGAATGG   12180

AGAGAGGTAA TTTAAAAGGC AGAGGACATT TTTCTCCTTG TTTTTACCTA TGCTGATCCC   12240

CTACCTGGTG TTGGAGCAGC TTCACTGTGA GTAAAATCTG AACAGTGTTT AAGCAGTAAA   12300

CCCACTATAT TGAGGAAAGC GTGACCTGCA CTTTTTTTTT TTTTTTTTTT CCTGAACATG   12360

ACTTGGTTGT TGCTCATCAT TTTGGTTGGT GATGGGTCTT TGACAAACCG ATATGCTCAC   12420

CATCCAAAGT TGTGTCCATG TTTAGATCAG CGCAGTATTC GATAGGGCAC GTTTCCTCAA   12480

GATACCAATT TTACAGGGAA GTCAAAGAGC ATCAGAGCTA TCATAAGGGG TGTTTTTCAG   12540

AAGCCAAATC CTGGGCCCCA TTCTCAGATG CTCTTATTCT AATGCTCTGG ATGGGCCCAG   12600

TAATCTGCAT TTTTAACATG TGCCCCAGGT GATTCTGACC ACTGTAACAT ACTTTGAGAA   12660

ATATGGCCTC AGTTGGGGAG CTCTCATTAG ATCATCTCAA GCTACCCCTG GATTTAGGAT   12720

AGAAACAGCC CTGTCAGGTC AACTATGACT TTCATAAAGG ATTCCGTTGG CTTAATTCAC   12780

CGAATTCATC TTTCCCTGCC AAGCCCGTGC CTGGGAATGC CAGCTGTCCA CAGGCAAGAG   12840

TGACTCATGA ATGGGCTGAA ATAGATTGAA TAGAAAGTTT GAAAACCAAG ACTTGTGGCC   12900

AGAAATCAGT GACAGGAGGG AGTGACTACA GAGGCAAAGC TGGATTCCAA GGCCAAGAGC   12960

AGGCAAGCCA AGGGTGAGGG ACTAGGCTCG AGTGGGAAAG GGCAGAGTGG ATATCCTGGG   13020

GACAGAGACA CTGTGTTTGC CTCCTGGAGT GAAGAACTAT GCCTTTGACT CACTTGACAC   13080

ACTTTACAAA TAGTATTACC CATGGTTTTT AGAAAAGTAT GGCCTGTCAT TGCTCCTTTT   13140

CCTGCTGTGG AATTAACTAA TACCTCTTAA CACCTTTAAG CAAGAATGAT AATAACAGAT   13200

CAATATCAAA AAAATATGTT GAGATCAAGT TCCAGAGACA GCCTTAGGCA TTTGATATCC   13260

ATATTCTTTT TGTATATGTC TGTGTTTTAA AATTTCACAT TTAGTTCACT CAAAAGTATA   13320

AAAATATTTA TTTAAAGAAT AATAAATACC CAAGTTGGCT TGAGAAATAG AACATTTCAT   13380

TAATTAAAAA ATATGCCCTC CCTGATCACA CCCTCTTCCT CCCCAAGAAG AAGAAACCAC   13440

CTAAATTGAA TTTTGGTTTA ATCATCTGCT GAATAAAATG TTTCTTTTCA CAATATTTTG   13500

AACTTTAAGA GAACATATAC TGAAACTATT TTTTTTTTTT TTTTTTGGC ACATTGTTAG   13560

ACTCATCCGT GTTGACTGGG AGATTCTATT TATTTTCACT GCTTTTTAGT TGTATCAGTT   13620

GAATATTTTA CGGTTTGTTA TTTCCCTTGC TGGGGGACAA TTGACTTTTA TTTTTTGTTT   13680

TAAAATTTTA AATGTAAATT GTGTTGATTC GTTGATTGCT GTTACAAACT ATGCTCCTAC   13740

GAACATTGTT AAATGCCTCT GATCACTTAG GTACTAGAAT GTCATAAAAA AGAGTGAACT   13800

TTAAATCCCA GCCCCAAATA CTTCCTGAGT AAGCTTGGAC GAGCTTCTCA CTGAGTCTTG   13860

GTTTCCTCCT CTGTAAAACA ACAATACTAG TATCTACTTT ATAGTGTTAC TATGAGATTA   13920

TTTGGGGCAA CACATCAATG TGGTTAGCTT CCCATCCACA GATCTACCCA CCTGCATCCC   13980

ACTCAAACCC ACCTAAGTTT TCTGCAGCCT TTACATTTCA GTAACTAGAA CTTCCCACGT   14040

GGTCTGTGTA TAGAGCAGCC ATGGTTTGGT GAATGACTGT GTCCTGAAAT GTAGTCTTTT   14100

GCGTATCTTC TTTTGGTAGTA GGAAACAGCT CATTATGCTA GGCTCTTCAG GATATTTTCT   14160

AGAATAGTTC CCTTTTTTCT GAGAGGGCCT TGAATGAGTA GAACACTAAC AAATGAGTGA   14220
```

```
AATAATGGTA CATAGGCCAG CATTCCCTAA GCACAATTTC TGTTTTTCCT TCATGAAATG    14280

CTGGAGGTGG CAGGCAGGAT TTCATATCCC ATTCTTCTCA TCACATGCAT ACTCCCTGAA    14340

ATTTGTATAG GATTTTAGGG TTTTCAGAGC TACTTCGTAT ATATGATTTC GTTTGGTCTT    14400

CGTCAACTCC TTTGAAGTGC TAGACATGTC TAGGTTTTAG GTGTGATTTT CTTAAATTTA    14460

CACACCCTGG GATTCAGATA AATAAGAAAC TGAGACTTGA CATCTGGGCC ATTGCTTTTT    14520

ATACTATCTC ATAGATAGCA GACTCTCCAA ATCAAAATAC AGAAATATTT TTACTAATAC    14580

ATAATAATTA TACACATTTA TGGGATATCT GTGACAATTT CATGCTTCCA TGCAATGTGT    14640

GGTGATCAAA ACAGGGTAAC TGGGATATCC ATCACCTCAA ACATTTATCA TTTCTTTGTG    14700

TGGGAGCAT TTTCTACCTA TTTGAACTA CACAATAAAT TATTGTTAAC TATAGTCACC    14760

CTCCTGTGCT GTCAAACACT AGAACTTATT CCTTCTAACT GTATTTTGT ATCCAGTAAA    14820

CAACCTCCCT TAATTCCCGT CCCCCAACCC CAACACTCAC TCTCTATAGC CTCTGTTAAC    14880

TACTGTTCTA CACTTTACCT CCATGAGATC AATTATTTTG GCTCCCACAT ATGAGTGAGA    14940

ATAAAGACAT TTGTCTTTCT GTGCCTGGTT TATTTCACTT AAAATAATGT CCTTGGTTCC    15000

ATCCGTGTTG CTGCAAATGA CCGGACCTCA TCCTTTTTAA CGGCTCAATA GTACTCCATT    15060

GTGTAGATGT ACCACATTTT CTTTATGCAT TCATCTGTTG ACGGATACTT AGGCTGGTTC    15120

CAAATCTTGG ATATTGTGAA CAGTACTGCA ATAAACGTGA GAGTGCAGAG ATCTCTTCAA    15180

CATGCCATGC TGTTTTTGTT ACTCCTACAG TTTTGCAGTA CATTTTGAAA TTCGCTAGCG    15240

TGATGCCTTC AGCTTTATTC TTTTGACTCA GTATTGCTTT CGCTACTTGG AGTCTTTTGT    15300

GGTTCCATAG AATTTTATGA TTTTTTTTTC TAATTTCTAT GAAGAAGTAT TTGGCATTTT    15360

CACGGGGATT GCATGAAATC TGTAGATCAC TTTTGGCAGA ATTGGTTATT TTAACAATAT    15420

TAATTCTTCC AACCTGTGAA CATGGGGTTG GGGTGTCTTT CTACTTTTTT GTGTAATCTT    15480

TAATTTATTT TGTAAGTTTT TTAATAGTTT TCCTTGTAGA GGTTTTTATC TCATTGGTTA    15540

AATTTATTCC TAGATACTTT ATTTTATTTT TTATACCTAT TATAAACGGG ATTGCTTTCT    15600

TGATTATTTT TTCCTGCTGG CTGCTTGTTG GTACACAGAA AGTCTAGTGG TTTTTGTATA    15660

TTAATTTTGT GTACTGCAAA TTTACTGAAT TCACTTATCA CTTCTGAAAG TTTTTTTGGT    15720

GGAGTTTTAA GGGTTTTGTG TCTGCAAACA AATTTACTGA ATTCATTTAT GACTACTGAA    15780

AGTTTTTTGG TGGAGTTTTA AAGGTTTTAT ATCTGCAAAC AGGGACAATT TGACTTCTTC    15840

CTTTCCAATC TGGATGCTCT TTTTTTTCCC TTGCCTAATT GCTGTGGCTA GAACTTCTGG    15900

TACTATGCTG AATAAAAGTT GTGAAGTGGA TATTTTTGTC TCTTCCGTAT GTTAGAGGAA    15960

ATCCTTTGAA TTTTTCCCTG TTCAGTATGA TGTTGGTTGT GGGTTATTA TATATGGCCT    16020

TTATTGTGTT CAGATATATT CCTTTTACGT CTGACTTGTG GAGAGTTTTT ATCATGAAGC    16080

CCTGTTGAAT TTTATCAAAT GTTTTTTCTG CATCTATTGA GATGATCACA TGGTTTTTGT    16140

TCTTCACTCT GTCAATGCGA TGTATCATAT TTAAGTTGGT TTGCATATGT GGAAACATCC    16200

TGTCATTTTG TTAATTATTT TCTGGTTGGT TTGTATAACC TTTGTTGATT TCTTTCTTAT    16260

TGTTTATCAT TGCAGTTTAG TATTTTCCTG TAGTGATAAA GTTTGATTGT TTTTCCTTTC    16320

TCCCTTGTAT ATCTGCTCTA CTGGGATGAA TCCCTTGCAT CCCTGGGATA AATCCCACTT    16380

GGTCATGGGG AATGATCTTT TTAATGTGCT GTTGGTTTCA GTTTCTTAGT ATTTGGTTGA    16440

GGTTTTTTGC GTTTCTGTTA ATCAGAGATA CTGGTCTATA GTTTTCTTTT TTTGTTGTGT    16500

CCTTGTCTGG ATTTGGTATC AGAGTAATGC TGACCTCAAA TAATGAACTT TGAAGAATTC    16560

TCTTCAACTT TCTGGAAGGG TTTGAGAAGA ATTGCTATTA TTTATTTAAA TTTGTGGTGT    16620
```

```
AATTCAGCAT TGAAGCCCTC AGTTCCTCAG TTATTTGATG GGAGGCTGTT TATTACAGAT   16680

TCAATCTTCT TACTCATAAT TGGTCTGTTC AGGTTTTCTA TTTCTTTTTT TTTTTTTTTT   16740

TTTTTTTTTT TTTTTTTGAG AGGGAGTCTC TCTCTGTCAC CCAGGCTGGA GTGCAGTGGT   16800

GCAATCTCGG CTCACTGCAA ACTCCTCCTT CCGGGTTCAT GCCAGTCTCC TGCCTCAGAC   16860

TCCTGAGTAG CTGGGACTAC GGGCACCTGT CATGATGCCC AGCTAACTTT TTTGTATTTT   16920

TAGTAGAGAT GGGGTTTCAC CGTGTTAGCC AGGATGGTCT CCATCTCCTG ACCTCATTAT   16980

CCGCCCGCCT CTGCCTCTCA AAGTGCTGGG ATTACAGCTG TGAGCCACCG TGCCCGGCCC   17040

GTGTTTTCTA TTTCTTACTG GTTCAATCTT GGTAGGTTTT ATGTGTCCAG GAATTTGTCT   17100

ATTTCTTTCT GCTAGGTTCT CTGATTTTTT GGTGTATAGT TGTTCAGAAT AGTCTGTAAT   17160

GATCCTTTAT ATTTCTCTGG TAGTCTCCTA TTTCATTTCT GATTTTATTT ATTTGAGTCT   17220

TTTTCTCTTT TATTCTTGGT TTGTGTAGCT AACCGTTTGC AAATTTTGTT TACCTTTTCA   17280

CAAAACCAAC TTTTTCTTTT GTTGATCTTC TGTATTTTTA TAGTCCCCAT TTTATTTCTG   17340

CTCTGATCTT CATTATGTTT TTCTTCTACT AATTTTGGTC ATGGTTTGCT CTTACTTTTC   17400

TAGTTCCTTG ATATGCATCG TTAGGTTTTT AATTTTATTT CCACTTTTCG GATACAGGTA   17460

TTTATTGCTG TAAGTTTTCC TCTTAAAATG GCTTTGTTGT ATCGCATAGG TTTTCAAATG   17520

TTGCTGTTTT CATTTGTTTC CAGAAATTTT TAAATTATCG TTTTAATTTT TTCATTTGAC   17580

TTCTCATTCA GGAGCATGTT GTTTAATTTC CATGTATTTG TGTAATTTCA AAAGTTACTC   17640

TTGTTATCGA TTTCTAGTTT TATTCCATTG TGATTAAGAG AAGATACTTA CCATGATTTC   17700

AGTTCATTTA AATTTGTTGA AACTTAATTG TGTGGATGAA CATGTGGTCT GTCCCCAAGA   17760

ACAGTCCATG TGCAGAATTT ACTGATGAAA AGCATGTGTA TTCTGCAGCT ATTGGATGAA   17820

ATGTTCTAGA AATGTCTGTT AGGTCTGTCT GGTCTCAGAT TCATTTCCTG TTAAATGTTT   17880

CTTTGTTGGT TTCTGTATAT ATATATATAT ATATATATGT ATATATATAG ATATCTGTCT   17940

AATGCAGAGA GTGAGTGTTG GAAGTCCCCA ACTATTACTA TATTGAAGTC TATCTCACCC   18000

TTTAGATTTA ATAATATTTG GTTTTTATAT ATCTGGGTGC TCTGATGTTG GGTGAATATA   18060

TATTCACAAT TGTTATATCC TCTGGCTCAA TTGGACCCTT TATCATTACA TAATGACCTT   18120

TTTGGTCTCT TTTTACAGTT TTTGACTTGA AGTCTGTTTC ATTTGATATG TATAGCTACT   18180

CTAATTCACT TTTGGTTTTG GTTCACATGG AATATCTTTT TCTGTTCCTT CACTTTCAGT   18240

CTATGTAATC ACACAAGTGT CTTTACAGGT GAAGTCAGTT ACTTGTAGGC AGCATCCAGT   18300

TGGGTAATTT TTTTTTTTTT TTTCAATCCA TTCTGCTAGC CTAAGTCTTT TATGTGAGGA   18360

ATTTAATCTG TTTACATTCA AGGTATTACT GATAGGTGAG GACTTACTCC TGTCATTTTG   18420

TTAATTATTT TCTTGTTGTT TTGTATATCC TTTGTTCATT TATTTCTGCC TTATTGTTTA   18480

TCGTTGCAGT TTGGTCATTT CTATAGTGAT ACGATTTGAT TATTATTCCT TTTGTTGTAT   18540

ATCTGCTCTA CCAGTGATCT TTATACTTGT ATATGTCTCT GTAATAGTGA TCATCATCTT   18600

TTTACTTCCA GATGTAGGAC TTCCTTAACC ATTTCTTGTA AGGCCAGTCT AGCACTGATG   18660

GACTCCCTCA GTTTTTGCTT GCTTTAGGCA GACTTTATTT CTCCCTCATT TATGAAGGAT   18720

TGCTTTGCTG GGAATAGCAT TCTTGACTGA ACTTCTTTTT TTTTTTTTT TTTTTTTAG    18780

CACGTTGAAT TATATCATCT CATTTTCTCC TGGCCTGTAA GACTTCTGCA GAGAAATCCA   18840

CTACTAGTCT AATGGAGATG CCCTTATATG TGACTTGATG CTTTTCTCTT GCTTTTGTAG   18900

AGAAAGACTT TCACGTGCAT CTGAGTTTTA GTGTGCCAGT TGAGAAGGGT GCAGTGACTC   18960
```

-continued

```
TTTTTCAAGA TAGTTGAAGT GGTATGGCCT CATTCAGCTT CTTTGGCTGC ATTCAATATC    19020

AGCAGTAGCT GTGAGTACCT CAGTTGCCTA GGCCATACAA GTTTGTGGTA GTGATGATGG    19080

CATAAGTTGT TAATAACCTC CATATCAAAG GCTTTGGGGG TTTTCTTCAT TCTCATTTTC    19140

CACACACTGG GGAGATTTAG ACAAGAGTAT CCTTTCTGGA TTCAGGTCTG ACATGGCCTA    19200

TAAGTAGCTA TAGCAGTGCT GGGTTCCAGG TTTAGGTGCT CCAAATGGCT ATGGTGCTAG    19260

GGTCCTAGGC TCAAGGTTTC ATGAACTATG TGTGGCACTT GGGTCTTGGG GTGCCTGTTT    19320

ATTCTCTGTG GTGAGGTTGA ATGCAGGTTG CCCAAAGAGC CAGGATCTGT GACTCTGAGG    19380

TACCCCCTAG CAGCTTGGTT ACAGGGATTT GGGTTGTAGC TGTGATTCTA TCCCTAGTGG    19440

CCAGGGAGCA GCACTGGACC AACTCTGGAG AAGAAGGGGT GCTCTGGATG TTTGGGCCTA    19500

GGGAGCAGGG TAGTGCTGCA ATTCAGGAAC CCAAGCCAAT AGGTATCAGT GGCAATGTGG    19560

GTCCCATTGT AGTAGTAGTA GTGGTAGTAG TAGTAGTAGT AGTAGTAGTA GTAGTAGTTG    19620

TAGCTGTAGT AGTAGTAGTA GTTGTTGTAG TTGTTGTAGT TGTAGTAGTA ATAGTTGTTG    19680

TAGTGGCAGT AGTAGTGACT CTAGACCTTG TGATGGTGGA GTCAGCAGTA TTCCAGATTC    19740

TGTGAGGCCA GGTGTAGCAG TAGCAAGTAC CCTGAATAGT GGAGCACAGC TGTCCTTTGG    19800

GCCCTGTTAG GCAGGAAACA GCACTGTGAT GATTTTACTT TCCAGGGAGA GGGGTGTCTC    19860

AGCAGCTCCC GCTCTTGGTG GCTAGTCCAG CTCTCCAGGG AATTAGGATA CTAGAGTTGT    19920

TTGGCCTGTA GGGCAGACTG TCTCAGTTCA GCCACGGTTT TGCCTCTCTG TGATGCAAGG    19980

TACTACAGCA GTTTAGCTCA GCTTGGCCAG GGCACTGATT CCCCAGGTGG CCCAGAGACC    20040

ATTTTCTGGG ATACAGGGCA CTGCTAAAAC TTAGGCACAG GGAGGCATGA CTGCTCAAAG    20100

TGACTAAGGT ATTGTTTTCT TGGAGGCAGG GTACTGTTTC AGATCTGGCC TGAGGAGTTA    20160

GGGGAAGAGT AGGTGGATCA GCTCCACCTC CACTTGGCCC CAGGAGAAGT GTGTAAGAGA    20220

TGCTTATAGC TCACCTTGGG GATGTTCAGT CACTAGGCTG GGGGTGTTTT GGTGGCAGTT    20280

TAGCCTCAGG GATGAAGGGG ACCTGTGCCT ACTTGAACCC TGAGCACGAC ACACTCCAGC    20340

CGTAGGTCTA GCTGCAAGAT GGTATAGCAC AGTAGACATG TGGGCCACAG AGGAGAACAT    20400

AGTGTTAGCT ACTTCTCTGA AGGGAGCACA GCTTTGTGAA CTCTAGACAG CTCCTTCAGG    20460

TGGGCTTAGG TAGTGCCTGT GAGGACCGTA GGGCACCTCT GCCATGGTGA GGTCTGTGGA    20520

TGTCCAAGGT GTTGATCGGG GTTGCTGGTG TTCTCTTGCT TACCTCCTCA CTGTATGAAG    20580

AAGTTCCTCT TTGTTCCTAG CTTATCTCAA TTTGGGATG GAGTGGTGAA GGCCTGGCAT    20640

TTCCTTCCAT TCTCTTTGTG GCTGTTCTGT TTCTGTGCTC ATCAGGGTTC CTGCTATTCC    20700

TCTGAGTTTC TCTGGAACTC TCCTTCAGTT ACTCTCATTA AAACGTAGTG TTTTTTTAGT    20760

CTTTCTGGCA TCTGTGATGG AGACAAGCTC TAGGGGCTTC TAGTCAGCCT TGCTCTTAAT    20820

TAATCCAAGA GACAGAAATA TTTTTGACTG GGCTTTATGA AAGCTATAAC TAGGACTATA    20880

ATGCGAAATG GACAACTTAA AATTGGAGGG AGAAAAAAAT TCAGTTAGAA TAGGTTGAGC    20940

TAAAATTTAC CATGTGTCAG CAGGCTCTGT ACAAAATTGC ATTAAGTAAC TCCCCTCATT    21000

TAATCCTTAC AACACCCTAG TGAAGTTATA TATTGTTCTT ATTTTTTATA TATGGGAACA    21060

CAAATACTTA CACTATAAAA TATCTTACCT AATGTCACAG AGCTAGTTAG CTACAGAGTC    21120

AGGGGTCTGA CTGCAGAGCC CCCCAGTTTA CCACCCTAAA TTCCTCTGTC ACTTAAACTT    21180

CAATCCCATC TCACTCCATG CCCTTTTCTT AGAAGGCAGT GGTTTACACA GAACAGATCT    21240

GATTTGTTTA GAATATGGAG AATCTTTTAA AAAATAATT TGTTGAGGTG AAATTAAAAT    21300

AATGAAATTA ACCATTTTAA AGTAGCACTA AGTAGATTCA TAATGTCTTA CAAACAGCAC    21360
```

```
CTCTATCTTA GTTCTAAAAT GTTTTCATCA TGCCGAAGTA AAAATACCTT TAAGCCGTTT    21420

TCCCCCATCC CTCTGCAACT GCAATCGCTG GAAACCACCT AGGTGCACTC TTACCTTTTC    21480

TGGATATTTC GTATAAATTG AATCATGCAG TATGTGATGT TTTATCTGCT TTCACTTAGC    21540

ATGTTTTCTT CACTTAGCAT ACATTGCAGC AGGTATCCAA TACTTCATTC CTTTTCATGG    21600

TTGAATAATA TTCCGTTCCG TGAATATACC ACATTATGTT TATCCATTCC CCCTGCTGGA    21660

CTTTTGGGCT GTTTCTACCT TTTGATTATT GTAAATAGTG CTGCTATGAA CATGTGTGCA    21720

CATGTACTTA TTTATGAGTC CCTATTTTCT TCTTTTTTAA TACTTTTATT TTAGGTTTGG    21780

GGGTACATGT GAAGGCGTGT TACACAGATA AACTCATGTC ATGGGAGTGT TTGTTGTACA    21840

GATTATTTCA TCACCCAGGA ATTAAACCCA GTACCCAACA GTTACCTTTT CTGCTCCTCT    21900

CTCTCCTCCC ACCCTCCTGC CTGAAGTGCG CCTCAGTGCC TGTTGTTTCC TTCTTTGTAT    21960

TCACAAGTTC TCATCATTTA GCTCCCACTT ATAAGTGAGA ACATGCAGTA TTTGGTTTTC    22020

TGTTCCTGCA CTAGTTTGCT GAGGATAATG GCCTCCAGCT CCATCCACTT CCTGCAAAAG    22080

ACATGATCTT GTTCTTTCTG TATGGCTACG TAGTATTTGA TAGTGTATAC GTACCACATT    22140

TGCTTTATCC AATTTGTCAT TGATGGGCAT TTAGGTTGAT TCCTTGTTTT TGCTATTGTG    22200

AATAGTGCTG CAATGAACAT TTGTGTGCAT TTGTCTTTAA GGCAGAATGA TTTATATTCC    22260

TCTGGGTATA TTCCCAGTAA TTGGATTGTT GGGTCGAATG GCAGTTCTGC TTTTAGCTGT    22320

TTGAGGGATT GCCGTACCGC TTTTCATAAG GGTTGAATGA ATTTACACTC CACCAATGGT    22380

GTATAAGGGT TCCCTTTTCT CTGCAACCTC ACTAGCATCT GTTATTTTTT GTTGAGTTCC    22440

GATTTTTAAT TCTCTGGGGT GTATACACAG CAATGAACTT AAGGGTCGTA TGGTAATTGT    22500

GTGTTTAATC ATTTGAGAGA TTGCCAAACT GTTTTCCACA GCAGCTGAAC CATATTACGT    22560

TATAACCAGC AATGTACAAG TTCTGATTTC TCACCAGCAC TTGTTAATTT TCCATTTAAA    22620

AAAAGTATAG CTATCCTAGA GGCTGTGAAG TGATACTTTA TTGTGGCCTT TATTTGCATT    22680

TCCCTACTGA CTAATGGTAT TGAACATTTG TAAAACATGT TTGTTTGCCA TTTGTATATA    22740

TTCTTTATAG AAATATCTAT TCAGTCCTTT GCTCCTTTTT AAATTGGATT GTTAGGTTTT    22800

TTGTAGTTGA GTTGTTAAAA GTTGTTTATA TGTATGTTCT CAATACTAGA TCTTTATTAA    22860

AATATGATTC ACAATTATTT TCACCCATTT TGTAGGCTGG ATTTTTACTT TCTTGGTAAT    22920

GTCCTTCCTT TGATGCATAA AATTTTAAAA TTTTGACAAA ATATAATTTA TCTATTTTTG    22980

TTTTTCATGC TTTTGGTGTC ATATGTAATA ATCTATTGCT GAATCCACTT TGAAGAAGAT    23040

TTACACCTGT GTTTTCTTCG AAGGGGTACA GTTTTAGCTT TTATATTTAG GTTATTGATT    23100

CATCTTGAGT TAACATTTTA TATAGTATGA AGTAGGGTCT CGACTTTCTT CTTTTGCATT    23160

TGGATATTCA GTTGTCCCAG CATCATTAAA GACAATTCTT TCCCCACTG AAAGGTCTTG     23220

GTACCTTTTT GTTTGTTGAA TAGTGATTGA AATCACTTTA GCTTAATCCA AACAATCAGT    23280

GAGACAAGGA AGTGCTGGGA CTCTGCCCCA TGTTTTCTTG ATATGTCTGT CATCCATGCA    23340

GGTTCTTCTC AAGGTTCAAA GAAGAACCCA AGTTCTTCTT TGAACCCAAG GTTCAAAGCC    23400

CCATCCCAAG TGTCCTCCTC TCCACTGGCT GCTTCTCCTA TTAGTAACAG ACTCTAAAGT    23460

TGAGGAAGTC ACCAGATTCT TCTCCCTAGT CCAGACCCAC AAGATGGTTC CTTGTTGTTA    23520

GCAAGGATAC CAACTGGATG CCATGGGTCT CATTCAGGCC CATTCACAGC CTTGTTGGTT    23580

TCACTATTTT TTCCTTCCTC CTTTTAATTT TAACAGGTTC ATTGCAATAT AATTACTGTA    23640

CATAAACTGC ACATATTAAA ATTGTACACC TTGCTGAGTT TTGACATATG TATACAACTG    23700
```

```
TGAAACCATC ACAACAGTGA AGATAAGAAA CATTCCCATC ATCTCATTGT AATTCATTCC    23760

CCAACCCACC CTCAACTAAT AATCTGTTTT CTGTCACTAT GAATTACTTC AAGCTTTCTA    23820

GAAGTTTATA TAAATGGAAT CATACAGTAT ATACCCTTTA GTCTGTGAAT TCTCTCATTT    23880

CTCATAATGA TTTTTAGATT CGTCTGTGTT GTTGCATGTA TCAATAGTTT CTTCCTTTTT    23940

ATTGCTGAGT AGTATTTCAT AATAAAGATT TTACACAATT TGTGTATCCG TTCTTATACT    24000

GATGGTCATT TGGGCTATTT CACGTTTGGG GCTATTGCAA ACAAAGGTGC TACTAACATT    24060

AGTGTGTAAG TCTTTGTGTA GATGTATGCT TTTATTTCTT TTGGGCAAAG ACCCAGGAAT    24120

TGAACAGCAA GGTCCTATGT TAGGTGCATT TTAAGTTTTT AAAGAAATTT CCACGCATTT    24180

TCTGGAAACA CACAAGAATA AATTAACATA TTCTTATCTC TTGTCATCTT TGTGCTACTA    24240

TAATATTTGG AGGTTCTTTT AAAAATAAAT GTGTACATCT TTGTCTCCTA TGCCTTTGAT    24300

TGCCTGGAGC AGATTTGTTT GTTCTTTTTT GCACCTTCAA TTCCTAAGAC AGTCCTTTGC    24360

ATAAAAGGAT GGTTAATCAG CTTTGGATGA ACGAATGTCA GATAATGGCT TATCTGAACC    24420

AAAATGAATG AGAGGGCAAA ATTGGAGAGG ATGAGAGGAG TAGAATAGGT AAATAAATAA    24480

AATAACACTG TCTTTTAAAA TTATGCACAT AATTCATGAT GGAAAAAGAT CCAAAAATAA    24540

AGAGTAGCTT AAAGAAGAAA ATAAAAATCA TCCATGATCC TTCATAGTCA CTCTTTAAAA    24600

AATTATTTTG TTGTTTTATT TTCTCCCCAA TATTCTCTTA AAGTTAAGGC CACTAGTTCT    24660

CAACTCTTCC TACACATCAG ACTACTCAGG AAGCTCTTTT AAATAGGTCC AATGTCTGGA    24720

TTCCATTAGA GATTCTAATT TTAATTGGTC TGAGGTGGAG TCTGGGTGTC AATAGTTTTT    24780

TTTTTTTTAA TCAATCTTTC AAAGGTAGTG ATTTACATAC AACAAAATGC ATTTATTTTA    24840

AGTGTACAGT TCAATGAGTT TTGACAAGTA TGTATCCTCC CTATAAACAC TGCTCTAATC    24900

AAGTATACAA TATTTCCATC ATCTTCAAAT ACCCCACATT TCATCCCAGG CAACCCCTGA    24960

TCTGGCTTGT TACTATAGAT TAATGGTGAT TATTCAAGAA TTTCATATAA ACAGAACCTA    25020

ACAGTCTGGC TTCTTTCACT CAGCATGTTT ATCAGAGTCA TCATATTGTT ACATATATCC    25080

ATAGTTTATT CTTTTTCACT ACTGATTAGT ATTTCATTGT ATGGAGGTAC CACATTTTGT    25140

TTATCCATTC ACCTCTTGAT GGACATCTGG GCTGTTTGCA CGTATTGACT GTTAGGAATA    25200

GAGCTTCTAT GTGCGTTCTT ATAAGTCTTT GTGTGGAGAT ATGTTTTCAT TTCTCTTGGG    25260

TAAATGTGTA GGAGTAGAAT TGCTGGGTCT TATGGTAAGT GTCTGTTTAA CTTTATAAGA    25320

AATTTACAAA TCATTTTTCT TTTTTTCTTT TTTTTCCAAG ACAGAATCTT GTTCTGCCTC    25380

CCAGACTTGA GTGCAATGGC GCGATCTCGA CTCACTGCAA CCTCGGCCTC CCAGGTTCAA    25440

GCAATTCTCC TGCCTCAGTC TTCTGAATAG CTGGGATTAC AGGCACGTGC CACCATGCCC    25500

GGGTAATTTT TGTGTTTTTA GTAGAGGCGT TGTTTTCACC ATGTTGGCCA GGCTGGTCTC    25560

CAACTCCTAA CCTCGTGATC TACCCTCCTC GGCCTACCAA AGTGCTGGGA TTACAGCCAT    25620

GAGCCACTGT GCCTAACCTC CAAACCATTT TTCAAAGTAG TTGTACTATT TCACACATCC    25680

ACCAGTGATG TGTGAGTGTT CAGTTGTCCT ACATTTTTGC CACACCACCA ATATTGTCAG    25740

TATCTTAAAT TTAAACCATT ATAGGGGTCA TTAGCAGTTT CTAAAAGCTC CCCTAGAAAT    25800

GTGTACTTCT CTGTATATAA TACATAGTAA AAAGTGAAGA AAAAATAACT CTCGAAATGA    25860

TTGTAATGTG CAGTCAATAT TGAGAACCAC TGAGAACCAC TGAGCAAGAC TAGACCGACA    25920

AGTCCCAAGT ATTTAAATAA TGACATATTT TCATTTGTGC GTTATTTTTT TCTTACCCAT    25980

TCATTTATTC AAAAATAACT ATACTAGCTC TATACTAAGT GTTGGCAACA TAGAGATCTA    26040

CAACAATATT TTTCTGCCCT CAAGAAGCTG ACAAATTTCT TTTTTCTCTT AAGAAAACAA    26100
```

```
AATTTCACCT GTGTGACCAC AGTCATTTCA GACAATTTAG TTTTTAATTG GTCTTTCTCA    26160

GTATTGTGCA GCCCAGGCCT TGAGTCGATC TTGATGAGGG GGAAAAAGTA ACGGGATCAT    26220

TCATGGTATT TGAGATGTTG CTTTCTTGAT TTTACTCTTT TCCTTCCCTG CTTCCTGTCT    26280

CCCGTATTTG CTTTCATACA TAATTCAGCT TTGGGAACAG TGTCTTTAAA TGAAGTCACC    26340

ACATGAGCCA TAACAATATA AATAAAACAA AAATACTTTG CCTCTGGAAT TGGCACTTTG    26400

GTGACTGCAC TCCATAGAGG CTATGGCTGA TTTCTAATTT TTGTATTTTA TTTTTCTCCT    26460

TTGTTTCTTT GATATAGGAA ATCTTCAGTA AAAAGCATAT TCTAATAAAA ATAAGACTAA    26520

CTAGTGTAAC ATTATAAAAT CCTCTCCAGA AGCCTATTAA ATAAGTATAG TAGATGGGTA    26580

AAAAATAATA TGGCCCATAA ACCCTACAAA ACTCACAAGT AAAATTATGT AATCAAATTG    26640

TAAAATATTC TCTTATTTGC TATTAAATGT ACACTATAAA AAAGACTTTG AAATTGTACA    26700

ATAATGTTTA CCTCCTTGGA ATTGTTAGAA ATAAGTACAT AATACTTAAT TTCTGTGCAG    26760

AATTTTTTTA ATATTCTAAG AATTGTTAAG GTCAGTGTGA GAAGTGTTAA CATTGGCTGC    26820

CACTTGCTTA CAAAAGAGGT TCTACATACA GCAACTGATA GGAGATTCCA TTTTCCTTTT    26880

TACTGGGGCT TTAGTGATTT CAGAGACTCC AACATTCTTG TGAAAAATTG ACTATAGAAG    26940

TCCAATAATG AGTAGAAAGT TATTTGTCTA GCTGTCGGTT TAAAGAAATT TCATCCCCAA    27000

CATAGGTGGC TTTCCATCAA GAAAATATTT TCCAGCACAA TCTCAAGCCA ATTTAATCCC    27060

TTGATTGTAT TCTGTACCAT GCAGCAAAGC CAGTTTCCAT GTTGCTGTG TTTAATTTTA    27120

TTTCACTGAA CTTTCTTTTC ACTGCAATTC TTTCCTTATT TTCATTGTTT TTACACAAAT    27180

TAGATTCATT GATCAGTTTT TTTGTATCAC ATTAATTTTT CCTTATTTAG TTTCAACCAC    27240

TGCAATTTTT GCTTTTGTTT TCCAAATCCA AATCTCTCTG ACATCAAATT TTGCAAGTCT    27300

AAATGTAAAG AAAATGTCTT TTGCAGCAAC TTGGGTGTAA CTGGAGGCCA TTATTCCAAA    27360

TGAAGTAACT TAAGAATGGA GATGCAGAAA CCATGTGTTC TCAGTTATAA GTGAGAGCTA    27420

AGCTATAAGG ACACAAAGAC ATTCAGAGTT ATACAATGGA CATCAGAGAA TCAAAAGGGG    27480

GAGAAGGTGG GTGAGGCATG AGGGCTAAAA GCTGCATATT GGGTACGATA TACACTACTC    27540

AGGTGATGGG TGCACTAAAA TTTCAGACTT CACCACTATA CAATTCATCC ATGTAACAAA    27600

AAACCACGTG CACCCCTAAA GCTATCGAAA TAAAAAATAA AAACAAAAAC AAAAAATAAA    27660

ATTTGAATGC ATTTTATCAA AAGGATGCGA GCCTTCTTTC CATTTTTAAC CAATAGCATT    27720

GTTGCCATGT GTGGTATCAT CTGTTGTCAG TTTTATTTTA TGCTGATTAT TTCTACCAGC    27780

CGTAACAATT GGGAAATAGG CAAAAAGTTG GTTGTATTTA TTTCCTAGAT AATCAATAAC    27840

AAACTTCAGA GCAATCTAAT GAGACAGAGT TATAGGTGCA CAGAAGAAGA AGAAAAGCTA    27900

CAGTTGTGTG GAGCATGGAT GGCTAAACTC CTGGTTAACT CGATGGGGTC AAAAGGACAA    27960

ATGTGGGCA GAGTTCAGAT CTTTTGACAG GGTCAACGGA TCTGGCATCA GTCCCTGGCT    28020

GCTCTCTTCT AAGTTTTCAG TCGTGCTCTT CTCCATTCCT CACCAGACCC CTGGCCTCTT    28080

TGGAGCTGCC TGGACAGGAG CTCTCCTGGC CTCTGGCAAA CTCCTGGCTG GGTTGCGGAT    28140

GGAAATTCCT GGTACCCTTA GTTGAGTTCA TACAAGCTGA ACGTTTTCAA AAGGAACTAA    28200

TTTTACTTGA GCCAACTAAA CAAAACTGAA ATACACACAG AAAATACAAA AGCACAGAAA    28260

TAGATGAGGG TTCCATGCCA TGGGCATTTT AATCATGTGT ATCAAGAACC TTTATAGAGT    28320

TCATGTCTGG CCCAGCCAAT CCACTTCTAG GAAGTTATCT CAAGGTGATG TACTGGATAT    28380

GAGTTGAAAG ATGTGTATAC GACGTATTTA TCAACAAAAA TTGGAACAAG GTAAATATGT    28440
```

```
TCTGATAGAG GAATAATTCA AATAGAGTAT TTTCATACCA TTTAATACTC AGCTACGAAG    28500

CAGGGCTGGT AAACTTTTCT GGAAAAGAAT AGATAGTAAG TATTGTAGAT TGTGGGCCA     28560

TATGGTGTCT GTCAGAAATA ATCGATTCTG CTATTGTAGC ACAGCAATGG GCATAGATAG    28620

TACATAAAGG AATCAGCACA TTCATGTTCC AATAAAACTT TGTTAATTTA CCAAAAAAAA    28680

AAAAAACACA AAACCCAGGT GGAATTGGCT TATGAGCCTT AATTTGCAGA CCCCTGGTTT    28740

ACAGAGATGA TATGGATTTG TATTTACTGA CAAAGAGAGC TGATTATAAT ATACTATTGG    28800

GCAAAAACAA AAGCAGATAC TAGTATAGCA TTTATGGTAT GATGTCACTT ATGCAAAATG    28860

AAGATTGATA TATATATATA TATATATATA TATATATATA TATATATATC AGTAGAGAAG    28920

TGTCTAGAAG GATGTTCAGC AAATACTAAC GAAGATATTA TCACTAGGTT GAAGAATTTG    28980

AGATGATTTT TTTCCTTTAT TTGTTTTCAC ATTTTTTCAT TACTAGAAAA AATATTTTTA    29040

TTTAATAATT CATACTCTTT GACAGAGTAC TTCCACGGTT GTTGTTGGGG TTGCCGCACA    29100

GCTGTGAAGC CTGTGCAGTT GCACACTTCC AGGAGATGCC ATCACATGGA CTACAATGTG    29160

AAGGATTCCC CCAGAGTTGT GTGGCGAGGC AGTCTTCCCA CCTCCCATTC TCTGTTCAGC    29220

TCTGTCCAAT TAATTCAGCA AGCATTTGTT TGTCATCTAC TACACTAGAC ATTGTTCTAG    29280

ACAGAAATAT CGGGAAACAA AGCATACAAA AATGTTTGCC CTTGTAGTGC TTTATGTTCT    29340

AGTGAAGGAG AAAGATGATA AGGAGAATAA AGAGTGACAC ATATGCAAGC TTCCTGGAGG    29400

TCAAGTAGCC CAGTTTTTGG CAGAGGGAAT AGCCAGTGGG AAGAAGGCAG GCAGGGCAAA    29460

TATTTACAAC CCTCGTTTTA CAGAAGAGAA CATTGGAACT TAGGGAGGTT TAAGGGATGG    29520

CTGAGGGTCA GAACGTGGTC AGCACCAGAA GCAAGGCCTT TCAATTGCAA GGTCAGGGTT    29580

CCTTCCACAC TGGGACAAGA GGCAGCACCT GCAAGATAAG GTAGAGGTGA ATGAACCTAG    29640

GTGGCTTTAG TTAGATTCTG CAGACTTTTA TGACAGGCCA ATGCATATAA ATGATAATAG    29700

CTGACATCAC ATTAAGAAAA AGATGCAGCA TCTCATGAGA TCTACTACAT GCTCCTGATT    29760

AGGAAAAGGA ATGTTGAAAA ATAGCACTGA GTTTATAAAA ATAGCGTTTA GGGTGTAATT    29820

CTCATTTTTT TAGTACATGA ATGCTTAAGA AAGATGTTCA TCAAATGTTA GCAATGCTTA    29880

TTACTTGATG GTAGGATTTC AAAGAGTTTT AAATTTTCTT CTTTATTCTT TTCTGAATTG    29940

TTTGAGTTTT TTGCAATGAG AGTGTGAAAA CAGAAGAAAT AAAAAAGTTT GATGTTAGAA    30000

AGATACCATT AAGCTAACAT TTACACACTC TGTGCTGTTC CACAGCACCT GTAGTACCAC    30060

TATTTCTTTG TAAATTCTTC CAGGGCAGAG ACTGTGTTTT ATTCATTCTT CTTTGCCCAG    30120

CATGTGGAAC CTCCTACAAA ACAAGCATTC AACAGGGTTT GTGGAACAAA TGCAAAGTGC    30180

ATTTGCGAAC TGCAGCTTAT ATAATCTACA ACAGACACCT AGGGGGGCTC AGGAATGACA    30240

CGAACAGTTT CCAGCCGAAG GGAATTTCAT TTTCTTTTCT AGTTGGAGTT TCCATGGCAC    30300

CCAGAAGACC AGGGATCCTG GTAAGAAAGT TTTAAAACGC TGAAGTGGTA AGTTTGTAAA    30360

TTTGTGATAC CTGGTGTCAA GTCCTACTTC AGGAATCTAC AAAAATTGGG CCTTTTGAAT    30420

AGAAGTGTTT TAGTGAATAA TGAGTGATGT GGCAACTTAT TCTGATAATA TTTCAATCTA    30480

GCTTTTTGCT TTTAATGGTA GTTGCCATTT CTATTGGGCT GCATCATTCC CAGGAAAGCC    30540

TTCTTTTAAA ATCAGTACAG GATGTGTGCA TCCTAATACA AAAATCCCAA ATCCAGAAAT    30600

GCCCCTGAAT CTGAAAGTTT TTCAGTGCTA ATATGAGATA GTGAAACCTT TGCTTTCAGA    30660

TGGTTCAGTG TACAAAAACA TTGTTTCATA GACAAAATTA TTTAAGGTGT TGTATAAAAT    30720

TACTTTCAGA CTATGTGCCT AAGGTATATA TGAAACATAA ATGAATTCCA TGTTTAGATT    30780

TGGGTCTCAC TCCCAGATAT CTCATTATAT ATATGCAAAT ATTCCAAAAT CAAAATCAAA    30840
```

-continued

```
AACAAACAAA CAAAAAAACC GCCAAATCCG AAACACTTCT GGTTTCAAGC ATTTTGGAGA    30900
AGGGATTTTC AGCCTCTCCC TAGAGATTAA TTTGTTTGAT GTGGTCAATT GCCTGATTAT    30960
TCAAACTCCT CAAAAAGTGC AGGTCTTTCC TCCATACCAC CTGTTTAGGT TTTGAATAGT    31020
TTAGAAAAAA AAATAAGTGA CTGTCTTTAA GTCATTGATT AAAAGTTAAT AGCCTTAAAA    31080
TGTTTCCATT CCTATTTTAT TACAAAGTAT TGCTCGAAAC AAGTTTTAAT AGTGAGAAGG    31140
AAAGTTGTCA CCCATAGGTT TAGGCACAAT TTTTCAGTCT CCTTTACTCA CTTAGCATTA    31200
GACTAGAAAC ACTTTCCCAA TGATTTTTTG AATACTTGTG TAGCATTTGA ACTTGTAGAT    31260
GACCACACTG TACAAAACCA TTGCAGAATT AGCATACATT CATATTAGTG TTAGTTTTTT    31320
AGTGATTTTT AATTGAACAG GGAAATTTTA CATATTTGGC TCTATTCTGT AACTACAAGC    31380
AAAATTCTAA CTGACTTTTC CCTCTTTCAG ATTCTTAATT ATTAAACTCA TCTGACCATT    31440
TTTATTTTTA TTTATTTAAT TGACAAAGAG CGTATATACT CAAGGTGTAC AATGCAATTA    31500
TTTGATATGC CTAAATTAGG TTGGTGCAAT TAGTTTGCAC CAACCTAATA CATTGTATAA    31560
TTACTACAAT CAAATTAATT AATACATACA TTATCACCCA TGCTATACAT TAGATTCTCA    31620
GAAATTGCTC ATCTTATAAC TGAAAGTTTG TCCCCTTTGG TCAAAATCTA CCCATTTCCC    31680
CCACCGCCAT TCCCTGGCAA CTGCCATGGT ACTCTATGTT TTGATGAGTT CAACTCTCTT    31740
ATATTCTGCA TATAATACAC TGTTGACCCT TGAACAGCGT GGAGTTTGAG CACTGACCCC    31800
TGCATAGTCG CAAATCAGCA TATAACTTTT TCTTAAGGCA TGGGGTCTCA CTATGTTTCC    31860
CAGACTGGGC CTTGAATTAC CTTGGCCTTA AAACTTGATT CTCCAAAAGC TTAACTACTA    31920
ATAGCCTACT ATTGACCAAT AGCCTTACCA ATAACGTAAA CACTTGATTA ACATGTATTT    31980
TGTATATGTA TTATATACTG TATTTGTACG CTAAAGTAAA CTATAGAAAA GATGGTGTTA    32040
TTAAGAAAAT CATAAGGAAA AGAAAATATA TTTACTATTC CTTAAGTCAA AGCGGAGAGG    32100
TCTTCATACT CCTTGTGTTC CTATTGGGTA GACTGAGGAA GAGAAGGAAG AGGAGGATTG    32160
GTCTTGCTGT CTCAGATGTG ACAGAAACAG AAGAAAATTC ACATATAAGT GGACCTGTAC    32220
CATTCAAACT CATGATGTTC TATTAGTCTA TGTGTTTGTT TTTATGCCAG TACCATACTC    32280
TTTAGATTAA CATAGCTTTG TAACATAGTT TGAAATCAGG AAATGTGATG CCTCCAGCTT    32340
CGCTCTTCTT TCTCAAGATT GCTTTGGTCA GGTTTTTTTG TGGTTCCATA TGAATCTTAG    32400
AATTATTTTT TCTCTATCTG TGAAGAATGC TGCCATTGGA ATTTTGATAG AGTTTGCAAT    32460
GAACCTATAG ATCACCTTGG GTAGTATGGA TATTTAATA ATATTAATTC TGATACATGA    32520
ACATGTGATG TCTTTCTTTT TATTTGTGTC ATCTTCAATT TATTTTCTCA GTGTTTTATA    32580
TGCTGATATT TAAACTTCTT GGTTAAATGT ATTCCTAAGT AATTTTATTG TGCTTGTTGC    32640
TATTGTAAGT AGGATTGTTT TCTTTCTTTC TTTTTCAGAT AATTTGTTGG TGCTGTATAG    32700
AAGTGCAATT CATTGTTCAA TTCCCACCAG TGATTGAGAA CGTGCGGTGT TTGGTTTTTT    32760
GTCCTTGCGA TAGTTTGCTG AGAATGATGG TTTCCAGCTT CATCCATGTC TCTACAAAGG    32820
ACATGAACTC ATCATTTTTT ATGGCAGCAT AGTATTCCAT GGTGTATATG TGCCACATTT    32880
TCTTAATCCA GTCTATCATT GTTGGAGTTA ATGGGTGCAG CACACCAACA TGGCACATGT    32940
ATACATATGT AACAAACCTG CACGTTGTGC ACATGTACCC TAAAACTTAA AGTATAATAA    33000
TAATAATAAT AATAATAATA ATAATGAAAG AATTGCAATT CAATTTTAAT GTTGATTTTG    33060
GTATTCTGGA ACTTTACTGA ATTCTCTTTT TAGGTCTAAC AGTTTTTTGG TGGAGTTTCT    33120
GTATACAAGG TCATGTCATC TACGGAGACA ATTTTGCTTC TTCCTTTCTG ATTTGGATAT    33180
```

-continued

```
TTTTTATTTC TTTTTCTTGC CTAACTGCTC TAGGTAGCAC TTGTGGTACT ATGCACAATA   33240

GAAGTGGTGA GTGTGGGCAC CCTTGTTCCT GATCATAGAA GAAAAGCTTT CTGCTTTTTA   33300

CCATTGGGTA TGATGTTGGC TGTGGGCTTG TCCAATATGG CATTTATTCT GTTGAGGAAC   33360

ATTCCTTGCA TACCTAATTT GGTGAGAGTT TTAACAGCAT TTTGAAGTAT AAGTGACATA   33420

AAATAAACAG CATATGTATC TAGTGTACAA TTTGATAAGT TTTGACATAC GTATATACCC   33480

ATGAAGCCGA TCAATATAGT GAACATAAAC ATCATCCCAA AAGGTATCCT TGTGCTCCTT   33540

TGTAATCTCT CCTTCCTGTC TCTCTCCATG TACCCTCTTC TCAGGCAACC ACTGATCTCC   33600

TTTCTGTCAT ACAGATTGGT TTTAATTGTC TAGAGGCATA TACCAATGTA ATAATACAAT   33660

AAGTAGTTTA TTTTGGTGTG GCTTCTTTTA TTCAGCATAA TTACTTTAAC ATTCATTCAT   33720

ATTGTTGTAT GTATCCATAG ACCTTTTTTT TTTTTTTTT TTTTTTTTG CTGAATAGTA   33780

TTTCATTGTA TGAATACACC AACATTTCTT TATCTAGTTA CCTGTTATGG ACATTTGGGT   33840

TGTTTTCAGT GTGAGACTTT TACAAATAAA GCTGCTATAA ACATTTATAT ATGAGTCACT   33900

TTATGATACG CTTTTAGTTC TCTTGGATAT ACAAGTGCTG GATCACATAG CAGGAATACG   33960

TCTGACTTTT TAAGAAACTG CAGGTTTTCC ATTTTTCGTT TCCAACAGTA TATCAGTTCT   34020

AATTCCTCCA CCTCCTTGAC AACATTTGGT ATTGTCAATC TTTTTAAATT TAGCTATTGT   34080

GGTAGGCATA TAATGCTTTT AACTTGTATT TTCCTAACTA CTAATGATTT TGAACATCTT   34140

TTCATATGCT TATTTCCCAT CCCTGTATCT TCTTTGTGGA AGTATCTGTT CAAGTATTTT   34200

GCCCATTGTT TTATTGTTTT TCTAACTCGA TTTTGAGAGT ACTTTATACA TTCTGGATGA   34260

AGGTTGTTAT CAGACATATT CTGTGCAAAT ATTTTCTCCC AGTCTGGCTT GTTTTCTCAT   34320

TCTCTTAGTA GCATCATCTG AAGAACAGAA GTTTTGAATT TTGATGAAAT CCAGTTTATC   34380

AGTTTGTTCT TTTATGGATC ATGCTTTTGG TGTTACAGCT AAGAAATCTT TGCCCAGTGC   34440

AAAGTCACAA AGATTTTCTT TTAGAAATGT TATCGTTTTT GGTTTCTAAC TTAGGCCTGT   34500

GACCCATTTT TCAGTTCATT TCTAGGTATA GTGTGAAGTA TGGATTTTGC ATATGGTAAC   34560

CAATTATTCT AGCACCATTT GTTGAAAAGA CTGTCCTTTC TCCACTTAAT TACATTTGCA   34620

CATTTGTAAA CACAAACACA CAGACAGACA GACAGACACA CACACACACA CACACACACA   34680

CACACACACA CACACACCCC ATATATATTT AGGTCTCTTT CTGGGCTCTC TATATTTTTT   34740

AATGATATCC CTTGTCTATT GTGATGTCAA TACCCACTAT TTTGGTTACT GTAGCTTAGT   34800

AATAAGTCTA GACGTGAGAC AGTGTTAATC CGCCTAGTTC TTCTTTTCCC AAATTGTTTT   34860

GTCTAGTATG GTTCCTTTTC ATTTCCACAT TAATCTTAGA GTCAGCTTGT CAATTTCTAT   34920

AAAATGTCTG CTAGGGTTTT GATTGTGATT CCATTGAATC CATAATTTGG AGATAATTGG   34980

CATATTAATA ATAATGAGTC TTTTAATCCA TAAACATGGT CTATCTCTCC ATTTATATAG   35040

GTCCTTAATT TCTTTTGGCA ATGTATTATA GTTTATAGTG TACACATCTT TCACATTTTA   35100

TGTCAGATTT ATCCCTATGT ATTTCATATT TTTATGTTAT TCAAAGTATT TTTAAAATTT   35160

CAACTTGTGA TTGTTCTTTG CTAGTCTGTA GAAATACAGT TGATTTTTA TTGATATTTT   35220

ATCCTAAAAC CTTAGCTAAA ATCAATTATT ACTTCTAACT TTTTTGTGTT TCTATTAGAT   35280

TTTCTAGATA GATAGTCATG TTGGCTATAT ATAAAGACAG TTTTATTTCT TCCATTCTGG   35340

ATGCATTTTT TTCATGTCTG ATTATATGTT CCAGTATCTC CAGCACAAGG TTGAATACAA   35400

GTGGTGAGAG CAGACATCCT TGTCTTAGTC CTGATCACAG AGGAAATGCA TTCAGTCTTT   35460

TATCATGAAG TAAGTTTTTA GCTATAGATT TTTCATAGAT GCTGTATTAT TCAGGAGTCT   35520

CCAGAGGAAC AGAACTAATA GGAGAGATGT GTATATGAAA GGGAATTTAT TAAGGAGTAT   35580
```

```
TGACTCACAT GATCACAAGG TGAAATCCCA TGATAGGCCG TCTACAAGCT GACGAGCAAG    35640

AAAGCCCAGT CCAAGCCCCA AAACCTCAAA AATAGGGAAG CCAACAGTGC CGCCTTCAGT    35700

CTGTGGCCGA AGGCCTGAGA GCCCTTAGCA AACCACTGGC ATCAAGCCTG AGACTCCAAA    35760

AGCTGAAAAA CATGCACTCC GATGTTTGAG GGCAGGAAGC ATCCAGCACA GGAGAAAGAT    35820

GAAAGCCGGA AGGCTCAGCA AGTCTAGTTC TTCCATGTTC TTCTGCCTGC TTTATTCTAG    35880

CTGTGCTGGC AGCTGATTAG ATTGTGGCCA CCCAGAATGA GGGTGGGTCT GCCTCTCCCA    35940

GTCTACTGAC TCAAATGTTA ATCTCCTTTG GCAACACCCT CACAGACACA CCCAGGAACA    36000

CTACTTCGCA TCCTTCAAGC TAGTCAAGTT AATACTCAGT ATTAACCATC ACAGATGCCC    36060

TTTATCAGTT TGAGGAAATG CTTTTCTATG CTTAGTTTGC TGAAAGTTTT TATTTAATAA    36120

TACATGTTAG ATTTTTGTTA CCTGCTTTTT CTGTGTCTTT TGAGATGATC ATGTGATTTA    36180

TCTCTTTGCT AACATGGAGA ATTGTACTGA TTTATTTTCA GTGTAAAATC ATCCTGAATT    36240

CCTAGGAAGT AAAATCCCAA TTTATCATGA TATTGTATTC TTTTTATAGA TTTTGAATTC    36300

AGCTTGCTAA AATTTTTATT TTTTTCTTCT ATATTCATGA AGAATCTTGG CCTATAGTTT    36360

GCTTTTTTGT TAACATCTTA GTAAGGTTTT TGTGCCATGG TAATTCTGGT CTCTTACAAA    36420

TATTCCCTGC CTCATAAGTT CTCTGGGATA GTTTGTATAG AATTGGTATT ATTTCTTCAT    36480

TAAATGTTTG GCAGAATTCA CTGGCAAAGC TATCTGGGTC TCAAATCTCC TTTGTGGGAA    36540

GATTTCTAAC TACAAATTGA AAATTTTTAC ATTTATTTTT ATTTGTACAT TTATTTATTT    36600

TCTGAGATGG AGTGTCTCTC TGTCACCTAG GCTGGAGCCC AGTGGTGCGA TCTCAGCTCA    36660

CTGCAACCTC TGTCTCCTGG GTTCAAGCAA TTCTTCTGCC CCAGTCTCCC TTGCAGCTGG    36720

GATTACAGGT GTGTGCCACC ATGCCCAGCT AATTTGTTTG AATTTTTAAT AGAGACAGGG    36780

TTTTGCCATG TTAGTCAGGC TGGTCTTGAA CTTCTGACTT CAGATGATCC ACCTGTCTCA    36840

GCCTCCCAGT GTGTTGGGAT TACAGGCGTG AGCCACCGTG CACACCCTAT ATTGATTTTT    36900

TTTTTTAAAT ATAAGGCTAT TATCTGTTTC TTTGTGACTG AGCTTTGATA TTTTATATGT    36960

TTTAGGACAT TTGTTAATTT CATTTCCATT GTAAAATTTA TGGGCATAAA ATTTTACAAG    37020

TGATATTCCC TTTTTATACT TTTTAATATC TTAGAAACCA CTGATACCCA TTCTCTCATT    37080

CCTAATGTGA AAAATTTTGA TCTCTCCTTT TTCCTAATCA ATCTATCTTG AGATTTATCC    37140

ATTTTCTTTT GCTTTGTTTT TTTTTTTTTT TTCCTCTCTG AGATGGAGAT TCAGTCTTGT    37200

TGCCCAGGCT GCAGTGCAAT GGGTTGATCT CGGCTCAATG GGGCAACCTC CGCCTCCTGG    37260

GTTCAGGCAA TTCTCCTGCG TCAACATCCT GAGTAGTTGG GATTACAGGT GTGCACCACC    37320

AAGCCCAGCT AATTTTTGCA TTTTTCAGTA GAGATGGTGT CTCACCATAT TGGTCAGGCT    37380

CATTTAGAAC TCCTGACCTC AGGTGATCCA CCTGCCCTGG CCTTCCAAAG TGTTGGGATT    37440

TCAGGCATGA GCCAGTGTGC CCAACTCCAT TTTATTTTTC TTGTCAAGAA ACCAACTTTG    37500

TTTTTGTTGA TTTTCTCTAT TTTTGTCTTC TATTTTATTG ATTTCTCTTT TGATCTTTAT    37560

TATTTCCTAC TGTCTGCTTC CTTTGAGTTT AATGTGCACT CTTGTTTTTA TTATTTATTT    37620

CTTGTGATGG ATCCTGAGGT CATTGCCTTG AATCATTTTT TTTTTTTTTT GTAAAATAGG    37680

TATTTGGTGT TATACAGTTC CATTAGTATT AGTATTAGAT GCCAAACATT AGTGGCATCC    37740

TACAAATTCT TATATACTGT ATTTTCATTT TCACTCACCT CAGAATATTT TGTAATTTCC    37800

CTTTTGATTT CTTCTTTGAA CTGTGAGTTA TTTAGAAGCA TGTTATTTAG TTTCTAGATA    37860

TTTGGGTATT TTTCAGTTAT CCCTCTTCTA TTGATTTCTA ATTTAATTTC ACTGTGGTCA    37920
```

-continued

```
AAGAACATAT TTGTATGACT TGAATCTTTT TACGTATATT GAGAATGGTT TTATGGCTCA    37980

GAATGTAGTT GGTCTTTGTA AATGGCCCAT GTGTACTTGA AAATAATATA TATTCTGCTG    38040

CCATTGGATG GAGTGTTGTA AAAATGTCAA TTAGGAGTTG TTTGATAGTA TTGTTCAAAT    38100

CTGTTATATC CTTGCTGATT TTCTGTCCAC TTGTTCTATT AATTATCGAG AAAGGATTAT    38160

TGAAATTCCC AGCTACAATT ATGGATGTGT TTATTTCTCC TTACAATCTA TTAGTTTTTG    38220

CCTCATGTAT TTGAAGCACT GTTATGAAGT ACCTAAACCC TTAGGATTGT CACATTTTCA    38280

TTAACTGACC AATTTGTCAT GCTGAAATGA CTCTCTGCCT ACGGTAACAT TTTTCACTCT    38340

AAGATTTACT TCTTTTAGTA TATTAATATA GCCTCTGTCG AGGGCTCAGC TGGAGAGAGA    38400

GCTGAGCTGC CAGGTTTTAA CGTGGTCAGT TAAGAAAACG GCCAAACTTA AAAGAAAAA    38460

AAAAAAAGAA ACCATCAAGA CTTTATTCAC TTATGCAACA GTATAAGCAA GAAGCAAAAA    38520

AGGAAGAAGT GCCAGCTCCC AGAATGTTCC ATGTTTTCCC CCATGGAGCA GCTCAGAGGA    38580

GGGGAGTTTG GGGTATGGGG ATGATCATCT CCCTGCTTAG CGAGACGGAC TGCCGAACAT    38640

GAGCCTCCTG CTATTTCGCT GTTGCTGGGA ATTTATGGAC CCTGTGGTGA AGGGTGGGAG    38700

TTTGGGGAAG GCTAGGAGTG GAAGATACTT AATACTGAGG ACCGCGGAGG CGGAGGTTGT    38760

TGCAGTGAGC CGAGATCGCG CCACTGCACT CCATCCTAAG CGACAGCATG AGACTCAGTC    38820

TCAAAAAAAA AAAAAAAAAA AAAAAAGAA GAAGAAGAGG AGGAGGAGGA GGGAGGGGA    38880

GGAGGAGGAG GAGGAGAATG AGAAGAAAAG AAAAAAGAAG AAGAAGAAGA GGAAGAAGGG    38940

GAAGAAGAAG AGAAGGAAGC GGAAGAGGAA GAAGAAGAAG GAGAAGAGGA AGAAGAAGAA    39000

GAAGCAGAAG AAGAAGAAGA GGAGGAAGAA GAAGAAGAAG AGAGAAAAGC ATGTTTTTCA    39060

GGTTACTCTC AAGAAGTTGG TGTCTAGTAG AGGCAGCCAA GAAAGACCTC TGCCAGGACC    39120

CTCCTGATCC GGGGACCTCT GCATGGACGT ATCTGGGCTG GGAATGCAGG TATGTGTAAG    39180

AACATAAGTG CGGGGGACG TGAGTCTTTG ATACAACTCC CCTAGGGGAC TGTGTGCTCT    39240

GGTTCTGGTT GTGCACCGAG GCCGGTGGGG AGGACCCATG GAACAAACTT GTGGTAAGGC    39300

CTTTGTAGTG GCTGAAAACT CACACACAGA GTTGGGTTTT GGCTCTCAGA AAACTGCTCA    39360

GCCACTCCAG CTTCCTCTTG GCCAGTGTCA GCAATGGCAT ACCCTTGTCA AAACTTAGAC    39420

TATTTGGCCA GGCCCCGTGG CTCATGCCTG TAATGCCGGT ACTTTGGGAG CTGGGGCAG    39480

GTGGATCCTG AGCGCAGGAG TTTGAGAACA GCCTGGCCTC AAGAAAAAAA AATTTTTTTT    39540

CACTTTTAAC CCATTTGTGT CTTTATATTT TAAAGTGCAT CTCTTGCAGG CAGCACAAAG    39600

TTGTCTTGCA TTTTTATCCA ATCTGACAGT CTGCCTTTTA ATGGGCTAA TTGGACTATT    39660

TTTATTTAAA CTTTTTATCT GTAATGGCTA ACTTTCACTC TATCACATTG GCATTTGTTT    39720

CTTATTTGTT CCACCTGTTC TTTGTTCCTT TTTTCCTCCC TCTCTGTCTT ATTTTAGATT    39780

AATTGGATTA ATTTAGATTA ACTGGATTGA TTTGAATTAG TTGAGTATTT TTATGATCTA    39840

TTTTTATCTC CTTTATAGAC TTATTAGCTT TAACTCTTTG TTTTATTATT TTAGTGGTAG    39900

CATACATCTT TTCTTATCAC GATATATTTT GAGGGATACT ATACCTCTTC ATATGTGGTA    39960

TGATATCCTC AAATGGGTAT ACTTCTATTT CTCCCCCCAC CAGCCTTTAT GTTATTGTTT    40020

TTGTCTTCCA ATTTATATAA GTCATAACCC CTATAATACA TGGTTATTAT TTATGTTTAA    40080

ATAGCCAATT ATCTCTTATT TGGTAATTTT TATTGTGATA AAATATACAT AACATAAAAT    40140

TTACCATTTT AACTGTTATC AGTGGTGAAT CCACACAAGA CTGCAGCAAC CTCAATTCTT    40200

ACCTCCTTCA GAAGAAAGAA TTCAACCAAA GGGAATAAGG CAGAGGGAGA AACTGAGGCA    40260

AGCTTAAGGG AAGGAGTGAA AGTTTATTAA GAAGTTTTAG AGCAAGAATG AAAGGAAGTG    40320
```

```
AAGTACGCTT GGAAGAGGGG CAAGCGGGTG ACTTGAGAGA TCAAGTGCAA GGTTTGACCG   40380

TTGACTTGGG TTTTTATGCT TCTGGGGTGA TTGTGCCCTT CTCCCCTGAT CCTTCCCTTG   40440

GGGTGGCCTG CCAGCACTTA GGAGGGGCCA CGTGTGCAGT GTGTTTACTA AAGTTGTATT   40500

CAGGCCGCCT TGAAACATTT TTCCCTTACC GGTTGAGTAT TCCCTAAGGA AGGTGAGGTA   40560

CCAGTTAATT CCACCATTTT GCCTCTTAGT GTGCATGCTT GAGTTCACTC ACCCAACTCC   40620

TGCCATCTAA TCAGGAAGCT GCTGATCATC AGTTTCAGGT GTTTTCTATC TATTGGGAGA   40680

CTGCGTTTCC CTGGCGCTGG CTGCAACCAA TTATTATTTT AGAGACAGTT TAACAACCAC   40740

CTCACTATCA CCTTATGGTC GCCTGACATT CCTGGTGAAG AGGGCCCTCT CCTTCCCTGC   40800

TCATGTCTGC CTAACTACCT ATGGTAACAA AAGCTTTTTT TTTTTTTTTT TTTTTGAGGC   40860

AAGGTCTTGC TCTGTCACCC CAGGTGTCGT GCAGTGGGGC AATCATGGTT CACTGCAACC   40920

TCAACCTCCA GGGCTCAATT GATCCTCCCA CCTTAGCCTC CTGAGTAGCC AGGACTACGG   40980

GTGTGTGCCA CCACACCTGG CTAATTTCTG TATTTTTTGT AGAGACAGGA TTTGCCTTGT   41040

TGCTTAGGCT GGTCTTGAAT TCCTGGGGTC AAGCTATCTG TTGGTCTCTG CCTCCCAAAG   41100

TGTTGGGATT ATAGGTGTGA ACCACTGTGC CTAGACCCCC AAATTATCTT TTTTTCAGAG   41160

ACAGTGTGAT AGTTCTCAAA CTATCACCTA ACATTCCTGG TAGGAGAGGA AAGATCTCTC   41220

TCTTGCCCCA GTCATGCCTG TCTAACTACG TGTAACTAGT TAGCTCAGCT TACTGTTATA   41280

ATTTTTCTCA CTGATAGAAT TTTTGCAAAG ACACTTTCAA TACTACCAAA ATAAATAGTA   41340

ATCAACCACT TGGAAAGCAT TTAGAAGTAA CTGAAGTCCC TACTTACACC AAATGAGGAA   41400

AAGCCAAACT ACACTGTGGG ACACACTGTA AGTCCCTGCA TCAGTCAGCT GTTGCTGTGC   41460

AAACACCTCC TCAAGACTCG GCAGGATAAA GCAATGACCA TTTATAATTG CTCACATGTC   41520

TGCAGGTCAG CTGCTTTTTG GCTGACCGAG GCAGGGCTTA GCTAGGCTGG CTCTGCAGCG   41580

TGTGTCTCTC ATTCTCCTCC TGTGGCAAAC AATGGCAGAT GACAATGGCA AATGTGGAAA   41640

GCCTTTAAAG AAGAAATCTC ATAAGGAGTT CCCTGTCACT CCCATTCATC TCAGTCTTTC   41700

AGCCAAAGCA AGTGATATGG CCAAACCCCA TATCAAGGGG TGGGGAAATA TAATTTGCTT   41760

ATTTATTAGG AGCAAAGTCA CATGGTGGTC ATTGCAGAAT GGGTTGAATG ACATAACCTA   41820

TCATCAGCCC TGAAGAAACT CATCATTCAT TTCCTTCCTC AAGACTCCCC TCATCCGGGC   41880

ATCTCCAGAT CTTACTCTTT CCCACACTCT GTATCAAACA GTCCACTCAC ACTAGCTACC   41940

CTGCTTCCTT TGGCACCCTC TTTCCACTAG ATAACCTGTT CACTCAGCAT TTCTATTTTC   42000

ATTTGCATCT CCACCCTTTG CCCATTACCC CAGCAGCTCA CAGAGGACCC TGACAGAATA   42060

GGCAAAACCC AGAAGTTGGG TGGGTAGATA ATGTGTGAAA GCTCACACGG TTCTGACGCC   42120

TCCTTGACGC AGCACATTAC TAGCGAATGA CATGTATAGG GCCTGGGGTG TTTGCAGAAC   42180

CAAATCAGGT GTGGAGGAAA TTATATGTAA ATACCTCCAT GGGTGTGTGA TTGTATCATA   42240

CCTCACCATA ACAAAGCTCA AATGACATTT CATTTCCAAA TGTGGCTAGG TTTCCCTGTG   42300

TTATATGTCG TTGAAAGCCA GTATAAATAA ATATCTGTGA AAGTCCTAGC TGACTGCCTG   42360

CTTTGTTTCT GCCACTAAAC TGTAAGCTCC TCATGAACAG AGTGTTTCTG TACAATTCAC   42420

TAGCTGTCTC TATCTTTACC TCACAGCCAA TCCACAAATG AACGCTGTCA GCCTTGCCCC   42480

CCATCATATC CCAACCATCC ATGTCTGGCT ACTCCATTGC TAGTCCAACC GAAGCCCCTT   42540

GCATCTCATG CCTGGGTTAT TTCACAGCCT TCTAGGCTGG TAACTCCCGC TGCTACTGTG   42600

CCTGGCTCCA GTCTATTCTG TACATGGTGA AGAGGATCCT TTGAAAAATG GATAAAATGA   42660
```

-continued

```
GTAGCAAATT GTGTTTCTCC TGCACTCAGA ATCCTCCTCT GGCTCCTCAC TGTAACCTCT    42720

GGCTTCAGTA GTTACGGCAA ATATTTAAAA GTCAGCCTGC AGGAAGAACC CTGATTTACT    42780

GAGTTTTCCA ATGTTAGTAG TATAAATACT CATCATGGCC AATTTTAAGC TGGCTTCTTT    42840

CCTTCACTCC GTCCCTCCCT CCTCCCCTTC TCCCCTCCTT CTCTTCTCCC CTCTTTCCTT    42900

CATTTCCTCC CTCCCTCCCT CATTTCTTCT GTCCTTCTCT CCTTCCCTTC CTTTCCTTCT    42960

CACGTCCTTC TTTCCTTTCT TCCCTCCTCC CGTCCTTTCT TCCCTATTCT CTGCCTCCTA    43020

CTCTAGAATT GACATTTCAT GACAGGCAAT CCATGTCTGT CTTAGTTATT GCTTAGAAGT    43080

ACCTGGCACA TAATGGAAGG CTCAGTACAT ATTTCTTGAA CAAATAGTTG ACTAATTGAA    43140

TAGATGATCC TTTCTTAATT CTGTACCAGG ATTTAAGAAT TATTCAAAGA AGATGTCATT    43200

GTTTTAAAAT GACCAAGTAC TGCTCAGCAC TTTCAAGTTC ACAAAGCATG CCTCATGCAT    43260

CATCTCTATG ATCTGTACCC GGGTGCCATC CTGAGAAGCT GGGAAAGGCT TTTCTCTTCC    43320

TCCTCACTTT ACAAATGAGG AAACAAAGAC TCAGAGGGAT GGAGGTTCCC GCTCAAGGCC    43380

AAACAGTAAG TATGTATCCA CAAGTCTGAC TCTCAGTCTG GCAGTCTTCT CAGTGGTCTC    43440

CAGGAACTGT TTAGCTCTTG GGGGGATCTC ATAAGGGAAG CCTGGAGGCT TCAGGGAGAG    43500

CTGTCCCAAG GAAGAGGAGA GAAACACATG GTGGCGAGGA AGGAGGATTG ACGACCAGGG    43560

AAGGCCTTAC GTAGGCCTCT ACCAGGCTGA GCCTCTGGTG TCAGGCCAGT AACATAGTAA    43620

TTCAGGTCCC CAATCCTGAT TCTGTCTCTA GATTCCCACT AACCTCCCCA CAGACATGGA    43680

GCATTGAGCC CCCCTTCCCC ACTTATAGAG TACCCCAGAT AGCATAGGCT CCACACCTAG    43740

CACCCACCTT CTTGCAAGTC TATAGCAATG AGCAGCAGAG CGCCAGCTGA GATCC          43795
```

(2) INFORMATION FOR SEQ ID NO:102:

(i) SEQUENCE CHARACTERISTICS:
        (A) LENGTH: 40328 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:102:

```
GATCTCTAGT AAAGCTGTGT AGAATCAGTA ACTTCTAGGC TCTAATTAAC AAAGCAGGAA      60

CCCTCCTTTC TTATTAACTT CTATAACATT ACTGTGTTCA AAAAGATAAC GCAGTTTCTT     120

TTGTCTTTTG TTTTCTTTCA GACAGGTATA TGTGTAATAG CTTTCTCTTT TGCAGCATTT     180

TGTACTGACA TTTGTGAAGT CAACAGCACT TCACCAATGA TTTTTAAATT AATGATGTGT     240

CATAGTTTCC TGATGTGTCA ATTAGTTCTT AATTAAAATT TTTTCAAAAT AAGTCAGCTA     300

AATAGTGAAG CCAAAAAAGA AACTTGAAAA CAAATCGGCT GAAAATAAAT TCAAATAACA     360

GGACACTAAC TTACATTGGC ACACCACTTG TACCACTTTA TACGTACAAA ATGAATTCAC     420

AGATGTGATC TCATGTCATT CTCAAAGCAC TTTGCCCACA GATACATAGC TGGCAAGTAG     480

GTGGCTTATA ACCACTTACC TGTAAGGGAC ATAAACCTAG ATCTCCTGAC TGAATTATTT     540

GTTTCACTAT GCTATATTGT TTCTCCAACG TATATATTAC TTATGAATAC TACTTCAGAA     600

AATTTTACAT TAACCTTAGA GTCTGCTGTG GAAAGAATAA AGACAGTTCT GATCAGAATC     660

TAGAAAATTA GTGAGTTATA TGTATGTGTT TTTTTATCTG AAAATAAAGA TGGTATCATT     720

TATATCTATC AGCCCACTGT GAAAATCAGA ATTATCAGTC AGACTGATTC CGTGTTACTC     780

AGGAAGAAAA ATGTTATTTC AAAAGATGCT TTGAACACCC TAGCGTTAGG GAAGAGGATT     840
```

-continued

```
GTAACAAATT GGTTTAAAAC GTTGAGGCTT ATTTTCTTTT TGGTGGGGCT TTTTTTTTTT       900

TTTTTTTTTT TAAGATTTAT CTTTAGTCTA CTCAGTAAAG TGAAAAGTTG TTTATGAATA       960

TAGAACAGGA TGATTTTAAT AACTTTAATT TTTACAAATC TAAACTCTCT AGTTTTGGGT      1020

GTCTTTTTTA ACTACTTCAC GTAGTACTTT CACAAATACT AAATGGGTAT TCTTCCACAG      1080

CATTATACAA GACTCGGTGA TGAGCGGCAC TAGGTTTAAG AAAGTACTGT ATCCTTCGGT      1140

TAAAATTCCA TGCTGATGTA CTCTGATAAG TTTAAATCCT GAGCCTGAAC TGAGCTGCAC      1200

TGGTGACTGA ATTACAATGA AAGTAATTTA TATAAAATAT ACTTAAAATA CAAAAATGGT      1260

ATTTCACATT ATGTATGGGT TTTGCCTGCA TACGTAATTA TGATGTCTAC TTTCCAAATT      1320

ACAGTCTGCT GCAAATCCTG AGACTCCAAA CTCAACCATC TCCAGAGAGG CCAGCACCCA      1380

GTCTTCATCA GCTGCAGCTA GCCAAGGCTG GGTGTTACCA GAAGGCAAAA TCGTGCCAAA      1440

CACTGTTTTT GTTGGTGGAA TTGATGCTAG GGTATTGTAT TCGTACCTCA TTTTTACCTT      1500

AACATACATC ATGAACAATG GGATGTGGGC CCTGTTACAA ACTTAAATTT TTTTTTGTAC      1560

TTCCTGGAGG TTTAGAATTG CTTTTAGGTT TGACCCATAG GTACTAAAAA TATCTTTGAC      1620

AAAGGGCTGC TGGTCATTCG GGGATAAATG GGGGAGAAAT TTCCACCTCA TGGTAGTAAA      1680

ATTGTAGTAA AGTTGAAATT TTTGAATGCT GAATTTTTAC TCTGACGTTC AGTTCTTTTC      1740

CATAGATGGA TGAAACTGAG ATTGGAAGCT GCTTTGGTAG ATACGGTTCA GTGAAAGAAG      1800

TGAAGATAAT CACGAATCGA ACTGGTGTGT CCAAAGGGTG AGTAATTTTA TCAAAAATAT      1860

GTGAACTCCA GTCACCTATT CTATAAGTAT CAGACAAGAC TTCAAAACTG ATATTCTGAC      1920

CCTTGTATAA ATGCAATATT CTGCAGTGTT AATTTCTTTC ACGTAGGGGA TAAAAGGCTA      1980

TTACCAGTTC TTCTATTTGA CCATTTTTCT AATGTTTGTA TTTAAATGTC TCCAGTTTCT      2040

ATTTCATACA GATGAGTTAA TCAGTTTTCT CAAATAATTG TTTTCTTCAT ACACTGCAGA      2100

GCATCTTAAA TTTTAACCAC CTTGTCTTAG ACAGTAAGTT AAACTCAGGT TCACAGATAT      2160

GAATTCTTTG CTAATCAATA AAGTTGTCAC ACTGCCCTAA TCCTAGCACA TTTTGACATA      2220

GTTCTGCTTA AGAAAAGTG GTATTTGTAG AGGATCTGTC ATGTACATCT TAGCAAATAC       2280

TTATCATGGT ATATTATTCG TCTTTTGTCA TGACCACTTC TGTATATAGA ATAGTAGACC      2340

TTCTGAACCA CGTACTGTAT GATGGTGATT TTATGCTTCA TTTGTCTGCC TTTATAGCTA      2400

TGGATTTGTT TCGTTTGTTA ATGACGTGGA TGTCCAGAAG ATAGTAGGAG TAAGTAATCT      2460

AATAGAAAAA TCTCTTATTT ATCTTATTGC TACAACGTTT AGTGTCAGTG ATACACTCGG      2520

ACTTGTGTAA AATTTGGGGA AAGACACACT TCCTGTTCAA AATCCAAACT CAGAGTAACC      2580

TCACGTAGCT TGTTTGATCC TGTTTATTTT TGACTGGACA CCTAGTTTCA TGAACTACAG      2640

ACAGGAAGGG TTGGAGACAG GGTGATGGAA AGTTTTTGAT CAACTTTCAC TTGATGCCTC      2700

TTGACACTGA TTAGAGTAGT AAGGGTAAGT AAGGTAGCTT CGTGATGACA AATTTTAATT      2760

TGGTGCGTAG TTGTCCCCGA TCTTCTATGA TGATAGGTAC TTTAGAAGAC TTCAGGTGTT      2820

TACCCAAGTC TTGGAAGCTA ACACTTGAAA ATTGATTCTA GTTTTGTTAA CGGTTCTATT      2880

TTCAGTCACA GATACATTTC CATGGTAAAA AGCTGAAGCT GGGCCCTGCA ATCAGGAAAC      2940

AAAAGTTATG TGAGTAGGAA AAGAAATGGT TCTTTTCTGA CCCGTGTAGC TTTTCAAATA      3000

ACTAAAAATA GGCTTTTTTC TTCTTGCTTT TTAAAAAGGT GCTCGTCATG TGCAGCCACG      3060

TCCTTTGGTA GTTAATCCTC CTCCTCCACC ACAGTTTCAG AACGTCTGGC GGAATCCAAA      3120

CACTGAAACC TACCTGCAGC CCCAAATCAC GCCGAATCCT GTAACTCAGC ACGTTCAGGT      3180

AAGAACTGCT TATGTTCCTG TTCTCTTGTT TATTCTAGTC ATCCTTCCCT CTGTGGAATT      3240
```

```
GTATCTACAC TTTCCATAGT AAGTGGCAAT AGAATCCCTG TTTGAACAGT GTGAGTAACG    3300

GGAAATCTGT TACTTTTGTT AGAAATTTCT TATTCTTCGT GTTCGTCATT TGAGCTAAGA    3360

ATCTTCTGTA TACTTGGCGA AGCTTTCTCT TAGAAATGAC CTCTGTAGAC ACATGAACAA    3420

ATCTCTTCCT ATCTCTGCCT CTTTCACCTC ATATAACTAG TCCTAAAGTA TTTGGAAGCA    3480

GCCCTCCTTA TGTGTCTGCC TAGTTTATTG TTCTCTAAGG TTAGCAGTTA ACCTAGCTAT    3540

TCTTTACTTG CAGTGATTTC CAGATGCCTC CTCATATAAA TTGCTTGACT TCTGGGTATA    3600

TTCTGGTTCT GGGATGGGTA GATTTCTGAT CTCTTTTGCT CTATCTAGAA ATCCCGTGAG    3660

TTTCTGGCAC GTAATTTCTC TGATGCTGGT TGCTTTGATA TTTAAAGTAG GATTTGACAT    3720

ACTCTTGTCA CTTACTGGTG ATAAATAACG TTTAGTTTGT TCTTCGTTCA TTTTATTTAT    3780

GTGTTAGTTT TTAAAAAGAG GTTTTCTTCG ATGGAAAATA AAGTAACCAA ATAGTAGTGA    3840

ATTAGTTCTT CAATGTCTCT CATTTGTTGA CATTTTCCAT GTACTTGAAA CGTGTGGGGT    3900

ACACCTCTTC TTCTTTTTCC TTCTCTGAGC AATGGCTAGA AGAAAAGCCC TACTTGTTTG    3960

TAGCATTTAC TGTGAGCCAT TACTGAATGT GGGTGTATTG ATGAATGATG CTACCTGTAT    4020

GTTTTTAATC AGTAAGTATT TATTGAAAAG TAGAAGACAT TATACTGTCT CTTTTCCAGC    4080

TGTGGCTTAC TTACTGCCCT TAATTTGTGG AAAAGAAGTA CAGAGAAAGC CGTAACATCT    4140

GCCGAAGAAC TACAGTATTA CCCTATAATA TCATCAGATA GCAAACAGTC TAGAAGTATT    4200

TTGCCAAAGA AAGAGCAAAT GTATTATTTT AACTTACGTT GAAATCTATC TTAATAGAGC    4260

CTTATCAGCA GCGTAAGAAA TAACTTCTGG GTGGGCATAA GTACACAGTA TAAATATGGT    4320

AGACTTTGGC CGGTGCAACA GTCACTTGTT TTGTCATTTG TCTCTTCCCC CTCCCCGCCC    4380

AAAGGGTAGC ACTTGACAGA GAATATTTGT TTCTTCATGT CAGTCATTCA TTTAGAAATC    4440

TGTATTTCTG TATGTAGAAA AATAATTACC ATTTCAAGGT TTTTCGTATT TTTGTTATTT    4500

TGGGAATGAT ATTTCTTTCT AGTTAAAGAA AATGTTTTAC CGTATTAATC CATTCTTTCT    4560

GTAAACTTTA TTTTCAGGCT TACTCTGCTT ATCCACATTC ACCAGGTCAG GTCATCACTG    4620

GATGTCAGTT GCTTGTATAT AATTATCAGG TAATTGAAGA GGGAGTAAGA TGATTTACTT    4680

TCAGCTACTA TTGAGGCCTC AACTTGCTTA TACAAATTGC TTGAATAGGT TGTCCTTTTA    4740

AACTAGTGAA CTGTACCTAA AATTTAAGAA ATCACTTAGA ATTAGTGTAA TGAGGACCTC    4800

TGTTTTGTTT AGAAGTGATG AAATAAGATT TTGACAGGAG GGTACTTAGC AATAACTTTT    4860

CCGTAGAACA ATTTCTGAGA TTTGGTGTTC CCTTCTTTGT TTCAGCATGT ATTTTGTTAT    4920

CTTTGCTGTC AAAGAGCTGA AACATCCAGA CTGACTTTCC TGAATCTTGT AGAGATACAG    4980

AGTGAAATAA AAGCTTTACC GAATTCTTAG AGCACAGAAT TTCAGTTGTA TTTTTATTTT    5040

AGCTTGCTGC TTCATGATAG CAGTTCTCTG GGTCTCTTTT CAATGGTACA ACTATTATCT    5100

GTGACCCATA ATTGTATCTG TGGTAACAAA TTCAAAGAAT TAATATCTTT GAGGGTTCCA    5160

CAATTCTGTT TCCATAAAAT TGGGAAAAAG GTGAGGTTTT CTGTGTAGAA GTAACAACAA    5220

GAACTTTGGG GATTAGAAAC CTAAAGTACT TCTTTTTTCT ATTCTGTTTC TTTTATTATA    5280

ACAAAGGAGC CATCATGATA AATACTCCAA TATTATGTAA CTCATGTGTT TTTGAAAACG    5340

TGTAGGAGTA TTTAAATAAT TGTGGTTACT TTTTTTTTTT TTTTTTTTT TTTTAATTT     5400

AAGATTCCAC TGCACTGGCC TGTTGGGCG CAAAGGAGTT ATGTTGTTCC TCCGGTAAAG    5460

CGAATGAGTG AAACATATAC CTGCTCTTCT TTCTTGATTT TTTGTGTGGC ACATATGCCT    5520

ATAAATATTT TTAATGATTC TTTATATTGA TGTGTTAACG TTTTGTTACT TTCTTTTTAA    5580
```

```
CCCAATTATA ATCTCCCATG GGAGAAACAG TGCCTTTTTC TCTCTCAGGT TTTTGTATGC   5640

TTAAGCAATG GCTTCTCCAA ATTATGACAA GTGTTCAGTT ACTTGTCGAT AGATTATTTA   5700

ATCTAAGAAA GGTAGTCCTA ATGTGGCTTT ATCTAAGAAA GGTAGTATTA ATTTGGCTTT   5760

AGAATAGCAT GTATCTGATG AGAATCTGCA TCTGGATGTA CCAACCATAA AAAATTTCAT   5820

AAAGAGAAAC AGAAATGTTT TGCTGTTAAT TACTCTTAAA TAAGAATAGG ATTAAAAGA    5880

GTATTACCTC TATAACACCT GAGCTGCTTT CCCCCATATA ACTAAAATAT TTAAAAGCAG   5940

TTCTCCTCAT GTGTCTGCCT GCTTTATTCT TCTCTAAGTT TAGCAGTTAA TCCAGGTATT   6000

CTTTATTTGA AATGATTTCC AGATGCCTCT GCATATTAAA TTGCTGACTT CCAGATATAT   6060

TCTGGTTCTG GAATGGGTAG ATTTCTGATA TGTTTTAGGT ATCTGTAAAT CCCGCAAGTT   6120

TCTGGCATGT AGTGTCTCTG ATCCTTGTTA GTTTGCTATT TAAAGTAGAT TTGACATATT   6180

CTGTCACTTA CTGGTGGTAA ATAACGTTTA TTTTCTTCTT AGTTCATTTT ATTTATATCT   6240

TAGTTTAAAA GACATTTTCT TTGATGGAAA ATAAAGTAAC AGAATAGTAG TGAAGTAGTT   6300

ATATTCAGTG TTTCTCATTT GTTGACATTT TCCCTGTACT TGAAACATGT ACGGTATACC   6360

TCATCTTCTT TTTCCTTCTG TGAACAATGG CTGGAATAAA AGCCCTACTT CTATCATTTA   6420

CTGTGAGCCA TTACTGAATC TGGGTGTATT GATGCATGCT GCTTACCTAT ATGTGTTGAA   6480

ACAATAAGTA TTTATTGAAA CATATGAGAC ATTATACTGT CTCTTTTCCA GTATTGGATT   6540

CTATACTGCA CTTAGTTTTT CAACATGAAG TACAGAAAAC GCCGTAAATT CTGCAGAACT   6600

ACGTATTACC TTATAATATT GTCAAATACA CATCAGTCTG GAAGCATTTT TACAGGGAAA   6660

TAGCAAATGT ATTAATTTAA CTTACATTGA ACTCTGTCTT AATGCAGCCT TATCACCAGT   6720

GCAAGAAATA ACTTCTGGGT GGGCATAAGT ACACAATATA AGTAAGGTTA ACTTTGCCTG   6780

GTGTCATAGC CAGTTCTTTT GACATTTGTC TGTTCCCCCT CCACGCCCAA CCATAGCACT   6840

TGACCGAGAA TAATACGTTC TTCATAAATC AGTCAGTCAC TTACAATTCT ACATTGTTGC   6900

AGATAGAAAA ATAATTAGTA TTTCGAAATT TTTCATAGTT TTGTTATATT GGGACTAATT   6960

CTTCCTAATT AAAAATAATG TTTTAACGTA TTAATTCATT CTTTCTGTAT AATTTATTTT   7020

CAGGAATATC CTACTTATCC CGATTCAGCA TTTCAGGTCA CCACTGGATA TCAGTTGCCT   7080

GTATATAATT ATCAGGTAAT GTAAGAGGGA GTAAAATGAT TTGCTTTCAG GTATTATTGG   7140

GGCCTTTAAC TTTTTTAGAC AAATTTCCTG AACAGTTGGT CATTTAAAAC TAGTGAAGTG   7200

TACCTAAAAT TTAAGGAAAC ACTTAGAATT AGTGTAGAAT GAAGACATCT GTCTTATTTA   7260

GAAGTAATGA AGTAGTATTT TGAGAGGAAT ATACCTGGCA ATAACATTTC TGTAGAAGAG   7320

ATTTCTGAGA TGTGGTGTTC TCTCCTTTAC TTCTGGATGT AGTTTTCATC TTTACTGTGA   7380

AATAGCTGAA TGAAACATCC AAACTGACTT TCATGAATTT TCTTAGGGAG ATAGAGTGAA   7440

ATAAATTTCT GCTGCACTTT TCAGAGCACA GAATCCCAAT TACATTTTCA TTTTAGCTGG   7500

CTGTTTGAAG ATAGTAATTC TCTGGATCTC TTTTCATAGA TACAAGTATA TCTATGACCC   7560

ATAATTATAT CTATGGTAAT AAACTGAAAG AGGTAGTATC TTGGAGGTTT CCACATTGCC   7620

AACTCCTGAA AATTTGGAGA AGATGAAGT TTCAAATATA AAAGTAAGAA GAATGTCATG    7680

GACTAGAAAC ATGATGTACT TAAGTTTTCC TTTCTGTTAC TTTTATTATA ATAAAAAAGG   7740

AGACAGCAGG ATAAGGACTT CAATATTGTG TTTCTCATGA GTTTTTGAAA ATGTGTAGGA   7800

ATACTTTAAT AGTTTGGTG TCCTTTTTTT TTTTTTTTT TTTTTTTTTA AGATGCCACC     7860

ATAGGGGCCT GTTGGGGAGC AAAGGGATTC CGTTCTTGAC GTTAAGTGAA TTAGCCAAAC   7920

ATAGACTTCC TGTTCATTCT TGATTTTTTT CCATGTCATA TATGCCTATA AATATTTTTA   7980
```

```
AGTGATTCTT TATATTAATT TTTTTGTCGT TGTTACTTTC TTGTTAACCC GATTATGAAC      8040

TCCCATGGGA GCAAGAGTGC CTTTTTTGCC CTCAGGTTTT TATGTGCCTA AGCAATGGCA      8100

GGTCCACATA ATGATAGACT ATATAATCAC AGAAAAGTAG TATTCACTTG ACTTTAGAAT      8160

TATCACGTAT CTGCCAATAA TCTGCCTCTG GCTTTACCAG CAATAGAAAA TTTATAGAAG      8220

AGAAACAGAA TTGCTTTGCT GTTAATGACG CTTAAATAAG AACAGGAGTG AACGAGAGTA      8280

TTACCTCCAA ATCACCGGAG CTGCTTTCCC CCTTATAAGC AGTTCCTAAA GTGAATGAAA      8340

GCAGCTCTCC TTATGTGTCT GCCTACTTTA TTCTTCGGTA AGTTTAGCAG TTCATCTAGC      8400

TATCCTTTAT TTGAAATGAT TTCCAGATGC CTCCTCATAT AAATTGCTGA CTTCTGGATA      8460

TTTCCTGGTT CTGGAATGGG TAGATTTCTG ATGTGGTTTA GTATATATAT GTAAACCCCG      8520

TGAGCTTCTG GCATCTAATT TCTCTGATCC TGGTTACATT GATATTTAAA GTAGGGTTTG      8580

ACATACTCTG TCACCTACTG TTGATAAATA ACGTTTATAT TCTTCTTAGT TCATTTTATT      8640

GACGTGTTAG CTTTAAAGAC ATTTTCTTTG ACGGAAAATG AAGTAACAAA ATAATAGTGA      8700

AATAGTTATG CAGTGTCTCT AATTTGTTGA TATTTTCCAT GTACTTGAAA CTTGTATGGT      8760

ATACCTCTTC TTTTTCCTTC TCTGAACAAT GGCTAGAAAA AAAGTCCTAC TTTTTTCTGT      8820

CATTTACTGT GAGGCATCAC TGATTCTGGG TGTATTCATG TATGCTGCTA CCTGTATGTT      8880

TTCAAACAAT AAGAATTTAT TGAAACATGT AAGACATTAT ACTTTCTCTT CTCCAGTATT      8940

GGATCATAGA CTGCACTTAG TTTTTCGTAA TGAAGTACAG ACAAAGCCAT AACATCTGTC      9000

GAACTACATA TTACCCTATA ATATTGTCTG ATACAAAACA GTCTAGAAAT ATTCTTACAG      9060

AGAAATTGCA AATGTATTAA TTTAACTTAC CTTGCAATCT CTCTTAATGG AGCCTTACCA      9120

CCAGTGTAAG AAATAACGTC TGGGTGTGAA TAAGTACACA GTATAAGGTA AACTTTGGTG      9180

AAGTAGTCAA TTCTTTTGTC ATTTGTTCCC CCTTCACACC CATAGTGTAG CACTTGACCT      9240

AGAATCTTTC TTTCTTCATA AAGTCAGTCA TTCATTTGGA ATTCTGCATT GTTGTACGTA      9300

GAAAAAGGAT ATTTTACCTT TTGTAATATT TTTGTTATAT TGGGAATTAT ATTTCTTTGT      9360

AATTTTAAAA AGTGGTTTAC CATATTCATT TTTTTCTGCA ACCTTTCTTT TCAGCCATTT      9420

CCTGCTTATC CAAGTTCACC ATTTCAGGTC ACTGCTGGAT ATCAGTTGCC TGTATATAAT      9480

TATCAGGTAA TGTAAGAAGG AGTAAAATGA TTTACTTTCA GGTATTATTG AGGCATTCAA      9540

CTTGTTTATA CAAATTTCCT GAATAGCTGG TCATTTTAAA TTAGTGAAGT GTACCTAAAA      9600

TTTAAGGAAA CACGTAGAAG TAGTGTAGAA TGAAGACCTC TGTCTTATTT AGAAGTAATG      9660

AAGTAGTATT TTGAGAGGAA TATACTTGGC AATAACTTTT CTGTAGAAGA GATTTCTGAG      9720

ATGTGGTGTT CTCTTCTTTA TTTCTGGATG CAGTTTTCAT CTTTACTGTG AAATAGCTGA      9780

ATGAAACATC CAAACTGACT TTCATGAATT TTCTTAGGGA GATAGAGTGA AATAAATTTA      9840

TGCTGCACTT TTCAGAGCAC AGAATCCCAA TTACATTTTC ATTTTAGCTG GCTGTTTGAA      9900

GATAGTAATG CTCTGGATCT CTTTTCATAG ATACAAGTAT ATCTATGACC CATAATTACA      9960

TCTATGGTAA GAAACTGAAA GAGGTAGTAT CTTTGAGGTT TCCACCTTGC CAACTCCCGA      10020

AAATTTGGAG AAAGGTGAAG TTTCCAATAT AAAAGTAACA AGAATGTCAT GGACTAGAAA      10080

CATAAAGTAC TTAAGTTTTC CTTTCTGTTA CTTTTATTAT AATGAAAAAG GAGACAGCTG      10140

GATAAGTACT TCAATGTTGT ATTTCTCATG TGTTTTTGAA AATGTGTAGG AATACATATA      10200

ATACTTTCGG TGTCCTTTTT TTTTCTTTCT TTTTCTTTCT TTTTTTTTTT TAAGATGCCA      10260

CCATAAGGTC CTGTTGGGGA GCAAAGGATT ATGTTGTCCT TGACGTTAAG TGAATTAGCC      10320
```

```
AAACATAGAT TTCCTGTTCA TTCTTGATTT TTTTCCATGT CATATATGCC TATAAATATT    10380
TTTAAGTGAT TCTTTATATT AATTTTTTTG TTGTTGTTAC TTTCTTGTTA ACCCGATTAT    10440
AAACTCCCAT GGGAGCAAGA GTGCCTTTTT AGCCCTCAGG TTTTTATGTG GTTAAGCAAT    10500
GGCAGGTCCA TATAATGACA GACTATATAA TCAAAGAAAG GTAGTGTTCA TGTGACTTTA    10560
CAATTAGCAT GTATCTGCAT AGAATCTGCC TCTGGCTTTA CCAGCAATAG AATATTTATA    10620
GAAGAGAAAC AGAAATGCTT TGCTGTTAAT GACGCTTAAA TGAGAATAGG AGTAAACGAG    10680
AGTATTACCG CCAAATCACC GGAGCTGCTT TCCCCCTTAT AACCAGTTCC TAAAGTGAAT    10740
GAAAGCAGCT CCCCTTATGT GTCTGCCTAC TTTATTCTTT GGTAAGTTTA GCAGTTCATC    10800
TAGCTATTCT TTATTTGAAA TGATTTCCGG ATGCCTCCTC ATATAAATTG CTGACTTCTG    10860
GAAATATTCT TCTTCTGGAA TGGGTAGATT TCTGATGTGG TTTAGTATAT ATATAAACCC    10920
CGTGAGCTTC TGGCGTCTAA TTTCTCTGAT TCTGGTTACA CTGATATTTA AAGTAGGGTT    10980
TGACATACTC CATCACTTAA TGTTGATAAC TAACCTTTAT ATTCTTCTTA GTTCGTTTTA    11040
TTTATGTGTT AGCTTAAAAG ACATTTTCTT TGATGGAAAA TGAAGTAACA AAATAATAGT    11100
GAAATAGTTC TGCGGTTGTC TCTAATTTCG TGATATTTTC CATGTACTTG AAACATGTAT    11160
GGTATACCTC TTCTTTTTCC TTCTCTGAAC AATGGCTAGA AAAAAAGCCT TACTTGTTTC    11220
TGTCATTTAC TGTGAGCGAT TACTGAATCT GGGTGTATTC ATGTATGCTG CTACCTGTAT    11280
GTTTTCAGAT AATAAAAATT TTTTGAAACA TATAAGACAT TATACTTTCT CTTGTCCAGT    11340
ATTGGATTAT AGACTGCACT TAGTTTTTCG TAATGAAGTA CAGACAAAGC CATAACATCT    11400
GTCAAACTAT ATATTGTCCT ATAATATTGT CTGATACAAA ACAGTCTAGA AATATTCTGA    11460
CAGGGAAATA GCAAATGTAT TAATTTAACT TACCTTGCAA TCTCTCTTAA TGGAGCCTTA    11520
CCACCAGTGT AAGAAATAAC TTCTGGGTGT GAATAAGTAC ACAGTATAAG GTAAACTTTG    11580
GTGAAATAGT CAATTCTTTT GTCATTAGTT CCCCCTTCAC TCCCAAAGTG TAGCACTTGT    11640
CATAGAATCT TTCTTTCTTC ATAAAGTCAG TCATTCATTT AGAATTCTGC ATTATTGTAT    11700
GTAGAAAAAC AATATTTTAC CTATTTTTGT TATATTCAGA ATTATATTTC TTTCTAATTT    11760
TAAAAAAATG GTTTACCGTA TTCATTTTTT TCTGGAACCT TTCTTTTCAG GCATTTCCTG    11820
CTTATCCAAA TTCACCATTT CAAGTCGCCA CTGGATATCA GTTCCCTGTA TACAATTATC    11880
AGGTAATGTC AGAGGGAGTA AAATGATTTG CTTTTAGGTA TTATTGAGGC CTTTAACTTG    11940
TTCATACAAA TTTCCTGAAT AGTTGCTCAT TTTAAACTAG TGAATTGTAC CTAAAATTTA    12000
AGGAAACACT TAGTGTAGAA TGAAGACCTC TGTGTTATTT AGAATAATGA GGTAGTATTT    12060
TGACAGGAAT ATACTTGGCA ATAACTTTTC TGTAGAACAG ATTTCTGAGA TTTGGTGTTC    12120
TCTTCTTCAT TTCTGGATGT AGTTTTCATC TTTACTGTCA AATAGCTAAA TGAAACGTCC    12180
AAAGTGTCTT TCATGAATTT TCTTAGGGAG ATAGACTGAA ATAAAATTAT GCTGCACTTT    12240
TCAGAGCACA GAATCCCAAT TACATTTTCA TTTTAGCTGG CTGTTTGAAG ATAGTAATGC    12300
TCTGGATCTC TTTTCATAGA TACAAGTGTA TCTGTGACCC ATAATTATAT CTATGGTAAT    12360
AAACTGAAAG AGCTAGTATC TTTGAGGTTT CCACATTGCG AAATCCCGAA AATGTGGAGA    12420
GAGCTGAAGT TTCCAATGTA AAAGTAACAA GAATGTCATG GACTAGAAAC ATAAAGTATT    12480
TGAGTTTTCC TTTCTGTTAC TTTTATTACA ATAAAAAAGG AGACAGCAGG ATAAGTACTT    12540
TAATATTGTG TTTCTCATGT GTTTTGAAA ATGTGTAGTA ATACTTCAAT AGTTTTGGTT    12600
TCCTTTTATT TATTAATTGA TTTTTTAAGA TTCCACCTTA GGGGCCTGTT GGGTAGCAAA    12660
GGGATTATGT TGTCCTTGAC ATTAAGGGAA TTAGCCAAAC ATAGACTTCC TGTTCATTCT    12720
```

```
TGATTTTTTT CCATGTCATA TATGCCTACA AATATTTTTA AGTGACTTTT TATGTTAATG   12780

TTTTTTTTGT TGTTGTTTCC TTCTTGTTAA CCCGATTATA AACTCCCATG GCAGCAACAG   12840

TGCCTTTTTT GTCCTCAGGT TTTTATGTGC TTAAGCAATG GCAGGTCTAC ATAATGATAG   12900

ACTATATAAT CAAAGAAAGG GAGTATTCAC GTGACTTTAG AATTAGCATG TGTCTGCACA   12960

GAATATGCCT CTGGCTTTAC CAGCAGTAGA AAATTTATAG AAGAGAAACA GAAATGCTTT   13020

GCTGTTAATG ACGCCTAAAT AAGAAGAGGA GTAAAGGAGA GTATTACCTC CAACTCACCG   13080

GAGCTGCTTT CCCCCTTATA AGCAGTTCCT AAAGTGAATG AAAGCAGCTC TCCTTATGTG   13140

TCTGCCTACT TTATTCTTCG GTAAGTTTAG CAGTTTATCT AGCTATCCTT TATTTGAAAT   13200

GATTGCCACA TGCCTCCTCA TATAAATGGC TGACTTCTGG ATATATTCTG GTTCTGGAAT   13260

GGGCAGATTT CTGACGTGGT TTAGTATATA TATATAAACC CGGTGAGTTT CTGGCATGTA   13320

ATTTCTCTGA TCGTGGTTAC ATTGATATTT AAAGTAGGGT TTGACATAGT GTGTCACTTA   13380

CTGTTGATAA ATATCGTTTA TTTTCTTCTT AGTTCATTTC ATTGATGTGT TAGCTTAAAA   13440

GACATTTTCT TTGACAGAAA ATGAAGTAAT GAAATAATAG TGAAATCGTT CTGCTGTGTC   13500

TCTAATTTGT TGATATTTTC CATGTACTTG AAACATGTAT GGTATACCTC TTCTTTTTCC   13560

TTCTCTGAAC CATGGCTAGA AAAAAAGCCC TACTTGTTTC TCTCGTTTAC TGTGAGGCAT   13620

TAGTGATTCT GGGTGTATTC ATGTATGCTG CTACCTGTAT GTTTTCAAAC AATAAGAATT   13680

TGTTGAAACA TGTCAGACAT TATACTTTTT ATTCTCCAGT ATTGGAATAT AGACTGCAAT   13740

TAGTTTTTTG GAATGAAATA CAGACAAAGC CATAACATCT ATAGAACTAC ATATTACCCT   13800

ACAATATTGT CTGATACAAA ACAGTCTGGA AATATTCTTA CAGCGAAATT GCAAATGTAT   13860

TGATTTACCT TACATTGCAA TCTGTCTTAG TGGAACCTTA TCACCAGTGT AAGACATAAT   13920

TTCTGGGTGT GAATAAGTAC ACAGTATAAG GTAAATTTTG GTGAAGTAGT CAGTTCTTTG   13980

TCATTTGTTC CCCCTTCACA CCCAAAGTGT AGCACTTGAC ATAGAATCTT TCTTTCCTCA   14040

TAAAGTCATT CATTTGGAAT TCTGCATTGT TGTATGTAGA AAAAGGATAT TTTCCGTTTT   14100

GTAATATTTT TCTTATATTG GGAATTATAT TTCTTTCTAA TTTTAAAATG TGGTTTACCA   14160

TATTCATTTT TTCTGCAACC TTTTCAGGCA TTTCCTGCTT ATCCAAATTC ACCAGTTCAG   14220

GTCACCACTG GATATCAGTT GCCTGTATAC AATTATCAGG TAATGTAAGA GGTAGTAAAA   14280

TGGTTTGCTT TCAGGTATTA TTGAGGCCTT TAACTTGTTT ATAGAAATTT CCTGAATAGT   14340

TGGTCATTTT TAACTAGTGA AGTGTCCCTA AAATTTAAGG AAAGACTTAG TGTAGAATGA   14400

AGACCTCTGT CTTATTTAGA AGTAATGAAG TAATATTTTT ACAGGAATAT CCTTGGCAAT   14460

AACATTTGTG TAGAAGAGAT TTCTGAGATT TGGTGTCCCC TTCTTCATTT GTGGATATAG   14520

TTTTCATCTT TGCTGTCAAA TAGCTGAATG AAACATCCAA ACTGACTTTC ATGAATTTTT   14580

TTAGGGAGAT AGAGTGAAAT AAAATTATGA TCCACTTTTC AGAGCACAGA ATTCCAATTA   14640

TATTTTCATT TTAGCTGGCT GTTTGACGGT AGTCATTCTC AGGATCTCTT CTCATAGATA   14700

CAAGTATATC TATGACCCAT AACTATATCT ATGGTAATAA ACTGAAAGAG CTAGTATTTT   14760

TGAGGTTTCC ACATTGCCAA CTCCCAAAAA TTTGGAGAAA GGTGAAGATT CAAATTTAAA   14820

GTAACAAGAA TGTCATGGAC AAGAAACATA AAGTACTTAA GTTTTCCTTT CTGTTACTTT   14880

TATTATAATA AAAAGGAGA CAGCGGAATA AGTACTTCAA TACTGTGTTT CTCATGTGTG   14940

TTTGAAAATA TGTAGGAATA GTTAATAGT TTTGGTTTCC TTTTTTTTTT TTTTTTTAA    15000

AGATGCCACC TTAGGGCCT GTTGGGGAGC AAAGGGATTA TGTTGTCCTT GACGTTAAGG    15060
```

```
-continued

GAATTAGCCA AACATAGACT TCCTGTTCAT TCTTGATTTT TTTTCCATGT CATATATGCC    15120

TATAAATATT TTTAAGTGAC TCTCTATATT AATGTTTGTT GTTGTTGTTG TTACTTTCTT    15180

GTTAACCCGA GTATAAACTC CCATGGCAGC AACAGTGCCT TTTTTGCCCT CAGGGTTTTA    15240

TGTGCTTAAG CAATGGCAGC TCCACATAAT GATAGACTAT ATAATCAAAG AAAGGTAATA    15300

TTCACGTGAC TTTAGAATTA GCATGTAGCT GCATAGAATC TGCCTCTGGC TTTACCAGCA    15360

GTAGTAAATT TATAGAAGAG AAACAGAAAT GCTTTGCTGT TAATTATGCT TAAATAAGAA    15420

TAGAAGTAAA GGAGAGTATT ACCTGCAAAT CACCAGAGCA GCTTTCCCCC GTATAAGCAG    15480

TTCCTAAAGT GAATGAAAGC AGCTCTCCTT ATGTGTCTGC CTACTTTATT CTTCCGTAAG    15540

TTTAGCAATT CATCTAGCTA TCCTTTATTT GAAATGATTT CCAGATGCCT CCTCATATAA    15600

ATTGCTGACT TCTGGATATA TTCTGGTTCT GGAATGGGTA GATTTCTGAT GTGATTTAGT    15660

ATATATATAT AAACCGCTTG AGTTTCTGGC ATCTAATTTC TCTGATCCTG GTGACATTGA    15720

TATTTAAAGT AGGGTTTGAC ATACTCTATC ACTTACTGTT GATAAATAAC GTTTATATTC    15780

TTCTTAGTTC ATTTCATTGA TGTGTTAGCT TAAAAGACAT TTTCTTTGAT GGAAAATGTA    15840

GTAACAAAAT AATAGTGAAA TAGTTCTGCA GTGTTTCTAA TTTGTTGATA TTTTCCATGT    15900

ACTTGAAACA TGTATGGTAT ACCTCTTATT TTTCCTTCTC TGAACAATGG GTAGAAGAAA    15960

AGCTCTACTT GTTACTGTCA TTTACTGTGA GCCATTACTG AATCTGGGTG TATTCATGTA    16020

TGCTACTGCC TGTATGTTTT CAAACAATAA GCATTATTG AAACATATAA GACATTATAC     16080

TTCCTCTTCT CCAGTATTGG ATTATAGACT GCACTTAGTT TTTTGGAATG AAGTACAGAC    16140

AAAGCCATAA CATCTATAGA ACTACATATT ACCCTATAAT ATTGTCTGAT ACAAAACAGT    16200

CTAGAAATAT TCTTACAGCA AATTGCAAAT GTATTAATTT AACTTACATT GCAATCTGTC    16260

TTAATGGAGC CTTATCACCA GTGTAAGAAA TAACTTCTGG GTGTGAATAA GTACACAGTA    16320

TAAGGTAAAC TTTGGTGAAG TAGTCAATTC TTTTTTTTTT TTAAATTATG CTTTAAGTTT    16380

TAGGGTCCAT GTGCACATTG TGCAGGTTAG TTCCATATGT ATACATGTGC CATGCTGGTG    16440

CTCTGCACCC TCTAACTCCT CATCTAGCAT TAGGTATATC TCCCAGTGCT ATCCCTCCCC    16500

CCTCCCCCCA CCCCACAACA GTCCCCAGAG TGTGATATAT CCCTTCCTGT GTCCATGTGA    16560

TCTCATTGTT CAATTCCCAC CTATGAGTGA GAATATGCGG TGTTTGGTTT TTTGTTCTTG    16620

CGATAGTTTA CTGAGAATGA TGATTTCCAA TTTCATCCAT GTCCCTACAA AGGACATGAA    16680

GTCATCATTT TTTATGGCGG CATAGTATTC CATGGTGTAT ATGTGCCACA TTTTCTTAAT    16740

CCAGTCTATC ATTGTTGGAC ATTTGGGTTG GTTCCAAGTC TTTGCTATTG TGAATAATGC    16800

CGCAATAAAC ATACGTGTGC ATGTGTCTTT ATAGCAGCAT GATTTATAGT CCTTTGTGTA    16860

TACACCCAGT AATGGGATGG CTGGGTCAAA TGCTATTTCC AGTTCTAGAT CCCTGAGGAA    16920

TCGCCACACT GACTTCCACA ATGGTTGAAC TAGTTTACAG TCCCGCCAAC AGTGTAAAAG    16980

TGTTCCTGTT TCTCCACATC TTCTCCAGCA CCTGTTGTCT CCTGACTTTT AAATGATTGC    17040

CATTCTAACT GGTGTGAGAT GGTATCTCAC TGTGGTTTTG ATTTGCATTT CTCTGATGGC    17100

CAGTGATGAT GAGCATTTTT TCATGTGTTT TTTGGCTGCA TAAATGTCTT CTTTTGAGAA    17160

GTGTCTGTTC ATGTCCTTCA CCCACTTTTT GATGAGGTTG TTTGTTTTTT CTTGTAAATT    17220

TGTTTTAGCT CATTGTAGAT TCTGGATATT AGCCCTTTGT CAGATGAGTA GGTTGTGAAA    17280

ATTTTCTCCC ATTTTGTAGG TTGCCTGTTC ACTCTGATGG TAGTTCTTT TTCTGTGCAG     17340

AAGCTCTTTA GTTTAATTAG ATCCCATTTG TCAATTTTGT CTTTTATTGC CATTGCTTTT    17400

GGTGTTTTAG ACGTGAAGTC CTCGCCTATG CCTATGTCCT GAATGGTAAT GCCTAGGTTT    17460
```

```
TCTTCTAGGG TTTTTATGGT TTTACGTCTA ACGTTTAAGT CTTTAATCCA TCTTGAATTG   17520

ATTTTTGTAT AAGGTGTAAG GAAGGGATCC AGTTTCAGCT TTCTACATAT GGCTAGCCAG   17580

TTTTCCCAGC ACCATTTATT AAATAGGGAA TCCTTTCCCC ATTGCTTGTT TTTCTCAGGT   17640

TTGTCAAAGA TCAGATAGTT GTAGATATGC GGCGTTATTT CTGAGGGCTC TGTTCTGTTC   17700

CATTGATCTA TATCTCTGTT TTGGTACCAG TACCATGCTG TTTTGGTTAC TGTAGCCTTG   17760

TAGTATAGTT TGAAGTCAGG TAGTGTGATG CCTCCAGCTT TGTTCTTTTG CTTAGGATT    17820

GACTTGGCAA TGCGGGCTCT TTTTTGGTTC CATGTGAACT TTAAAGTAGT TTTTTCCAAT   17880

TCTGTGAAGA AAGGCATTGG TAGCTTGATG GGGATGGCAT TGAATCTGTA AATTACCTTG   17940

GGCAGTATGG CCATTTTCAC GATATTGATT CTTCCTACTC ATGAGCATGG AATGTTCTTC   18000

CATTTGTTTG TATCCTCTTT TATTTCCTTG AGCAGTGGTT TGTAGTTCTC CTTGAAGAGG   18060

TCCTTCACAT CCCTTGTAAG TTGATTTCCT AGGCATTTTA TTCCCTTTGA AGCAATTGTG   18120

AATGGGAGTT CACTCATGAT TGGGCTCTCT GTTTGTCTGT TGTTGGTGTA TAAGAAAGCT   18180

TGTGATTTTT GTACATTGAT TTTGTATCCT GAGACTTTGC TGAAGTTGCT TATCAGCTTA   18240

AGGAGATTTT GGGCTGAGAC AATGGGGTTT TCTAGATATA TAATCATGTT GTCTGCAAAC   18300

AGGGACAATT TGACTTCCTC CTTTCCTAAT TGAATACCCT TTATTTCCTT CTCCTGCCTA   18360

ATTGCCCTGG CCAGAACTTC CAACACTATG TTGAATAGGA GTGGTGAGAG AGGGCATCCC   18420

TCTCTTGTGC CAGTTTTCAA AGGGAATGCT TCCAGTTTTT GCCCATTCAG TATGATATTG   18480

GCTGTGGGTT TGTCATAGAT AGCTCTTACT ATTTTGAAAT ACGTCCCATC AATACCTAAT   18540

TTATTGAGAG TTTTTAGCAT GAAGGGTTGT TGAATTTTGT CAAGGGCTTT TTCTGCATCT   18600

ATTGAGATAA TCATGTGTTT TTTGTCTTTG GTTCTGTTTA TATGCTGGAT TACATTTATT   18660

GATTTGCGTA TATTGAACCA GCCTTGCATC CCAGCGATGA AGCCCACTTG ATCATGGTGG   18720

ATAAGCTTTT TGATGTGCCG CTGGATTCGT TTTGCCAGTA TTTTATTGAG GATTTTTGCA   18780

TCAATGTTCA TCAAGGATAT TGGTCTAAAA TTCTCTTTTT TGGTTGTGTC TCTGCCTGGC   18840

TTTGGTATCA GAATGATGCT GGCCTCATAA AATGAGTTAG GGAGGATTCT GTCTTTTTCT   18900

GTTGATTGGA ATAGTTTCAG AAGGAATGGT ACCAGTTCCT CCTTGTACCT CTGGTAGAAT   18960

TCGGCTGTGA ATCCATCTGG TCCTGGACTC TTTTTGGTTG GTGAGCTATT GATTATTGCC   19020

ACAATTTCAG CTCCTGTTAT TGGTCTATTC AGAGATTCAA CTTCTTCCTG GTTTAGTCTT   19080

GGGAGAGTGT ATGTGTCGAG GAGTTTATCC ATTTCTTCTA GATTTTCTAG TTTATTTGCG   19140

TAGAGGTGTT TGTAGTATTC TCTGATGGTA GTTTGTATTT CTGTGTGATC AGTGGCGATA   19200

TCCCCTTTAT CATTTTTTAT TGCGTCTATT GGATTCTTCT CTCTTTTTTT CTTTATTAGT   19260

CTTGCTAGCG GTCTGTCACT TTTGTTGATC CTTTCAAAAA ACCAGCTCCT GGATTCATTA   19320

ATTTTTTGAA GGGTTTTTTG TGTCTCTATT TCCTTCAGTT CTGCTCTGAT CTTAGTTATT   19380

TCTTGCCTTC TGCTAGCTTT TGACTGTGTT TGCTCTTGCT TTTCTAGTTC TTTTAATTGT   19440

GATGTTACGG TGTCAATTTT GGATCTTTCC TGCTTTCTCT TGTGGGCATT TAGTGCTATA   19500

AATTTCCCTC TACACACTGC TTTGAATGCA TCCCAGAGAT TCCGGTATGT TGTGTCTTTG   19560

TTCTCGTTGG TTTCAAAGAA CATCTTTATT TCTGCCTTCA TTTTGTTATG TACCCAGTAG   19620

TCATTCAGGA GCAGGTTGTT CAGTTTCCAT GTAGTTGAGT GGTTTTGAGT GAGATTCTTA   19680

ATCCTGAGTT CTAGTTTGAT TGCACTGTGG TCTGAGAGAT AGTTTGTTAT AATTTCTGTT   19740

CTTTTACATC CGCTGAGGAG AGCTTTACTT CCCAGTATGT GGTCAGTTTT GGAATAGGTG   19800
```

```
TGGTGTGGTG CTGAAAAAAA ATGTATATTC TGTTGATTTG GGGTGGAGAG TTCTGTAGAT    19860

GTCTATTAGG TCCACTTGGT GCAGAGCTGA GTTCAATTCC TGGGTATCCT TGTTGACTTT    19920

CTGTCTCGTT GATCTGTCTA ATGTTGACAG TGGGGTGTTA AAGTCTCCCA TTATTAATGT    19980

GTGGGAGTCT AAGTCTCTTT GTAGGTCACT CAGGACTTGC TTTATGAATC TTGGTGCTCC    20040

TGTATTGGGT GCATATATAT TTAGGATAGT TAGCTCTTCT TGTTGAATTG ATCCCTTTAC    20100

CATTATGTAA TGGCCTTCTT TGTCTCTTTC GATCTTGTT GGTTTAAAGT CTGTTTATC     20160

AGAGACTAGG ATTGCAACCC CTGCCTTTTT TTGTTTTCCA TTTGCTTGGT AGATCTTCCT    20220

GCATCCTTTT ATTTTGAGCC TATGTGTGTC TCTGCACGTG AGATGGGTTT CCTGAATACA    20280

GCACACTGAT GGGTCTTGAC TCTTTATCCA GTTTGCCAGT CTGTGTCTTT TAATTGGAGC    20340

ATTTAGTCCA TTGACATTTA AAGTTAATAT TGTTATGTAT GAATTTGATC CTGTCATTAT    20400

GATGTTAGCT GGTTATTTTG CTTGTTAGTT GATGCAGTTT CTTCCTAGTC TCGATGGTCT    20460

TTACATTTTG GCATGATTTT GCAGCGGCTG GTACCGGTTG TTCCTTTCCA TGTTTAGTGC    20520

TTCCTTCAGG AGCTCTTATA AGGCAGGCTT GGTGGTGACA AAATCTCTCA GCATTTGCTT    20580

GTCTGTAAAG TATTTTATTT CTCCTTCGCT TATGAAGCTT AGTTTGGCTG GATATGAAAT    20640

TCTGGGTTGA AAATTATTTT CTTTAAGAAT GTTGAATATT GGCCCCCACT CTCTTCTGGC    20700

TTGTAGGGTT TCTGCCGAGA GATCCACTGT TAGTCTGATG GGCTTCCCTT TGAGGGTAAC    20760

CCGACCTTTC TCTCTGGCTG CCCTTAACAT TTTTTCCTTC ATTTCAACTT TGGTGAATCT    20820

GACAATTATG TGTCTTGGAG TTGCTCTTCT CGAGGAGTAT CTTTGTGGTG TTCTCTGTAT    20880

TTCCTGAATC TGAACGTTGG CCTGCCTTGC TAGATTGGGG AAGTTCTCCT GGATAATATC    20940

CTGCAGAGTG TTTTCCAGCT TGGTTCCATT CTCCCGATCA CTTTCAGGTA CACCAAGCAG    21000

ACGTAGATTT GGTCTTTTCA CATAGTCCCA TATTTCTTGG AGGCTTTGCT CATTTCGTTT    21060

TATTCTTTTT TCTCCAAACT TCCCTTCTCA CTTCATTTCA TTCATTTCAT CTTCCATTGC    21120

TGATACCCTT TCTTCCAGTT GATCGCATCA GCTCCTGAGG CTTCTGCATT CTTCACGTAG    21180

TTCTTGAGCC TTGGTTTTCA GCTCCATCAG CTCCTTTAAG CACTTCTCTG TATTGGTTAT    21240

TCTAGTTATA CATTCTTCTA CATTTTTTTT TTCCAAAGTT TTCAACTTCT TTGCCTTTGG    21300

TTTGAATGTC CTCCCGTAGC TCAGAGTAAT TTGATCGTCT GAAGCCTTCT TCTCTCAGCT    21360

CGTCAAAGTC ATTCTCCATC CAGCTTTGTT CCGTTGCTGG TGAGGAACTG CGTTCCTTTG    21420

GAGGAGGAGA GGTGCTCTGC TTTTTAGAGT TTCCAGTTTT TCTGTTCTGT TTTTTCCCCC    21480

TCTTTGTGGT TTTATCTACT TTTGGTCTTT GATGATGGTG ATGTACAGAT GGGTTTTTGG    21540

TGTGGATGTC CTTTCTGTTT GTTAGTTTTC CTTCTAACTG AGAGGACCCT CAGCTGCAGG    21600

TCTGTTGGAA TACCCTGCCG TGTGAGGTGT CAGTGTGCCC CTGCTGGGGG GTGCCTCCCA    21660

GTTAGGCTGC TCGGGGGGTC AGGGGTCAGG GACCCACTTG AGGAGGCAGT CTGCCCGTTC    21720

TCAGATCTCC AGCTGCGTGC TGGGAGAACC ACTGCTCTCT TCAAAGCTGT CAGACAGGGT    21780

CATTTAAGTC TGCAGAGGTT ACTGCTGTCT TTTTGTTTGT CTGTGCCCTG CCCTAGAGG     21840

TGGAGCCTAC AGAGGCAGGC AGGCCTCCTT GAGCTGTGGT GGGCTCCACC CAGTTGGAGC    21900

TTCCCTGCGG CTTTGTTTAC CTAATCAAGC CTGGGCAATG GCGGGCGCCC CTCCCCCAGC    21960

CTCGTTGCCG CCTTGCAGTT TGATCTCAGA CTGCTGTGCT AGCAATCAGT GAGACTGCGT    22020

GGGCGTAGGA CCCTCCGAGC CAGGTGCGGG ATATAATCTA GTGGTGTGCC GTTTTTTAAG    22080

CCCGTCGGAA AAGCGCAGTA TTCGGGTGGG AGTGACCCGA TTCTCCAGGT GGCATCCGTC    22140

ACCCCTTTCT TTGACTCAGA AGGGAACTCC CTGACCGCTT GCGCGTCCCA AGTGAGGCAA    22200
```

-continued

| | | | | | |
|---|---|---|---|---|---|
|TGCCTCGCCC|TGCTTCCGCT|CGCACGCGGT|GAGCCCACCC|ACTGACCTGC|GCCCACTGTC 22260|
|TGGCACTCCC|TAGTGAGATG|AACCCGGTAC|CTCAGATGGA|AATGCAGAAA|TCACCCGTCT 22320|
|TCGGCGTCGC|TCACGCTGGG|AGCTGTAGAC|TGGAGCTGTT|CCTATTCGGC|CATCTTGGCT 22380|
|CCTCCCCCAC|CCCCCTTTTT|TTTTCAAGAT|GCCACCATAG|GGGCCTGTTG|GGGAGCAAAG 22440|
|GGATTATGTT|TTCCTTGATG|TTAAGTGAAT|TAGCCAAACA|TAGACTTCCT|GTTCATTCTT 22500|
|GGTTTTTTTC|CACGTCGTAT|ATGCCTATTA|CTATTTTTAA|GTGATTTTTA|TATCAATGTT 22560|
|TTAGTTTATT|TTTTTACTTT|CTTGTTAACC|CGATTATAAA|CTCCCATGGG|AGCAACAGTG 22620|
|CCTTTTTTGC|CCTGAGGTTT|TTATTTGCTT|AAGCAATGGC|AGGTCCACTT|AATGATAGAC 22680|
|CATATCATCA|AAGAAAGGTA|GTATTCATGT|GGCTTTTGAA|TTAGCATGCA|TCTGCGTAGA 22740|
|TTCTGCCTCT|GGCTTTACCA|GCAACAGAAA|ATTTGTAGAA|CAGAGACAGA|AATGCTTTGC 22800|
|TGTTAATTGC|GCTTAAATAA|GAATAGGAGT|AAACGAGAGT|ATTACCTCCA|AAGCACCAGA 22860|
|GCTGCTTTCC|TCCTTATAAC|CAGTTCCTAA|AGTGAATGAA|AGCAGCTCTC|CTTATGTGTC 22920|
|TGCCTACTTC|ATTCTTCGGT|AAGTTTAACA|GTTCATCTAG|CTACCCTTTA|TTTGAAATGA 22980|
|TTTCCAGATG|CCTCCTCATA|TAAATTGCTG|ACTTCTGGAT|ATATTCTGGT|TCGGGAATGG 23040|
|GTAGATTTCT|GATGTGGTTT|AGTAGGTATA|TAAATCCCGT|GAGCTTCTTG|CATCTAATTT 23100|
|CTCTGATCCT|GCTTACACTG|ATATTTAAAG|TAGGTTTTGA|CATACTCCAT|CACTTAATGT 23160|
|TGATAAAGGA|CGTTTATATT|CTTCTTAGTT|CGTTTTATTT|ATGTGTTAGC|TTTAAAGACA 23220|
|TTTTCTTTGA|CGGAAAGTGA|AGTAACAAAA|TAATAGTCGA|ATAGTTCTGC|CGTGTCTCTA 23280|
|ATTTGTTGAT|ATTTTCCATG|TACTTGAAAC|ATGTATGGTA|CACCTCTTCT|TTTTCCTTCT 23340|
|CTGAACAATG|GCTAGAAAAA|AAACCCTACT|TCTTTCTGTC|ATTTACTGTG|AGGCATTACT 23400|
|GAATCTGGGT|GTATTCATGT|ATGCTGCTAC|CTGTATGTTT|TCAAACAATA|AGAATTCATT 23460|
|GAAACATATA|AGACATTATA|CTTTCTCTTC|TCCAGTATTG|GATTATAGAC|TGCACTTAGT 23520|
|TTTCCGGAAT|GAAGTACAGA|CAAAGCCATA|ACGCGTGTAC|AACTACACAT|TGTCCTATAA 23580|
|TATTGTCTGA|TAAAAAACAG|TGTAGAAATA|TTCTGACAGG|GAAATAGCAA|ATGTATTAAT 23640|
|TTAACTTACC|TTGCAATCTC|TCTTAATGGA|GCCTTATCAC|CAGTGTAAGA|AATAACGTCT 23700|
|GGGTGTGAAT|ACGTACACAG|TATAAGGTAA|ACTTTGGTGA|AGTCGTCAAT|TCTTTTGTCA 23760|
|TTTCTTCCCC|CTTCACAGCC|AAAGTGTAGC|ACTTGACATG|GAATCTTTCT|TTCTTCATAA 23820|
|ATCAGTCATT|CATTTGGAAT|TCTGCATTGT|TGTATGTAGA|AAAACGATAT|TTTCCCTTCT 23880|
|GTAATATTGT|TGTTATATTG|GGAATTATAT|TTCTTTGTAA|TTTTAAAAAG|TGGTTTACCA 23940|
|TATTCATTTT|TTTCTGCCAA|CCTTTCTTTT|CAGGCATTTC|CTGCTTATCC|AAGTTCACCA 24000|
|TTTCAGGTCA|CCACTGGATA|TCAGTTGCCT|GTATATAATT|ATCAGGTAAT|GTAAGAAGGA 24060|
|GTAAAATTAT|TTGCTTTCAG|GTATTATTGA|GGCCTTTAAC|TTGTTTATAC|AAATTTCCGG 24120|
|AATAGTTGGT|CATTTTAAAC|TAGTGAAGTG|TACCTAAAAT|TTAAGGAAAC|ACTTAGAATT 24180|
|AGTGTAGAAT|GAAGACCTCT|GTCTTATTGA|GAAGTAATGA|AGTCGAATTT|TGACAGGAAT 24240|
|ATACTTGGGA|ATAACTTTCC|TGTAGAACAG|ATTTCTGAGA|TTTGGTGTCC|CATTCTTCAT 24300|
|TTCTGGATGT|AGTTTTCATC|TTTACTGTCA|AATAACTGAA|TGAAACATCC|AAACTGACTT 24360|
|TCATGAATTT|TCTTAGGGAG|ATAGAGTGAA|ATAAAATTAT|GACCCACTTT|GCAGAGCACA 24420|
|GAATTCCAAC|TATATTTTCA|TTTTAGCTGG|CTGTTTCACG|ATAGCAATTC|TCTGGGTCTC 24480|
|TTTTCACAGA|TACAAGTACA|TCTATGCCCA|ATAATTATAT|CTATGGTAAT|AAACTGAAAG 24540|

```
AGCTAGTATC TTTGAGGTTT CCACATTGCC AACTCCCGAA AATGTGGAGA AGGGTGAAGT    24600

TTCTAATATA AAAGTAACAA GAATGTCATG GACTAGAAAC ATAAAGTACT CAAGTTTTCC    24660

TTTCTGTTAC TTGTATTATA ATAAAAAAGG AGACAGCAGG ATAAGTGCTT CAATATTGTG    24720

TTTCTCATGT GTTTTTGAAA ATGTGTAGGA ATATTTTAAT AGTTTTGGTT TCCTTTTTTT    24780

TTTTTTTTTT AAGATGCCAC CATAGGGGCC TGTTGGGGAG CAAAGGGATT ATGTTTTCCT    24840

TGATGTTAAG TGAATTAGCC AAACATAGAC TTCCTGTTCA TTCTTGGTTT TTTTCCACGT    24900

CGTATATGCC TATTACTATT TTTAAGTGAT TTTTATATCA ATGTTTTAGT TTATTTTTTT    24960

ACTTTCTTGT TAACCCGATT ATAAACTCCC ATGGGAGCAA CAGTGCCTTT TTTGCCCTGA    25020

GGTTTTTATT TGCTTAAGCA ATGGCAGGTC CACTTAATGA TAGACCATAT CATCAAAGAA    25080

AGGTAGTATT CATGTGGCTT TTGAATTAGC ATGCATCTGC GTAGATTCTG CCTCTGGCTT    25140

TACCAGCAAC AGAAAATTTG TAGAACAGAG ACAGAAATGC TTTGCTGTTA ATTGCGCCTA    25200

AATAAGAATA GGAGTAAACG AGAGTATTAC CTCCAAAGCA CCAGAGCTGC TTTCCTCCTT    25260

ATAACCAGTT CCTAAAGTGA ATGAAAGCAG CTCTCCTTAT GTGTCTGCCT ACTTCATTCT    25320

TCGGTAAGTT TAACAGTTCA TCTAGCTACC CTTTATTTGA AATGATTTCC AGATGCCTCC    25380

TCATATAAAT TGCTGACTTC TGGATATATT CTGGTTCGGG AATGGGTAGA TTTCTGATGT    25440

GGTTTAGTAG GTATATAAAT CCCGTGAGCT TCTTGCATCT AATTTCTCTG ATCCTGCTTA    25500

CACTGATATT TAAAGTAGGT TTTGACATAC TCCATCACTT AATGTTGATA AAGGACGTTT    25560

ATATTCTTCT TAGTTCGTTT TATTTATGTG TTAGCTTTAA AGACATTTTC TTTGACGGAA    25620

AATGAAGTAA CAAAATAATA GTCCAATAGT TCTGCAGTGT CTCTAATTTG TTGATATTTT    25680

CCATGTACTT GAAACATGTA TGGTACACCT CTTCTTTTTC CTTCTCTGAA CAATGGCTGG    25740

AAAAAAAGCC CTACTTGTTT CTGTCATTTA CTGTGCGGCA TTACTGAATC AGGGCATATT    25800

CATGTGTGCT GCTACCTGTA TGTTTTCAAA CAATAAGAAT TCATTGAAAC ATATAAGACA    25860

TTATACTTTC TCTTCTCCAG TATTGGATTA TAGACTGCAC TTAGTTTTTT GGAATGAAGT    25920

ACAAACATAG CACTAATATC TATAGAACTA CATATTACCC TTTAATATTG TCTGATACAA    25980

AACAGTCTAG AAATATTCTG ACATTGAAAT AGCAAATGTA TAAATTTAAC TTACATTGCA    26040

ATCTGTCTTA ATGGAGCCTT ATCACCGGTG TAAGAAAGAA TTTCTGGGTG TGAATAAGTA    26100

CACAGTATAA GGTAAACTTT GGTGAAATAG TCAATTCTTT TGTCATTTGT TCCCCCTTCA    26160

CACCCAAAGT GTGGCACATG ACATAGACTA TTTCTTTCTT CATAAAGTCA GTCATTCATT    26220

TAGAATTCTG CATTGTTGTA TGTAGAAAAA TGATATTTTA ACGTTTTAA TATTTTTGTT    26280

ACATTGGGAA TGATATTTCT TTCTAATTTT AAAAAATGGT TTACCATATT CTTTTTTTTC    26340

TGCCACCTTT CTTTTCAGGC ATTTCCTGCT TATCCAAATT CAGCAGTTCA GGTCACCACT    26400

GGATATCAGT TCCATGTATA CAATTACCAG GTAATGTAAG AAGGAATGAA ATGATTTGCT    26460

TTCAGGTATT ATTGAGGCCT TTAACTTGTT TATACAAATT TCCTGAATAG TTGGTCATTT    26520

TAAACTAGTG AAGTGTACCT AATATTTAAG GAAACACTTA GAATTAGTGT AGAATGAAGA    26580

CCTCTGTCTG ATTTAGAAGT AATGAGGTAA TATTTTGACA GGAATGTACT TGGCAATAAC    26640

TTTTCTGTAG AACAGTTTTC TGAGATTTGA CCCTTCTATA TTTCAGGATA TAGTTTTCAT    26700

CTTTGCTGTC AAATAGCTGA ATGAAACCTC CAGGATGACT TTCATGAATT TTTTAGGGAT    26760

ATAGAGTAAA TAAAATTATT ACCCAATTCT TAGAGCACAT AATTCAAATT ATAGTTTCAT    26820

TTAGTAGGCT GTTTCCCGAC AATTGTTGTC TGGTTCTCTT TTCATAGTAG AGAGGACTCT    26880

ATCTATGACC AATAATCATA TGTAGCATAA TAAGTTCAAA GTAGTAACAT CTTTGAGATT    26940
```

-continued

```
TCCACAATGC CAAATCCAAA AATTGGGGAA AAGGTGTGGT TTCGTATTTG TATGTGGAAG    27000

TAACAACAAG AATGTCAGGA ATTAGAACCA TAAAGTACTT CTTTTTTCCA TTGTCTTTCT    27060

TTTATTATAA TAACAAAGGA GCCAGCATAG GTACTTCAAT ATTTTATATA TCATTTGTTT    27120

TTGAAAATGT TTATGAATAT TTGAATAATT TTGTTTTCCT ATTTTTTTTT TAAGATGCCA    27180

CCGCAGTGCC CTGTTGGGGA GCAAAGGAGG TAGGTTGTAC CTCTGGTAAA GTGAATTAGC    27240

CTACCATGTA CTTCTGTTCT TTCTGGATTA TTTTCCATAT CATTTATGCC TTATAAATAT    27300

TTTAAATGAT TCTTTATATT AATGTGTTAC ATTTTGTTAC TTTCTTTTTA ACCCAGTTAC    27360

AATCTCCCAT GGGTGCAACA GTGCCTTTTT CTCTCTCAGG TTTTTGTGTG CTTAAGGAGT    27420

GGCTGGTCCA CATAATAAGT GTTCAGTTAC TTGTTGATAG ACTGTGTAAT CTAAGAAAGA    27480

TAGTATTAAT GTCACTTTAG AATTAGCATG TATCTGCGTA GGGTCTGCCT CTGGTTTTAC    27540

CAGCCACAAA AAATTTGTTG AAGAGAAACA GAAATGTTTT GCTGTTAATT ACTCTTAAAT    27600

AAGAATAGGA ATAAAAAAAG AGTATTACCT CTAAAATACC TGAACTTCTT TCCCCCATTA    27660

TACCTAGTTC TGAAAACATT TGAAAGCAGC TGTTCTAATG TTTCTGCCTA GTTTATTCTT    27720

TAAGGATAGC GATTAATCTA GCTCTTCTTT ACTTGCAATG ATTTCCAGTT GACTCCTCAT    27780

ATAAACTGCT GACTTCGGGA TATATTCTCG GTCTGGAATG TATAGATTTC TGACCTATTT    27840

TACTGTACCT ATAAATCCTG TGAATTTCTG GCATGTAATT TCTCTGATCC TGATTACTTT    27900

GATATTTAAA GTAGGATTTG ACATACTCTA TCACTTATTG GTGATAAATA ACGTCTGTTT    27960

TCTTCTTAGT CCATTTTATT TATGTGTTAG TTTAAAAGAC ATTTTCTTTG ATGGAAAATA    28020

AAGTAACAAA ATAGTAGTGA AATAGTTCTT CAGTGTCTCT CATTTATTGA CATTTTCTGT    28080

GTACTTGAAA TGTGTAGGAT ATACCTCTTC TTCTTTTTTC TTCTCTGAAC AATGGCTAGA    28140

GACAAAGCCC TACTTGTTTC TAACATTTAC GGTGAGCCAT TACTGAATTT GGGTGTATTC    28200

ATGTATGCTG CTTCCTATAT GTTTTCAAAC AATAAGTATT TATCGAAACA TATAAGACAT    28260

CGTACTGTCC TTCTCCAGTT TTGGATTGTA CACTGCCCTT AGTTTTTCGA AATGAAGTAC    28320

AGAAAAAAAA CATAACATCT GTAGGAGAAC TACATATTAC CCTGTAATAT TGTCAAACAC    28380

AAAACTATCT GGAAGTATAT TGACAAAGAA ATAGCAAATG TATTAACTTA ACTTACATTG    28440

AGATCTGTCT TAATGGAGCC TTACCAGCAG TGTAAGAAAC AACTTCTGGG TGGGCATAAG    28500

TACACAGTGT CAGTAAGGTG AACTTTGCCT GGTGAAATAG TCACTACTTT GTCATTTGTG    28560

TGTTCCCCCG CCCCACCCAA AGGGGCTTAG CACTTGACAG AGAATATTTA TTTCTTCCTG    28620

AAGTCATTCA TTCATTTAGA ATTCTGCATT GTTTTATATA GAAAATTAAT AAATATTTTA    28680

AAGTTTTTCA TTTTTTTTAT TTTGGGAATA ATATTTTTTT CTAATTTAAA AAGATGTTTT    28740

ACCATATTCA TTCTTTCTGT AAACTTACTT TCAGACATAT CCTACTTATC CAAATTCACC    28800

AGGTCAGGTC ACCACTGGGT GTCAGTTGCC TGTATGTAAT TATCAGGTAA TTGAAGAGGG    28860

AGTAAAATGA TTTGTTTTCA GATATTATTG AAGCCTTTAA CTTGTTTATA TGAATTTCCC    28920

AAATAGTGTG TCATTTTAAA CTAGTGAAAT GTACCTAAAA TTTAGGAAAA CACTTGCAAT    28980

GGTCTAGAAT GAAGCCCTCT GTATTATTTA GAAGTAATGA ATTAACATTT TGACAGGGAT    29040

ATACTTAGCA ATAACTTTTC TGTAAAACAG TTTTCTGAGA TTCGTTGTCC CCTTCTATAT    29100

TTCAGCGTGT ATTTTTTCAT CTTTTTCATC TTTTTATCAT CCCATTCTTA GAGCACAGAA    29160

TTCCAATTAT ATTTTTATTT TAAGCTTGCT GCTTCATGAT AGTAGTTCTC TGGGCCTCTT    29220

TTCATAGATA TGACTACATC TGTGACCCAT AATCATATCT ATGGTGATAA GTAATAAATT    29280
```

```
-continued

GAAAAAACTA GTATCCTTGA GATTTCCACA ATGCCAACTC CAGAAAATTG GGAAAATGGC   29340

GAGGTTTTAT GTATAAAAGT AACAAGAACA TCAGGGATTA GAAACATAAA GTACTTCTTT   29400

TTTTTTTTTT ACTCTGTTTC TTTCACTTTA ATAACAAATG AGCCAGCATG ATAAGTGCTT   29460

CAATATTGTG TATCTCATGA GTTTTTGAAA ATGTGTAGGA ATATTTTAAT AGTTTTGGTT   29520

TCCTTCTTTT TATTTTTTTA AGGTGCTACC GCAGTGGCCT GTTGGGGAGC AAAAGGGGTT   29580

ATGGAGTAAA GTGAATTAGT GAAACGTATA CTTCCTCATC TTTCTTGACT TTTTTCTATG   29640

CCATATATGC CTGTAGATAT TTTTAAATGG TTCTTTATAT TAATGTTTTA TGTTTTGTTA   29700

CTTTATTTTT AACCCAATTA TAAACTCCCA TGGGAGCAAC AGTGCCTTTT TGTCTCTCAC   29760

ATTTTTGTGT GCTGAAACAG TGGCTGGTCC ACATAATGAT AAGTGTTCAG TTACTTGTTG   29820

ATAGATTATA TAATCCAGGA ATGGCGGTAT TAACTGGCTT TAGAATTAGC ATGTATCTGC   29880

CTAGAATATG CCTCTGGCTT TACTAGCCAT AAAACATTTG TTGAGGAGAA ACCGAAATGT   29940

TTTGCTATTA ATTACTCTTA AAGAGGAATA GGAATAAAAC AAGAGTATTA CCTCTAATAC   30000

AACAGAGCTG CTGTCTTACA TCACGATTGG ATATTTGAAG GATATAGTAA GTGTTAAAAT   30060

TCTCAAACAC TCCCTTAACT ACATTTGTTT CTTAGAATCC TTCTACCTCT GATTATGTTG   30120

ATACCTGGAA GACGTTTTAA AACAAAAGGC TGCCTTAATG CATTTCAACT TTTCGTTTAA   30180

AACAAGGTTT CTGAAGTAAC ACAATTGAAT TTCAACACAA CCTACATTGA AACTTTTGAT   30240

ACCAGCTCAC CTTTTTGAGG AATAAATAAG TAGCTTTTAA ACGTATCTGT ATTATCTGTT   30300

TAATTACACT TTCATTATTT TAAATATAGG CTTATTCAGC TCTTAACTGT CACTGTAGTG   30360

AAGTTGATAC AGGAGGTGAT GTTGTGCTAA ATGAATGCTC AATTCATGAA GCTACCCCAC   30420

CCTCTGGAAA TGGCCCACAA AAGGCAAACA TCTAATTTTG AATTTTTTTT ACAATATATA   30480

TTTCATATTT TTTTCTAATT TGAATGACTT TTTTTGAGAA GCAAACATTT TTGCCCAAAT   30540

TTAAAAATGT TAGCCATAAA TCATGGAGCT TAAATAATGG ACTGATAGTC AGCAGTTAAT   30600

GTAAAGGTTG TTGAAATTTC AGATACCCCA AATTTTCAGT ATATACCTAA AGTTTCTGAT   30660

TCAGCAAGTC CTTTCCTGTA TTTCAGTTTC ACTAATTTTA AAAAGCCATT CTTTAATAAA   30720

TACTGTATTA ATATGATTTG GCAGAATGCT ATGGGAGGGT TTCCTCTAGA ATTCTACTCA   30780

AAAGAAGAAT TAGTACGAAT TGTATGTCCC TTTTCTTTTA CAACAGTTTT GATCTTAAGC   30840

AGTGAAAAAT ACCATTTAAA TAAGCATTCT CTCCATAACA TTATATGTGG CAGAAGTTTC   30900

CAACAGTGGT GAAGTCAGTA GTAATTATTC AAACACTGAA ATAGACAGGG TTGTTTCTTT   30960

TTTTTATCAT TAGTGCAAAT TTCTGTAATA ACAGTACTGT CACTCCTGGC GTCACATATG   31020

TTCTGTTAGA TAGGTGGGCG TGTGGAAGTA GTTGATGTGC TGGTAATATG TATAATACCC   31080

AAGAAGTCCC ATTGCAGTGT AAATTCCTTG ATTTGATATT GGATTTTAAA ATGTGAATAA   31140

ATATGAAAAC ATAACTCTTA CAGTATAATT GTCTGGTTTT GTTCTGAGTA TGTTTTCTTG   31200

AAACATTGGA ATTCACTTAG GGATTTAACA AATTCAGCTT TTTAAACCAG TATTCTATCG   31260

CTAAGGTTCT AAAATAATTC TTCGATTTGT CAGAAAACGT ACATACTGAG GATATGTGGC   31320

AGGAATTATG AATCACATTT TTATGAATTT CTTTTTTTTT TTGAGACAGG GTCTTGCGGT   31380

GTCGCCCAGG CTGGAAGTGC AGTGGTGTGA TCTCGGCTCA CTGCAACTTC TGTCTCCTAG   31440

GTTCCAGTAA TTCTCCCTGC CTCAGCCTCC CCAATAGGTG GAATTACAGG CACCCGTCAC   31500

CCAGCTAATT TTTGTATTTT TTAGTGGAGA AGGGGTTTCG CCATGTTGGC CAGGATAGTC   31560

TTGAACTCCT GATATCAGGT GATGCGTCCT CCTCGGCCTC CCAAAGTGCT GGGATTAGAG   31620

GTGTGAGCCA CTGCTCCCAG CCTCTTTTAG CATTTTTGCA TTTCTTTGGA AATAAACTGA   31680
```

```
TATGTTCATT AAACCATCAA AAGAAAAACC AAAACACACC CTTATTAAGA GTGAGTGAAA    31740

GAAAGAGTTG TCTTTACATT ACTGAAAACT TCTGTGTTTC AGAAATCTGT GGACCGAAGC    31800

ATACAAATGG TGGTATCTTG TCTGTTTAAT CCAGAGAAGA GACTGATAAA TTCCGTTGTT    31860

ACTCAAGATG ACTGCTTCAA GGTATGAAAG GAATGGCATG CATAATTAAA AAGCACACTT    31920

GTTCCCTCTC AAGTTAGCTG TTTTCCTTGT GGCACATGTA TTTTGGGCTT TCTTAGAGGA    31980

ATTTTTTTTC TTTTTTTTTT GTTTTGAGAC GGAGTCTCCT CTGTGCGCCC AGGCTGGAGT    32040

GCAGTGAGTG GCCCCATCTA GGCTCACTGC AAGCTCCACC TCCCAGGTTT ACTTAACGCC    32100

ATTCTCCTGC CTCAGCCTTC CGAGTAGCTG GGACTACAGG CGCCCACCAC CACGCCCAGC    32160

TAATTTTTTG TATTTTTAGT AGAGACGGGG TTTCACCGTG TTAGCCAGGA TGGTCTCGAT    32220

CTCCTGACCT CGTGATCCAC CTGCCTCAGC CTCCCAAAGT GCTGGGATTA CAGGCATGAG    32280

CCACCGTGCC CGGCCTAGAA CATTTAATTG AACTGTTGGC ATTTGACTGT AACCCAGTAA    32340

ACCAGTGTGG GTTTTACCTG GCAGTATATT TTCTGCTGCC GAGCCTTGAT ATAATGTAGT    32400

CAAATTTAGG GAAGAATCCT GCAGCAGAAA TTTGTAATTG AAAGGGTTTA CTAGAGAAGA    32460

GAGTTAGTTG ACTACCTTGA CCAAATAGTA AAATAAAATT TTAGATACAG AAAGGAGATC    32520

TTGGCTGGGT GCAGAGGCTC ACGCCTGTAA TCCCAACACT TTGGGGGGCT GAGGTGGGTG    32580

GATTGCTTGA GCTCAGGAGT TCGAGGCCAC CCTGGGTAAC AAGGCAAAAC ACCATCTCTA    32640

CAAAAAAATA CAAAAATCAG CCAGTTGTGA TGGTACATGC CTGTAGTGCC AACTACTCCA    32700

GAGGAGTCTG AGGCAGGAGG ATCGCTTGAG CCTGGGAAGT TGAGGCTGCA CTGAGCCATG    32760

ATTGTGCCGT TGTAGTCCAG CCTGGGCAAC AGAGTGAGAC ACCTTGTCTC AAAAAAAAAA    32820

AAAAAAAAAA AAAAGTAGA ACTTAATACA TGCATATTGG ACTAAAGAGA AGAAAAGAAA    32880

TGATTTACTC AGATGATACA CCTGAACAGT GTGAAGGGAG AAAAGGGGTA AAATGAAGCA    32940

GTAAAAAGTT GAGTAGAAAG AGAGGTTGAT TCAGAGTTGG TGAAGCGGAA GAGAATGTGG    33000

CTAGTTGAAT TCCAGAAAGA TCTGACTTCT GATCCCACTT TCTATCCATG TTGGATAGAT    33060

AAATCTTTTA TTAAGGCTCT AATTCTTACA AGTCTAAAAT GAGAAGGTAC AGGACTAAAG    33120

GTTTCTGGGT CCCTGTGGTT CTAAGTCTAT AAATACGAAA AAGAACTAAC TTGGTCAGTC    33180

CGGTGGGAGA AAAATATTAT GGTTAATAAA GGGAAGGTGT TTTTTAAATA ACAATTTTAT    33240

TAAAATAATA CCAGTAATAC AATTTATGTA TTTAAAATGT GCACTTCACT GTTTTTTCAT    33300

ATATTCAAAG TTGTGCAACC ATGTCCACAA TCAATTTTAG AATATTTAAA TCACCTCAAA    33360

AATCACCCCC GTACCTTAGC AGTCACCTGC TATTTTCCTG GAACTTGTGT GTATCCCTAG    33420

GCAAACACTA ATTTACTTTT TTCCTCTAAG GATTTTCCTG TCCTGGAGAT TTCTTGTATA    33480

TGGAATCATA CATAATGATG TGGCATTTTG TGACTGGATT TTTTCACTCA GCATAATGTT    33540

TGTAAGGTTC ATCAATATTC TAGCACGTAT CAGAACTTAA TCATTTCTTT TTATTTGTAG    33600

ATATTACCTT ATTCTGTTTA TGCATTCATC TGTTAAAGAC ATTTGGATTA TTTCCACTTT    33660

TTAGCTGTTA TAACTAATGC TGTGAACATT CATGTACAAG TTACTGTGGG GACATACGTG    33720

CTTACCTCTC TTGCGTATAT ACTTGGGAAT GGAATTGCTA AGTCATATTT AACCTTTAGT    33780

GGAACTGCCA GATTTGTCAA AACTGGCTAC ACACTTTACA TTCAAAAGAA AATGTTTAAC    33840

CATCACTTTG TGTCTTACAA CAGAACTAGC TTATTTTTGT CTGTGAATGG ATATGGGATG    33900

AAGCCTAAGC CTTTTTAAAG GGTTATATTA TGAATCTTCT GTATAATGTA GAAGAGTAGA    33960

GCCAGATAGC AGAATTAAGT TCTTAACATC TTTGCAACAT GGAGTAAATA TATTTAAATT    34020
```

-continued

```
TGACATTTGT TCTCTTGTTG CTTCGTTCTA TATAGATAGT ACAATTTAGA AAAGAAAGAA    34080

CTGGAATTGT ACATCAGCTT ATCTTGCCGA AAATTCTGAT TACATTGGTG TCTACAGTAG    34140

TACTTAAGTG ATTTTCAAAG CAGAAGATAG TTTTTTGTGT TTCTTTCTTT CTTTCTTTTT    34200

TTTTTTTTTG AGGTGACCTC ATTTGGTCAT CCAGGCTGGA GTGCAGTGTC GCAATCACAG    34260

CTTACTACAA CCTCAAACTC CTGCACTCAA GGGATCCTTC TGCCTCAGCG TCCCAAATAG    34320

GACGACAGAC GTGCACCACC ACACTTAGCT AGTTAAAAAG AAATTTTTTT TTTTTTTTT    34380

TGAGACAGAG TCCCACTGTG TCACCCAGGT TGGAGTGCAG TGGTGCGATC TTGGCTCACT    34440

GCAAGTTCTG CCTCCCAGGT TCATGCCATT CTCCTGCCTC AGCCTCCCGA GTGGCTGGGA    34500

CTACAGGTGC CTGCCACCAC GCCCAGCTAA TTTTTTGTGT TTTTAGTAGA GATGGGGTTT    34560

CATCGTGTTA GCCAGGATGG TCTCGATCTC CTGACCTTGT GATCTGCCCG CCTCGGCCTC    34620

CCAAATTGCT GGGATTACAG GTGTGAGCCA CCGTGCCCAG CCAAAAGATT TTTTTTAAG    34680

AGAGAATCTT ACTATATTGC CCTGGCTCGT CTTGAACTCC TGGGCTCAAG TGATCCTCCT    34740

GCCTCAGCCT CCCAAAGTGC TGGGATTACA GGCGTATGCC ACCATGTCCA GCCCAGAAAA    34800

TATTTTTTA AACTTGAGTT CTCACCTGGT GGTAGACAAA AGACTCGCTT TGAAACTTCC    34860

AGAGTTTTCT GCTTATTTGG GAGAGGAATC AGAAGTTGGC ATCCTGCAGT TGTCTGACAT    34920

TTAGACCTAT TTTAATTGAC TGCACGTTGT TATATTGAAT TAGAATGCCT GAGATATTTT    34980

TGAATGTATT TACAATTTCC ATAGCCGATT TCTCTTCATT GTCTTAGTTA TCTAGCCCTT    35040

TCACAATCTT GTTTCCTACA TGACCTCTGA ATATACATGT TGGTGACCAG TTTTCTAGAT    35100

TTTAACCTAA ATTGATTATC ACTCTTTTGA CAGATGAGGT AACTTCCAGA AGCCACTTTT    35160

ATTTATATGA AAATGAAACT GAAGTCTTAA AAAAAGGGCA CAGCTTTGTA GAAAAGGAAA    35220

TGTTATTACT CGTTCACTCA TTCCCATTCC TCCTTGTAAG ACCTCTCACT TCTCTCTGCA    35280

CGTCTGCAGG CAACATAGAG TGAAAAGAAA GTTTTGCATG TATTTTAAAG TTTTATCTTC    35340

CTTTCTAAAG AATGATATGT CTTCACAGGT TAATGATATG TTCTTCAAAT GCCAAAACTT    35400

ACATATTTTA ATCTAAAAAC ACGAAATTTC AGATTGGAGA GCAGTTCGCA AGCTGTAGTT    35460

GGTATTAAAT GCAGTTCAAT TAGTGAAAAA AGTATTCTTT ACAATTACAT TTTCTACCAG    35520

CTGTCTTTGG GACATTACTG CAAAATTATT AACTAAGAAG TACATAAAAT GATACTGAGT    35580

TTAAGTCCTT TTATTTCTCA GTTTACTGGA ATTTGTTTTA TTTAATTATT GATTTCTTTT    35640

TTTAACTGTT TAATAAAACT AGCCATCTTG GTACATTTGT TATCCCAGTG TTCAAATATG    35700

CTTCCTGAAA AGAATCATCT TTTTTTCTCA TTATTTATAA TGTTTAAACC CAAAACAAAT    35760

GGTTTAAGTT TTGACAACTT TCAGATCCAT AGTAGTCATC AGAAATTTTC AGTAAAATAA    35820

AAGGACTATT TCTGTCTTTT CCAGGGTAAA AGAGTGCATC GCTTTAGAAG AAGTTTGGCA    35880

GTATTTAAAT CTGTTGGATC CTCTCAGCTA TCTAGTTTCA TGGGAAGTTG CTGGTTTTGA    35940

ATATTAAGCT AAAAGTTTTC CACTATTACA GAAATTCTGA ATTTTGGTAA ATCACACTGA    36000

AACTTTCTGT ATAACTTGTA TTATTAGACT CTCTAGTTTT ATCTTAACAC TGAAACTGTT    36060

CTTCATTAGA TGTTTATTTA GAACCTGGTT CTGTGTTTAA TATATAGTTT AAAGTAACAA    36120

ATAATCGAGA CTGAAAGAAT GTTAAGATTT ATCTGCAAGG ATTTTAAAA AATTGAAACT    36180

TGCATTTTAA GTGTTTAAAA GCAAATACTG ACTTTCAAAA AAGTTTTTAA AACCTGATTT    36240

GAAAGCTAAC AATTTTGATA GTCTGAACAC AAGCATTTCA CTTCTCCAAG AAGTACCTGT    36300

GAACAGTACA ATATTTCAGT ATTGAGCTTT GCATTTATGA TTTATCTAGA AATTTACCTC    36360

AAAAGCAGAA TTTTTAAAAC TGCATTTTTA ATCAGTGGAA CTCAATGTAT AGTTAGCTTT    36420
```

```
ATTGAAGTCT TATCCAAACC CAGTAAAACA GATTCTAAGC AAACAGTCCA ATCAGTGAGT    36480

CATAATGTTT ATTCAAAGTA TTTTATCTTT TATCTAGAAT CCACATATGT ATGTCCAATT    36540

TGATTGGGAT AGTAGTTAGG ATAACTAAAA TTCTGGGCCT AATTTTTTAA AGAATCCAAG    36600

ACAAACTAAA CTTTACTGGG TATATAACCT TCTCAATGAG TTACCATTCT TTTTTATAAA    36660

AAAAATTGTT CCTTGAAATG CTAAACTTAA TGGCTGTATG TGAAATTTGC AAAATACTGG    36720

TATTAAAGAA CGCTGCAGCT TTTTTATGTC ACTCAAAGGT TAATCGGAGT ATCTGAAAGG    36780

AATTGTTTTT ATAAAAACAT TGAAGTATTA GTTACTTGCT ATAAATAGAT TTTTATTTTT    36840

GTTTTTTAGC CTGTTATATT TCCTTCTGTA AAATAAAATA TGTCCAGAAG AGGCATGTTG    36900

TTTCTAGATT AGGTAGTGTC CTCATTTTAT ATTGTGACCA CACAGCTAGA GCACCAGAGC    36960

CCTTTTGCTA TACTCACAGT CTTGTTTTCC CAGCCTCTTT TACTAGTCTT TCAGGAGGTT    37020

TGCTCTTAGA ACTGGTGATG TAAAGAATGG AAGTAGCTGT ATGAGCAGTT CAAAGGCCAA    37080

GCCGTGGAAT GGTAGCAATG GGATATAATA CCTTTCTAAG GGAAACATTT GTATCAGTAT    37140

CATTTGATCT GCCATGGACA TGTGTTTAAA GTGGCTTTCT GGCCCTTCTT TCAATGGCTT    37200

CTTCCCTAAA ACGTGGAGAC TCTAAGTTAA TGTCGTTACT ATGGGCCATA TTACTAATGC    37260

CCACTGGGGT CTATGATTTC TCAAAATTTT CATTCGGAAT CCGAAGGATA CAGTCTTTAA    37320

ACTTTAGAAT TCCCAAGAAG GCTTTATTAC ACCTCAGAAA TTGAAAGCAC CATGACTTTG    37380

TCCATTAAAA AATTATCCAT AGTTTTTTTA GTGCTTTTAA CATTCCGACA TACATCATTC    37440

TGTGATTAAA TCTCCAGATT TCTGTAAATG ATACCTACAT TCTAAAGAGT TAATTCTAAT    37500

TATTCCGATA TGACCTTAAG GAAAAGTAAA GGAATAAATT TTTGTCTTTG TTGAAGTATT    37560

TAATAGAGTA AGGTAAAGAA GATATTAAGT CCCTTTCAAA ATGGAAAATT AATTCTAAAC    37620

TGAGAAAAAT GTTCCTACTA CCTATTGCTG ATACTGTCTT TGCATAAATG AATAAAAATA    37680

AACTTTTTTT CTTCAAATGT GTTTTGGCT TTCCGATGTA ATAATGTAAA ATGGTGGGGA    37740

GTTGCGTGGG AACTGTGTAA CAAGGTTTAA ATTCGTATAA CAAGCTTTAG ATTCTTAAAA    37800

TGCAGAAGTA TAAAGTTCAG TATACTAATC TGTCTGAGTT AGCCCATAAA AGCAAATGTA    37860

GGTACAAAGA TAAGTTTAAG AGGTGCATCA ACAGCAGTGC AGACTAGGAA TGCTGATGAA    37920

CACATCCGAC TCTGCTATCT CACGGCTAAG GTCCCTCACA TTTTGGACCC TATGAAGCAT    37980

TTTGTCTACT GTACACTTTG GGCCTAGTCT CTAGATCATT TATTTCGGGG TATTGCAGTT    38040

GCCTAAGGGA GCTTAATTTT TTTATATTGC AGGTACTTCC TGTGGATACC ATAAAAAAAA    38100

AAAATCAGTA CCGCTTCTTC TAGCTTTAGT GTTAGTACTC AGTTCTATAA GCTGAGTCCA    38160

GTGGAGAGGA AACTCCTCAG ACACTCCTGT ATTTCATTAG TTAGTAAGCT TGCTGATTCA    38220

TAACCAGAAA GTTGACTCCA AGGATACGCA GGATAGCAAA CAGTGCTTTC TGCATCACCA    38280

AAGATTAAAT TGTGATGTTT AGTGTCCAAT AATAGGCAAA AAATTAGTAA TTCTTTTATG    38340

TGCCTATGTG TATATATGTG TACATATGTG TCTATATATG CATATATTTA TGGTTATGTA    38400

CATACTAACG ATTATCCAGA ATATTTGGTT CTAGCTGATC AAGCTAGTAG GTTTTCAGTA    38460

TTTTCAGACC CCAAAACTAG ACTACATATG GTTAAGATA GTTGCTTTAC ACCAGCTTGT     38520

TTCTAGTTTC CTATTAAATT ATTACCACAA AAATCTTTGG AATTGAAAAA TAACAGTTAA    38580

GCACTTTTTT GTAAAAAGTT CAAGTTATGG TGAAATCAAG CAGCTCTAAA AAGGTTGGTC    38640

ACCTCCTTAA GTGTATTCTG CATGTTGGTT TTTTTCTTTT TCTAAAATCA GATTACCTTT    38700

AATTCAAAAT AACTTCAGAA TTGGTAGTAC CTGTCTGGCA AGGAAGTCAT TGACTCTTAA    38760
```

-continued

```
AAATAAATAC TCCACAGCAT TTCCCTCTCG TTATAAAGCA CCTCTAGCCC CCTCTTCACT    38820
AAATTTTTCT TGGCTTTTTT TTAAAGGTAA ACTGATAAAA ATGGGCTGCC ACATTGCTTA    38880
ATCGCCTTGC CTGCTTTCCT TGCTGTCAGT TGAGGGTAAT GAGGAGCAGC AACGATAAGG    38940
CAGCGTGCCA CCTTGCTTTC ACAAAGATGC CAATAGAGAA AGTGGGGAAA CATAAGGGAG    39000
AAAAAAGTAG CAGTATTTTA CATTGACCAA GTCTTGTGAA TGGGCCAGCT ATTGAGTATG    39060
ATCATTTGGA ATCCCTAGAT AAGGATTGCT CCTGTACATA TTTTGATAAG TGTAATCTAT    39120
CCCTTCCCAA CATGTGTAGT ATGTCTCTGT ATGTAACTGA TTGTTGTGAG CAATTCCTTG    39180
CCACTCACCA AAGACAGAAC TTTCCATCTG TAGACAGTAC ATTTTGTAGT AGAAAACAAT    39240
AGACATAAGA AGTTCAAACT ATAAACATGT TTTTGAATGC TCATGAAAGA TAATCTGCAT    39300
AGCAAAGAAA TAATAGACAA TTCAACATTG CATTTAGAGT TAAAAACATC TGTCCAGTAT    39360
GGATGTAGCT GTGGGCCAAT CCTAAGTAAA CGCAAAAAAA AAAAAAAAAA AAAATTGTCT    39420
CTTGGTACAG AAGTTGAAAC TACCACTCTA CCACTGTACA ATTAAACTCT ATGGTCGCTG    39480
TATTTTACGT TTTTAACTGG TCTGAAACAG TTCTCTAGTT AAGTCTGTAG TTCGTTTTCC    39540
CAAGACAAGG CTTTGTATCT TACGTGCACC TTCATTAATG CTGCATGCCA GGAATTCCAC    39600
ATGAAACTTC AAGATGCCGG TTCACTAGGT CTTTTCCACA TGAAACTTCA AGATACCGGT    39660
TCACTAGGTC TTTAACAATA GAACAAATAC TTGCATGACT GGGATATTCA GGTCATGAAC    39720
ACTCCTTATA AATTTGAAGC AATAGTAACA TTTTAAGCAC TTTGGAAAAT TGGAGGTTTC    39780
ATAACCCTCA ATCAGATCTT TTTATAGAAT AACAAAAATA CACTAAGGTT CTAATCACAT    39840
CTATTGTCTT TGCCCAAAAT AACATGGATA GAGACACACT CCATTCTGGC TCAATCTTAG    39900
ATGAAACTCC AGAAGAAAGG CAGTTGATAA TGATACAGCC AGGCCAGCTG TTTAAGTGGA    39960
CGTGTCCCCT CTGCCCTTGT ACATTTGTTT AAAAATTTTG ATAGGACTCT TCCCGCCTCC    40020
TTCACACCCT CCATAAATCT GACTAGGCCC ATAAGAATGG AGAGAGGTAA TTTAAAAGGC    40080
AGAGGACATT TTTCTCCTTG TTTTTACCTA TGCTGATCCC CTACCTGGTG TTGGAGCAGC    40140
TTCACTGTGA GTAAAATCTG AACAGTGTTT AAGCAGTAAA CCCACTATAT TGAGGAAAGC    40200
GTGACCTGCA CTTTTTTTTT TTTTTTTTC CTGAACAAGA CTTGGTTGTT GCTCATCATT    40260
TTGGTTGGTG ATGGGTCTTT GACAAACCGA TATGCTCACC ATCCAAAGTT GTGTCCATGT    40320
TTAGATCC                                                            40328
```